US011536715B2

(12) United States Patent
Jungmann et al.

(10) Patent No.: US 11,536,715 B2
(45) Date of Patent: Dec. 27, 2022

(54) QUANTITATIVE DNA-BASED IMAGING AND SUPER-RESOLUTION IMAGING

(71) Applicant: President and Fellows of Harvard College, Cambridge, MA (US)

(72) Inventors: Ralf Jungmann, Munich (DE); Peng Yin, Brookline, MA (US); Mingjie Dai, Brookline, MA (US); Maier S. Avendano Amado, Brookline, MA (US); Johannes B. Woehrstein, Munich (DE)

(73) Assignee: President and Fellows of Harvard College, Cambridge, MA (US)

( * ) Notice: Subject to any disclaimer, the term of this patent is extended or adjusted under 35 U.S.C. 154(b) by 69 days.

(21) Appl. No.: 16/559,490

(22) Filed: Sep. 3, 2019

(65) Prior Publication Data

US 2020/0064340 A1    Feb. 27, 2020

Related U.S. Application Data

(62) Division of application No. 14/908,333, filed as application No. PCT/US2014/048977 on Jul. 30, 2014, now abandoned.

(60) Provisional application No. 61/934,759, filed on Feb. 1, 2014, provisional application No. 61/884,126, filed on Sep. 29, 2013, provisional application No. 61/859,891, filed on Jul. 30, 2013.

(51) Int. Cl.
| | |
|---|---|
| *G01N 33/53* | (2006.01) |
| *G16B 40/00* | (2019.01) |
| *G16B 45/00* | (2019.01) |
| *C12Q 1/6816* | (2018.01) |
| *C12Q 1/6804* | (2018.01) |
| *G06T 7/246* | (2017.01) |
| *C12Q 1/6841* | (2018.01) |
| *G16B 40/10* | (2019.01) |
| *G06V 10/28* | (2022.01) |
| *G06V 10/50* | (2022.01) |
| *G06V 10/75* | (2022.01) |
| *C07K 16/18* | (2006.01) |
| *G06K 9/62* | (2022.01) |

(52) U.S. Cl.
CPC ......... *G01N 33/5308* (2013.01); *C07K 16/18* (2013.01); *C12Q 1/6804* (2013.01); *C12Q 1/6816* (2013.01); *C12Q 1/6841* (2013.01); *G06K 9/6298* (2013.01); *G06T 7/248* (2017.01); *G06V 10/28* (2022.01); *G06V 10/50* (2022.01); *G06V 10/754* (2022.01); *G06V 10/758* (2022.01); *G16B 40/00* (2019.02); *G16B 40/10* (2019.02); *G16B 45/00* (2019.02); *C07K 2317/76* (2013.01); *G01N 2333/36* (2013.01); *G01N 2458/10* (2013.01)

(58) Field of Classification Search
CPC ......... C12Q 1/68; C12Q 1/6816; G01N 33/53
See application file for complete search history.

(56) References Cited

U.S. PATENT DOCUMENTS

| | | | |
|---|---|---|---|
| 5,424,413 A | 6/1995 | Hogan et al. | |
| 5,491,063 A | 2/1996 | Fisher et al. | |
| 5,681,943 A | 10/1997 | Letsinger et al. | |
| 5,888,778 A | 3/1999 | Shuber et al. | |
| 6,083,486 A | 7/2000 | Weissleder et al. | |
| 6,110,687 A * | 8/2000 | Nilsen .................... | C07K 16/40 |
| | | | 435/6.19 |
| 6,146,828 A | 11/2000 | Lapidus et al. | |
| 6,150,173 A | 11/2000 | Schubert | |
| 6,451,588 B1 | 9/2002 | Egholm et al. | |
| 6,468,785 B1 | 10/2002 | Wang et al. | |
| 6,534,041 B1 | 3/2003 | Licha et al. | |
| 6,815,164 B2 | 11/2004 | Kurn | |
| 6,833,246 B2 | 12/2004 | Balasubramanian | |
| 6,924,115 B2 | 8/2005 | Schubert | |
| 8,481,714 B2 | 7/2013 | Fujimoto et al. | |
| 9,944,972 B2 | 4/2018 | Yin et al. | |
| 9,975,916 B2 | 5/2018 | Yin et al. | |
| 10,006,917 B2 | 6/2018 | Dai et al. | |
| 10,024,796 B2 | 7/2018 | Yin et al. | |
| 10,041,108 B2 | 8/2018 | Barish et al. | |
| 10,190,151 B2 | 1/2019 | Yin et al. | |
| 10,294,510 B2 | 5/2019 | Yin et al. | |
| 11,092,606 B2 | 8/2021 | Lara Gutierrez et al. | |
| 2002/0015679 A1 | 2/2002 | Kotov | |
| 2002/0051986 A1 * | 5/2002 | Baez ................ | C12Q 2521/501 |
| | | | 435/6.11 |
| 2002/0106648 A1 | 8/2002 | Lizardi et al. | |
| 2002/0173053 A1 | 11/2002 | Damaj et al. | |
| 2002/0177149 A1 | 11/2002 | Rimm et al. | |

(Continued)

FOREIGN PATENT DOCUMENTS

| | | |
|---|---|---|
| DE | 4421891 A1 | 1/1996 |
| EP | 2703816 A1 | 3/2014 |

(Continued)

OTHER PUBLICATIONS

Heidel et al., Molecular Conjugates. Advances in Biochemical Engineering and Biotechnoogy. 99 : 7-39 (Year: 2005).*
Hendrickson et al.,High sensitivity multianalyte immunoassay using covalent DNA-labeled antibodies and PCR. Nucleic Acids Research 23(3) : 522-529 (Year: 2005).*
Aitken et al., An oxygen scavenging system for improvement of dye stability in single-molecule fluorescence experiments. Biophys J. Mar. 1, 2008;94(5):1826-35. Epub Oct. 5, 2007.

(Continued)

*Primary Examiner* — Ethan C Whisenant
(74) *Attorney, Agent, or Firm* — Wolf, Greenfield & Sacks, P.C.

(57) ABSTRACT

The present disclosure provides, inter alia, methods and compositions (e.g., conjugates) for imaging, at high spatial resolution, targets of interest.

17 Claims, 38 Drawing Sheets

Specification includes a Sequence Listing.

(56) References Cited

U.S. PATENT DOCUMENTS

| | | | |
|---|---|---|---|
| 2002/0182601 A1* | 12/2002 | Sampson | C12Q 1/6872 435/6.12 |
| 2003/0044353 A1 | 3/2003 | Weissleder et al. | |
| 2003/0064398 A1 | 4/2003 | Barnes | |
| 2003/0073149 A1 | 4/2003 | Archer et al. | |
| 2003/0118595 A1* | 6/2003 | Niemeyer | A61K 47/557 424/184.1 |
| 2003/0165925 A1 | 9/2003 | Saito et al. | |
| 2003/0175852 A1 | 9/2003 | Kalra et al. | |
| 2004/0121382 A1 | 6/2004 | Liu et al. | |
| 2004/0121385 A1 | 6/2004 | Andersson et al. | |
| 2004/0248325 A1 | 12/2004 | Bukusoglu | |
| 2005/0014163 A1 | 1/2005 | Dong et al. | |
| 2005/0095595 A1 | 5/2005 | Pittaro et al. | |
| 2005/0169843 A1 | 8/2005 | Weissleder et al. | |
| 2005/0171434 A1 | 8/2005 | Madden et al. | |
| 2005/0266419 A1 | 12/2005 | Pappas et al. | |
| 2005/0287578 A1 | 12/2005 | Davis | |
| 2006/0204999 A1 | 9/2006 | Macevicz | |
| 2006/0228733 A1* | 10/2006 | Pierce | C12Q 2525/301 435/6.14 |
| 2007/0009914 A1 | 1/2007 | Wallace et al. | |
| 2007/0048759 A1 | 3/2007 | Luo et al. | |
| 2007/0117109 A1 | 5/2007 | Rothemund | |
| 2007/0259345 A1 | 11/2007 | Sampas | |
| 2008/0004185 A1* | 1/2008 | Labgold | C12Q 1/6825 506/9 |
| 2008/0044834 A1 | 2/2008 | Heyduk | |
| 2008/0118934 A1 | 5/2008 | Gerdes et al. | |
| 2008/0182336 A1 | 7/2008 | Zhuang et al. | |
| 2008/0242560 A1 | 10/2008 | Gunderson et al. | |
| 2009/0011956 A1 | 1/2009 | Yin et al. | |
| 2010/0068710 A1 | 3/2010 | Buela et al. | |
| 2010/0081134 A1 | 4/2010 | Mirkin et al. | |
| 2010/0151472 A1 | 6/2010 | Nolan et al. | |
| 2011/0092381 A1 | 4/2011 | Sood et al. | |
| 2011/0244457 A1 | 10/2011 | Nadeau et al. | |
| 2011/0311966 A1* | 12/2011 | Hennig | C12Q 1/6804 435/6.1 |
| 2012/0004132 A1 | 1/2012 | Zhang et al. | |
| 2012/0071330 A1 | 3/2012 | Kokoris et al. | |
| 2012/0107798 A1 | 5/2012 | Santangelo | |
| 2012/0178081 A1 | 7/2012 | Nguyen et al. | |
| 2012/0251552 A1 | 10/2012 | Horlick | |
| 2012/0258870 A1* | 10/2012 | Schwartz | C07H 21/00 506/4 |
| 2013/0027518 A1 | 1/2013 | Mackay et al. | |
| 2013/0261019 A1 | 10/2013 | Lin et al. | |
| 2014/0057254 A1 | 2/2014 | Bodepudi et al. | |
| 2014/0248710 A1 | 9/2014 | Heyduk et al. | |
| 2014/0256588 A1 | 9/2014 | Glezer et al. | |
| 2014/0275482 A1* | 9/2014 | Polukhtin | C07D 207/46 530/363 |
| 2015/0004598 A1* | 1/2015 | Gao | C12Q 1/6841 435/6.11 |
| 2015/0329584 A1 | 11/2015 | Yin et al. | |
| 2016/0033411 A1 | 2/2016 | Barish et al. | |
| 2016/0161472 A1 | 6/2016 | Jungmann et al. | |
| 2016/0169903 A1 | 6/2016 | Dai et al. | |
| 2016/0312272 A1 | 10/2016 | Barish et al. | |
| 2016/0319328 A1 | 11/2016 | Yin et al. | |
| 2016/0369321 A1 | 12/2016 | Landegren et al. | |
| 2017/0015698 A1 | 1/2017 | Iinuma et al. | |
| 2017/0038391 A1* | 2/2017 | Lara Gutierrez | C12Q 1/6816 |
| 2017/0137864 A1 | 5/2017 | Yin et al. | |
| 2018/0037950 A1 | 2/2018 | Gunderson et al. | |
| 2018/0216159 A1 | 8/2018 | Yin et al. | |
| 2018/0224461 A1 | 8/2018 | Gutierrez et al. | |
| 2019/0203291 A1* | 7/2019 | Hindson | C12Q 1/6806 |
| 2019/0323061 A1 | 10/2019 | Yin et al. | |
| 2022/0003776 A1 | 1/2022 | Gutierrez et al. | |

FOREIGN PATENT DOCUMENTS

| | | |
|---|---|---|
| EP | 3696277 A2 | 8/2020 |
| JP | H 07-503139 A | 4/1995 |
| JP | H08-070876 A | 3/1996 |
| JP | 2004-537257 A | 12/2004 |
| JP | 2008-545142 A | 12/2008 |
| JP | 2013-507941 A | 3/2013 |
| JP | 2013-539867 A | 10/2013 |
| WO | WO 1998/18961 A1 | 5/1998 |
| WO | WO 00/03034 A2 | 1/2000 |
| WO | WO 00/20641 A1 | 4/2000 |
| WO | WO 00/58507 A1 | 10/2000 |
| WO | WO 02/079771 A1 | 10/2002 |
| WO | WO 03/003810 A2 | 1/2003 |
| WO | WO 2004/009848 A1 | 1/2004 |
| WO | WO 2005/017485 A2 | 2/2005 |
| WO | WO 2005/047468 A2 | 5/2005 |
| WO | WO 2012/051386 A2 | 4/2012 |
| WO | WO 2012/058638 A2 | 5/2012 |
| WO | WO 2012/071428 A2 | 5/2012 |
| WO | WO 2013/010023 A2 | 1/2013 |
| WO | WO 2014/028538 A2 | 2/2014 |
| WO | WO 2014/145620 A2 | 9/2014 |
| WO | WO 2015/017586 A1 | 2/2015 |
| WO | WO 2015/070037 A2 | 5/2015 |
| WO | WO 2015/089506 A2 | 6/2015 |
| WO | WO 2015/138653 A1 | 9/2015 |
| WO | WO 2020/045984 A1 | 3/2020 |

OTHER PUBLICATIONS

Azcona et al., Development and clinical evaluation of automatic fiducial detection for tumor tracking in cine megavoltage images during volumetric modulated arc therapy. Med Phys. Mar. 2013;40(3):031708. doi:10.1118/1.4791646.

Baines et al., Peptide aptamers as guides for small-molecule drug discovery. Drug Discov Today. Apr. 2006;11(7-8):334-41.

Betzig et al., Imaging intracellular fluorescent proteins at nanometer resolution. Science. Sep. 15, 2006;313(5793):1642-5. Epub Aug. 10, 2006.

Bird et al., Single-chain antigen-binding proteins. Science. Oct. 21, 1988;242(4877):423-6.

Derr et al., Tug-of-war in motor protein ensembles revealed with a programmable DNA origami scaffold. Science. Nov. 2, 2012;338(6107):662-5. doi: 10.1126/science.1226734. Epub Oct. 11, 2012.

Fukusaki et al., SELEX for tubulin affords specific T-rich DNA aptamers. Systematic evolution of ligands by exponeential enrichment. Bioorg Med Chem Lett. Nov. 19, 2001;11(22):2927-30.

Giannone et al., Dynamic superresolution imaging of endogenous proteins on living cells at ultra-high density. Biophys J. Aug. 9, 2010;99(4):1303-10. doi: 10.1016/j.bpj.2010.06.005.

Greenwood et al., Proximity assays for sensitive quantification of proteins. Biomol Detect Quantif. May 20, 2015;4:10-6. doi: 10.1016/j.bdq.2015.04.002. eCollection 2015.

Gullberg et al., Cytokine detection by antibody-based proximity ligation. Proc Natl Acad Sci U S A. Jun. 1, 2004;101(22):8420-4. Epub May 21, 2004.

Hein et al., Stimulated emission depletion (STED) nanoscopy of a fluorescent protein-labeled organelle inside a living cell. Proc Natl Acad Sci U S A. Sep. 23, 2008;105(38):14271-6. doi:10.1073/pnas.0807705105. Epub Sep. 16, 2008.

Hell et al., Breaking the diffraction resolution limit by stimulated emission: stimulated-emission-depletion fluorescence microscopy. Opt Lett. Jun. 1, 1994;19(11):780-2.

Hell et al., Microscopy and its focal switch. Nat Methods. Jan. 2009;6(1):24-32. doi: 10.1038/nmeth.1291.

Hu et al., Visualization of interactions among bZIP and Rel family proteins in living cells using bimolecular fluorescence complementation. Mol Cell. Apr. 2002;9(4):789-98.

Huang et al., Three-dimensional super-resolution imaging by stochastic optical reconstruction microscopy. Science. Feb. 8, 2008;319(5864):810-3. doi: 10.1126/science.1153529. Epub Jan. 3, 2008.

(56) References Cited

OTHER PUBLICATIONS

Huston et al., Protein engineering of antibody binding sites: recovery of specific activity in an anti-digoxin single-chain Fv analogue produced in Escherichia coli. Proc Natl Acad Sci U S A. Aug. 1988;85(16):5879-83.

Johnson-Buck et al., Super-resolution fingerprinting detects chemical reactions and idiosyncrasies of single DNA pegboards. Nano Lett. Feb. 13, 2013;13(2):728-33. doi:10.1021/nl304415b. Epub Jan. 31, 2013.

Jones et al., Fast, three-dimensional super-resolution imaging of live cells. Nat Methods. Jun. 2011;8(6):499-508. doi: 10.1038/nmeth. 1605. Epub May 8, 2011.

Jungmann et al., Single-molecule kinetics and super-resolution microscopy by fluorescence imaging of transient binding on DNA origami. Nano Lett. Nov. 10, 2010;10(11):4756-61. doi: 10.1021/nl103427w.

Jungmann et al., Multiplexed 3D cellular super-resolution imaging with DNA-PAINT and Exchange-PAINT. Nat Methods. Mar. 2014;11(3):313-18. doi: 10.1038/nmeth.2835. Epub Feb. 2, 2014.

Lew et al., Three-dimensional superresolution colocalization of intracellular protein superstructures and the cell surface in live Caulobacter crescentus. Proc Natl Acad Sci U S A. Nov. 15, 2011;108(46):E1102-10. doi: 10.1073/pnas.1114444108. Epub Oct. 26, 2011.

Lin et al., Submicrometre geometrically encoded fluorescent barcodes self-assembled from DNA. Nat Chem. Oct. 2012;4(10):832-9.

Liu et al., Super-resolution imaging and tracking of protein-protein interactions in sub-diffraction cellular space. Nat Commun. Jul. 17, 2014;5:4443. doi: 10.1038/ncomms5443.

Lubeck et al., Single-cell systems biology by super-resolution imaging and combinatorial labeling. Nat Methods. Jun. 3, 2012;9(7):743-8. doi:10.1038/nmeth.2069.

Ni et al., Nucleic acid aptamers: clinical applications and promising new horizons. Curr Med Chem. 2011;18(27):4206-14.

Niemeyer et al., Oligonucleotide-directed self-assembly of proteins: semisynthetic DNA-streptavidin hybrid molecules as connectors for the generation of macroscopic arrays and the construction of supramolecular bioconjugates. Nucleic Acids Research. 1994;22(25):5530-9.

Nieves et al., DNA-Based Super-Resolution Microscopy: DNA-PAINT. Genes (Basel). Dec. 11, 2018;9(12). pii: E621. doi: 10.3390/genes9120621. 14 pages.

Paige et al., Fluorescence imaging of cellular metabolites with RNA. Science. Mar. 9, 2012;335(6073):1194. doi: 10.1126/science. 1218298.

Paige et al., RNA mimics of green fluorescent protein. Science. Jul. 29, 2011;333(6042):642-6. doi:10.1126/science.1207339.

Rasnik et al., Nonblinking and long-lasting single-molecule fluorescence imaging. Nat Methods. Nov. 2006;3(11):891-3. Epub Oct. 1, 2006.

Ries et al., A simple, versatile method for GFP-based super-resolution microscopy via nanobodies. Nat Methods. Jun. 2012;9(6):582-4. doi: 10.1038/nmeth.1991. Epub Apr. 29, 2012.

Rust et al., Sub-diffraction-limit imaging by stochastic optical reconstruction microscopy (STORM).Nat Methods. Oct. 2006;3(10):793-5. Epub Aug. 9, 2006.

Schnitzbauer et al., Super-resolution microscopy with DNA-PAINT. Nat Protocols. 2017;12(6):1198-1228. Epub May 18, 2017.

Sharonov et al.,Wide-field subdiffraction imaging by accumulated binding of diffusing probes. Proc Natl Acad Sci U S A. Dec. 12, 2006;103(50):18911-6. Epub Dec. 1, 2006.

Söderberg et al., Direct observation of individual endogenous protein complexes in situ by proximity ligation. Nat Methods. Dec. 2006;3(12):995-1000. Epub Oct. 29, 2006.

Stadler et al., Fluorescent DNA nanotags featuring covalently attached intercalating dyes: synthesis, antibody conjugation, and intracellular imaging. Bioconjug Chem. Aug. 17, 2011;22(8):1491-502. doi: 10.1021/bc100485f. Epub Jul. 22, 2011.

Stoltenburg et al., SELEX—a (r)evolutionary method to generate high-affinity nucleic acid ligands. Biomol Eng. Oct. 2007;24(4):381-403. Epub Jun. 16, 2007.

Szychowski et al., Cleavable biotin probes for labeling of biomolecules via azide-alkyne cycloaddition. J Am Chem Soc. Dec. 29, 2010;132(51):18351-60. doi: 10.1021/ja1083909. Epub Dec. 8, 2010.

Tokunaga et al., Highly inclined thin illumination enables clear single-molecule imaging in cells. Nat Methods. Feb. 2008;5(2):159-61. doi: 10.1038/nmeth1171. Epub Jan. 6, 2008.

Ward et al., Binding activities of a repertoire of single immunoglobulin variable domains secreted from Escherichia coli. Nature. Oct. 12, 1989;341(6242):544-6.

Wei et al., Complex shapes self-assembled from single-stranded DNA tiles. Nature. May 30, 2012;485(7400):623-6. doi: 10.1038/nature11075.

Willig et al., Nanoscale resolution in GFP-based microscopy. Nat Methods. Sep. 2006;3(9):721-3.

Winckler et al., Identification and super-resolution imaging of ligand-activated receptor dimers in live cells. Sci Rep. 2013;3:2387. doi: 10.1038/srep02387.

Yin et al., Kinetics and dynamics of DNA hybridization. Acc Chem Res. Nov. 15, 2011;44(11):1172-81. doi: 10.1021/ar200068j. Epub Jun. 30, 2011.

Partial European Search Report dated Jun. 2, 2020, for Application No. EP 20164170.1.

Extended European Search Report dated Sep. 18, 2020, for Application No. EP 20164170.1.

[No Author Listed] DNA origami scaffolds for cryo-EM visualization of membrane associated complexes. University of Michigan. Project ID: 377. Last accessed from http://mcubed.umich.edu/projects/dna-origami-scaffolds-cryo-em-visualization-membrane-associated-complexes on Nov. 12, 2015.

[No Author Listed], Hybridization Probe. Wikipedia. Printed Jun. 26, 2020. 3 pages. Accessible at en.wikipedia.org/wiki/Hybridization_probe.

[No Author Listed], New England Biolabs, Inc. 2013-14 Catalog and Technical Reference, USER Enzyme, 2013, p. 129.

[No Author Listed], Stringency. Genscript. Printed Jun. 26, 2020. 2 pages. Accessible at www.genscript.com/molecular-biology-glossary/2822/stringency.

Ahern, Biochemical, reagents kits offer scientists good return on investment. The Scientist. Jul. 24, 1995;9(15):20. 7 pages. Http://www.the-scientist.com/article/print/16618/.

Asanuma et al., Enantioselective Incorporation of Azobenzenes into Oligodeoxyribonucleotide for Effective Photoregulation of Duplex Formation This work was partially supported by a Grant-in-Aid for Scientific Research from the Ministry of Education, Culture, Sports, Science and Technology, Japan (Molecular Synchronization for Design of New Materials System). The support by the Grant from "Research for the Future" Program of the Japan Society for the Promotion of Science JSPS-RFTF97I00301) is also acknowledged . . . . Angew Chem Int Ed Engl. Jul. 16, 2001;40(14):2671-2673.

Bai et al., Cryo-EM structure of a 3D DNA-origami object. Proc Natl Acad Sci U S A. Dec. 4, 2012;109(49):20012-7. doi:10.1073/pnas.1215713109. Epub Nov. 19, 2012.

Ben-Shem et al., The structure of the eukaryotic ribosome at 3.0 Å resolution. Science. Dec. 16, 2011;334(6062):1524-9. doi: 10.1126/science.1212642. Epub Nov. 17, 2011.

Chapman et al., Femtosecond X-ray protein nanocrystallography. Nature. Feb. 3, 2011;470(7332):73-7. doi: 10.1038/nature09750.

Cheng et al., A primer to single-particle cryo-electron microscopy. Cell. Apr. 23, 2015;161(3):438-49. doi:10.1016/j.cell.2015.03.050.

Douglas et al., DNA-nanotube-induced alignment of membrane proteins for NMR structure determination. Proc Natl Acad Sci U S A. Apr. 17, 2007;104(16):6644-8. Epub Apr. 2, 2007.

Eggeling et al., Photobleaching of Fluorescent Dyes under Conditions Used for Single-Molecule Detection:? Evidence of Two-Step Photolysis. Anal Chem. Jul. 1, 1998;70(13):2651-9. doi: 10.1021/ac980027p.

Fedorov et al., Modern methods for modulation and imaging of endogenous microRNA. Bulletin of Almazov Federal Heart, Blood and Endocrinology Center. Oct. 2012;5:77-81.

(56) References Cited

OTHER PUBLICATIONS

Fujimoto et al., Site-specific photochemical RNA editing. Chem Commun (Camb). Oct. 28, 2010;46(40):7545-7. doi:10.1039/c0cc03151h. Epub Sep. 17, 2010.

Ghauharali et al., Fluorescence photobleaching-based image standardization for fluorescence microscopy. J Microscopy. May 2000;198(2):88-100.

Jenner et al., Crystal structure of the 80S yeast ribosome. Curr Opin Struct Biol. Dec. 2012;22(6):759-67. doi:10.1016/j.sbi.2012.07.013. Epub Aug. 8, 2012. Review.

Jones et al., Nanomaterials. Programmable materials and the nature of the DNA bond. Science. Feb. 20, 2015;347(6224):1260901. doi:10.1126/science.1260901.

Kato et al., High-resolution structural analysis of a DNA nanostructure by cryoEM. Nano Lett. Jul. 2009;9(7):2747-50. doi: 10.1021/nl901265n.

Ke et al., DNA brick crystals with prescribed depths. Nat Chem. Nov. 2014;6(11):994-1002. doi: 10.1038/nchem.2083. Epub Oct. 19, 2014.

Manning et al., Fabrication of patterned surfaces by photolithographic exposure of DNA hairpins carrying a novel photolabile group. J Exp Nanoscience. Feb. 1, 2010;5(1): 26-39.

Manning et al., Use of oligonucleotides carrying photolabile groups for the control of the deposition of nanoparticles in surfaces and nanoparticle association. Int J Mol Sci. 2011;12(10):7238-49. doi: 10.3390/ijms12107238. Epub Oct. 24, 2011.

Martin, Functional Synthetic DNA Nanostructures. Dissertation. Technische Universität München, Laboratory for Biomolecular Nanotechnology. Filed on Mar. 12, 2013.

Meserve et al., A double-stranded molecular probe for homogeneous nucleic acid analysis. Analyst. Aug. 2008;133(8):1013-9. doi:10.1039/b804853c. Epub Jun. 6, 2008.

Mittag et al., Sequential photobleaching of fluorochromes for polychromatic slide-based cytometry. Cytometry A. Mar. 2006;69(3):139-41.

Nannenga et al., High-resolution structure determination by continuous-rotation data collection in MicroED. Nat Methods. Sep. 2014;11(9):927-30. doi: 10.1038/nmeth.3043. Epub Aug. 3, 2014.

Nannenga et al., Protein structure determination by MicroED. Curr Opin Struct Biol. Aug. 2014;27:24-31. doi: 10.1016/j.sbi.2014.03.004. Epub Apr. 5, 2014.

Pinheiro et al., Challenges and opportunities for structural DNA nanotechnology. Nat Nanotechnol. Nov. 6, 2011;6(12):763-72. doi:10.1038/nnano.2011.187.

Rodgers et al., Transient association of Ku with nuclear substrates characterized using fluorescence photobleaching. J Immunol. Mar. 1, 2002;168(5):2348-55.

Shi et al., Three-dimensional electron crystallography of protein microcrystals. Elife. Nov. 19, 2013;2:e01345. doi:10.7554/eLife.01345.

Shi, A glimpse of structural biology through X-ray crystallography. Cell. Nov. 20, 2014;159(5):995-1014. doi: 10.1016/j.cell.2014.10.051.

Wahlby et al., Sequential immunofluorescence staining and image analysis for detection of large numbers of antigens in individual cell nuclei. Cytometry. Jan. 1, 2002;47(1):32-41.

Wang et al., Caged molecular beacons: controlling nucleic acid hybridization with light. Chem Commun. 2011;47:5708-10.

Winfree et al., Design and self-assembly of two-dimensional DNA crystals. Nature. Aug. 6, 1998;394(6693):539-44.

Wlodawer et al., Protein crystallography for aspiring crystallographers or how to avoid pitfalls and traps in macromolecular structure determination. FEBS J. Nov. 2013;280(22):5705-36. doi:10.1111/febs.12495. Epub Sep. 18, 2013.

Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.

Zhang et al., Structural DNA nanotechnology: state of the art and future perspective. J Am Chem Soc. Aug. 13, 2014;136(32):11198-211. doi:10.1021/ja505101a. Epub Jul. 28, 2014.

Zheng et al., From molecular to macroscopic via the rational design of a self-assembled 3D DNA crystal. Nature. Sep. 3, 2009;461(7260):74-7. doi:10.1038/nature08274.

Lutz et al., Detecting Nanoscale Distribution of Protein Pairs by Proximity-Dependent Super-resolution Microscopy. bioRxiv preprint. Mar. 27, 2019. doi: 10.1101/591081/ 10 pages.

Xing et al., Techniques for the Analysis of Protein-Protein Interactions in Vivo. Plant Physiol. Jun. 2016;171(2):727-58. doi: 10.1104/pp.16.00470. Epub Apr. 25, 2016.

Anderson, M.L.M. Nucleic Acid Hybridization. 1999. Garland Science. Chapter 5:49-51 https://doi.org/10.1201/9781003076780.

Chozinski et al., Twinkle, twinkle little star: photoswitchable fluorophores for super-resolution imaging. FEBS Lett. Oct. 1, 2014;588(19):3603-12. Epub Jul. 7, 2014.

Galbraith et al., Super-resolution microscopy at a glance. J Cell Sci. May 15, 2011;124(Pt 10):1607-11.

Li et al., Switchable Fluorophores for Single-Molecule Localization Microscopy. Chem Rev. Sep. 26, 2018;118(18):9412-9454. Epub Sep. 17, 2018. Author Manuscript, 104 pages.

* cited by examiner

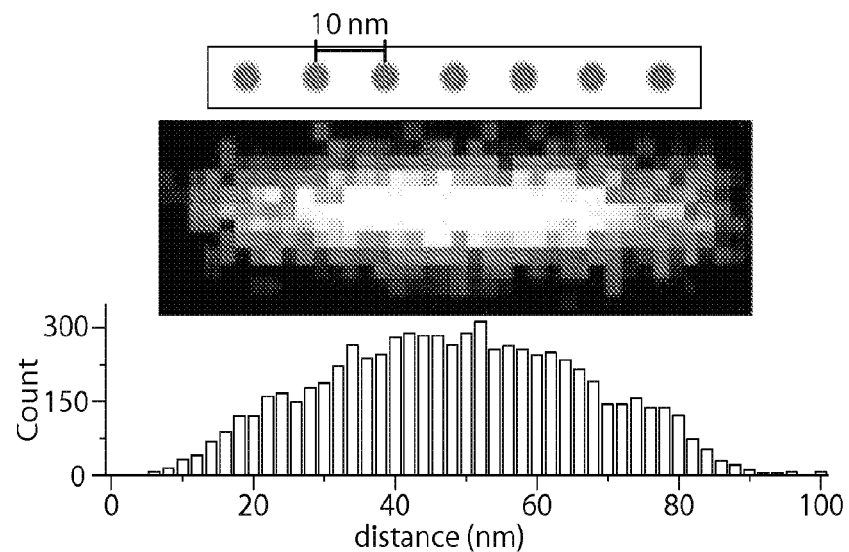
Fig. 4B1
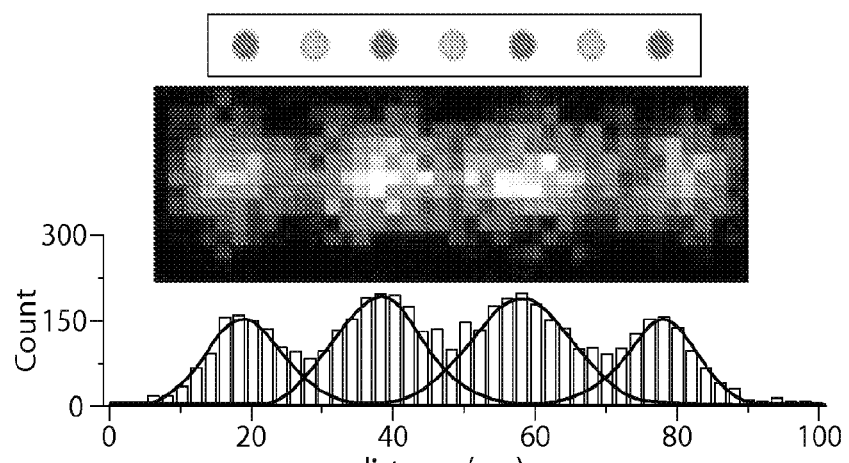
Fig. 4B2
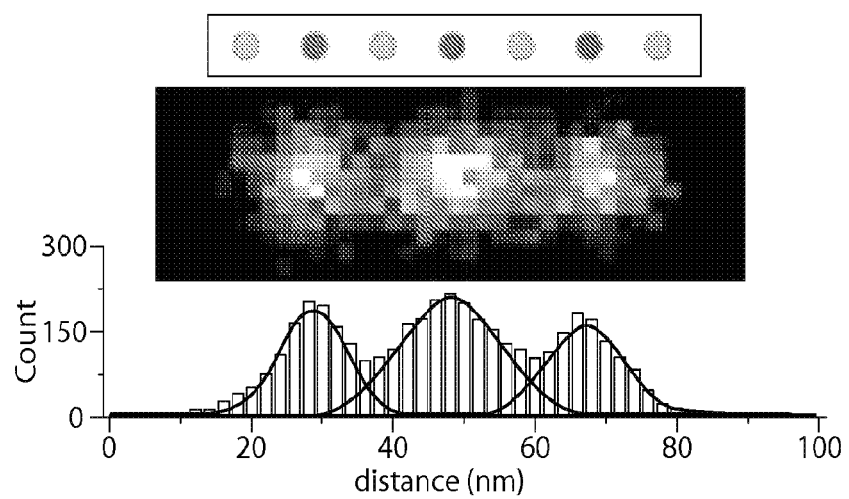
Fig. 4B3

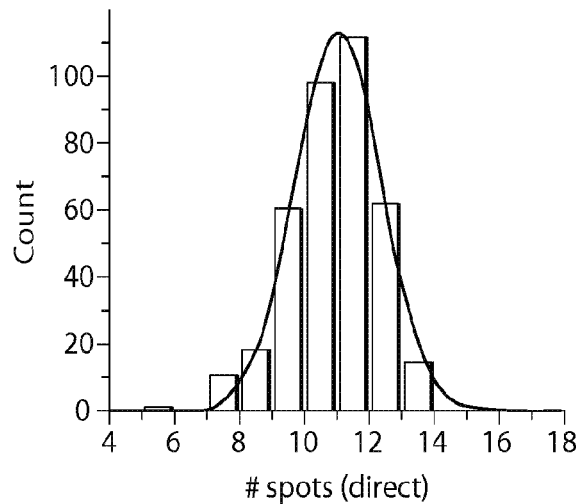
Fig. 7D1
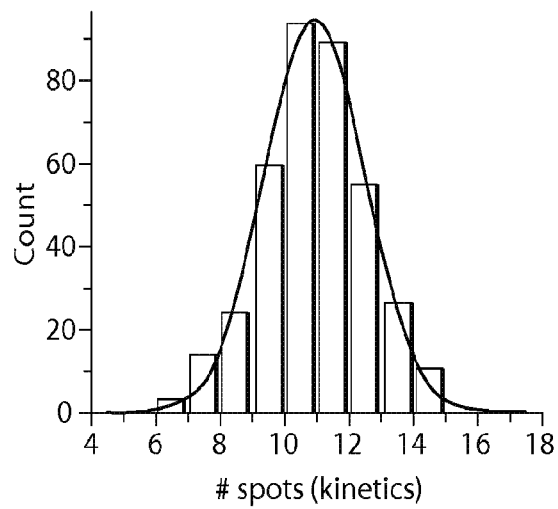
Fig. 7D2
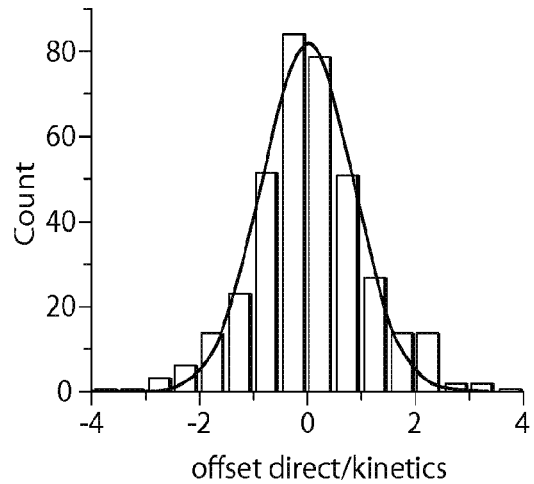
Fig. 7D3

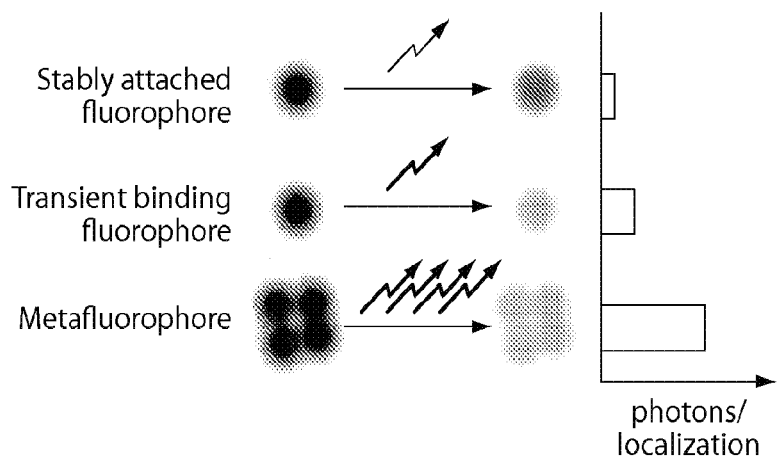
Fig. 11A
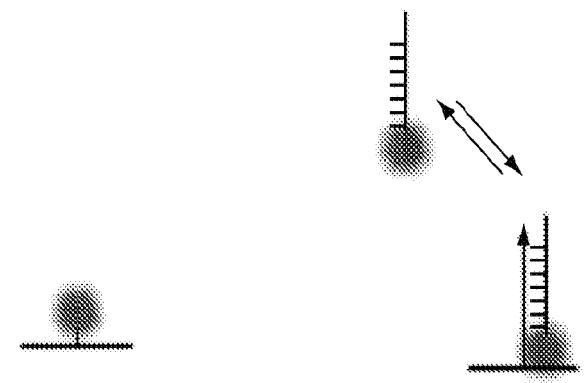
Fig. 11B1     Fig. 11B2

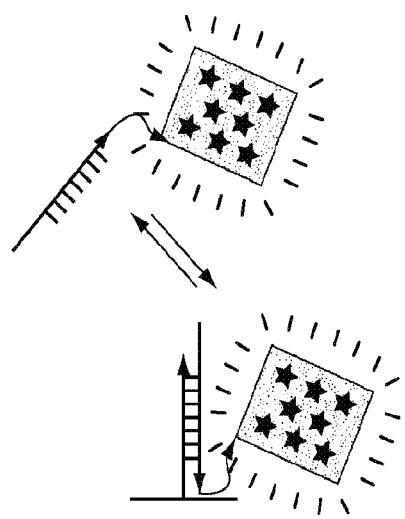
Fig. 11B3
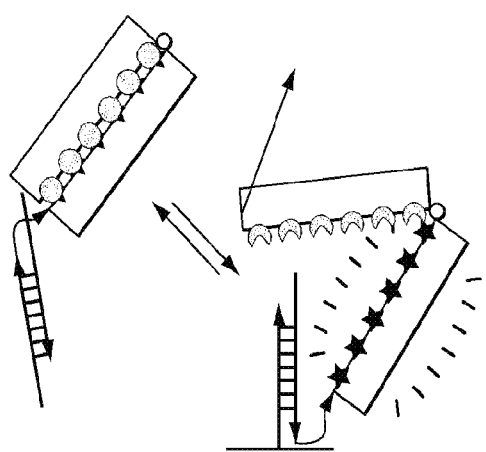
Fig. 11B4

The drift markers

The drift correction principle

~ 110 nm

QUANTITATIVE DNA-BASED IMAGING AND SUPER-RESOLUTION IMAGING

RELATED APPLICATIONS

This application is a divisional of U.S. application Ser. No. 14/908,333, filed Jan. 28, 2016, which is a national stage filing under 35 U.S.C. § 371 of international application number PCT/US2014/048977, filed Jul. 30, 2014, which was published under PCT Article 21(2) in English and claims the benefit under 35 U.S.C. § 119(e) of U.S. provisional application No. 61/934,759, filed Feb. 1, 2014, U.S. provisional application No. 61/884,126, filed Sep. 29, 2013, and U.S. provisional application No. 61/859,891, filed Jul. 30, 2013, each of which is incorporated by reference herein in its entirety.

FIELD OF THE INVENTION

The present disclosure relates generally to the field of detection and quantification of targets.

BACKGROUND OF THE INVENTION

Far-field fluorescence microscopy has seen major advances since the advent of methods that circumvent the classical diffraction limit, e.g., super-resolution microscopy (refs. 1, 2). Most implementations switch molecules between fluorescent ON- and OFF-states to allow consecutive localization of individual molecules. Switching is traditionally obtained in one of two ways: "targeted" switching actively confines the fluorescence excitation to an area smaller than the diffraction of light (e.g., stimulated emission depletion microscopy, or STED (ref. 3)), whereas "stochastic" switching uses photoswitchable proteins (photoactivated localization microscopy, or PALM (ref. 4)) or photoswitchable organic dyes (stochastic optical reconstruction microscopy, or STORM (ref. 1)). Although these methods offer enhanced spatial resolution, they tend to require either expensive instrumentation or highly specialized experimental conditions, and thus have not yet been developed into common biological laboratory techniques.

SUMMARY OF THE INVENTION

The present disclosure provides, inter alia, methods, compositions (e.g., conjugates) and kits for imaging, at high or low spatial resolution, targets (e.g., biomolecules) of interest in, for example, a cellular environment. The methods, compositions and kits of the present disclosure take advantage of repetitive, transient binding of short, labeled (e.g., fluorescently labeled) oligonucleotides (e.g., DNA oligonucleotides), or "imager" strands, to complementary "docking" strands, which are attached to targets of interest, in some embodiments, through an intermediate molecule such as an antibody such as a primary or a secondary antibody, to obtain stochastic switching between fluorescent ON- and OFF-states (FIGS. 1A and 1B). In the unbound state, only background fluorescence from partially quenched (ref. 8) imager strands is observed (depicted by dimmer fluorescence of unbound imager strands in FIG. 1A). This is considered an "OFF" state. Upon binding and immobilization of an imager strand, fluorescence emission is detected using, for example, total internal reflection (TIR) or highly inclined and laminated optical sheet (HILO) microscopy (ref. 9). This is considered an "ON" state. In general, the methods, compositions and kits as provided herein increase the imaging resolution and thus the sensitivity of detection. In some aspects, they also increase the specificity as well as the number of utilizable fluorophores available for detecting targets of interest including but not limited to, e.g., naturally-occurring biomolecules.

By linking a short docking strand to a binding partner (e.g., a protein-binding moiety or a nucleic acid-binding moiety, whether primary or secondary), such as an antibody including a primary and a secondary antibody, different species of targets (e.g., biomolecules, optionally in a cellular environment) can be labeled and subsequently detected by introducing fluorescently-labeled imager strands that are complementary to and bind to the docking strands through transient Watson-Crick interactions. Unlike existing detection methods, the methods of the present disclosure are not limited by the number of spectrally distinct fluorophores available for detecting distinct targets (e.g., biomolecules). Rather, the programmability of nucleic acid (e.g., DNA and/or RNA) molecules and sequential time-lapsed imaging are used herein to provide images of up to hundreds of distinct species of targets using, in some embodiments, only a single optimized fluorophore. Further, these different species of targets (e.g., biomolecules) can be quantified using predictable kinetics of binding of single fluorescently-labeled imager strands to their complementary target docking strands.

In some instances, the methods can be used to generate super-resolution images, significantly even without the need for a super-resolution microscope. It should be understood that while the methods, compositions and kits as provided herein may be described for use in super-resolution imaging, they may also be used, in some embodiments, for imaging that does not require super-resolution. Thus, in some embodiments, the methods, compositions and kits of the present disclosure may be used for imaging, generally.

In some aspects, provided herein is a protein-nucleic acid conjugate, comprising a protein linked to a docking strand that is capable of transiently binding to a complementary labeled imager strand. In some aspects, provided herein is a protein-nucleic acid conjugate, comprising a protein linked to a docking strand that is transiently bound to a complementary labeled imager strand. Imager strands, in some embodiments, are labeled with a detectable label. The detectable label may be, for example, a fluorescent label or other detectable label, e.g., gold nanoparticle. While various aspects and embodiments herein refer to fluorescently-labeled imager strands, it should be understood that such fluorescent labels, in many instances, can be interchanged with other detectable labels. Thus, in some embodiments, a fluorescently-labeled imager strand (which may be detected by, for example, fluorescent microscopy) may be interchanged with an imager strand labeled with, for example, gold nanoparticles (which may be detected by, for example, dark field microscopy). It is also to be understood that the docking strands may be capable of transiently binding a plurality of complementary labeled strands (e.g., the docking strand may comprise a plurality of binding sites for complementary labeled strands).

In some embodiments, a method may be carried out involving a plurality of docking strand and imager strand pairs. Such a method can be used to detect a plurality of targets (e.g., with each docking strand-imager strand pair corresponding to one target). The docking strand-imager strand pairs in the plurality must share an approximately equal probability of hybridizing under a single environment or condition (as defined for example by temperature, salt concentration, strand molarity, etc.), such that if there is an observed difference between the level of binding (and thus the detection) of a population of imager strands, an end user can conclude that such difference is a function of the amount of docking strand and thus ultimately the amount of target. In some embodiments, the docking and imager strands are typically selected such that their bound states have a thermal stability in the range of about +/−0.5 kcal/mol. With this range of thermal stability, it is possible to select at least 200 orthogonal (e.g., different) sequences to be used in these multiplexing methods.

In some embodiments, a protein is an antibody such as a primary antibody or a secondary antibody, an antigen-binding antibody fragment, or a peptide aptamer.

In some embodiments, a protein is linked to the docking strand through an intermediate linker. In some embodiments, the intermediate linker comprises biotin and streptavidin.

In some embodiments, an antibody is a monoclonal antibody.

In some embodiments, a complementary fluorescently-labeled imager strand comprises at least one fluorophore.

In some embodiments, a complementary labeled, optionally fluorescently labeled, imager strand is about 4 to about 30 nucleotides, or about 8 to about 10 nucleotides, in length. In some embodiments, a complementary labeled imager strand is longer than 30 nucleotides.

In this and other aspects and embodiments described herein, the docking strand may comprise a plurality of domains, each complementary to a labeled imager strand. The domains may be identical in sequence (and thus will bind to the identical imager strands) or they may be of different sequence (and thus may bind to imager strands that are not identically labeled). Such domains may also be referred to herein as binding sites for imager strands.

In some embodiments, a docking strand includes at least two or at least three domains, each respectively complementary to a labeled imager strand.

In some aspects, provided herein is a target bound to at least one protein-nucleic acid conjugate.

In some embodiments, the target is a protein. In some embodiments, the target is a nucleic acid (e.g., DNA or RNA).

In some aspects, provided herein is a plurality of protein-nucleic acid conjugates. In some embodiments, the plurality comprises at least two subsets of the protein-nucleic acid conjugates, and the protein-nucleic acid conjugates of each subset bind to different targets.

In some aspects, provided herein is a composition or kit comprising a plurality of protein-nucleic acid conjugates, optionally wherein at least one of the protein-nucleic acid conjugates is bound to at least one target.

In some aspects, provided herein is a composition or kit comprising at least one protein-nucleic acid conjugate that comprises a protein linked to a docking strand, optionally wherein the at least one protein-nucleic acid conjugate is bound to a target, and at least one complementary labeled, optionally fluorescently labeled, imager strand that is transiently bound to (or is capable of transiently binding to) the at least one protein-nucleic acid conjugate.

In some embodiments, a composition or kit comprises at least two complementary labeled, optionally fluorescently labeled, imager strands, wherein the at least two complementary labeled imager strands are identical. In some embodiments, the composition or kit comprises at least two complementary labeled imager strands, wherein the at least two complementary labeled imager strands are different.

In some embodiments, the number of complementary labeled, optionally fluorescently labeled, imager strands is less than, greater than or equal to the number of protein-nucleic acid conjugates.

In some embodiments, a composition or kit comprises at least 2, 3, 4, 5, 6, 7, 9 or 10 different complementary labeled, optionally fluorescently labeled, imager strands. In some embodiments, the composition or kit comprises at least 50 or at least 100 different complementary fluorescently-labeled imager strands.

In some aspects, provided herein is a composition or a kit comprising a (e.g., one or more) docking strand and an (e.g., one or more) imager strand. The docking strand may be modified to include an affinity label, thereby facilitating its subsequent attachment to one or more binding partners, such as an antibodies. For example, the docking strand may be biotinylated or it may be attached to avidin or streptavidin. Other affinity labels can be used instead. The imager strands may be labeled, such as fluorescently labeled. The imager strands may be a plurality of identical imager strands (e.g., with respect to sequence and label) or they may be a plurality of different imager strands (e.g., with respect to sequence and label). The composition or kit may further comprise a target-specific binding partner, such as an antibody. It is to be understood that the components may be bound to each other or they may be unbound, including physically separated from each other, in such compositions and kits. These and other compositions and kits may further comprise one or more buffers including oxygen scavengers.

In some aspects, provided herein is a composition or kit comprising an antibody-nucleic acid conjugate, wherein the antibody is a "secondary antibody" having specificity for an antibody, typically specificity for a particular isotype or an Fc domain of an antibody from a particular species (e.g., a mouse antibody that is specific for a human IgG1 antibody). The nucleic acid in the conjugate is a docking strand, as described herein. The composition or kit may further comprise one or more imager strands (or one or more subsets or populations of imager strands), as described herein. These and other compositions and kits may further comprise one or more buffers including oxygen scavengers.

In some aspects, the present disclosure provides an antibody-DNA conjugate, comprising a monoclonal antibody linked to a docking strand that is bound to a complementary labeled, optionally fluorescently labeled, imager strand, wherein the antibody and the docking strand are each biotinylated and linked to each other through an avidin or streptavidin linker or a biotin-streptavidin linker.

In some aspects, provided herein is an aptamer-nucleic acid conjugate, comprising a nucleic acid aptamer linked to a docking strand that is transiently bound to a complementary labeled, optionally fluorescently labeled, imager strand.

In some aspects, provided herein is a method of detecting a target in a sample, the method comprising contacting a sample with (a) at least one protein-nucleic acid conjugate that comprises a protein linked to a docking strand and (b) at least one fluorescently-labeled imager strand that is complementary to and transiently binds to the docking strand of the at least one protein-nucleic acid conjugate, and determining whether the at least one protein-nucleic acid conjugate binds to the target in the sample. In some embodiments, the determining step comprises imaging transient binding of the at least one fluorescently-labeled imager strand to the docking strand of the at least one protein-nucleic acid conjugate.

In some aspects, provided herein is a method of detecting a target in a sample, the method comprising contacting a sample with (a) at least one protein-nucleic acid conjugate that comprises a protein linked to a docking strand and (b) at least one fluorescently-labeled imager strand that is complementary to and transiently binds to the docking strand of the at least one protein-nucleic acid conjugate, and imaging transient binding, optionally using time-lapsed imaging, of the at least one fluorescently-labeled imager strand to the docking strand of the at least one protein-nucleic acid conjugate.

In some embodiments, a protein of the protein-nucleic acid conjugate is an antibody, an antigen-binding antibody fragment, or a peptide aptamer. In some embodiments, an antibody is a monoclonal antibody.

In some embodiments, a protein of the protein-nucleic acid conjugate is linked to the docking strand through an intermediate linker. In some embodiments, an intermediate linker comprises biotin and/or streptavidin.

In some embodiments, a complementary fluorescently-labeled imager strand comprises at least one fluorophore.

In some embodiments, a complementary labeled, optionally fluorescently labeled, imager strand is about 4 to about 10 nucleotides, or about 8 to about 10 nucleotides in length.

In some embodiments, a sample is a cell or cell lysate.

In some embodiments, a target is a protein. In some embodiments, a target is a nucleic acid (e.g., DNA or RNA).

In some embodiments, a target is obtained from a cell or cell lysate.

In some aspects, provided herein is a method of detecting at least one or at least two targets in a sample, the method comprising contacting a sample with (a) at least two protein-nucleic acid conjugates, each comprising a protein linked to a docking strand, and (b) at least two labeled (optionally spectrally distinct, or fluorescently labeled, or spectrally distinct and fluorescently labeled) imager strands that are complementary to and transiently bind to respective docking strands of the at least one, or at least, two different protein-nucleic acid conjugates and determining whether the at least two protein-nucleic acid conjugates bind to at least two targets in the sample. In some embodiments, the determining step comprises, in the following order, imaging transient binding of one of the at least two labeled imager strands to a docking strand of one of the at least two protein-nucleic acid conjugates to produce a first image (e.g., of a fluorescent signal), and imaging transient binding of another of the at least two labeled imager strands to a docking strand of another of the at least two protein-nucleic acid conjugates to produce at least one other image (e.g., of a fluorescent signal). In some embodiments, the method further comprises combining the first image and the at least one other image to produce a composite image of signal (e.g., fluorescent signal), wherein the signal of the composite image is representative of the at least two targets.

In some embodiments, a protein of the protein-nucleic acid conjugate is an antibody, an antigen-binding antibody fragment, or a peptide aptamer. In some embodiments, an antibody is a monoclonal antibody.

In some embodiments, a protein of the protein-nucleic acid conjugate is linked to the docking strand through an intermediate linker. In some embodiments, an intermediate linker comprises biotin and streptavidin.

In some embodiments, each of the at least two spectrally distinct, fluorescently-labeled imager strands comprises at least one fluorophore.

In some embodiments, each of the at least two labeled, optionally spectrally distinct, fluorescently labeled, imager strands is about 4 to about 10 nucleotides, or about 8 to about 10 nucleotides in length.

In some embodiments, a sample is a cell or cell lysate.

In some embodiments, at least two targets are proteins. In some embodiments, at least two targets are nucleic acids (e.g., DNA or RNA).

In some embodiments, at least two targets are obtained from a cell or cell lysate.

In some aspects, provided herein is a method of detecting at least one, or at least two, protein targets in a sample, comprising (a) contacting a sample with at least two protein-nucleic acid conjugates, each comprising a protein linked to a docking strand and (b) sequentially contacting the sample with at least two labeled (e.g., optionally spectrally indistinct, or fluorescently labeled, or spectrally distinct and fluorescently labeled) imager strands that are complementary to and transiently bind to respective docking strands of the at least two protein-nucleic acid conjugates, and determining whether the at least one or at least two protein-nucleic acid conjugates bind to at least two targets in the sample. In some embodiments, a method comprises, in the following ordered steps, contacting the sample with a first protein-nucleic acid conjugate and at least one other protein-nucleic acid conjugate, contacting the sample with a first labeled, optionally fluorescently labeled, imager strand that is complementary to and transiently binds to the docking strand of the first protein-nucleic acid conjugate, imaging the sample to obtain a first image, optionally using time-lapsed imaging, removing the first labeled imager strand, contacting the sample with at least one other labeled imager strand that is complementary to and transiently binds to the docking strand of the at least one other protein-nucleic acid conjugate, and imaging the sample to obtain at least one other image, optionally using time-lapsed imaging.

In some embodiments, a method comprises, in the following ordered steps, contacting a sample with a first protein-nucleic acid conjugate, contacting the sample with a first labeled, optionally fluorescently labeled, imager strand that is complementary to and transiently binds to the docking strand of the first protein-nucleic acid conjugate, imaging the sample to obtain a first image, optionally using time-lapsed imaging, removing the first labeled imager strand, contacting the sample with at least one other protein-nucleic acid conjugate, contacting the sample with at least one other labeled, optionally fluorescently labeled, imager strand that is complementary to and transiently binds to the docking strand of the at least one other protein-nucleic acid conjugate, and imaging the sample to obtain at least one other image, optionally using time-lapsed imaging.

In some embodiments, a method further comprises determining whether the first protein-DNA conjugate binds to a first target and/or whether the at least one other protein-DNA conjugate binds to at least one other target.

In some embodiments, a method further comprises assigning a pseudo-color to the signal (e.g., fluorescent signal) in a first image, and assigning at least one other pseudo-color to the fluorescent signal in the at least one other image.

In some embodiments, a method further comprises combining a first image and the at least one other image to produce a composite image of the pseudo-colored signals, wherein the pseudo-colored signals of the composite image are representative of the at least two targets.

In some embodiments, the protein of the protein-nucleic acid conjugate(s) is an antibody, an antigen-binding antibody fragment, or a peptide aptamer. In some embodiments, the antibody is a monoclonal antibody.

In some embodiments, the protein of the protein-nucleic acid conjugate(s) is linked to the docking strand through an intermediate linker. In some embodiments, the intermediate linker comprises biotin and/or streptavidin.

In some embodiments, each of the fluorescently-labeled imager strands comprises at least one fluorophore.

In some embodiments, each of the fluorescently-labeled imager strands is about 4 to about 30 nucleotides, or about 8 to about 10 nucleotides in length.

In some embodiments, a sample is a cell or cell lysate.

In some embodiments, a target(s) is a protein. In some embodiments, a target(s) is a nucleic acid (e.g., DNA or RNA).

In some embodiments, a target(s) is obtained from a cell or cell lysate.

In some aspects, provided herein is a method of detecting a target, optionally a naturally-occurring biomolecule, comprising contacting a sample containing at least one target, optionally a naturally-occurring biomolecule, with (a) at least one BP-NA conjugate, optionally each BP-NA conjugate comprising a protein or nucleic acid linked to a docking strand, and (b) at least one labeled, optionally fluorescently labeled, imager strand that is complementary to and transiently binds the docking strand of the at least one BP-NA conjugate, and determining whether the at least one BP-NA conjugate binds to at least one target, optionally a naturally-occurring biomolecule, in the sample. In this and other aspects or embodiments described herein, it is to be understood that the method may be carried out using a sample that is suspected of containing at least one target or a sample that an end-user desires to analyze for the presence of the at least one target without any prior knowledge of the sample respecting its likelihood of containing the target.

In some embodiments, the determining step comprises imaging transient binding of the at least one labeled, optionally fluorescently labeled, imager strand to the docking strand of the at least one BP-NA conjugate.

In some embodiments, a sample is a cell or cell lysate.

In some embodiments, an at least one target, optionally a naturally-occurring biomolecule, is obtained from a cell or cell lysate.

In some embodiments, a protein is an antibody, an antigen-binding antibody fragment, or a peptide aptamer. In some embodiments, an antibody is a monoclonal antibody.

In some embodiments, a protein is linked to the docking strand through an intermediate linker. In some embodiments, an intermediate linker comprises biotin and/or streptavidin.

In some embodiments, a nucleic acid is a nucleic acid aptamer.

In some embodiments, a fluorescently-labeled imager strand comprises at least one fluorophore.

In some embodiments, an imager strand, optionally a fluorescently-labeled imager strand, is about 4 to about 30, or about 8 to about 10 nucleotides in length.

In some aspects, provided herein is a method of detecting a target, optionally a naturally-occurring biomolecule, comprising contacting a sample containing at least two targets, optionally naturally-occurring biomolecules, with (a) at least two different BP-NA conjugates, optionally each BP-NA conjugate comprising a protein or nucleic acid linked to a DNA docking strand, and (b) at least two labeled (optionally spectrally indistinct, or fluorescently labeled, or spectrally distinct and fluorescently labeled) imager strands that are complementary to and transiently bind to respective docking strands of the at least two BP-NA conjugates, and determining whether the at least two BP-NA conjugates bind to at least one or at least two naturally-occurring biomolecules in the sample.

In some embodiments, a method comprises, in the following ordered steps, contacting the sample with a first BP-NA conjugate and at least one other BP-NA conjugate, contacting the sample with a first labeled, optionally fluorescently labeled, imager strand that is complementary to and transiently binds to the docking strand of the first BP-NA conjugate, imaging the sample to obtain a first image, optionally using time-lapsed imaging, removing the first labeled imager strand, contacting the sample with at least one other labeled, optionally fluorescently labeled, imager strand that is complementary to and transiently binds to the docking strand of the at least one other BP-NA conjugate, and imaging the sample to obtain at least one other image, optionally using time-lapsed imaging.

In some embodiments, a method comprises, in the following ordered steps, contacting the sample with a first BP-NA conjugate, contacting the sample with a first labeled, optionally fluorescently labeled, imager strand that is complementary to and transiently binds to the docking strand of the first BP-NA conjugate, imaging the sample to obtain a first image, optionally using time-lapsed imaging, removing the first labeled imager strand, contacting the sample with at least one other BP-NA conjugate, contacting the sample with at least one other labeled, optionally fluorescently labeled, imager strand that is complementary to and transiently binds to the docking strand of the at least one other BP-NA conjugate, and imaging the sample to obtain a at least one other image, optionally using time-lapsed imaging.

In some embodiments, a method further comprises determining whether the first protein DNA conjugate binds to a first target, optionally a naturally-occurring biomolecule, and/or whether the at least one other protein-DNA conjugate binds to at least one other target, optionally a naturally-occurring biomolecule.

In some embodiments, a method further comprises assigning a pseudo-color to the signal (e.g., fluorescent signal) in a first image, and assigning at least one other pseudo-color to the signal (e.g., fluorescent signal) in at least one other image.

In some embodiments, a method further comprises combining a first image and at least one other image to produce a composite image of pseudo-colored signals, wherein the pseudo-colored signals of the composite image are representative of at least one, or at least two, targets (e.g., naturally-occurring biomolecules).

In some aspects, provided herein is a method of determining the number of targets in a test sample, comprising obtaining a sample that comprises targets transiently bound directly or indirectly to labeled, optionally fluorescently labeled, imager strands, obtaining a time-lapsed image, optionally a time-lapsed diffraction-limited fluorescence image, of the sample, performing spot detection (e.g., fluorescence spot detection) and localization (e.g., through the use of Gaussian fitting) on the diffraction-limited image to obtain a high-resolution image of the sample, calibrating $k_{on} \cdot c_{imager}$, optionally using a control sample with a known number of targets, wherein $k_{on}$ is a second order association constant, and $c_{imager}$ is concentration of labeled (e.g., fluorescently labeled) imager strands in the test sample, determining variable $\sigma_d$, optionally by fitting the fluorescence OFF-time distribution to a cumulative distribution function, and determining the number of test targets in the sample based on the equation, number of test targets= $(k_{on} \cdot c_{imager} \cdot \tau_d)^{-1}$.

In some aspects, provided herein is a method of determining a relative amount of targets in a test sample, comprising obtaining a sample that comprises targets transiently bound directly or indirectly to labeled imager strands, obtaining a time-lapsed image of the sample, performing spot detection and localization on the image to obtain a high-resolution image of the sample, determining variable $\tau_d$, and determining the relative amount of two or more test targets in the sample based on $\tau_d$.

In some embodiments, test targets are protein targets.

In some embodiments, protein targets are bound to protein-nucleic acid conjugates that comprise a protein linked to a docking strand, and the labeled (e.g., fluorescently labeled) imager strands are complementary to and transiently bind to respective docking strands of the protein-nucleic acid conjugates.

In some embodiments, the protein of the protein-nucleic acid conjugate is an antibody, an antigen-binding antibody fragment, or a peptide aptamer.

In some embodiments, test targets are single-stranded nucleic acids.

In some embodiments, single-stranded nucleic acids are DNA or RNA.

In some embodiments, each of the fluorescently-labeled imager strands comprises at least one fluorophore.

In some embodiments, each of the labeled, optionally fluorescently labeled, imager strands is about 4 to about 30 nucleotides, or about 8 to about 10 nucleotides in length.

In some embodiments, a time-lapsed fluorescence image is obtained over a period of about 25 minutes.

In some embodiments, the number of test targets is determined with an accuracy of greater than 90%.

In some aspects, provided herein is a single-stranded DNA probe comprising a target binding domain of about 20 nucleotides in length linked, optionally at its 3' end, to a docking domain of at least one, at least two, or at least three subdomains, wherein the at at least one, least two, or at least three subdomains are respectively complementary to at least one, at least two, or at least three labeled, optionally fluorescently labeled, imager strands of about 4 to about 30, or about 8 to 10 nucleotides in length, and wherein the target binding domain is bound to a complementary domain of a single-stranded mRNA target strand.

In some embodiments, at least one of the at least one, at least two, or at least three subdomains is transiently bound to at least one labeled, optionally fluorescently labeled, imager strand.

In some aspects, provided herein is a method of performing drift correction for a plurality of images, wherein each of the plurality of images comprises a frame of a time sequence of images, wherein the time sequence of images captures a plurality of transient events, the method comprising determining a time trace for each of a plurality of drift markers identified in the plurality of images, wherein a time trace for each drift marker corresponds to movement of an object in the image over the time sequence of images, determining, with at least one computer processor, a first drift correction from at least one of the plurality of drift markers based, at least in part, on the time traces for the plurality of drift markers, determining a time trace for each of a plurality of geometrically-addressable marker sites from a plurality of drift templates identified from the plurality of images, wherein each drift template in the plurality of drift templates describes a geometrical relationship between the plurality of geometrically-addressable marker sites of transient events in the drift template, determining a second drift correction based, at least in part, on the time traces for the plurality of geometrically-addressable marker sites from the plurality of drift templates, correcting the plurality of images based, at least in part, on the first drift correction and the second drift correction, and outputting a final image based on the corrected plurality of images.

In some embodiments, a method further comprises identifying a plurality of localizations in each of the plurality of images, creating a two-dimensional histogram of the plurality of localizations, and identifying locations of the plurality of drift markers based, at least in part, on the two-dimensional histogram, wherein determining the time traces for each of the plurality of drift markers comprises determining the time traces based, at least in part, on the locations of the plurality of drift markers.

In some embodiments, identifying a plurality of localizations comprises identifying a plurality of spots on each of the plurality of images, and determining a fitted center position of each of the plurality of spots using a local Gaussian fitting algorithm, wherein each of the plurality of localizations comprises the spot identified on an image and its associated fitted center position.

In some embodiments, each of the plurality of localizations further comprises a detected photon count corresponding to the localization.

In some embodiments, creating the two-dimensional histogram of the plurality of localizations comprises binning all localizations into a two-dimensional grid and using a total number of localizations in each bin as a histogram count.

In some embodiments, creating the two-dimensional histogram of the plurality of localizations comprises binning all localizations into a two-dimensional grid and using a total number of photon count of the plurality of localizations in each bin as a histogram count.

In some embodiments, identifying locations of the plurality of drift markers based, at least in part, on the two-dimensional histogram comprises at least one of the following: binarizing the two-dimensional histogram using one or more selection criteria, wherein the one or more selection criteria include a lower-bound threshold of a histogram value or a upper-bound threshold of a histogram value; partitioning the binarized image into partitions and filtering the partitions based on one or more selection criteria, wherein the one or more selection criteria include one or more of a lower-bound threshold of an area of a partition area, an upper-bound threshold of the area, a lower-bound or an upper-bound of a longest or shortest linear dimension of a partition longest, and a lower-bound or an upper-bound of an eccentricity of a partition; and expanding and shrinking the binarized image using one or more binary image operations, wherein the one or more binary image operations include one or more of the following: dilate, erode, bridge, close, open, fill, clean, top-hat, bottom-hat, thicken, thin, and more.

In some embodiments, determining a first drift correction based, at least in part, on the time traces for the plurality of drift markers comprises: determining a relative time trace for each of the plurality of drift markers, wherein the relative time trace is determined by comparing the time trace for the drift marker with the average position of the same trace; and determining a combined time trace based on the relative time traces for each of the plurality of drift markers, wherein determining the first drift correction based, at least in part, on the time traces for the plurality of drift markers comprises determining the first drift correction based, at least in part, on the relative time traces for each of the plurality of drift markers.

In some embodiments, determining the first drift correction based, at least in part, on the relative time traces for each of the plurality of drift markers comprises performing a weighted average of the relative time traces for each of the plurality of drift markers.

In some embodiments, performing the weighted average comprises: determining a quality score for each of the relative time traces, wherein the quality score is determined based, at least in part, on a measure of variability over time associated with the time trace and/or a measure of localization uncertainty of individual localizations within the time trace.

In some embodiments, the measure of variability over time comprises a standard deviation of the time trace over time.

In some embodiments, the measure of localization uncertainty of individual localizations comprises, at least in part, an estimate of uncertainty from a Gaussian fitting or a comparison with other simultaneous localizations, wherein the other simultaneous localizations are from within a same image and from other time traces from the plurality of drift markers, wherein the comparison comprises a mean and standard deviation of all simultaneous localizations.

In some embodiments, the method further comprises determining that a first drift marker of the plurality of drift markers is not present in at least one frame of the time sequence of images, and linearly interpolating the time trace for the first drift marker for the at least one frame to produce a smoothed time trace for the first drift marker.

In some embodiments, determining a time trace for each of a plurality of geometrically-addressable marker sites from a plurality of drift templates identified from the plurality of images comprises: identifying a plurality of localizations in each of the plurality of images; creating a two-dimensional histogram of the plurality of localizations; and identifying the plurality of drift templates based, at least in part, on the two-dimensional histogram, wherein identifying the plurality of drift templates comprises evaluating the two-dimensional histogram using an lower-bound and/or an upper-bound threshold in a histogram count.

In some embodiments, determining a time trace for each of a plurality of geometrically-addressable marker sites from a plurality of drift templates identified from the plurality of images comprises determining a time trace for each of a plurality of geometrically-addressable marker sites within each of the plurality of drift templates, and wherein determining the second drift correction comprises determining the second drift correction based, at least in part, on the time traces for each of the plurality of marker sites within each of the plurality of drift templates.

In some embodiments, determining the second drift correction based, at least in part, on the time traces for each of the plurality of geometrically-addressable marker sites from each of the plurality of drift templates comprises: identifying a plurality of geometrically-addressable marker sites within each of the plurality of drift templates; and determining a relative time trace for each of a plurality of geometrically-addressable drift markers for each of the plurality of drift templates, wherein determining the second drift correction based, at least in part, on the time traces for the plurality of drift templates comprises determining the second drift correction based, at least in part, on the relative time traces for each of the plurality of drift markers within each of the plurality of drift templates.

In some embodiments, identifying a plurality of geometrically addressable marker sites from each of the plurality of drift templates comprises determining a plurality of marker sites based on, at least in part, a two-dimensional histogram of the plurality of localizations in the corresponding drift template, and/or one or more selection criteria, wherein the one or more selection criteria include one or more of a total number of localizations, a surface density of localizations, and standard deviation of localizations.

In some embodiments, determining the second drift correction based, at least in part, on the relative time traces for each of the plurality of drift markers within each of the plurality of drift templates comprises performing a weighted average of the relative time traces for each of the plurality of drift markers within each of the drift templates.

In some embodiments, performing the weighted average comprises:

determining a quality score for each of the relative time traces, wherein the quality score is determined based, at least in part, on a measure of variability over time associated with the time trace and/or a localization uncertainty within the time trace.

In some embodiments, the measure of variability over time comprises a standard deviation of the time trace over time.

In some embodiments, the measure of localization uncertainty of individual localizations comprises an estimate of uncertainty from a Gaussian fitting or a comparison with other simultaneous localizations, wherein the other simultaneous localizations are from within a same image and from the other time traces from the plurality of marker sites from the plurality of drift templates, wherein the comparison comprises a mean and standard deviation of all simultaneous localizations.

In some embodiments, correcting the plurality of images based, at least in part, on the first drift correction and the second drift correction comprises correcting the plurality images using the first drift correction to produce a first corrected plurality of images, and wherein determining a time trace for each of a plurality of drift templates identified from the plurality of images comprises determining a time trace for each of the plurality of drift templates identified from the first corrected plurality of images.

In some embodiments, a method further comprises smoothing the first drift correction prior to correcting the plurality of images using the first drift correction.

In some embodiments, smoothing the first drift correction comprises processing the first drift correction using local regression with a window determined by a characteristic drift time scale of the first drift correction.

In some embodiments, a method further comprises smoothing the second drift correction prior to correcting the plurality of images using the second drift correction.

In some embodiments, smoothing the second drift correction comprises processing the second drift correction using local regression with a window determined by a characteristic drift time scale of the second drift correction.

In some embodiments, a method further comprises selecting a single drift marker of the plurality of drift markers; and determining a third drift correction based, at least in part, on the selected single drift marker, wherein correcting the plurality of images comprises correcting the plurality of images based, at least in part, on the third drift correction.

In some embodiments, correcting the plurality of images based, at least in part, on the third drift correction is performed prior to correcting the plurality of images based, at least in part on the first drift correction and the second drift correction.

In some embodiments, a method further comprises identifying locations of a first plurality of points in a first image of the plurality of frames; identifying locations of a second plurality of points in a second image of the plurality of images, wherein the second image corresponds to a neighboring frame of the first image in the time sequence of images; and determining a fourth drift correction based, at least in part, on differences between the locations of the first plurality of points and the second plurality of points, wherein correcting the plurality of images comprises correcting the plurality of images based, at least in part, on the fourth drift correction.

In some embodiments, the second image corresponds to a frame immediately following the frame corresponding to the first image in the time sequence of images.

In some embodiments, determining the fourth drift correction based, at least in part, on differences between the locations of the first plurality of points and the second plurality of points comprises: creating a histogram of distances between the locations of the first plurality of points and the second plurality of points; determining based, at least in part, on the histogram, pairs of points between the first image and the second image that correspond to the same transient event; and determining a location offset between each of the determined pairs of points, wherein determining the fourth drift correction is based on a vector average of the location offsets for each of the determined pairs of points.

In some embodiments, the plurality of images correspond to DNA-based images and wherein the plurality of transient events are binding events between an imaging strand and a DNA docking strand.

In some embodiments, the imaging strand is a fluorescent imaging probe configured to fluoresce when associated with the DNA docking strand.

In some embodiments, at least one of the drift markers is a DNA based nanostructure.

In some embodiments, the DNA based nanostructure is a DNA origami nanostructure with docking strands.

In some embodiments, at least one of the drift templates is a DNA based nanostructure.

In some embodiments, the DNA based nanostructure is a DNA origami nanostructure with docking strands.

In some embodiments, at least one of the drift templates is a three-dimensional drift template.

In some embodiments, the three-dimensional drift template is a tetrahedron.

In some embodiments, at least one of the drift templates includes multiple colors corresponding to different types of transient events.

In some embodiments, the different types of transient events include a first binding event of a first imaging strand with a first type of DNA docking strand and a second binding event of a second imaging strand with a second type of DNA docking strand.

In some embodiments, outputting the final image comprises displaying the final image on a display.

In some embodiments, outputting the final image comprises sending the final image to a computer via at least one network.

In some embodiments, outputting the final image comprises storing the final image on at least one storage device.

In some aspects, provided herein is a non-transitory computer readable medium encoded with a plurality of instructions that, when executed by at least one computer processor, performs a method of performing drift correction for a plurality of images, wherein each of the plurality of images comprises a frame of a time sequence of images, wherein the time sequence of images captures a plurality of transient events, the method comprising: determining a time trace for each of a plurality of drift markers identified in the plurality of images, wherein a time trace for each drift marker corresponds to movement of an object in the image over the time sequence of images; determining a first drift correction from at least one of the plurality of drift markers based, at least in part, on the time traces for the plurality of drift markers; determining a time trace for each of a plurality of geometrically-addressable marker sites from a plurality of drift templates identified from the plurality of images, wherein each drift template in the plurality of drift templates describes a geometrical relationship between the plurality of geometrically-addressable marker sites of transient events in the drift template; determining a second drift correction based, at least in part, on the time traces for the plurality of geometrically-addressable marker sites from the plurality of drift templates; correcting the plurality of images based, at least in part, on the first drift correction and the second drift correction; and outputting a final image based on the corrected plurality of images.

In some aspects, provided herein is a computer, comprising: an input interface configured to receive a plurality of images, wherein each of the plurality of images comprises a frame of a time sequence of images, wherein the time sequence of images captures a plurality of transient events; at least one processor programmed to: determine a time trace for each of a plurality of drift markers identified in the plurality of images, wherein a time trace for each drift marker corresponds to movement of an object in the image over the time sequence of images; determine a first drift correction from at least one of the plurality of drift markers based, at least in part, on the time traces for the plurality of drift markers; determine a time trace for each of a plurality of geometrically-addressable marker sites from a plurality of drift templates identified from the plurality of images, wherein each drift template in the plurality of drift templates describes a geometrical relationship between the plurality of geometrically-addressable marker sites of transient events in the drift template; determine a second drift correction based, at least in part, on the time traces for the plurality of geometrically-addressable marker sites from the plurality of drift templates; correct the plurality of images based, at least in part, on the first drift correction and the second drift correction; and determine a final image based on the corrected plurality of images; and output interface configured to output the final image.

BRIEF DESCRIPTION OF THE DRAWINGS

FIGS. 4B(1)-4B(3) show that reducing the image density simultaneously increases the achievable resolution by up to a factor of $2\sqrt{2} \ln 2 \approx 2.35$. Here, the resolution, previously defined as the FWHM of the reconstructed localizations, can be understood as the standard deviation of the localization as in localization microscopy with sparse points. FIG. 4B(1) shows seven points in a linear geometry spaced at 10 nm (top). Simulated super-resolution data with approximately 14 nm resolution (center). The points cannot be resolved. Cross-sectional histogram data shows a broad peak (bottom). FIGS. 4B(2) and 4B(3) show that imaging every other site allows the localization of individual spots. These localizations can then be combined to form the final image of the full pattern.

FIG. 5B(i) shows an exchange-PAINT schematic showing sequential imaging of multiple targets using imager strands labeled with the same fluorophore. FIG. 5B(ii) shows a schematic of a DNA origami (70 100 nm) displaying docking strands that resemble digit 4. FIG. 5B(iii) shows a combined overview image of all ten Exchange-PAINT cycles, demonstrating specific interaction with the respective target with no crosstalk between imaging cycles. Scale bar: 250 nm. FIG. 5B(iv) shows a four-"color" image of digits 0 to 3 that are all present on the same DNA origami (10,000 frames each, 5 Hz frame rate; schematic at the bottom). Scale bar: 25 nm. FIG. 5B(v) shows pseudocolor images of ten different origami structures, each rendered a distinct color (e.g., orange, green, blue, purple, pink, etc.; color rendering not shown), displaying digits 0 to 9 in one sample with high resolution (FWHM of bar-like features <10 nm) and specificity. Image obtained using only one fluorophore (Cy3b) through ten imaging-washing cycles (imaging: 7,500 frames per cycle, 5 Hz frame rate; washing: 1-2 minutes per cycle). Scale bar: 25 nm.

FIG. 7D(1) shows the binding site distribution for 377 origami structures obtained by direct visual counting. FIG. 7D(2) shows the binding site distribution for the same structures obtained by binding kinetic analysis (kinetics) of the present disclosure. FIG. 7D(3) shows the "offset" between direct and kinetic counting: the counting "error" or uncertainty for the method of the present disclosure is less than 7% (determined by the coefficient of variation of the Gaussian distribution).

FIG. 11A shows that in the traditional method of detection, where a single fluorophore is stably attached to the imaging surface (see FIG. 11B(1)), a limited number of photons per "switching" event is emitted (top panel), that extraction of all photons from "replenishable" imager strands (see FIG. 11B(2)) leads to higher localization accuracy per switching event (middle panel), and that a DNA metafluorophore (see FIG. 11B(3) and FIG. 11B(4)) yields a significantly larger number of photons per switching event than the single fluorophore in FIG. 11B(2) (bottom). FIGS. 11B(1)-11B(3) show schematics of current imaging methods and methods of the present disclosure. FIG. 11B(1) shows a traditional detection method (e.g., in STORM), which uses a fluorophore stably attached to the imaging surface. FIG. 11B(2) shows one embodiment of a detection method of the present disclosure with fluorophores transiently binding to the imaging surface. FIG. 11B(3) shows a bright metafluorophore with 8 fluorophores in a compact DNA nanostructure. FIG. 11B(4) shows a conditional metafluorophore decorated with both quenchers (dark dots) and fluorophores (stars) that only fluoresces when transiently bound to the surface.

FIG. 12A(ii) shows a schematic drawing of the major type of drift markers (e.g., DNA drift markers) used in each stage.

FIG. 16A shows that the four corners are clearly resolved. FIG. 16B illustrates the X-Z projection of the structures with a height of ~85 nm.

FIG. 18A shows a scatter plot of collected and filtered localizations, represented by crosses. FIG. 18B shows a binned 2-D histogram view of the above structure. FIG. 18C shows a 1-D histogram by projecting all localizations in the rectangle in FIGS.

18A and 18B onto the x-axis, and least square fitting with 8 Gaussian components. The fitted Gaussian peaks all have standard deviation in the range of 1.5-2.4 nm, allowing for 3.5-5.6 nm resolution in principle; and spacing between neighboring peaks in the range of 9.8-11.0 nm, consistent with the DNA origami design. A few (5 in this case) spots are missing in the structure because of imperfect incorporation of staples in the assembly reaction, but not missed during the super-resolution imaging.

Figure 19A:
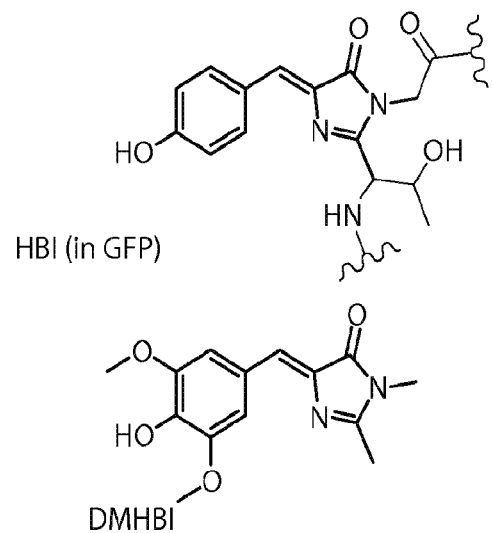
Figure 19B:
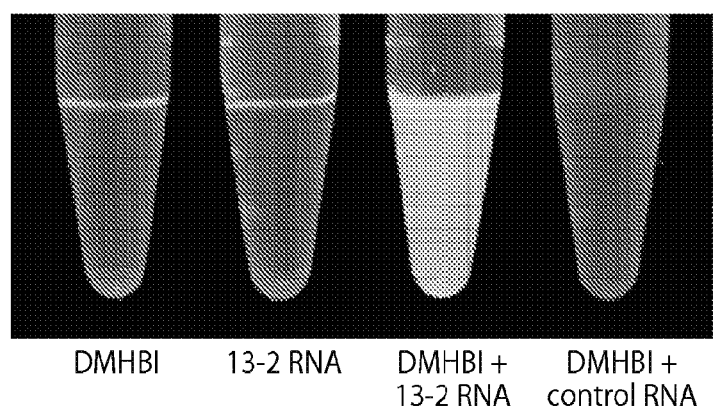

FIGS. 19A and 19B show that RNA aptamers modulate the fluorescence of GFP-like fluorophores. FIG. 19A shows structures of HBI (green), in the context of GFP, and DMHBI. FIG. 19B shows that the 13-2 RNA aptamer enhances the fluorescence of DMHBI by stabilizing a particular molecular arrangement favorable for fluorescence emission. Solutions containing DMHBI, 13-2 RNA, DMHBI with 13-2 RNA, or DMHBI with total HeLa cell RNA were photographed under illumination with 365 nm of light. The image is a montage obtained under identical image-acquisition conditions. (Image from Paige et al., ref. 19)

Figure 20A:
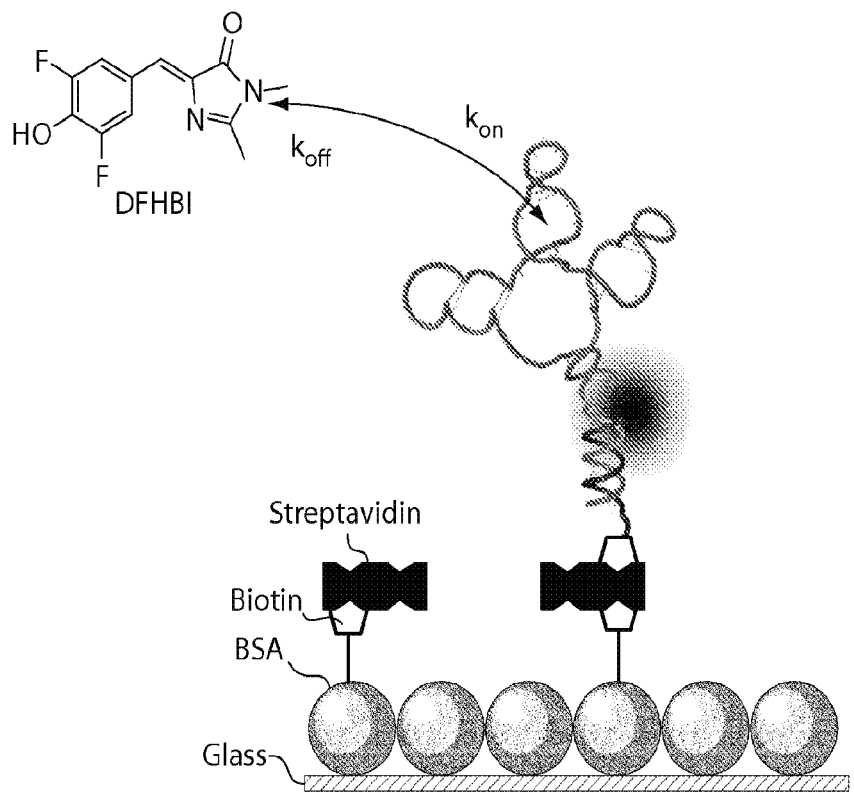
Figure 20B:
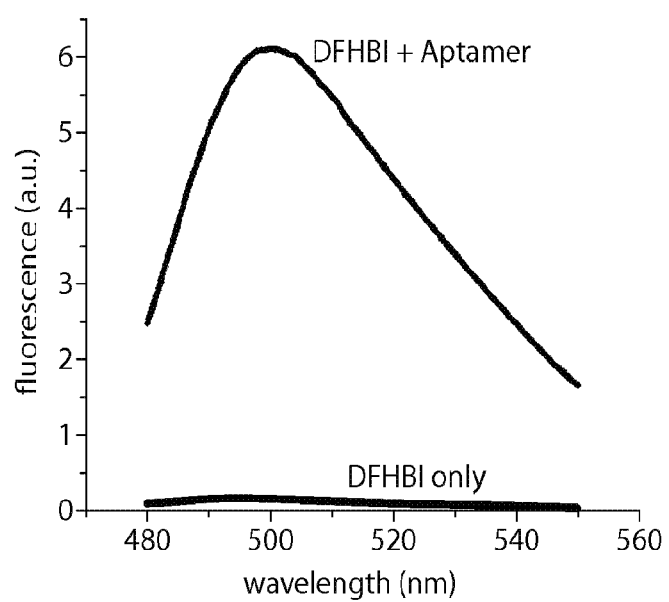

FIGS. 20A and 20B show single-molecule fluorescence characterization of the DFHBI binding kinetics. FIG. 20A shows a 5'-extended Spinach (green) is immobilized on a BSA/Biotin-coated glass substrate using a biotinylated DNA capture sequence (labeled with a red dye, e.g. Alexa647; color rendering not shown). FIG. 20B shows a bulk fluorescence measurement of the Spinach-DFHBI before (bottom line) and after (top line) addition of the aptamer shows that the DFHBI binding activity is well maintained after the addition an extension to Spinach required for immobilizing to the glass surface in FIG. 20A.

Figure 21A:
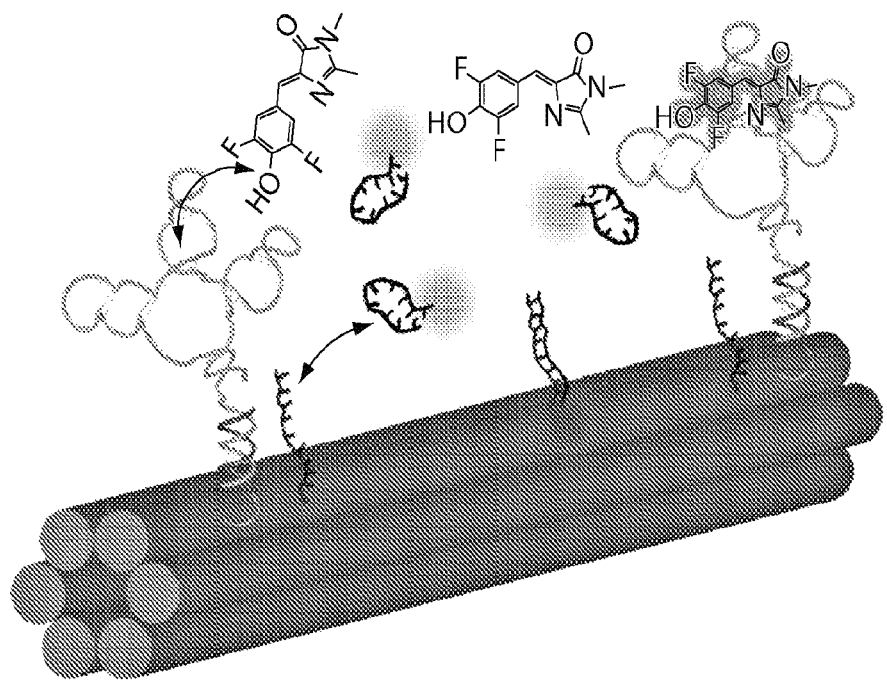
Figure 21B:
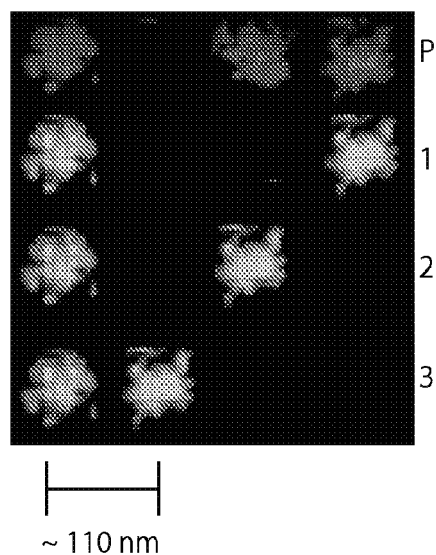

FIGS. 21A and 21B show benchmarking Spinach-PAINT performance. FIG. 20A shows a six-helix DNA origami structure used for placing two Spinach molecules in a defined distance. FIG. 20B shows a simulated representation of a super-resolved reconstruction using DNA-PAINT to localize the DNA structure (P) and Spinach-PAINT to localize the Spinach molecules in three different distances.

Figure 22:
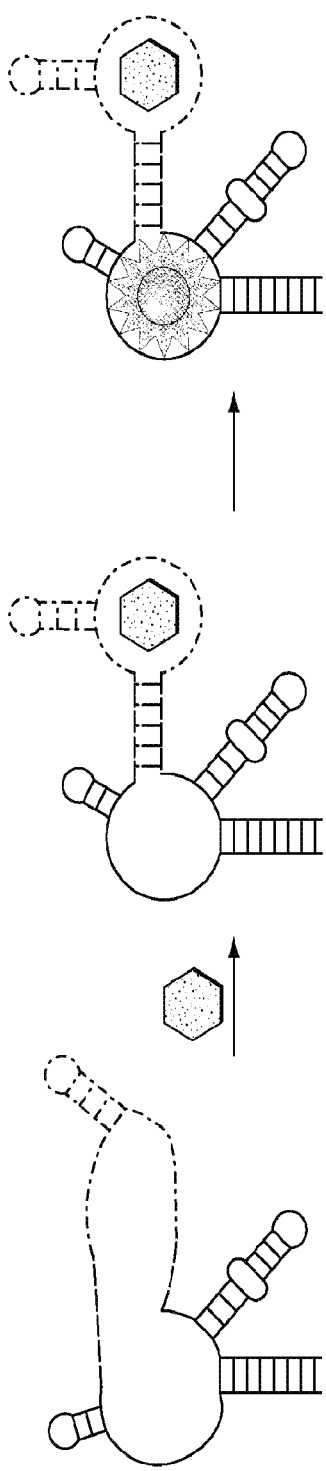

FIG. 22 shows Spinach-based sensors. The allosteric variant of the Spinach-based sensor (left) comprises the Spinach domain (black), the transducer module (medium gray), and the recognition module (light gray). In the absence of the target molecule, the transducer module is in a primarily unstructured state, which prevents the stabilization of the Spinach structure needed for activation of DFHBI. Upon binding of the target molecule, the transducer module forms a duplex, leading to structural rigidification of the Spinach module, and activation of DFHBI fluorescence (ref. 24).

Figure 23A:
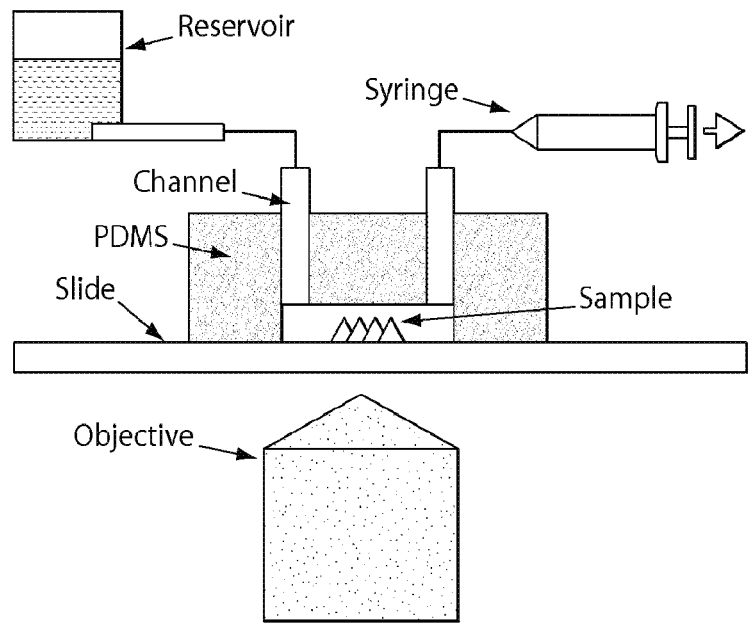
Figure 23B:
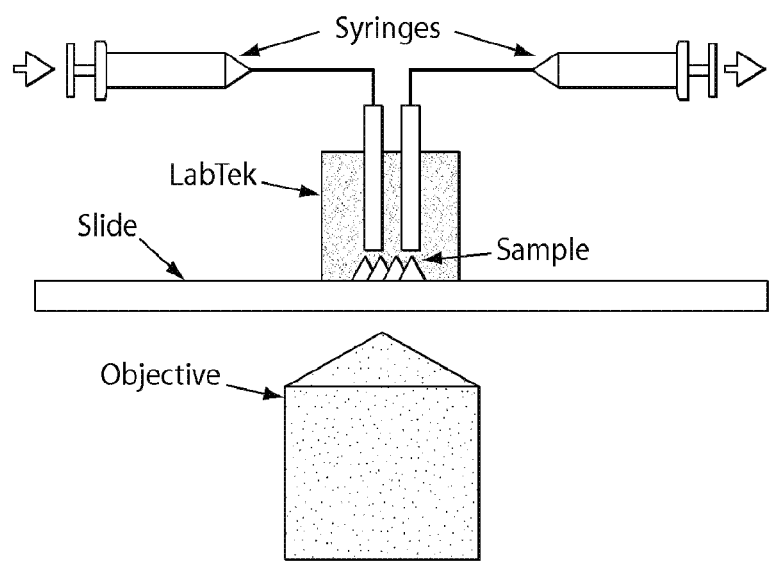

FIGS. 23A and 23B show examples of in vitro and in situ Exchange-PAINT chambers.

DESCRIPTION OF THE INVENTION

The present disclosure provides, inter alia, methods, compositions and kits for multiplexed imaging, for example, in a cellular environment using nucleic acid-based imaging probes (e.g., DNA-based imaging probes). The methods, compositions and kits for multiplexed fluorescence imaging are not limited by the degree of resolution attained. Thus, the methods, compositions and kits as provided herein may be used for imaging, generally.

In some aspects, the present disclosure further provides, inter alia, methods, compositions and kits for multiplexed super-resolution fluorescence imaging, for example, in a cellular environment using nucleic acid-based imaging probes (e.g., DNA-based imaging probes). As used herein, "super-resolution" imaging refers to the process of combining a set of low resolution images of the same area to obtain a single image of higher resolution. Many aspects of the present disclosure may be used to "switch" targets (e.g., biomolecules) of interest between fluorescent ON- and OFF-states to permit consecutive, or in some instances simultaneous, localization of individual targets. A fluorescent "ON" state is a state in which fluorescence is emitted. A fluorescent "OFF" state is a state in which fluorescence is not emitted. Switching between the two states is achieved, in some embodiments, with diffusing molecules that are labeled with a detectable label (e.g., fluorescent molecules) that interact transiently with the targets using an intermediate moiety that comprises the detectable label (e.g., fluorescent molecule(s)) and binds to the target. The methods, compositions and kits of the present disclosure are useful, in some aspects, for detecting, identifying and quantifying target targets of interest.

Binding partner-nucleic acid conjugates ("BP-NA conjugates") of the present disclosure transiently bind to complementary labeled, optionally fluorescently labeled, imager strands. As used herein, "binding partner-nucleic acid conjugate," or "BP-NA conjugate," refers to a molecule linked (e.g., through an N-Hydroxysuccinimide (NHS) linker) to a single-stranded nucleic acid (e.g., DNA) docking strand. The binding partner of the conjugate may be any moiety (e.g., antibody or aptamer) that has an affinity for (e.g., binds to) a target, such as a biomolecule (e.g., protein or nucleic acid), of interest. In some embodiments, the binding partner is a protein. BP-NA-conjugates that comprise a protein (or peptide) linked to a docking strand may be referred to herein as "protein-nucleic acid conjugates," or "protein-NA conjugates." Examples of proteins for use in the conjugates of the present disclosure include, without limitation, antibodies (e.g., monoclonal monobodies), antigen-binding antibody fragments (e.g., Fab fragments), receptors, peptides and peptide aptamers. Other binding partners may be used in accordance with the present disclosure. For example, binding partners that bind to targets through electrostatic (e.g., electrostatic particles), hydrophobic or magnetic (e.g., magnetic particles) interactions are contemplated herein.

As used herein, "antibody" includes full-length antibodies and any antigen binding fragment (e.g., "antigen-binding portion") or single chain thereof. The term "antibody" includes, without limitation, a glycoprotein comprising at least two heavy (H) chains and two light (L) chains interconnected by disulfide bonds, or an antigen binding portion thereof. Antibodies may be polyclonal or monoclonal; xenogeneic, allogeneic, or syngeneic; or modified forms thereof (e.g., humanized, chimeric).

As used herein, "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_H$, $V_L$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_H$ and $V_L$ domains of a single arm of an antibody, (v) a dAb fragment (Ward et al., Nature 341:544 546, 1989), which consists of a $V_H$ domain; and (vi) an isolated complementarity determining region (CDR) or (vii) a combination of two or more isolated CDRs, which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see, e.g., Bird et al. *Science* 242:423 426, 1988; and Huston et al. *Proc. Natl. Acad. Sci. USA* 85:5879-5883, 1988). Such single chain antibodies are also encompassed within the term "antigen-binding portion" of an antibody. These antibody fragments are obtained using conventional techniques known to those with skill in the art, and the fragments are screened for utility in the same manner as are intact antibodies.

As used herein, "receptors" refer to cellular-derived molecules (e.g., proteins) that bind to ligands such as, for example, peptides or small molecules (e.g., low molecular weight (<900 Daltons) organic or inorganic compounds).

As used herein, "peptide aptamer" refers to a molecule with a variable peptide sequence inserted into a constant scaffold protein (see, e.g., Baines I C, et al. *Drug Discov. Today* 11:334-341, 2006).

In some embodiments, the molecule of the BP-NA conjugate is a nucleic acid such as, for example, a nucleic acid aptamer. As used herein, "nucleic acid aptamer" refers to a small RNA or DNA molecules that can form secondary and tertiary structures capable of specifically binding proteins or other cellular targets (see, e.g., Ni X, et al. *Curr Med Chem.* 18(27): 4206-4214, 2011). Thus, in some embodiments, the BP-NA conjugate may be an aptamer-nucleic acid conjugate.

As used herein a "docking strand" refers to a single-stranded nucleic acid (e.g., DNA) that is about 5 nucleotides to about 50 nucleotides in length (or is 5 nucleotides to 50 nucleotides in length). In some embodiments, a docking strand is about 4 to about 60, about 6 nucleotides to about 40 nucleotides, about 7 nucleotides to about 30 nucleotides, about 8 to about 20 nucleotides, or about 9 nucleotides to about 15 nucleotides in length. In some embodiments, a docking strand is (or is about) 4, 5, 6, 7, 8, 9, 10, 11, 12, 13, 14, 15, 16, 17, 18, 19, 20 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more nucleotides in length.

A docking strand may have one domain or more than one domain (i.e., a plurality of domains), each domain complementary to a respective imager strand. As used herein, a "docking strand domain" refers to a nucleotide sequence of the docking strand that is complementary to a nucleotide sequence of an imager strand. A docking strand, for example, may contain one, two three, or more domains, each domain complementary to an imager strand. Each complementary imager strand can contain a distinct label (e.g., a red fluorophore, a blue fluorophore, or a green fluorophore), or all complementary imager strands can contain the same label (e.g., red fluorophores). For example, for a three-domain docking strand, the strand may contain a first domain complementary to an imager strand labeled with a red fluorophore, a second domain complementary to an imager strand labeled with a blue fluorophore, and a third domain complementary to an imager strand labeled with a green fluorophore. Alternatively, each of three docking domains may be complementary to imager strands labeled with a red fluorophore. In some embodiments, a docking strand has at least 2, at least 3, at least 4, at least 5, or more domains, each respectively complementary to an imager strand. In some embodiments, a docking strand has 1 to 5, 1 to 10, 1 to 15, 1 to 20, 1 to 25, 1 to 50, or 1 to 100 domains, each respectively complementary to an imager strand.

As used herein, an "imager strand" is a single-stranded nucleic acid (e.g., DNA) that is about 4 to about 30 nucleotides, about 5 to about 18 nucleotides, about 6 to about 15 nucleotides, about 7 to about 12 nucleotides, or about 8 to 10 nucleotides in length and is fluorescently-labeled. In some embodiments, the imager strand may be (or may be about) 4, 5, 6, 7, 8, 9, 10, 11, 12, 13, 14, 15, 16, 17, 18, 19, 20, 21, 22, 23, 24, 25, 26, 27, 28, 29 or 30 nucleotides in length. An imager strand of the present disclosure is complementary to and transiently binds to a docking strand. Two nucleic acids or nucleic acid domains are "complementary" to one another if they base-pair, or bind, with each other to form a double-stranded nucleic acid molecule via Watson-Crick interactions. As used herein, "binding" refers to an association between at least two molecules due to, for example, electrostatic, hydrophobic, ionic and/or hydrogen-bond interactions under physiological conditions. An imager strand is considered to "transiently bind" to a docking strand if it binds to a complementary region of a docking strand and then disassociates (unbinds) from the docking strand within a short period of time, for example, at room temperature. In some embodiments, an imager strand remains bound to a docking strand for about 0.1 to about 10, or about 0.1 to about 5 seconds. For example, an imager strand may remain bound to a docking strand for about 0.1, about 1, about 5 or about 10 seconds.

Imager strands of the present disclosure may be labeled with a detectable label (e.g., a fluorescent label, and thus are considered "fluorescently labeled"). For example, in some embodiments, an imager strand may comprise at least one (i.e., one or more) fluorophore. Examples of fluorophores for use in accordance with the present disclosure include, without limitation, xanthene derivatives (e.g., fluorescein, rhodamine, Oregon green, eosin and Texas red), cyanine derivatives (e.g., cyanine, indocarbocyanine, oxacarbocyanine, thiacarbocyanine and merocyanine), naphthalene derivatives (e.g., dansyl and prodan derivatives), coumarin derivatives, oxadiazole derivatives (e.g., pyridyloxazole, nitrobenzoxadiazole and benzoxadiazole), pyrene derivatives (e.g., cascade blue), oxazine derivatives (e.g., Nile red, Nile blue, cresyl violet and oxazine 170), acridine derivatives (e.g., proflavin, acridine orange and acridine yellow), arylmethine derivatives (e.g., auramine, crystal violet and malachite green), and tetrapyrrole derivatives (e.g., porphin, phthalocyanine and bilirubin). Other detectable labels may be used in accordance with the present disclosure, such us, for example, gold nanoparticles or other detectable particles or moieties.

As used herein, "spectrally distinct" molecules of the present disclosure (e.g., conjugates and/or imager strands) refer to molecules with labels (e.g., fluorophores) of different spectral signal or wavelength. For example, an imager strand labeled with a Cy2 fluorophore emits a signal at a wavelength of light of about 510 nm, while an imager strand labeled with a Cy5 fluorophore emits a signal at a wavelength of light of about 670 nm. Thus, the Cy2-labeled imager strand is considered herein to be spectrally distinct from the Cy5-labeled imager strand. Conversely, "spectrally indistinct" molecules of the present disclosure herein refer to molecules with labels having the same spectral signal or wavelength—that is, the emission wavelength of the labels cannot be used to distinguish between two spectrally indistinct fluorescently labeled molecules (e.g., because the wavelengths are the same or close together).

Figure 1A:
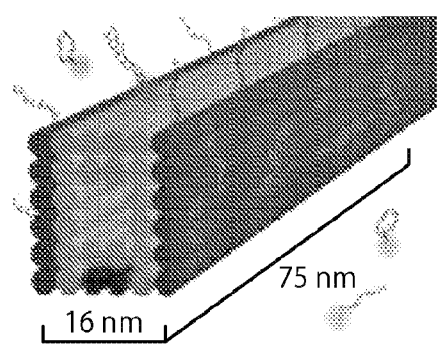
FIG. 1A shows microtubule-like DNA origami polymers "labeled" with single-stranded DNA docking strands on a pair of opposite faces (colored in dark gray) spaced approximately 16 nanometers (nm) apart. Complementary fluorescently-labeled imager strands transiently bind from solution to the docking strands. Biotinylated DNA strands (present on the bottom two center helices) are used to bind the microtubule-like DNA structures to glass surfaces for fluorescence imaging.
Figure 1B:
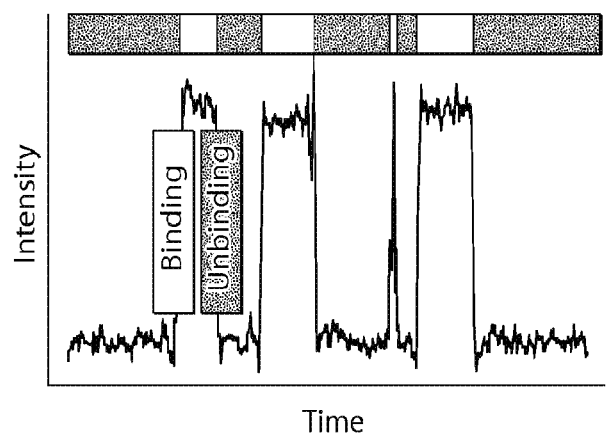
FIG. 1B shows a graph demonstrating that transient binding of fluorescently-labeled imager strands to the docking strands produces fluorescence "blinking" (fluorescence intensity vs. time trace). This blinking is used to consecutively localize points below the diffraction limit.
Figure 1C:
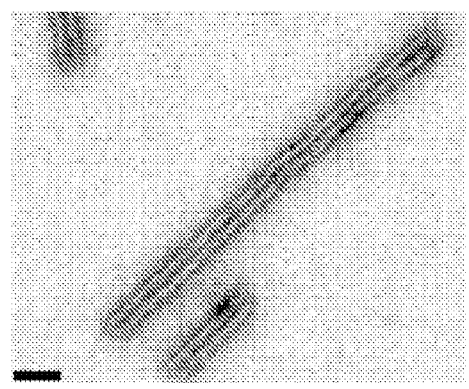
FIG. 1C shows a transmission electron microscope (TEM) image of DNA origami polymers with a measured width of 16±1 nm (mean±stdv) [scale bar: 40 nm].
Figure 1D:
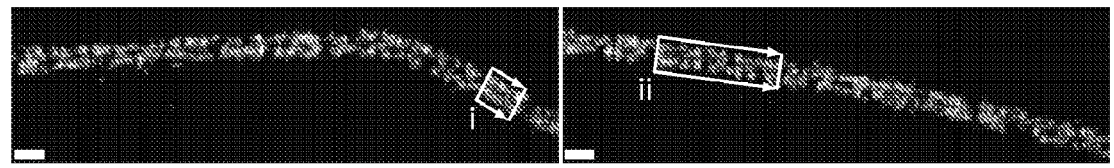
FIG. 1D shows super-resolution fluorescence images obtained using Cy3b-labeled imager strands (15,000 frames, 5 Hz frame rate). Two distinct lines are visible [scale bars: 40 nm].
Figure 1E:
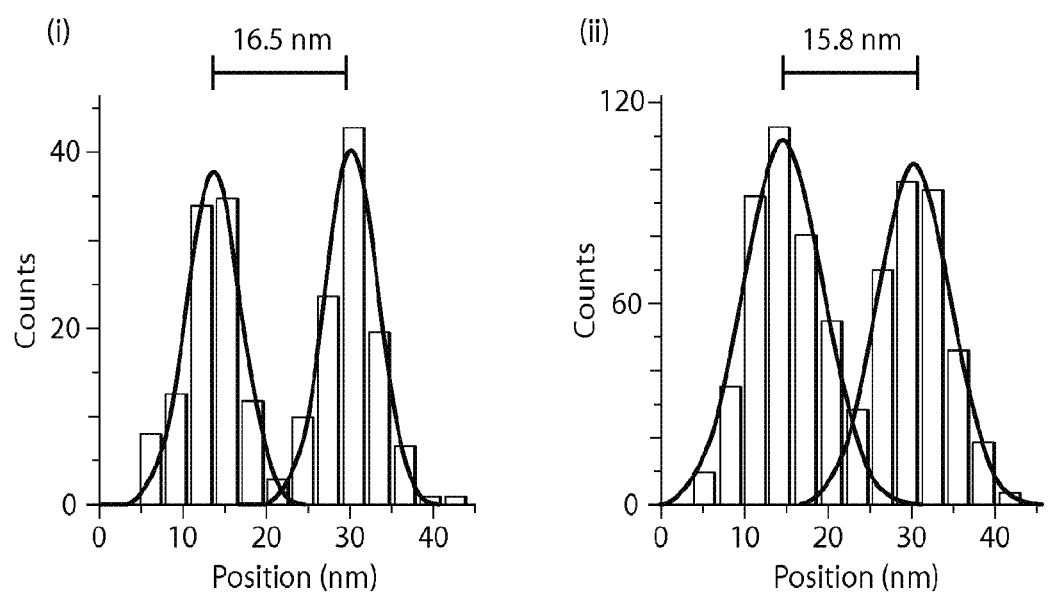
FIG. 1E shows a cross-sectional histogram of highlighted areas <i> and <ii> in FIG. 1D (arrows denote histogram direction), which show that the designed distance of approximately 16 nm is clearly resolved (full width at half maximum (FWHM) of each distribution is observed to be approximately 9 nm).
Figure 2:
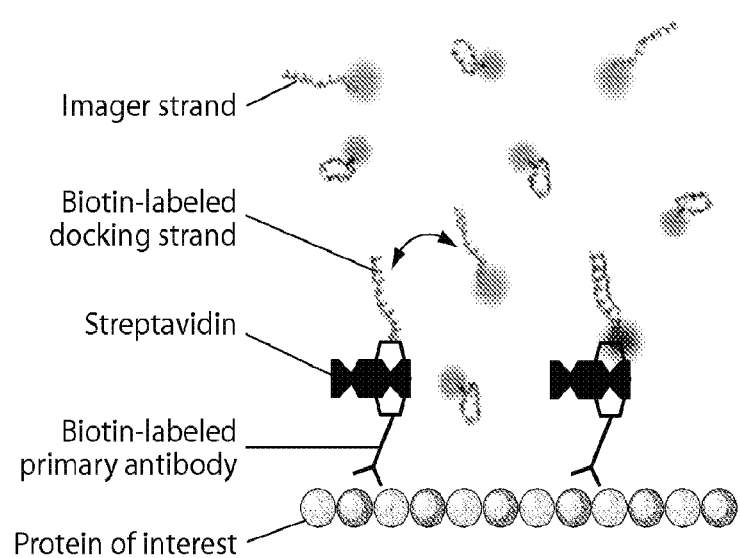
FIG. 2 shows an example of a biomolecule labeling scheme of the present disclosure where a protein (e.g., protein target) is labeled with antibody-DNA conjugates of the present disclosure and complementary fluorescently-labeled imager strands. The antibodies are linked to the docking strands through a linker that contains biotin and streptavidin (e.g., biotin-streptavidin-biotin linker).

The BP-NA conjugates (e.g., protein-nucleic acid conjugates) of the present disclosure may, in some embodiments, comprise an intermediate linker that links (e.g., covalently or non-covalently) the molecule to a docking strand. The intermediate linker may comprise biotin and/or streptavidin. For example, in some embodiments, an antibody and a docking strand may each be biotinylated (i.e., linked to at least one biotin molecule) and linked to each other through biotin binding to an intermediate streptavidin molecule, as shown in FIG. 2. Other intermediate linkers may be used in accordance with the present disclosure. In some embodiments, such as those where the molecule is a nucleic acid, an intermediate linker may not be required. For example, the docking strand of a BP-NA conjugate may be an extension (e.g., 5' or 3' extension) of a nucleic acid molecule such as, for example, a nucleic acid aptamer.

Pluralities of BP-NA conjugates (e.g., protein-nucleic acid conjugates) and imager strands are provided herein. A plurality may be a population of the same species or distinct species. A plurality of BP-NA conjugates of the same species may comprise conjugates that all bind to the same target (e.g., biomolecule) (e.g., the same epitope or region/domain). Conversely, a plurality of BP-NA conjugates of distinct species may comprise conjugates, or subsets of conjugates, each conjugate or subset of conjugates binding to a distinct epitope on the same target or to a distinct target. A plurality of imager strands of the same species may comprise imager strands with the same nucleotide sequence and the same fluorescent label (e.g., Cy2, Cy3 or Cy4). Conversely, a plurality of imager strands of distinct species may comprise imager strands with distinct nucleotide sequences (e.g., DNA sequences) and distinct fluorescent labels (e.g., Cy2, Cy3 or Cy4) or with distinct nucleotide sequences and the same fluorescent (e.g., all Cy2). The number of distinct species in a given plurality of BP-NA conjugates is limited by the number of binding partners (e.g., antibodies) and the number of docking strands of different nucleotide sequence (and thus complementary imager strands). In some embodiments, a plurality of BP-NA conjugates (e.g., protein-nucleic acid conjugates) comprises at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ BP-NA conjugates. Likewise, in some embodiments, a plurality of fluorescently-labeled imager strands comprises at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ fluorescently-labeled imager strands. In some embodiments, a plurality may contain 1 to about 200 or more distinct species of BP-NA conjugates and/or imager strands. For example, a plurality may contain at least 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200 or more distinct species. In some embodiments, a plurality may contain less than about 5 to about 200 distinct species of BP-NA conjugates and/or imager strands. For example, a plurality may contain less than 5, 6, 7, 8, 9, 10, 15, 20, 25, 30, 35, 40, 45, 50, 55, 60, 65, 70, 75, 80, 85, 90, 95, 100, 125, 150, 175 or 200 distinct species.

Figure 8A:
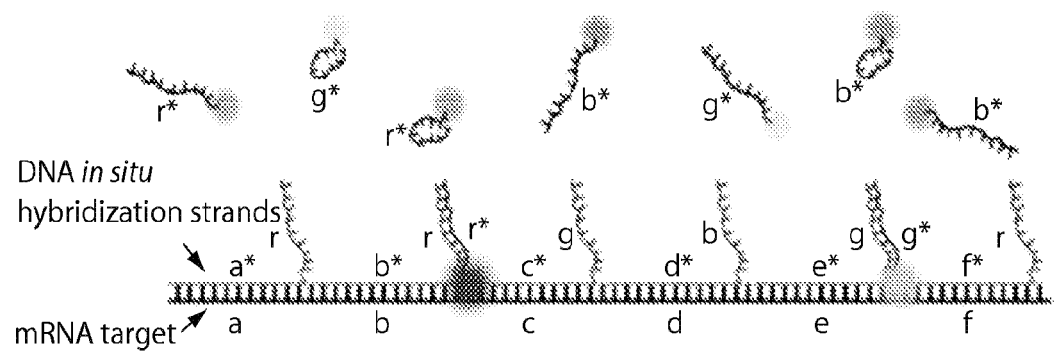
FIG. 8A shows mRNA molecules of interest in fixed *Escherichia coli* cells tagged using docking strands in a FISH-like hybridization scheme.
Figure 8B:
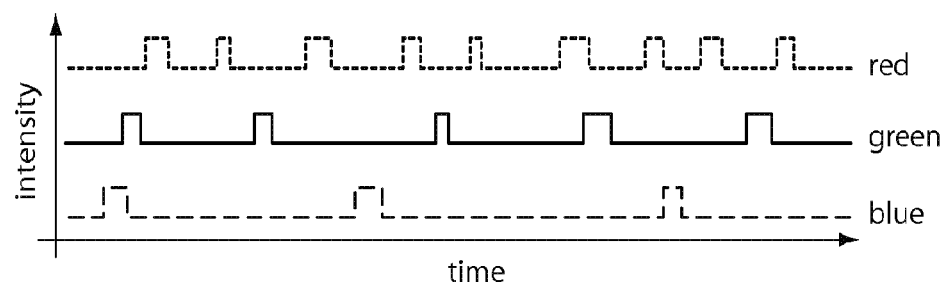
FIG. 8B shows a readout scheme used to determine the binding frequency for each imaging color. The intensity vs. time profile of each single mRNA location yields a specific transient binding pattern (blinking) per color. The frequency of binding events depends on the number of binding sites allowing the use of the binding frequency to distinguish between different integer numbers of binding sites.

The present disclosure also contemplates docking strands that can bind directly to a target. For example, as shown in FIG. 8A, a docking strand may contain, in additional to imager-binding domain(s) (e.g., one, two, three, or more, with the same or distinct fluorophores), a target domain that is complementary to and binds to a target, such as, for example, mRNA or other nucleic acid.

Methods

Methods provided herein are based, in part, on the programmability of nucleic acid docking strands and imager strands. That is, for example, docking strands and imager strands can be designed such that they bind to each other under certain conditions for a certain period of time. This programmability permits transient binding of imager strands to docking strands, as provided herein. Generally, the methods provided herein are directed to identifying one or more target(s) (e.g., biomolecule(s) such as a protein or nucleic acid) in a particular sample (e.g., biological sample). In some instances, whether or not one or more target(s) is present in sample is unknown. Thus, methods of the present disclosure may be used to determine the presence or absence of one or more target(s) in a sample suspected of containing the target(s). In any one of the aspects and embodiments provided herein, a sample may contain or may be suspected of containing one or more target(s).

Methods provided herein can also be used to identify the absolute quantity of a single target (e.g., such as, for example, a particular protein), or the quantity of a single target relative to one or more other targets.

Further, methods provided herein may be used to identify the location of a target within a sample or relative to other targets in the sample.

Methods provided herein may comprise, in some embodiments, contacting a sample with (a) at least one BP-NA conjugate (e.g., protein-nucleic acid conjugate) that comprises a binding partner linked to a docking strand and (b) at least one labeled, optionally fluorescently labeled, imager strand that is complementary to and transiently binds to the docking strand of the at least one BP-NA conjugate, and then determining whether the at least one BP-NA conjugate binds to at least one target (such as a biomolecule target) in the sample. In some embodiments, the determining step comprises imaging (e.g., with time-lapsed fluorescent microscopy techniques) transient binding of the at least one labeled, optionally fluorescently labeled, imager strand to the docking strand of the at least one BP-NA conjugate.

Other methods provided herein may comprise, in some embodiments, contacting a sample with (a) at least two BP-NA conjugates, each comprising a binding partner linked to a docking strand, and (b) at least two labeled, optionally spectrally distinct, fluorescently labeled, imager strands that are complementary to and transiently bind to respective docking strands of the at least two different BP-NA conjugates, and then determining whether the at least two BP-NA conjugates bind to at least one, or at least two, targets (such as biomolecule targets) in the sample. Binding of the BP-NA conjugates to respective targets can be determined by imaging transient binding of one of the at least two labeled, optionally spectrally distinct, fluorescently labeled, imager strands to a docking strand of one of the at least two BP-NA conjugates to produce a first image, and then imaging transient binding of another of the at least two labeled, optionally spectrally distinct, fluorescently labeled, imager strands to a docking strand of another of the at least two BP-NA conjugates to produce a second image. In some embodiments, the methods further comprise combining the first image and the second image to produce a composite image of signals (e.g., fluorescent signals), wherein the signals (e.g., fluorescent signals) of the composite image are representative of the at least two targets. As used herein, a "composite image" refers to a single image produced by combining (e.g., overlaying) multiple images of the same (or substantially similar) area. A composite image may also be referred to as a super-resolution image, as described elsewhere herein.

FIG. 3 demonstrates one embodiment of the present disclosure in which two distinct species of BP-NA conjugates (e.g., antibody-nucleic acid conjugates) are used to label biomolecules in a fixed HeLa cell sample. One species of antibody-nucleic acid conjugate comprises an antibody that recognizes and binds to an epitope on mitochondria. The mitochondrial specific antibody is linked to a docking strand with a sequence complementary to a Cy3b-labeled imager strand. The other species of antibody-nucleic acid conjugate comprises an antibody that recognizes and binds to an epitope on microtubules. The microtubule specific antibody is linked to a docking strand with a sequence complementary to an ATTO655-labeled imager strand. Two spectrally distinct species of imager strands are then introduced at the same time: one species is labeled with Cy3b and is complementary to the docking strand that is linked to the mitochondrial specific antibody, and the other species is labeled with ATTO655 and is complementary to the docking strand that is linked to the microtubule specific antibody. While both the Cy3b-labeled imager strand and the ATTO655-labeled imager strand are present at the same time in solution with the sample, imaging is carried our sequentially in Cy3b and ATTO655 channels.

Yet other methods provided herein may comprise, in some embodiments, contacting a sample with (a) at least two BP-NA conjugates, each comprising a protein linked to a docking strand and (b) at least two spectrally indistinct (e.g., labeled with the same fluorophore) fluorescently-labeled imager strands that are complementary to and transiently bind to respective docking strands of the at least two BP-NA conjugates, and then determining whether the at last two BP-NA conjugates bind to at least two targets (e.g., biomolecule targets) in the sample. In some embodiments, the methods comprise, in the following ordered steps, contacting the sample with a first BP-NA conjugate and at least one other BP-NA conjugate, contacting the sample with a first fluorescently-labeled imager strand that is complementary to and transiently binds to the docking strand of the first BP-NA conjugate, determining whether the first BP-NA conjugate binds to a first target, removing the first fluorescently-labeled imager strand, contacting the sample with at least one other fluorescently-labeled imager strand that is complementary to and transiently binds to the docking strand of the at least one other BP-NA conjugate, and determining whether the at least one other BP-NA conjugate binds to at least one other target.

Alternatively, in other embodiments, methods comprise, in the following ordered steps, contacting the sample with a first BP-NA conjugate, contacting the sample with a first fluorescently-labeled imager strand that is complementary to and transiently binds to the docking strand of the first BP-NA conjugate, determining whether the first BP-NA conjugate binds to a first target (e.g., biomolecule), removing the first fluorescently-labeled imager strand, contacting the sample with at least one other BP-NA conjugate, contacting the sample with at least one other fluorescently-labeled imager strand that is complementary to and transiently binds to the docking strand of the at least one other BP-NA conjugate, and determining whether the at least one other BP-NA conjugate binds to at least one other target.

Figure 4A:
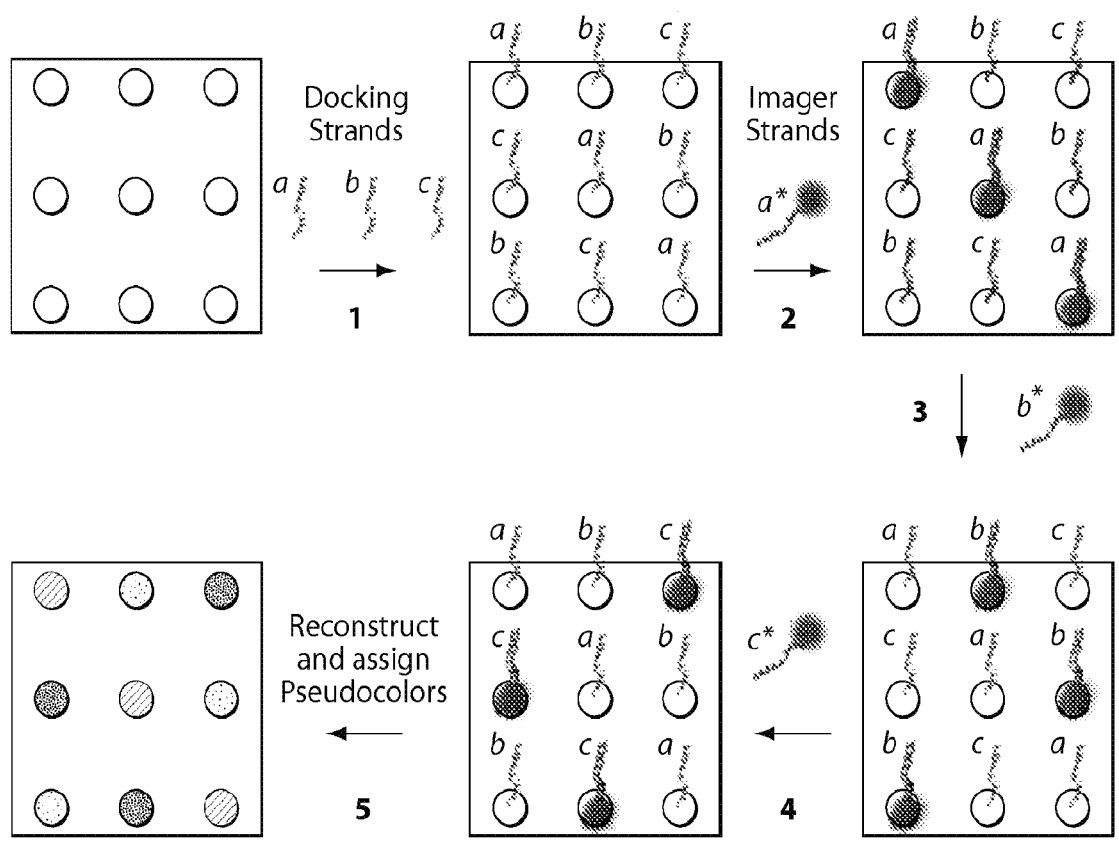
FIG. 4A shows one embodiment of the present disclosure using spectrally indistinct imager strands (e.g., each labeled with the same color fluorophore). In step [1], three different species of docking strands (a,b,c) label a surface. Such labeling may occur using the docking strand alone or linked to a protein-binding (e.g., antibody) or a nucleic acid-binding molecule that binds to the surface/biomolecule of interest. In step [2], multiple copies of the imager strand a* are introduced (where a* has a sequence complementary to a), and points labeled with docking strands a are imaged. In step [3], copies of the imager strand a* are flushed away, and imager strand b* is introduced to image the b labeled points. Images are obtained, and imager strands b* are washed away. In step [4], c labeled points are imaged in the same manner. In step [5], images from [2-4] are assigned pseudo-colors and combined to create the final image. Although pseudo-colors may be used in the final rendering of the image, all imager strands are actually labeled with the same color dye (e.g., fluorophore).

In some embodiments, the first determining step comprises imaging transient binding of the first fluorescently-labeled imager strand to the docking strand of the first BP-NA conjugate to produce a first image, and the second determining step comprises imaging transient binding of the at least one other fluorescently-labeled imager strand to the docking strand of the at least one other BP-NA conjugate to produce a second image. In some embodiments, the methods further comprise assigning a pseudo-color to the fluorescent signal in the first image, and assigning at least one other pseudo-color to the fluorescent signal in the second image. Further still, in some embodiments, the methods comprise combining the first image and the second image to produce a composite image of the pseudo-colored signals, wherein the pseudo-colored signals of the composite image are representative of the at least two targets (e.g., biomolecule targets). As illustrated in FIG. 4A, step [1], three distinct species of docking strands (a,b,c) label the surface of a grid (chosen for illustrative purposes). In step [2], multiple copies of the imager strand a* are introduced, and points labeled with docking strands a are imaged. In step [3], copies of the imager strand a* are flushed away, and imager strand b* is introduced to image the b labeled points. In step [4], c labeled points are imaged in the same manner. In step [5], images from steps [2-4] are assigned artificial pseudo-colors (e.g., using a software program) and combined to create the final composite image. All imager strands may be labeled with the same fluorophore—that is, the imager strands are spectrally indistinct. In some embodiments, the docking strands are linked to binding partners (e.g., proteins such as antibodies, or nucleic acids such as DNA or nucleic acid aptamers).

An advantage of the methods of the present disclosure is that partitioning and sequential imaging can be used to obtain multiplexed super-resolved images of up to hundreds of different species using only a single optimized fluorescent dye. Using these methods, the number of distinct nucleotide sequences (e.g., DNA sequences), as opposed to the number of spectrally distinct dyes, limits the multiplexing capability. In some methods of the present disclosure, for example, those that use an imager strand with a length of 9 nucleotides, there are several hundred species within tight bounds for binding kinetics that may be used for a single sample, representing a tremendous increase in multiplexing compared to direct "traditional" imaging approaches.

Figure 5A:
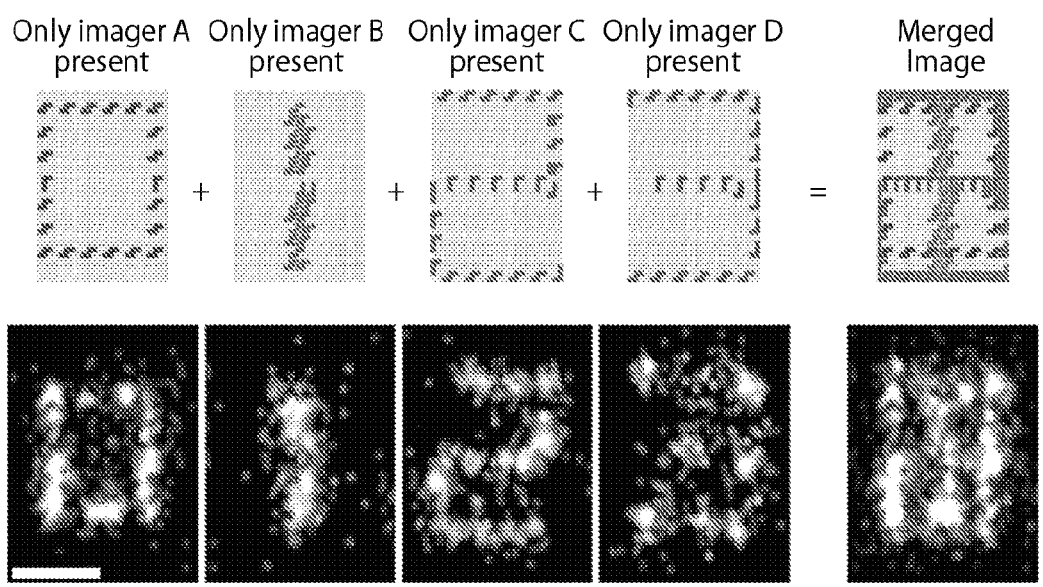
FIG. 5A shows one embodiment of the present disclosure using DNA origami structures with different species of docking strands at designated positions resembling numbers 0-3 (0, 1, 2 and 3). For each round, the respective imager strand sequence is added to an imaging chamber, image acquisition is carried out and the imager strands are washed out. In each imaging round the designed number is imaged, showing a very sequence-specific interaction with no crosstalk between different rounds [Scale bar: 50 nm]. Note that all imager strands are labeled with the same color dye, though each structure (e.g., 0-3 (0, 1, 2 and 3)) is rendered a distinct color (e.g., purple, yellow, blue, or red; color rendering not shown).

FIG. 5A illustrates another embodiment of the present disclosure using spectrally indistinct imager strands. A single DNA nanostructure displays four distinct species of docking strands (optionally linked to protein binding partners or nucleic acid binding partners) designed to resemble the digits from 0 to 3, respectively. Imaging is performed sequentially using a simple flow chamber setup, first flushing in fluorescently-labeled imager strands complementary to the docking strands of the number 0, and then exchanging the solution for fluorescently-labeled imager strands with a sequence complementary to docking strands of the number 1, and so forth. The resulting images have been pseudo-colored to represent the respective imaging cycles. As used herein, an "imaging cycle," or "imaging round" refers to the process of introducing fluorescently-labeled imager strands complementary to docking strands under conditions that allow the imager strand to bind to the docking strand, even if such binding is transient, and obtaining an image (or imaging an area).

Aspects of the present disclosure contemplate multiplex detection using multi-domain docking strands (e.g., docking strands with more than one domain), as described above. For illustrative purposes, the following embodiments are described in terms of a docking strand binding to a target, e.g., without an intermediate binding partner. It should be understood, however, that multi-domain docking strands may be linked to a binding partner (e.g., of a BP-NA conjugate, as provided herein.

In some embodiments, methods comprise contacting one or more target(s) with one or more docking strands, each containing two or more binding domains. In other embodiments, methods comprise contacting one or more target(s) with two or more docking strands, each containing one binding domain. The docking strand domains may have orthogonal sequences. In the examples that follow, all three targets (protein #1-#3) are present in the sample.

Detection Based on Spectral Resolution.

An exemplary multiplexed target detection method follows. A sample contains, or is suspected of containing, three target species—protein #1, protein #2, and protein #3. Three docking strands are designed such that: the first, containing imager binding domain A, binds to protein #1; the second, containing imager binding domain B, binds to protein #2; and the third, containing imager binding domains A and B, binds to protein #3. Complementary imager strand A' binds to imager binding domain A of a docking strand and is labeled with a blue fluorophore, and imager strand B' binds to imager binding domain B of a docking strand and is labeled with a red fluorophore. The sample is first contacted with the docking strands, and subsequently contacted with the imager strands A' and B'. The sample is then imaged. The sample containing the docking strands and the imager strands is first imaged under conditions that detect the blue fluorophore. Imaging the blue fluorophore detects protein #1 and protein #3, each bound by an imager strand labeled with the blue fluorophore. Imaging the red fluorophore detects protein #2 and protein #3, each bound by an imager strand labeled with the red fluorophore. Overlapping images of the red and blue fluorophores detects protein #3 only, the only protein bound by an imager strand labeled with a red fluorophore and an imager strand labeled with a blue fluorophore. Thus, the identification and location of proteins #1-#3 are identified by the overlay of images respectively detecting the red and blue fluorophores.

Detection Based on Exchange of Imager Strands.

Another exemplary multiplexed target detection method follows: A sample contains, or is suspected of containing, three target species—protein #1, protein #2, and protein #3. Three docking strands are designed such that: the first, containing imager binding domain A, binds to protein #1; the second, containing imager binding domain B, binds to protein #2; and the third, containing imager binding domains A and B, binds to protein #3. Complementary imager strand A' binds to imager binding domain A of a docking strand and is labeled with a blue fluorophore, and imager strand B' binds to imager binding domain B of a docking strand and is also labeled with a blue fluorophore. The sample is first contacted with the docking strands, and subsequently contacted with imager strands A'. The sample is then imaged under conditions that detect the blue fluorophore. Imaging the blue fluorophore detects protein #1 and protein #3, each bound by imager strand A' labeled with the blue fluorophore. The sample is then washed to remove imager strands A'. Next, the sample is contacted with imager strands B'. The sample is then imaged again under conditions that detect the blue fluorophore. Imaging the blue fluorophore now detects protein #2 and protein #3, each bound by imager strand B' labeled with the blue fluorophore. Overlapping images of the blue fluorophores (e.g., resulting in a stronger signal relative to non-overlapping fluorophores) detects protein #3 only, the only protein bound by two imager strands labeled with a blue fluorophore. Thus, the identification and location of proteins #1-#3 are identified by the overlay of images detecting the blue fluorophores and is based on signal intensity.

Detection Based on a Combination of Spectral and Exchange Detection.

Yet another exemplary multiplexed target detection method follows: A sample contains, or is suspected of containing, fifteen target species. The docking strands are designed such that each target species binds to a docking strand, each docking strand containing a single distinct domain or a distinct combination of domains A-D (e.g., A, or A and B (i.e., A/B), or A/C, or A/D, or A/B/C, or A/B/D, or A/C/D, or A/B/C/D, or B, or B/C, or B/D, or B/C/D, or C, or C/D, or D). The imager strands are divided into two sets: the first set (set #1) contains imager strand A' labeled by a red fluorophore and imager strand B' labeled by a blue fluorophore; the second set contains imager strand C' labeled with a red fluorophore and imager strand D' labeled with a blue fluorophore. The sample is first contacted with the docking strands, and subsequently contacted with imager strand set #1. The sample is then imaged under conditions that detect blue and red fluorophores. Targets bound by imager strands A' will be detected red and targets bound by imager strands B' will be detected blue. Thus, all target species with docking domains A and B will be detected in a first image or first set of images. The sample is then washed to remove imager strand set #1. Next, the sample is contacted with imager strand set #2. The sample is then imaged again under conditions that detect blue and red fluorophores. Targets bound by imager strands C' will be detected red and targets bound by imager strands D' will be detected blue. Thus, all target species with docking domains C and D will be detected in a second image or second set of images. By combining all images collected, each of the 15 target species can be identified using only four imager strands and two fluorophores. It should be understood that more than four imager strands can be used as well as more than two fluorophores, depending on, for example, the number of targets.

Detection Based on Duration of Transient Binding.

In some embodiments, the disclosure contemplates contacting target species with different docking strands domain sequence and different lengths of those sequences. The length of a docking strand imager binding domain affects the duration of transient binding to an imager strand. Docking strands with longer binding domains bind to respectively complementary imager strands for longer durations relative to shorter binding domains. In the following exemplary embodiment, a sample contains, or is suspected of containing, four target species. Four docking strands are designed such that: the first, containing binding domain A of 10 nucleotides in length (A10), binds to protein #1; the second, containing imager binding domain A10 and imager binding domain B of 8 nucleotides in length (B8), binds to protein #2; the third, containing imager binding domain A of 8 nucleotides in length (A8) and imager binding domain B of 10 nucleotides in length (B10), binds to protein #3; and four, containing imager strand binding domain B10. Imager strand A' is 10 nucleotides in length, binds to both A8 and A10, and is labeled with a blue fluorophore. Imager strand B' is 10 nucleotides in length, binds to both B8 and B10, and is labeled with a red fluorophore. The sample is first contacted with the docking strands, and subsequently contacted with imager strands A' and B'. The sample is then imaged under conditions that detect the blue fluorophore. Imaging the blue fluorophore detects protein #3 and protein #4 with a longer bound time (i.e., time of binding between imager strand and docking strand) and protein #2 with a shorter bound time. Imaging the red fluorophore detects protein #1 and protein #2 with a longer bound time and protein #3 with a shorter bound time. Overlapping images of the blue and red fluorophores detects each of the four protein targets.

The present disclosure also contemplates combining multiplexed detection based on spectral resolution and duration, exchange and duration, and spectral resolution, exchange and duration.

A "sample" may comprise cells (or a cell), tissue, or bodily fluid such as blood (serum and/or plasma), urine, semen, lymphatic fluid, cerebrospinal fluid or amniotic fluid. A sample may be obtained from (or derived from) any source including, without limitation, humans, animals, bacteria, viruses, microbes and plants. In some embodiments, a sample is a cell lysate or a tissue lysate. A sample may also contain mixtures of material from one source or different sources. A sample may be a spatial area or volume (e.g., a grid on an array, or a well in a plate or dish). A sample, in some embodiments, includes target(s), BP-NA conjugate(s) and imager strand(s).

A "target" is any moiety that one wishes to observe or quantitate and for which a binding partner exists. A target, in some embodiments, may be non-naturally occurring. The target, in some embodiments, may be a biomolecule. As used herein, a "biomolecule" is any molecule that is produced by a living organism, including large macromolecules such as proteins, polysaccharides, lipids and nucleic acids (e.g., DNA and RNA such as mRNA), as well as small molecules such as primary metabolites, secondary metabolites, and natural products. Examples of biomolecules include, without limitation, DNA, RNA, cDNA, or the DNA product of RNA subjected to reverse transcription, A23187 (Calcimycin, Calcium Ionophore), Abamectine, Abietic acid, Acetic acid, Acetylcholine, Actin, Actinomycin D, Adenosine, Adenosine diphosphate (ADP), Adenosine monophosphate (AMP), Adenosine triphosphate (ATP), Adenylate cyclase, Adonitol, Adrenaline, epinephrine, Adrenocorticotropic hormone (ACTH), Aequorin, Aflatoxin, Agar, Alamethicin, Alanine, Albumins, Aldosterone, Aleurone, Alpha-amanitin, Allantoin, Allethrin, α-Amanatin, Amino acid, Amylase, Anabolic steroid, Anethole, Angiotensinogen, Anisomycin, Antidiuretic hormone (ADH), Arabinose, Arginine, Ascomycin, Ascorbic acid (vitamin C), Asparagine, Aspartic acid, Asymmetric dimethylarginine, Atrial-natriuretic peptide (ANP), Auxin, Avidin, Azadirachtin A—$C_{35}H_{44}O_{16}$, Bacteriocin, Beauvericin, Bicuculline, Bilirubin, Biopolymer, Biotin (Vitamin H), Brefeldin A, Brassinolide, Brucine, Cadaverine, Caffeine, Calciferol (Vitamin D), Calcitonin, Calmodulin, Calmodulin, Calreticulin, Camphor—$C_{10}H_{16}O$, Cannabinol, Capsaicin, Carbohydrase, Carbohydrate, Carnitine, Carrageenan, Casein, Caspase, Cellulase, Cellulose—$(C_6H_{10}O_5)$, Cerulenin, Cetrimonium bromide (Cetrimide)—$C_{19}H_{42}BrN$, Chelerythrine, Chromomycin A3, Chaparonin, Chitin, α-Chloralose, Chlorophyll, Cholecystokinin (CCK), Cholesterol, Choline, Chondroitin sulfate, Cinnamaldehyde, Citral, Citric acid, Citrinin, Citronellal, Citronellol, Citrulline, Cobalamin (vitamin B12), Coenzyme, Coenzyme Q, Colchicine, Collagen, Coniine, Corticosteroid, Corticosterone, Corticotropin-releasing hormone (CRH), Cortisol, Creatine, Creatine kinase, Crystallin, α-Cyclodextrin, Cyclodextrin glycosyltransferase, Cyclopamine, Cyclopiazonic acid, Cysteine, Cystine, Cytidine, Cytochalasin, Cytochalasin E, Cytochrome, Cytochrome C, Cytochrome c oxidase, Cytochrome c peroxidase, Cytokine, Cytosine—$C_4H_5N_3O$, Deoxycholic acid, DON (DeoxyNivalenol), Deoxyribofuranose, Deoxyribose, Deoxyribose nucleic acid (DNA), Dextran, Dextrin, DNA, Dopamine, Enzyme, Ephedrine, Epinephrine—$C_9H_{13}NO_3$, Erucic acid—$CH_3(CH_2)_7CH=CH(CH_2)_{11}COOH$, Erythritol, Erythropoietin (EPO), Estradiol, Eugenol, Fatty acid, Fibrin, Fibronectin, Folic acid (Vitamin M), Follicle stimulating hormone (FSH), Formaldehyde, Formic acid, Formnoci, Fructose, Fumonisin B1, Gamma globulin, Galactose, Gamma globulin, Gamma-aminobutyric acid, Gamma-butyrolactone, Gamma-hydroxybutyrate (GHB), Gastrin, Gelatin, Geraniol, Globulin, Glucagon, Glucosamine, Glucose—$C_6H_{12}O_6$, Glucose oxidase, Gluten, Glutamic acid, Glutamine, Glutathione, Gluten, Glycerin (glycerol), Glycine, Glycogen, Glycolic acid, Glycoprotein, Gonadotropin-releasing hormone (GnRH), Granzyme, Green fluorescent protein, Growth hormone, Growth hormone-releasing hormone (GHRH), GTPase, Guanine, Guanosine, Guanosine triphosphate (+GTP), Haptoglobin, Hematoxylin, Heme, Hemerythrin, Hemocyanin, Hemoglobin, Hemoprotein, Heparan sulfate, High density lipoprotein, HDL, Histamine, Histidine, Histone, Histone methyltransferase, HLA antigen, Homocysteine, Hormone, human chorionic gonadotropin (hCG), Human growth hormone, Hyaluronate, Hyaluronidase, Hydrogen peroxide, 5-Hydroxymethylcytosine, Hydroxyproline, 5-Hydroxytryptamine, Indigo dye, Indole, Inosine, Inositol, Insulin, Insulin-like growth factor, Integral membrane protein, Integrase, Integrin, Intein, Interferon, Inulin, Ionomycin, Ionone, Isoleucine, Iron-sulfur cluster, K252a, K252b, KT5720, KT5823, Keratin, Kinase, Lactase, Lactic acid, Lactose, Lanolin, Lauric acid, Leptin, Leptomycin B, Leucine, Lignin, Limonene, Linalool, Linoleic acid, Linolenic acid, Lipase, Lipid, Lipid anchored protein, Lipoamide, Lipoprotein, Low density lipoprotein, LDL, Luteinizing hormone (LH), Lycopene, Lysine, Lysozyme, Malic acid, Maltose, Melatonin, Membrane protein, Metalloprotein, Metallothionein, Methionine, Mimosine, Mithramycin A, Mitomycin C, Monomer, Mycophenolic acid, Myoglobin, Myosin, Natural phenols, Nucleic Acid, Ochratoxin A, Oestrogens, Oligopeptide, Oligomycin, Orcin, Orexin, Ornithine, Oxalic acid, Oxidase, Oxytocin, p53, PABA, Paclitaxel, Palmitic acid, Pantothenic acid (vitamin B5), parathyroid hormone (PTH), Paraprotein, Pardaxin, Parthenolide, Patulin, Paxilline, Penicillic acid, Penicillin, Penitrem A, Peptidase, Pepsin, Peptide, Perimycin, Peripheral membrane protein, Perosamine, Phenethylamine, Phenylalanine, Phosphagen, phosphatase, Phospholipid, Phenylalanine, Phytic acid, Plant hormones, Polypeptide, Polyphenols, Polysaccharides, Porphyrin, Prion, Progesterone, Prolactin (PRL), Proline, Propionic acid, Protamine, Protease, Protein, Proteinoid, Putrescine, Pyrethrin, Pyridoxine or pyridoxamine (Vitamin B6), Pyrrolysine, Pyruvic acid, Quinone, Radicicol, Raffinose, Renin, Retinene, Retinol (Vitamin A), Rhodopsin (visual purple), Riboflavin (vitamin B2), Ribofuranose, Ribose, Ribozyme, Ricin, RNA—Ribonucleic acid, RuBisCO, Safrole, Salicylaldehyde, Salicylic acid, Salvinorin-A—$C_{23}H_{28}O_8$, Saponin, Secretin, Selenocysteine, Selenomethionine, Selenoprotein, Serine, Serine kinase, Serotonin, Skatole, Signal recognition particle, Somatostatin, Sorbic acid, Squalene, Staurosporin, Stearic acid, Sterigmatocystin, Sterol, Strychnine, Sucrose (sugar), Sugars (in general), superoxide, T2 Toxin, Tannic acid, Tannin, Tartaric acid, Taurine, Tetrodotoxin, Thaumatin, Topoisomerase, Tyrosine kinase, Taurine, Testosterone, Tetrahydrocannabinol (THC), Tetrodotoxin, Thapsigargin, Thaumatin, Thiamine (vitamin B1)—$C_{12}H_{17}ClN_4OS \cdot HCl$, Threonine, Thrombopoietin, Thymidine, Thymine, Triacsin C, Thyroid-stimulating hormone (TSH), Thyrotropin-releasing hormone (TRH), Thyroxine (T4), Tocopherol (Vitamin E), Topoisomerase, Triiodothyronine (T3), Transmembrane receptor, Trichostatin A, Trophic hormone, Trypsin, Tryptophan, Tubulin, Tunicamycin, Tyrosine, Ubiquitin, Uracil, Urea, Urease, Uric acid—C5H4N4O3, Uridine, Valine, Valinomycin, Vanabins, Vasopressin, Verruculogen, Vitamins (in general), Vitamin A (retinol), Vitamin B, Vitamin B1 (thiamine), Vitamin B2 (riboflavin), Vitamin B3 (niacin or nicotinic acid), Vitamin B4 (adenine), Vitamin B5 (pantothenic acid), Vitamin B6 (pyridoxine or pyridoxamine), Vitamin B12 (cobalamin), Vitamin C (ascorbic acid), Vitamin D (calciferol), Vitamin E (tocopherol), Vitamin F, Vitamin H (biotin), Vitamin K (naphthoquinone), Vitamin M (folic acid), Wortmannin and Xylose.

In some embodiments, a target may be a protein target such as, for example, proteins of a cellular environment (e.g., intracellular or membrane proteins). Examples of proteins include, without limitation, fibrous proteins such as cytoskeletal proteins (e.g., actin, arp2/3, coronin, dystrophin, FtsZ, keratin, myosin, nebulin, spectrin, tau, titin, tropomyosin, tubulin and collagen) and extracellular matrix proteins (e.g., collagen, elastin, f-spondin, pikachurin, and fibronectin); globular proteins such as plasma proteins (e.g., serum amyloid P component and serum albumin), coagulation factors (e.g., complement proteins, C1-inhibitor and C3-convertase, Factor VIII, Factor XIII, fibrin, Protein C, Protein S, Protein Z, Protein Z-related protease inhibitor, thrombin, Von Willebrand Factor) and acute phase proteins such as C-reactive protein; hemoproteins; cell adhesion proteins (e.g., cadherin, ependymin, integrin, Ncam and selectin); transmembrane transport proteins (e.g., CFTR, glycophorin D and scramblase) such as ion channels (e.g., ligand-gated ion channels such nicotinic acetylcholine receptors and GABAa receptors, and voltage-gated ion channels such as potassium, calcium and sodium channels), synport/antiport proteins (e.g., glucose transporter); hormones and growth factors (e.g., epidermal growth factor (EGF), fibroblast growth factor (FGF), vascular endothelial growth factor (VEGF), peptide hormones such as insulin, insulin-like growth factor and oxytocin, and steroid hormones such as androgens, estrogens and progesterones); receptors such as transmembrane receptors (e.g., G-protein-coupled receptor, rhodopsin) and intracellular receptors (e.g., estrogen receptor); DNA-binding proteins (e.g., histones, protamines, CI protein); transcription regulators (e.g., c-myc, FOXP2, FOXP3, MyoD and P53); immune system proteins (e.g., immunoglobulins; major histocompatibility antigens and T cell receptors); nutrient storage/transport proteins (e.g., ferritin); chaperone proteins; and enzymes.

In some embodiments, a target may be a nucleic acid target such as, for example, nucleic acids of a cellular environment. As used herein with respect to targets, docking strands, and imager strands, a "nucleic acid" refers to a polymeric form of nucleotides of any length, such as deoxyribonucleotides or ribonucleotides, or analogs thereof. For example, a nucleic acid may be a DNA, RNA or the DNA product of RNA subjected to reverse transcription. Non-limiting examples of nucleic acids include coding or non-coding regions of a gene or gene fragment, loci (locus) defined from linkage analysis, exons, introns, messenger RNA (mRNA), transfer RNA, ribosomal RNA, ribozymes, cDNA, recombinant nucleic acids, branched nucleic acids, plasmids, vectors, isolated DNA of any sequence, isolated RNA of any sequence, nucleic acid probes, and primers. Other examples of nucleic acids include, without limitation, cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), locked nucleic acids ("LNA"), and nucleic acids with modified backbones (e.g., base- or sugar-modified forms of naturally-occurring nucleic acids). A nucleic acid may comprise modified nucleotides, such as methylated nucleotides and nucleotide analogs ("analogous" forms of purines and pyrimidines are well known in the art). If present, modifications to the nucleotide structure may be imparted before or after assembly of the polymer. A nucleic acid may be a single-stranded, double-stranded, partially single-stranded, or partially double-stranded DNA or RNA.

In some embodiments, a nucleic acid (e.g., a nucleic acid target) is naturally-occurring. As used herein, a "naturally occurring" refers to a nucleic acid that is present in organisms or viruses that exist in nature in the absence of human intervention. In some embodiments, a nucleic acid naturally occurs in an organism or virus. In some embodiments, a nucleic acid is genomic DNA, messenger RNA, ribosomal RNA, micro-RNA, pre-micro-RNA, pro-micro-RNA, viral DNA, viral RNA or piwi-RNA. In some embodiments, a nucleic acid target is not a synthetic DNA nanostructure (e.g., two-dimensional (2-D) or three-dimensional (3-D) DNA nanostructure that comprises two or more nucleic acids hybridized to each other by Watson-Crick interactions to form the 2-D or 3-D nanostructure).

The nucleic acid docking strands and imager strands described herein can be any one of the nucleic acids described above (e.g., DNA, RNA, modified nucleic acids, nucleic acid analogues, naturally-occurring nucleic acids, synthetic nucleic acids).

Quantitative Imaging

The present disclosure also provides methods for quantitating fluorescent moieties or emitters in a dense cluster that cannot be spatially resolved using prior art imaging techniques. Prior to the invention, no systematic model existed that describes the kinetics of photoswitching of fluorescent signals.

Stochastic super-resolution imaging using transient binding of short oligonucleotides (e.g., imager strands) to their targets offers a unique possibility to quantitatively count integer numbers of labeled molecules in a diffraction-limited area. "Switching" molecules from a fluorescent OFF- to an ON-state in the method of the present disclosure is facilitated by single-molecule nucleic acid (e.g., DNA) hybridization events, which are governed by a very predictable kinetic model with a second order association rate $k_{on}$ and a first order dissociation rate $k_{off}$:

$$S_{imager} + S_{docking} \xrightarrow{k_{on}} S_{imager} : S_{docking}$$

$$S_{imager} : S_{docking} \xrightarrow{k_{off}} S_{imager} + S_{docking}$$

Figure 7A:
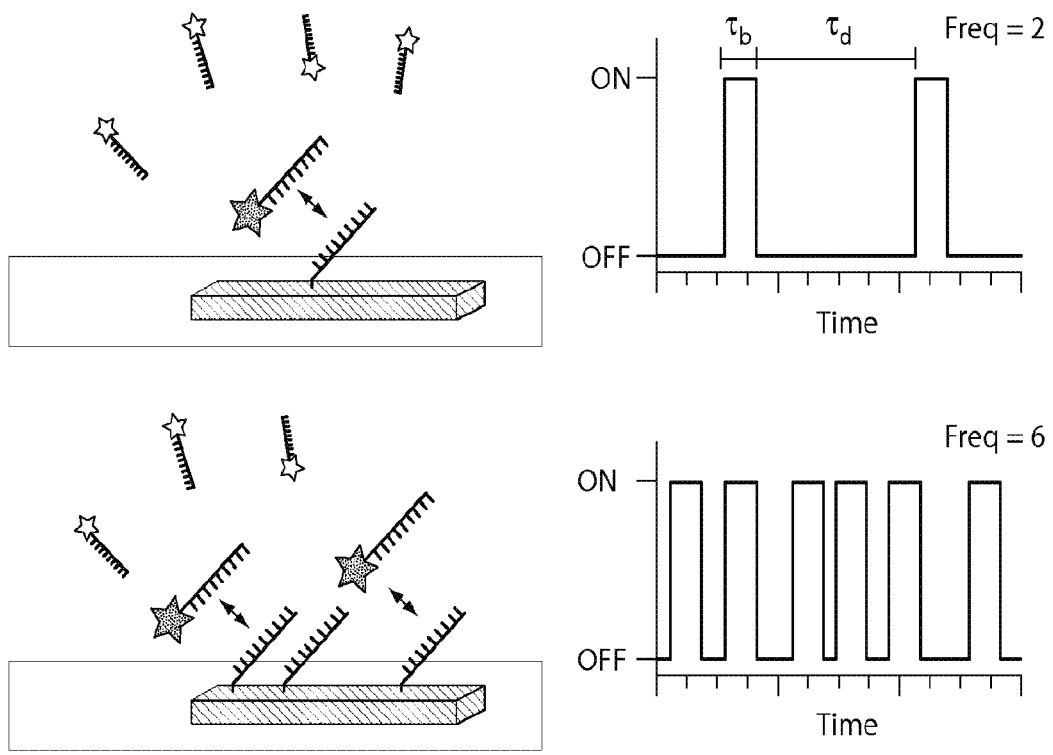
FIG. 7A shows that fluorescently-labeled imager strands transiently bind from solution to complementary docking strands on a structure or molecule of interest. The transient binding produces an apparent blinking as shown in the binding vs. time trace with characteristic fluorescence ON- and OFF-times ($\tau_b$ and $\tau_d$, respectively). The detected binding frequency of imager strands from solution is linearly dependent on the number of available docking strands in a given image area (i.e., the more docking strands, the higher the binding frequency). The time in-between binding events, i.e., the fluorescence OFF-time (rd), is inversely proportional to the number of docking strands.
Figure 7B:
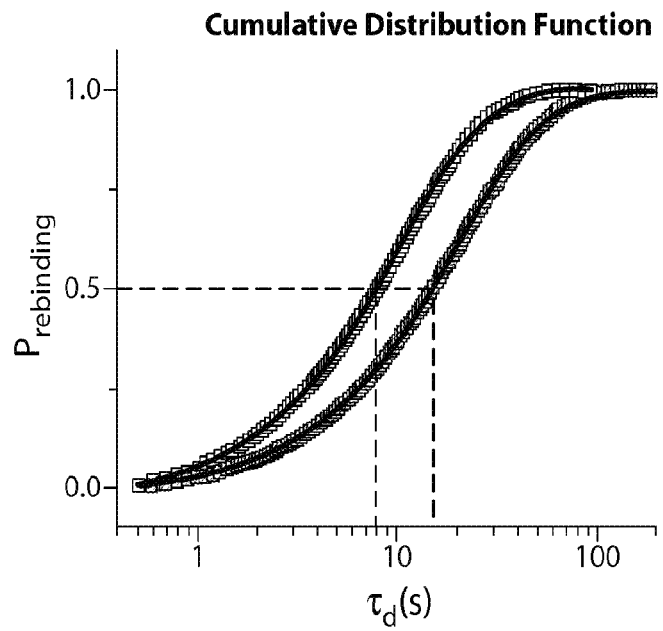
FIG. 7B shows that the average fluorescence OFF-time ($\tau_d$) can be determined by calculating a cumulative distribution function (CDF) for the OFF-time distribution. Given a known association constant $k_{on}$ and imager strand concentration c, the number of binding sites can be calculated by: number of binding sites=$(\tau_d \cdot c \cdot k_{on})^{-1}$.

The kinetic parameters $k_{on}$ and $k_{off}$ are now directly linked to fluorescent ON- and OFF-times ($\tau_b$ and $\tau_d$, respectively) depicted in FIG. 7A. The fluorescence ON-time $\tau_b$ is determined by the dissociation rate $k_{off}$: $\tau_b=1/k_{off}$, and the fluorescence OFF-time $\tau_d$ is determined by the association rate $k_{on}$, the concentration of imager strands in solution $C_{imager}$, and the number of observed binding sites bs:

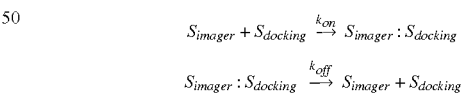

After calibrating $k_{on} \cdot c_{imager}$ using a sample with a known number of binding sites bs (which can be easily done using, e.g., a DNA nanostructure), the number of binding sites for an unknown molecule or area can be obtained according to the equation:

$$bs = \frac{1}{k_{on} \cdot c_{imager} \cdot \tau_d}$$

Accordingly, the quantification of a fluorescence image may be done automatically using binding kinetics analysis software. In brief, a typical image is recorded in a time-lapsed fashion (e.g., 15000 frames with a frame rate of 10 Hz). Fluorescence spot detection and fitting (e.g., Gaussian fitting, Centroid fitting, or Bessel fitting) is performed on the diffraction-limited image, and thus a super-resolved image is obtained. In the next step, a calibration marker is selected (e.g., a DNA origami structure with a defined number of spots as in FIG. 7C). The software automatically calculates the fluorescence dark time Td by fitting the OFF-time distribution to a cumulative distribution function. Using the equations described above, the product of $k_{on} \cdot c_{imager}$ can be calculated. This product is used to calculate the number of docking sites, and thus targets in the imaged area.

In some embodiments, the selection of areas of interest in the resolved (e.g., super-resolved) imaged can be performed automatically by applying a second spot detection step, e.g., to calculate the number of targets in a cluster.

Thus, in some embodiments, the methods of the present disclosure comprise providing a sample that comprises targets transiently bound directly or indirectly to fluorescently-labeled imager strands, obtaining a time-lapsed diffraction-limited fluorescence image of the sample, performing fluorescence spot detection and fitting (e.g., Gaussian fitting, Centroid fitting, or Bessel fitting) on the diffraction-limited image to obtain a high-resolution image of the sample, calibrating $k_{on} \cdot c_{imager}$ using a sample with a known number of targets, wherein $k_{on}$ is a second order association constant, and $c_{imager}$ is the concentration of fluorescently-labeled imager strands in the sample, including unbound imager strands, determining variable $\tau_d$ by fitting the fluorescence OFF-time distribution to a cumulative distribution function, and determining the number of targets in the sample based on the equation, number of targets= $(k_{on} \cdot c_{imager} \cdot \tau_d)^{-1}$.

Some aspects of the present disclosure relate to fitting functions. A "fitting function," as used herein, refers to a mathematical function used to fit the intensity profile of molecules. Examples of fitting functions for use as provided herein include, without limitation, Gaussian fitting, Centroid fitting, and Bessel fitting. It should be understood that while many aspects and embodiments of the present disclosure refer to Gaussian fitting, other fitting functions may be used instead of, or in addition to, Gaussian fitting.

Compositions

Provided herein are compositions that comprise at least one or at least two (e.g., a plurality) BP-NA conjugate(s) (e.g., protein-nucleic acid conjugate(s)) of the present disclosure. The BP-NA conjugates may be bound to a target of interest (e.g., biomolecule) and/or transiently bound to a complementary fluorescently-labeled imager strand. A composition may comprise a plurality of the same species or distinct species of BP-NA conjugates. In some embodiments, a composition may comprise at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ BP-NA conjugates. In some embodiments, a composition may comprise at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ complementary fluorescently-labeled imager strands. In some embodiments, a composition may contain 1 to about 200 or more distinct species of BP-NA conjugates and/or imager strands. For example, a composition may contain at least 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200 or more distinct species. In some embodiments, a composition may contain less than about 5 to about 200 distinct species of BP-NA conjugates and/or imager strands. For example, a composition may contain less than 5, 6, 7, 8, 9, 10, 15, 20, 25, 30, 35, 40, 45, 50, 55, 60, 65, 70, 75, 80, 85, 90, 95, 100, 125, 150, 175 or 200 distinct species.

It should be understood that the number of complementary fluorescently-labeled imager strands imager stands in a composition may be less than, equal to or greater than the number of BP-NA conjugates in the composition.

Kits

The present disclosure further provides kits comprising one or more components as provided herein. The kits may comprise, for example, a BP-NA conjugate and/or a fluorescently-labeled imager strands. The kits may also comprise components for producing a BP-NA conjugate or for labeling an imager strand. For example, the kits may comprise a binding partner (e.g., antibody), docking strands and intermediate linkers such as, for example, biotin and streptavidin molecules, and/or imager strands. The kits can be used for any purpose apparent to those of skill in the art, including, those described above.

The kits may include other reagents as well, for example, buffers for performing hybridization reactions. The kit may also include instructions for using the components of the kit, and/or for making and/or using the BP-NA conjugates and/or labeled imager strands.

In some embodiments, a kit comprises at least one docking strand and at least one labeled imager strand that is capable of transiently binding to a docking strand. The docking strands may or may not be conjugated to a binding partner. In some embodiments, the docking strands are conjugated to "generic" non-target-specific affinity molecule (e.g., biotin or streptavidin), which may be used to link a docking strand to binding partner chosen by an end user. In some embodiments, the affinity molecule is a secondary antibody. Thus, in some embodiments, a kit comprises at least one docking strand, at least one affinity molecule such as a secondary antibody, and at least one imager strand.

In some embodiments, a kit comprises (a) at least one docking strand linked to a binding partner such as a protein (e.g., a protein that binds to a target) and (b) at least one (e.g., at least 2, at least 3, at least 4, at least 5, at least 10, at least 100) labeled imager strand that is capable of transiently binding (e.g., transiently binds) to a docking strand. A docking strand may comprise, for example, at least two domains or at least three domain, wherein each domain binds to a respective complementary labeled imager strand. The number of labeled imager strands may be, for example, less than, greater than or equal to the number of docking strands. The binding partner may be a protein such as, for example, an antibody (e.g., monoclonal antibody), an antigen-binding antibody fragment, or a peptide aptamer. In some embodiments, a kit comprises at least two different binding partners (e.g., proteins), each specific for a different target. A binding partner (e.g., protein), in some embodiments, is linked to a docking strand through an intermediate linker such as, for example, a linker that includes biotin and streptavidin (e.g., a biotin-streptavidin-biotin linker). In some embodiments, a docking strand is modified to contain an affinity molecule that can be used to link the docking strand to a binding partner. In some embodiments, the affinity molecule is a secondary antibody. An imager strand, in some embodiments, is labeled with at least one fluorescent label (e.g., at least one fluorophore). In some embodiments, the length of an imager strand is 4 to 30 nucleotides, or longer. For example, the length of an imager strand may be 4, 5, 6, 7, 8, 9, 10, 11, 12, 13, 14, 15, 16, 17, 18, 19, 20, 21, 22, 23, 24, 25, 26, 27, 28, 29 or 30 nucleotides. In some embodiments, the length of an imager strand is 8 to 10 nucleotides. In some embodiments, a kit comprises at least two imager strands, each different from one another. In some embodiments, the thermal stability of a docking strand transiently bound to its complementary labeled imager strand is within 0.5 kcal/mol of the thermal stability of other docking strands transiently bound to their respective labeled imager strands.

In some embodiments, a kit comprises (a) at least one docking strand linked to a monoclonal antibody or an antigen binding fragment thereof (e.g., a monoclonal antibody or an antigen binding fragment thereof that binds to a target) and (b) at least one (e.g., at least 2, at least 3, at least 4, at least 5, at least 10, at least 100) labeled imager strand that is capable of transiently binding (e.g., transiently binds) to a docking strand. A docking strand may comprise, for example, at least two domains, wherein each domain binds to a respectively complementary labeled imager strand. The number of labeled imager strands may be, for example, less than, greater than or equal to the number of docking strands. In some embodiments, a kit comprises at least two different monoclonal antibodies or antigen binding fragments thereof, each specific for a different target. A monoclonal antibody or an antigen binding fragment thereof, in some embodiments, is linked to a docking strand through an intermediate linker that includes biotin and streptavidin (e.g., a biotin-streptavidin-biotin linker). An imager strand, in some embodiments, is labeled with at least one fluorescent label (e.g., at least one fluorophore). In some embodiments, the length of an imager strand is 4 to 30 nucleotides, or longer. For example, the length of an imager strand may be 4, 5, 6, 7, 8, 9, 10, 11, 12, 13, 14, 15, 16, 17, 18, 19, 20, 21, 22, 23, 24, 25, 26, 27, 28, 29 or 30 nucleotides. In some embodiments, the length of an imager strand is 8 to 10 nucleotides. In some embodiments, a kit comprises at least two imager strands, each different from one another. In some embodiments, the thermal stability of a docking strand transiently bound to a complementary labeled imager strand is within 0.5 kcal/mol of the thermal stability of other docking strands transiently bound to their respective labeled imager strands.

Applications

The BP-NA conjugates (e.g., protein-nucleic acid conjugates or antibody-nucleic acid conjugates) of the present disclosure can be used, inter alia, in any assay in which existing target detection technologies are used.

Typically assays include detection assays including diagnostic assays, prognostic assays, patient monitoring assays, screening assays, biowarfare assays, forensic analysis assays, prenatal genomic diagnostic assays and the like. The assay may be an in vitro assay or an in vivo assay. The present disclosure provides the advantage that many different targets can be analyzed at one time from a single sample using the methods of the present disclosure, even where such targets are spatially not resolvable (and thus spatially indistinct) using prior art imaging methods. This allows, for example, for several diagnostic tests to be performed on one sample.

The BP-NA conjugates can also be used to simply observe an area or region.

The methods of the present disclosure may be applied to the analysis of samples obtained or derived from a patient so as to determine whether a diseased cell type is present in the sample and/or to stage the disease. For example, a blood sample can be assayed according to any of the methods described herein to determine the presence and/or quantity of markers of a cancerous cell type in the sample, thereby diagnosing or staging the cancer.

Alternatively, the methods described herein can be used to diagnose pathogen infections, for example infections by intracellular bacteria and viruses, by determining the presence and/or quantity of markers of bacterium or virus, respectively, in the sample. Thus, the targets detected using the methods, compositions and kits of the present disclosure may be either patient markers (such as a cancer marker) or markers of infection with a foreign agent, such as bacterial or viral markers.

The quantitative imaging methods of the present disclosure may be used, for example, to quantify targets (e.g., target biomolecules) whose abundance is indicative of a biological state or disease condition (e.g., blood markers that are upregulated or downregulated as a result of a disease state).

Further, the methods, compositions and kits of the present disclosure may be used to provide prognostic information that assists in determining a course of treatment for a patient. For example, the amount of a particular marker for a tumor can be accurately quantified from even a small sample from a patient. For certain diseases like breast cancer, overexpression of certain proteins, such as Her2-neu, indicate a more aggressive course of treatment will be needed.

The methods of the present disclosure may also be used for determining the effect of a perturbation, including chemical compounds, mutations, temperature changes, growth hormones, growth factors, disease, or a change in culture conditions, on various targes, thereby identifying targets whose presence, absence or levels are indicative of a particular biological states. In some embodiments, the present disclosure is used to elucidate and discover components and pathways of disease states. For example, the comparison of quantities of targets present in a disease tissue with "normal" tissue allows the elucidation of important targets involved in the disease, thereby identifying targets for the discovery/screening of new drug candidates that can be used to treat disease.

The sample being analyzed may be a biological sample, such as blood, sputum, lymph, mucous, stool, urine and the like. The sample may be an environmental sample such as a water sample, an air sample, a food sample and the like. The assay may be carried out with one or more components of the binding reaction immobilized. Thus, the targets or the BP-NA conjugates may be immobilized. The assay may be carried out with one or more components of the binding reaction non-immobilized. The assays may involve detection of a number of targets in a sample, essentially at the same time, in view of the multiplexing potential offered by the BP-NA conjugates and fluorescently-labeled imager strands of the present disclosure. As an example, an assay may be used to detect a particular cell type (e.g., based on a specific cell surface receptor) and a particular genetic mutation in that particular cell type. In this way, an end user may be able to determine how many cells of a particular type carry the mutation of interest, as an example.

Devices

Also provided herein are fluidic chamber devices for liquid handling, as shown in FIGS. 23A and 23B. In some embodiments, the device is a polymer-based (e.g., polydimethylsiloxane (PDMS)) device comprising first and second channels, each connected at one end to a sample chamber. This configuration permits one or more fluid(s) to be sequentially administered to the sample at a controlled rate. For example, a syringe may be used to administer a first fluid to the sample through a first channel of the device. The syringe may then be used to administer a second fluid, which passes through the first channel of the device into the sample chamber, thereby forcing the first fluid out of the sample chamber, passing through a second channel and into, for example, a reservoir connected to the second channel (FIG. 23A). In some embodiments, the device is positioned on a glass slide to permit viewing from a microscope objective positioned below the device.

Super Resolution Imaging

Figure 3A:
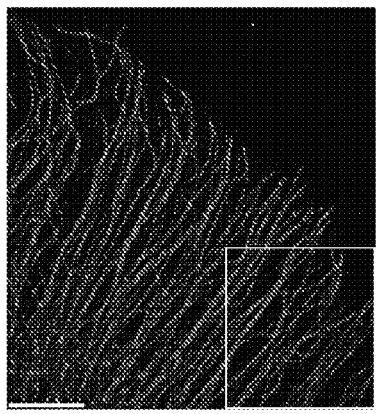
FIG. 3A shows a super-resolution image of a microtubule network inside a fixed HeLa cell using an antibody-DNA conjugate and Atto655-labeled imager strands (10,000 frames, 10 Hz frame rate) [scale bar: 5 μm].
Figure 3B:
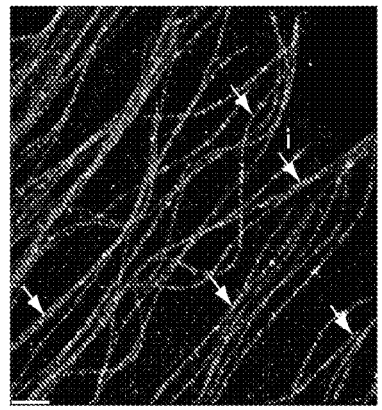
FIG. 3B shows a high magnification image of the highlighted area in FIG. 3A [scale bar: 1 μm].
Figure 3C:
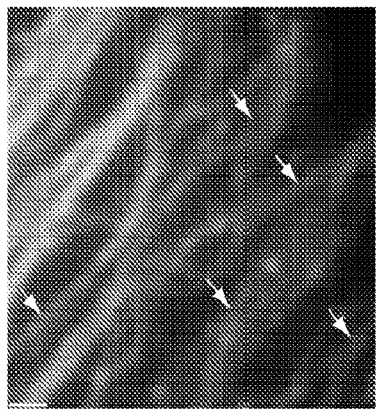
FIG. 3C shows a diffraction-limited representation of the same area in FIG. 3B. Arrows highlight positions where the increase in resolution of the image is clearly visible. Adjacent microtubules with an apparent width of approximately 46 nm at position <i> in FIG. 3B are separated by approximately 79 nm [scale bar: 1 μm].
Figure 3D:
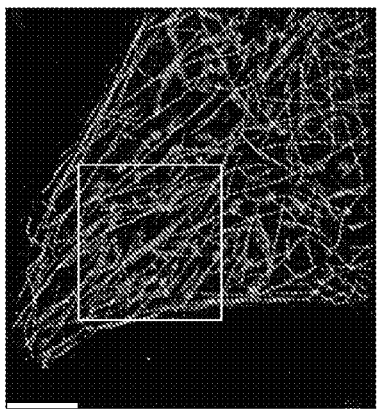
FIG. 3D shows a dual-color super-resolution image (15,000 frames, 10 Hz frame rate) of microtubules and mitochondria inside a fixed HeLa cell obtained using antibody-DNA conjugates, Cy3b-labeled imager strands for microtubules (linear-like structures) and Atto655-labeled imager strands for mitochondria (patch-like structures) [scale bar: 5 μm].
Figure 3E:
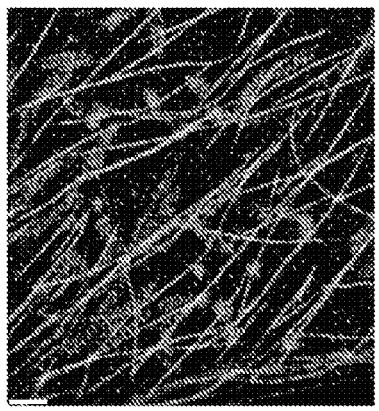
FIG. 3E shows a high magnification image of the highlighted area in FIG. 3D [scale bar: 1 μm].
Figure 3F:
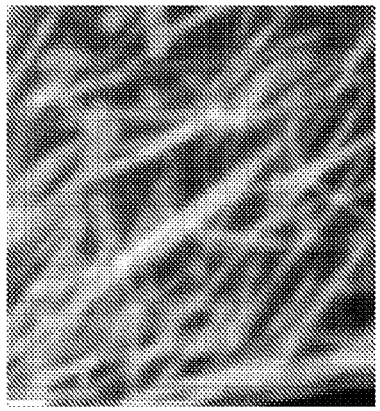
FIG. 3F shows a diffraction-limited image of the same area shown in FIG. 3E [scale bar: 1 μm].
Figure 4C:
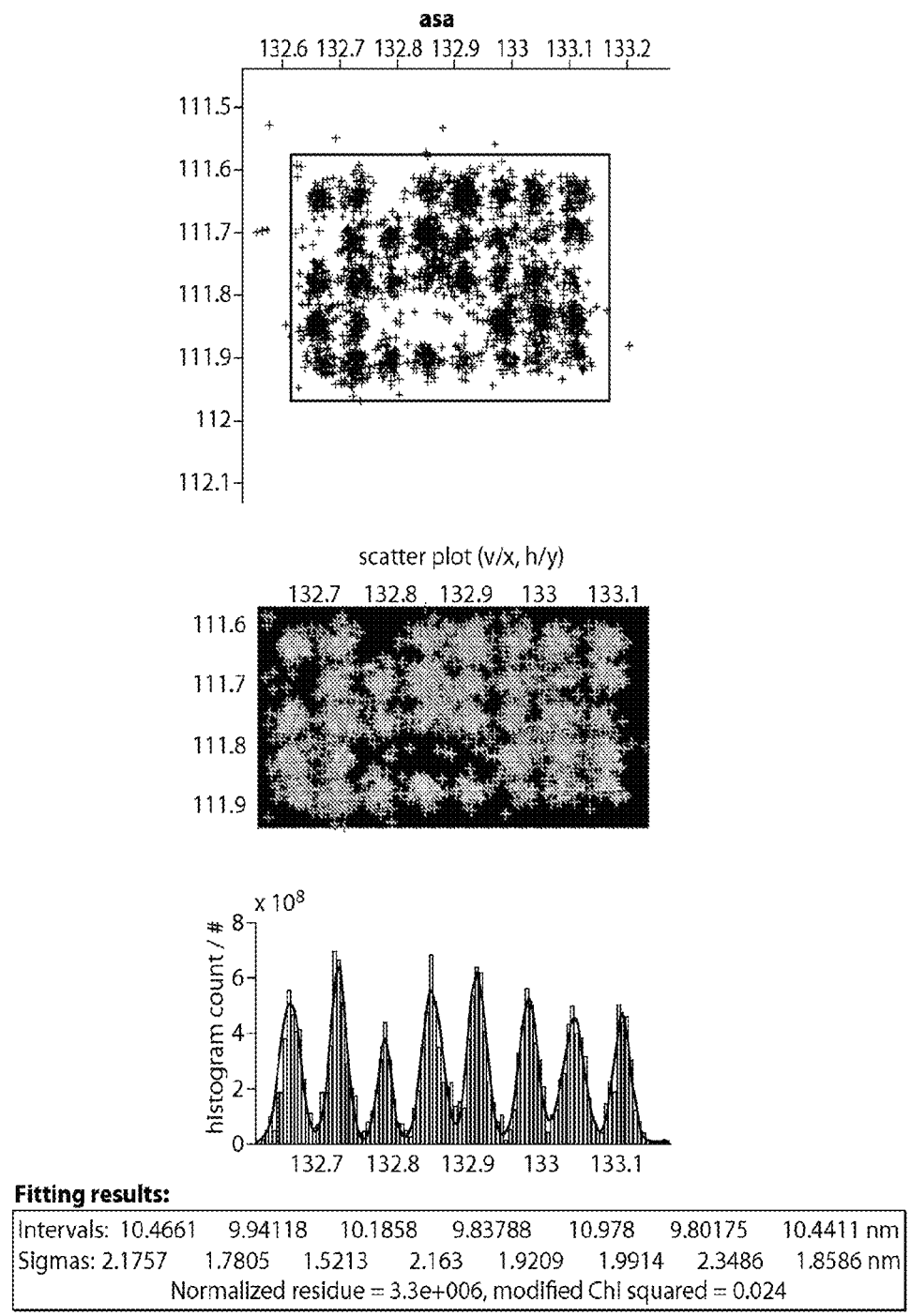
FIG. 4C shows an image of a DNA origami structure that displays docking strands spaced at 10 nm intervals.
Figure 11C:
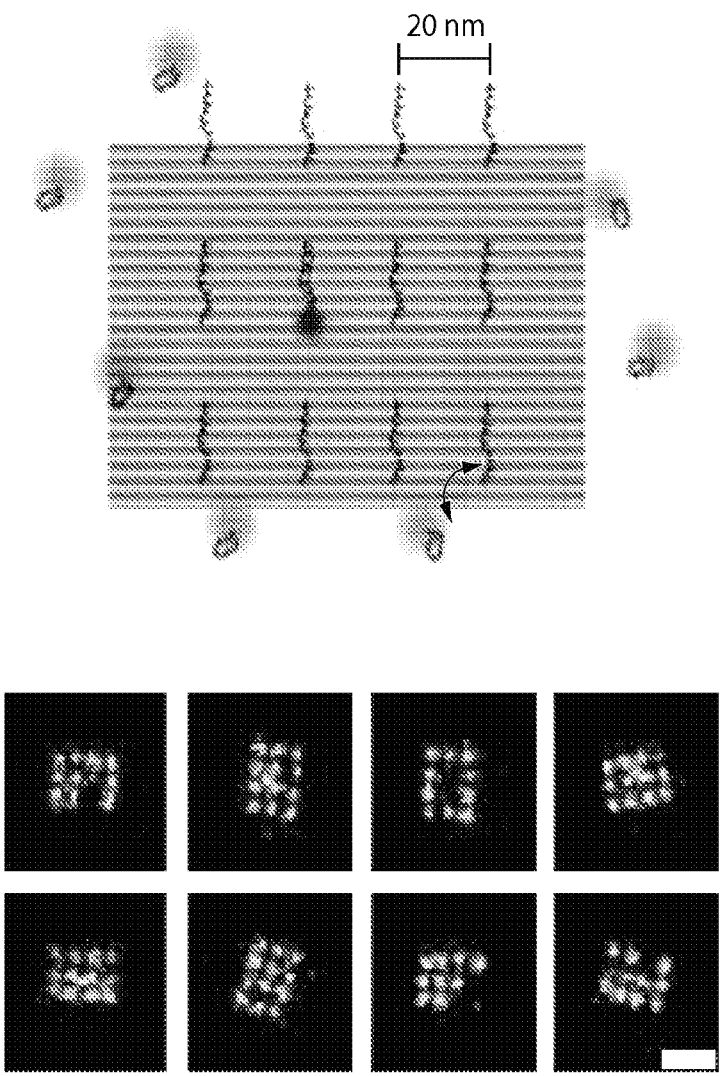
FIG. 11C shows a DNA origami structure with docking sites arranged in a 4×3 grid, spacing 20 nm. Single sites are optically localized with an accuracy of approximately 3 nm, currently the highest demonstrated resolution [scale bar: 50 nm].
Figure 11D:
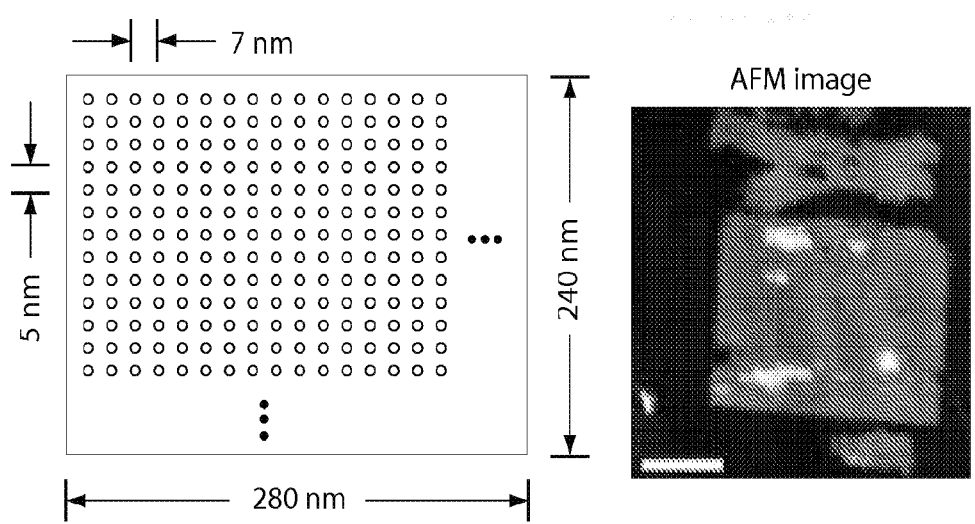
FIG. 11D shows a 280 nm×240 nm DNA nano-rectangle (single-stranded tile structure (15), 10× larger area than origami) displaying 2000 single-stranded docking strands (dots) with 7 or 5 nm spacing used as a test platform for ultra-resolution imaging [scale bar:100 nm].

Super-resolution imaging with increased spatial resolution (referred to herein as "ultra-resolution" imaging) may be achieved, in some embodiments, by increasing the number of photons per localization event using one of two strategies, depicted in FIG. 11A. In the first strategy, the maximum number of photons from single, replenishable fluorophores is extracted. High laser excitation power, in combination with fluorophore stabilization buffers (16,17) may be used to "bleach" transiently bound fluorophores at docking sites (or sites of docking strands), thus extracting the maximal number of photons per binding event and dye (FIG. 11A). The repetitive binding of imager strands permits "photobleaching" of every bound strand, thus making maximal use of emitted photons and resulting in a significant increase in localization accuracy over traditional imaging techniques. In the second strategy, bright metafluorophores are used. A fluorescent DNA nanostructure, or "metafluorophore," may be constructed by decorating a compact DNA nanostructure with many fluorophores (FIG. 11B3). The sum of the individual dye emissions from a metafluorophore are interpreted as originating from the same point source, and thus, using the metafluorophore in place of a standard fluorophore (e.g., Cy3) further improves the localization precision. A more advanced version of the metafluorophore with active background suppression is depicted in FIG. 11B4. Here, the clam-shell-like structure acts as a conditional fluorophore that only fluoresces when it is bound to the docking strand.

The present disclosure also provides algorithms used for spot detection, fitting and drift correction, as described below.

Software Algorithm for Drift Correction

Some embodiments are directed to methods and apparatus for correcting drift in images recorded in a time sequence. A non-limiting application of the techniques for performing drift correction, discussed in further detail below, is to correct for drift in molecular scale DNA-based imaging described herein involving transiently binding between docking strands and imaging strands. However, it should be appreciated that the techniques described herein may alternatively be used to correct for drift in other imaging applications where one or more transient imaging events are recorded during a time sequence of images, and embodiments related to drift correction are not limited to molecular scale DNA-based imaging.

In some embodiments, a DNA nanostructure can be used as a drift marker. Any suitable DNA nanostructure (see, e.g., (Rothemund US-2007/0117109 A1), single-stranded tiles (Yin et al., "Programming DNA Tube Circumferences," Science (2008): 321: 824-826), DNA hairpins (Yin et al. US-2009/0011956 A1; Yin et al., "Programming biomolecular self-assembly pathways," Nature (2008) 451:318-323) may be used, and may be made using, e.g., DNA origami techniques. Drift correction using DNA nanostructure-based drift markers in combination with advanced analysis and post-processing techniques has the advantage of high precision correction, compatibility with long time imaging and simplicity of implementation. Conventional nucleic acid-based imaging techniques incorporating drift markers based on fluorescent beads suffer from the limited length of imaging time before the beads are bleached; whereas bright field imaging requires specialized equipment, e.g. dual-field camera view.

Drift correction techniques in accordance with some embodiments described herein may include a plurality of stages, where each of the stages uses a different technique to perform drift correction. In some embodiments, the output from one stage is provided as input to a subsequent stage for additional drift correction processing. In a first stage, a coarse drift correction is performed by comparing localizations from neighboring frames. In a second stage, a single drift marker is selected and its time trace is used as a different coarse correction. In a third stage, a group of drift markers is selected, either automatically or with user input, and their time traces are then combined to compute a more precise drift correction. In a fourth stage, localizations are pooled from template-based drift markers displaying spots in a defined and spatially resolvable geometry (e.g., 4×3 grid points). In a fifth stage, a smoothing of the drift correction is performed to further reduce noise and enabling the resolution of the final image to approach molecular-scale resolution.

Any number and/or combination of these five stages may be performed in accordance with the techniques described herein. For example, in some embodiments, an amount of drift in the time sequence of images may be characterized using a quality measure, and based, at least in part, on the quality measure, one or more of the stages may be eliminated. In other embodiments, all five stages may be performed, as embodiments are not limited in this respect. In yet other embodiments, additional drift correction stages used in combination with at least one of the stages described herein may also be used.

In the following description of techniques for performing drift correction, the term FWHM (Full Width at Half Maximum) is used as the mathematical surrogate for "resolution." The approximation that FWHM~=sigma*2.35 for a Gaussian distribution, where sigma is the standard deviation, is also used. The techniques described herein for performing drift correction relate to processing a time sequence of images. The recorded image stack is referred to herein as a "movie" and each of the individual images as a "frame." Each frame of the movie is operated on with a spot finding algorithm, and then a local Gaussian fitting algorithm may be used for each identified spot; the spot and its fitted center position localization are interchangeably referred to herein as a "localization." The frames of the movie capture one or more transient events that are present in some frames but not others. In the illustrative application of the techniques where the frames of the movie related to nucleic acid-based imaging as discussed above, the hybridization of an imager strand to a docking strand until their disassociation is referred to herein as a binding "event"; thus an event could have, and typically will consist of, several localizations in a series of neighboring frames. Although binding events are discussed in further detail below as one illustrative transient event that may be analyzed using the techniques described herein for performing drift correction, it should be appreciated that other types of transient events imaged in a time sequence may alternatively be used. Within a certain area of the field of view, the collection of all localizations throughout the entire movie is collectively referred to as the "time trace," which reflects the movement of an observed structure, and is used for drift correction in several different ways, as described in more detail below.

Overview of Drift Correction Techniques

Figures 12A, 12B, 12C:
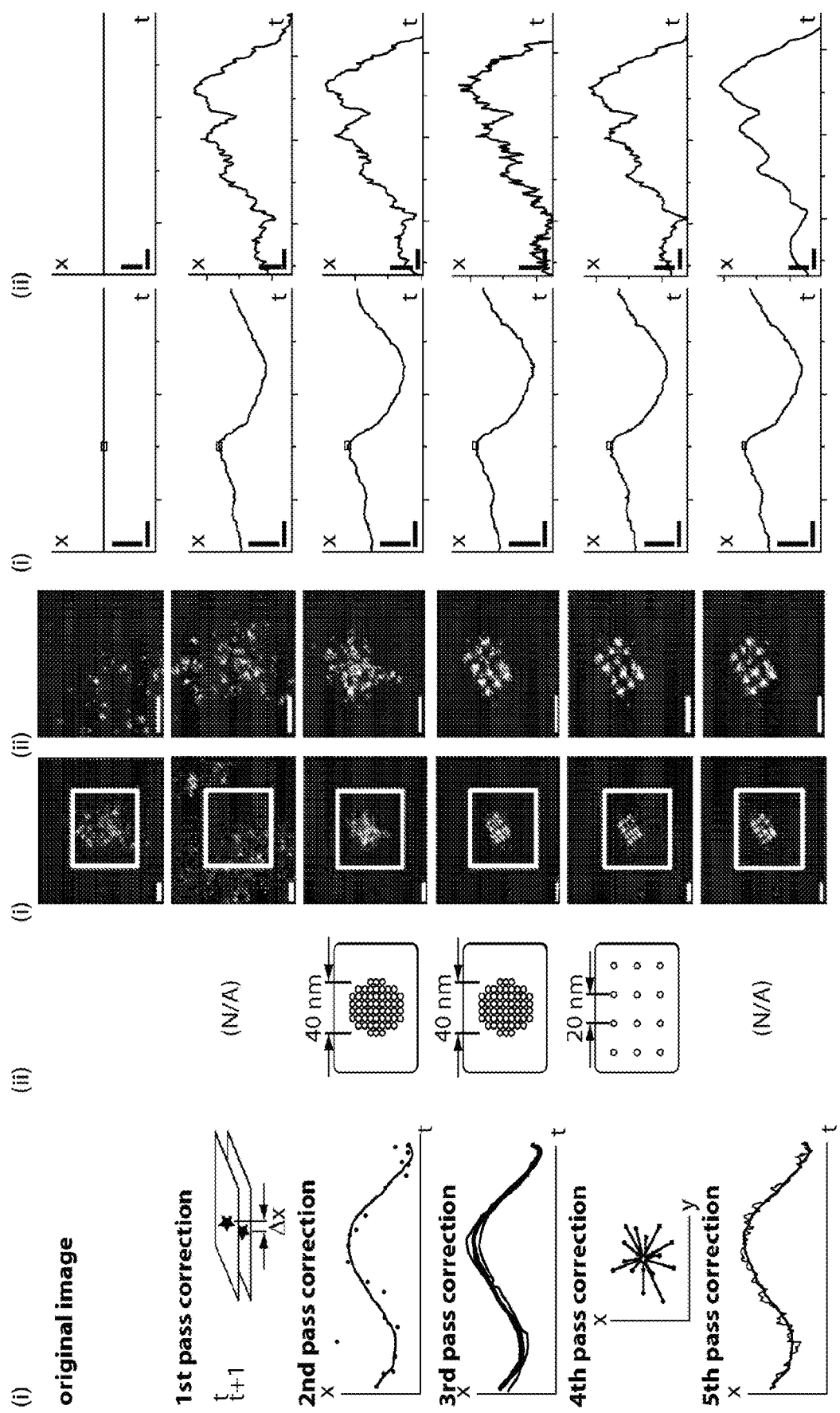
FIG. 12A(i) illustrates schematics showing the principle of each stage of drift correction. In each image, black markers and lines indicate source data, and gray values and curves indicate the calculated drift correction.
FIG. 12B(i) illustrates an example structure showing the imaging quality after each stage or correction, and FIG. 12B(ii) shows a zoomed image of the corresponding green rectangle in FIG. 12B(i) at each stage. The scale bars shown in FIGS. 12B(i) and 12B(ii) correspond to 50 nm.
FIG. 12C(i) illustrates an example drift trace after each stage of correction, and FIG. 12C(ii) shows a zoomed image of the corresponding rectangle in FIG. 12C(i) at each stage. The scale bars in FIG. 12C(i) correspond to x: 500 nm, t: 500 s, and the scale bars in FIG. 12C(ii) correspond to x: 10 nm, t: 10 s.
Figure 18A:
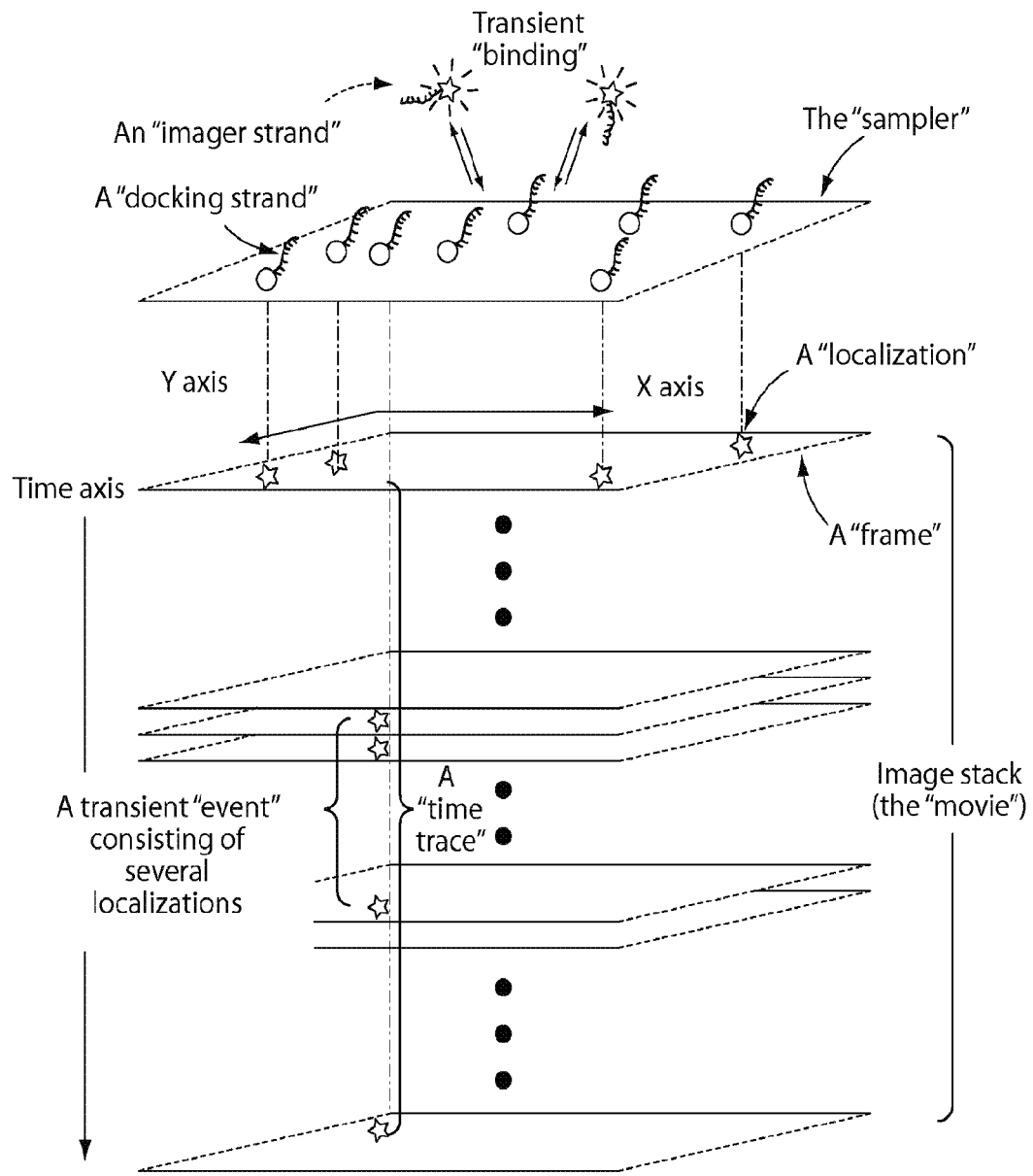
FIGS. 18A-18C illustrate an alternative representation of stages in a drift correction process in accordance with some embodiments of the present disclosure. A super-resolved image of a 10 nm-spaced regular grid on a single-molecule DNA origami nanostructure is shown. The DNA origami structure was designed to be a 5×8 square lattice of 10 nm spacing both vertically and horizontally.
Figure 18B:
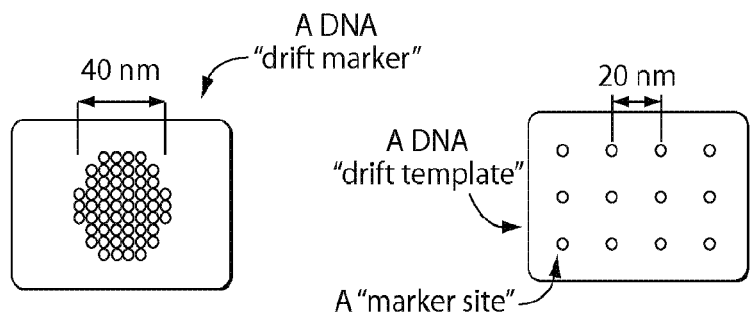
Figure 18C:
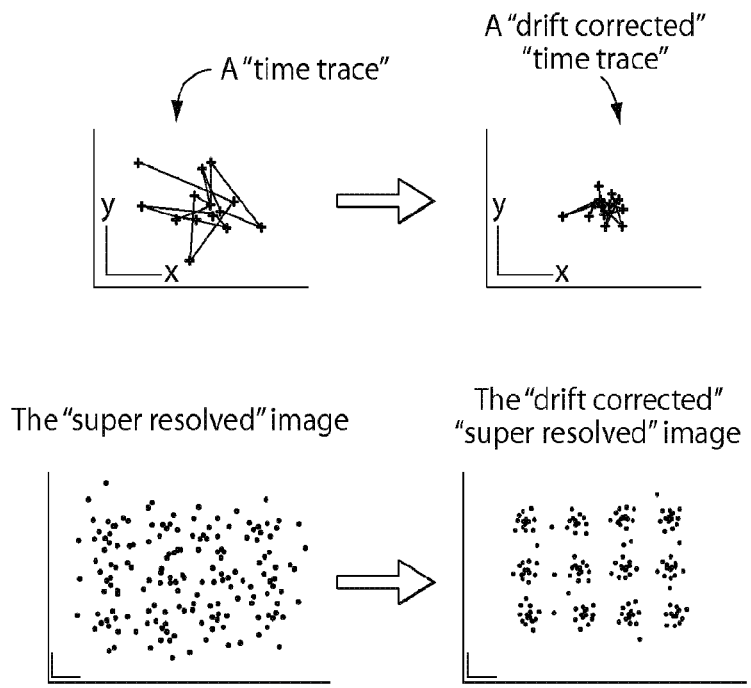

FIG. 12 illustrates a schematic overview of five stages of a drift correction procedure that may be performed in accordance with the techniques described herein. The stages are illustrated as being performed consecutively in an order from an unprocessed image to a final image that has been processed using the techniques of each of the five stages. Each of these stages will be discussed in more detail below. Briefly, FIG. 12A(i) illustrates schematics showing the principle of each stage of drift correction. In each image, black markers and lines indicate source data, and red values and curves indicate the calculated drift correction. FIG. 12A(ii) shows a schematic drawing of the major type of drift markers (e.g., DNA drift markers) used in each stage. FIG. 12B(i) illustrates an example structure showing the imaging quality after each stage or correction, and FIG. 12B(ii) shows a zoomed image of the corresponding green rectangle in FIG. 12B(i) at each stage. The scale bars shown in FIGS. 12B(i) and 12B(ii) correspond to 50 nm. FIG. 12C(i) illustrates an example drift trace after each stage of correction, and FIG. 12C(ii) shows a zoomed image of the corresponding green rectangle in FIG. 12C(i) at each stage. The scale bars in FIG. 12C(i) correspond to x: 500 nm, t: 500 s, and the scale bars in FIG. 12C(ii) correspond to x: 10 nm, t: 10 s. FIG. 18 illustrates an alternate representation of stages in a drift correction process in accordance with some embodiments.

In some embodiments, an image resolution output from the first stage may be on the order of 1 μm.

In some embodiments, an image resolution output from the second stage may be on the order of 200 nm.

In some embodiments, an image resolution output from the third stage may be on the order of 20 nm.

In some embodiments, an image resolution output from the fourth stage may be on the order of 5 nm.

In some embodiments, an image resolution output from the fourth stage may be on the order of less than 5 nm.

Imaging Quality and Limit of Achievable Resolution

The finest possible quality of a drift-corrected image is limited by the quality of individual localizations, which is determined by the various conditions used during an imaging session (e.g., a microscopy imaging session). To quantitatively assess and effectively compare between the quality of different imaging conditions, a quantity called Distance between Neighboring Frame Localizations (DNFL) is defined as the mean separation between localizations detected from consecutive image frames, which originated from the same transient event (e.g., a binding event).

The procedure for calculating the DNFL for an image is outlined as follows. For each pair of NF (Neighboring Frames, e.g. frame #1 and #2), all localizations from both frames are pooled and the distance between every pair of localizations from different frames (e.g. one localization from frame #1 versus another from frame #2) is calculated, assuming no drift between the frames. The resulting distances from all NF pairs are pooled to provide a bimodal distribution. The first mode of the bimodal distribution is broad, high in amplitude, and spans the width of the field of view. The second mode of the bimodal distribution is sharp, low in amplitude, and close to zero, and corresponds to localizations from the same binding event. The maximum of the second mode may be determined and a local Gaussian fitting algorithm may be performed around the maximum to determine the center of the peak. This value may be considered the DNFL of a certain image. Without combining localizations from consecutive frames, the DNFL value sets the limit of the finest possible resolution that can be achieved from a certain image, with a mathematical relation between the best achievable resolution and DNFL being: best achievable resolution=DNFL/sqrt(2)*2.35.

Drift Correction Quality and Supported Resolution

The quality of a final drift-corrected image may assessed by characterizing the Point Spread Function (PSF) of a single binding site. A statistical overlay of images of more than thousands of single docking sites may be produced as the reference for the PSF distribution. A 2-D Gaussian fitting may be performed on the statistical overlay to determine the standard deviation (sigma) of the PSF, which in turn determines the best supported resolution of the produced image, given by a similar formula as above: image supported resolution=sigma*2.35. The isolation and overlay of single isolated docking sites may be performed with the help of an auxiliary DNA nanostructure. This structure has a known pattern of well-separated docking sites (e.g., a lattice grid pattern), and may be the same structure used for the template-based drift correction stage, discussed in more detail below. Because of variation of laser intensity, unevenness of optical surface deposition and other systematic factors, as well as the possible stochastic nature of the imaging process, the above determined image quality of the whole image may not reflect the true imaging quality for each single sample object in the imaging field. Typically, structures closer to the center of the imaging field and better fixed to the optical surface, are better illuminated, and show better resolution than those that are on the periphery and are less well fixed. The image quality and resolution of a single molecule may be determined in a procedure similar to the one above. A projection of a single molecule of an auxiliary DNA nanostructure (same as above) may be taken along a direction that best separates the docking sites (in the case of lattice grid structures, this will be along any of the lattice directions), and a multi-Gaussian fit may be performed on the projected 1-D distribution. The standard deviation of the fitted Gaussian peaks may then be determined and similarly used to infer the resolution of a single-molecule image.

Drift Assessment and Choice of Drift Correction Stages

In some embodiments, the five stages incorporating techniques for performing drift correction, discussed in further detail below, operate in series to reduce the drift of an unprocessed image, where each consecutive stage reduces the drift further, and low enough for the successful operation of the next stage. Depending on the amount of drift in the captured images, less than all five stages may be used. For example, if it is determined that there is low drift in the original image, the localizations in each frame may be separable, and processing may begin from the second stage without requiring processing by first stage. If it is determined that there is even lower drift in the original image, processing may be begin from the third stage without significant loss of final image quality. Due to the complex origin of drift, which may involve, among other things, thermal fluctuation and expansion, microscope stage movement due to electric motor activation, vibration from the building and optical table complex, controlling drift in the original image tends to be difficult, and including the first two stages is often useful in producing a final image with desired resolution. For example, including all five stages described herein provides a robust strategy for drift correction that is applicable to images taken in most biology labs, without the requirement of specialized hardware or building requirements.

In some embodiments, the amount of drift and overall image quality of the original unprocessed image may be determined using any suitable technique, and the determined image quality may be used to select a choice of drift correction stages to use in performing drift correction. For example, a technique for determining image quality may compare different temporal segments of the same image. In this illustrative technique, the original image may be divided into two halves by separately pooling localizations from the first half and the second half of the movie, respectively. The cross-correlation between the two images may be calculated and a best offset may be estimated to provide an indication of the overall drift. The indication of overall drift may be compared to one or more threshold values to determine whether one or more of the drift correction stages may be skipped in performing drift correction in accordance with the techniques described herein.

Figure 13:
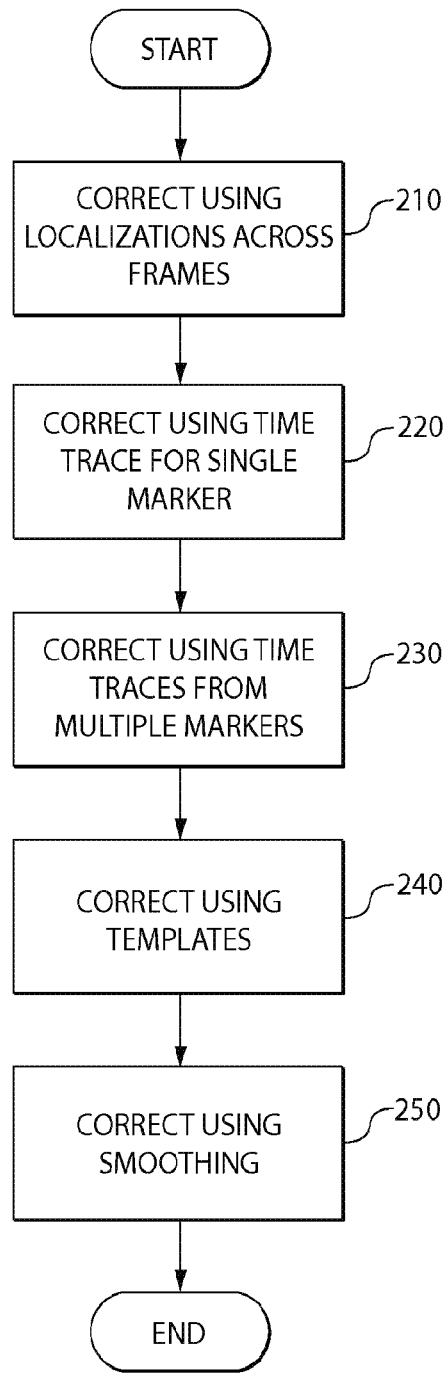
FIG. 13 illustrates a process for performing drift correction in accordance with some embodiments.

FIG. 13 illustrates a process for performing drift correction in accordance with some embodiments. In act 210, drift correction is performed by considering differences in localizations across neighboring frames of a movie. The process then proceeds to act 220, where a single drift marker is selected, a time trace describing the movement of the drift marker over time during the movie is determined, and the time trace for the single drift marker is used to perform drift correction of the image. The process then proceeds to act 230, where time traces are determined for each of a plurality of drift markers identified in the image. As discussed in more detail below, differences between the time traces may be used to provide a further drift correction in the final image. The process then proceeds to act 240, where drift correction using geometrically-constrained templates is performed. The process then proceeds to act 250, where the image is further drift corrected by smoothing the drift trace using suitable smoothing techniques, as discussed in more detail below. Each of the five stages for performing drift correction in accordance with the techniques described herein are described in further detail below. As should be appreciated from the foregoing discussion, not all embodiments require the use of all five stages for drift correction processing. For example, in some embodiments, only acts 230 and 240 may be performed. In other embodiments, acts 230, 240, and 250 may be performed. In yet other embodiments, acts 220, 230, 240 and 250 may be performed without including act 210.

First Stage Drift Correction

A first stage of drift correction (e.g., act 210 of FIG. 13) operates by comparing localizations from neighboring frames in a movie. A procedure similar to the DNFL calculation described above (or any other suitable technique) may be used to identify pairs of localizations originating from the same transient event (e.g., a single binding event). All pairs of localizations originating from the same transient event may be pooled to create a bimodal distribution. After creating a bimodal distribution of the localizations from neighboring images, a cutoff value may be automatically determined to separate those pairs of localizations from the same event (close localizations), from those that are different. Next, all pairs of close localizations for the same neighboring frame (NF) pair are pooled, and the offset between each pair is computed. The vector average of all offsets are output as the drift correction. For NF pairs with no qualifying close localizations being identified, a zero drift may be output. The first stage of drift correction typically corrects for global drift with high amplitude (farther than 1 µm in offset), which effectively removes interference between different drift markers and allows for incorporation of the next stage. As discussed above, in some embodiments where different drift markers may already be separable from each other, the first stage of processing may be omitted. A determination of whether the first stage of processing may be omitted may be made using an image quality factor analysis, as discussed above, or using any other suitable technique (e.g., manual inspection).

Second Stage Drift Correction

A second stage of drift correction (e.g., act 220 of FIG. 13) operates on a single drift marker or sample object. The single drift marker for use in this stage of drift correction processing may be selected in any suitable way. For example, in some embodiments, the single drift marker may be randomly selected from the set of all identified drift markers. In other embodiments, a particular drift marker associated with desirable qualities (e.g., an average amount of drift over the entire movie) may be selected as the single drift marker to use for this stage. After selecting the single drift marker, its time trace is automatically determined, smoothed, and output as the drift correction. Alternatively, a drift trace may be manually drawn in cases where separation between drift markers is hard to identify automatically.

The second stage of drift correction further reduces global drift in the movie (typically <200 nm), and allows automatic batch identification of drift markers in the following stages.

Third Stage of Drift Correction

A third stage of drift correction (e.g., stage 230 of FIG. 2) combines the time traces of a plurality of drift markers to compute drift correction with a finer resolution than the second stage of drift correction. Each drift marker has a large number of docking sites to allow a high temporal coverage; and a large number of these drift markers are deposited onto the imaging surface together with the samples. The number of binding sites on each drift marker and the concentration of drift markers on the surface may be selected appropriately to ensure a high quality drift correction, as the improvement in drift correction in performing this stage is primarily determined by the spread of each drift marker in the image and the effective number of drift markers per frame.

Figure 14:
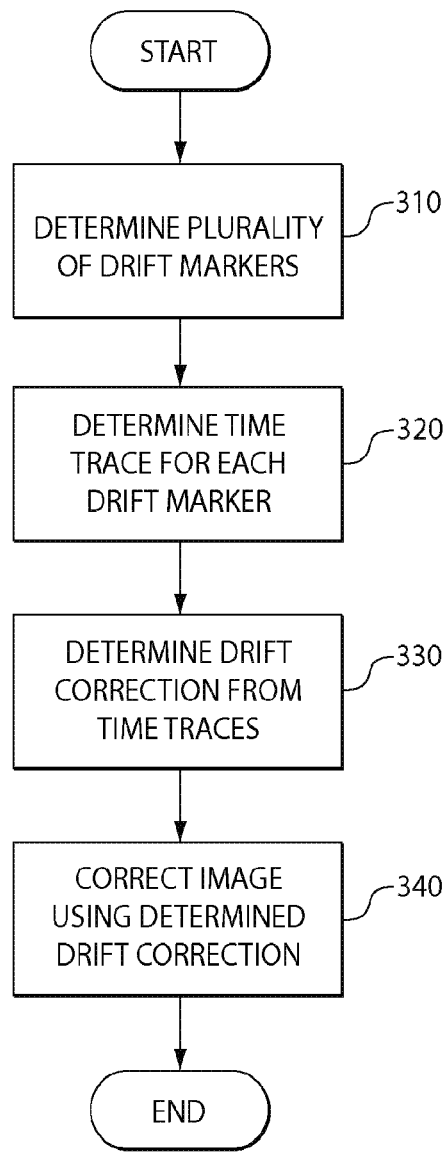
FIG. 14 illustrates a process for performing drift correction corresponding to stage 230 of FIG. 13.

FIG. 14 illustrates a process for performing drift correction corresponding to stage 230 of FIG. 2. In act 310, locations of a plurality of drift markers are identified. Identifying locations of the plurality of drift markers may include pooling localizations from all frames of the movie to calculate a two-dimensional (2D) histogram. Then, the locations of drift markers may be identified by appropriately tuning the histogram binning size and a combination of other selection criteria. For example, the binning size of the histogram may be tuned to reflect the feature size of the drift marker, e.g., a fourth or third of their overall size. The range of selection criteria includes, but it is not limited to, a lower-bound threshold of the histogram value and filtering based on geometrical properties (e.g., area, dimensions). Adequate separation between nearby drift markers is often necessary to exclude false localizations, which, for example, arise from spurious localizations of double-binding events. After the identification of a pool (e.g., thousands) of drift markers, the process to act 320, where the time trace for each drift marker is determined and the relative time trace determined as the offset of each time trace from the center of the combined trace is computed. Because the images capture transient events (e.g., nucleic acid-binding events), not all time traces for a drift marker may cover all time points in the movie. In such cases, the time traces may be linearly interpolated at the "missing points" to achieve a finer and smoother result.

After determining the time trace for each of the plurality of drift markers, the process proceeds to act 330, where the drift correction for the image is determined based on the time traces determined for each drift marker. Any suitable combination of the time traces may be used to determine the drift correction, and embodiments are not limited in this respect. In some embodiments, a weighted average of the time traces is used to determine the drift correction output from this stage. For example, a weighted average of the pool of relative time traces may be computed as the result of drift correction, where the correction is weighted by the quality of drift marker traces. The quality of drift marker traces may be determined in any suitable way including, but not limited to, determining the quality by assessing drift marker quality or individual localization quality. In some embodiments, the quality of each drift marker trace is computed by taking the standard deviation (sigma) of the trace over time. The inverse of this measure (e.g., 1/sigma) for each trace may be used as the weight factor. Alternatively, the quality of each individual localization within the time traces may be computed as the localization uncertainty given by the formula in Thomson, 2002. The inverse of the standard deviation of this calculation may be used as the weight factor for each time trace. After determining the drift correction, the process proceeds to act 340 where the image is corrected using the determined drift correction.

This stage of drift correction may be performed any number of times. In some embodiments, this stage of drift correction is iteratively performed with different parameters used for each iteration. As drift correction proceeds, the remaining drift amplitude is decreased further and further, the spatial spread-out of drift markers becomes smaller and smaller, and selection of drift markers may be performed more and more stringently. Consequently, in initial iterations, the threshold histogram count may be set to a lower value, and this value may be adjusted during later iterations to higher values. Additionally, in some embodiments, the valid area and dimensions of drift markers may be set to larger values in initial iterations, and later adjusted to smaller values during subsequent iterations. Yet further, in some embodiments, separation between drift markers may be shifted from larger values to smaller values in later iterations. In some embodiments, an interactive quality check (either manually or automatically performed) may be determined between iterations to facilitate a determination of further operations.

Depending on the imaging quality, this stage of drift correction typically brings the obtained image resolution to within a factor of two from the best allowed resolution (i.e. if the precision of each individual localization supports resolution of ~5 nm, then this stage usually yields ~10 nm resolution). Typically, with good imaging conditions, a resolution <10 nm may be obtained following processing with this stage.

Fourth Stage of Drift Correction

A fourth stage of drift correction (e.g., act 240 in FIG. 13) uses drift marker "templates," and thus this stage is termed "templated drift correction." One or more drift marker templates (e.g., DNA nanostructures with docking sites in a known and well-separated geometric arrangement) are deposited onto the imaging surface together with "ordinary" drift markers, discussed above in connection with stage three. The separation between these docking sites is preferably chosen not to be not smaller than twice the resulting resolution from the previous stage (e.g., stage three), allowing easy separation between localizations from different docking sites. The number of docking sites on these templates as well as the concentration of the docking sites on the surface, is preferably chosen to achieve effective template correction, similar that described for the third stage.

Figure 15:
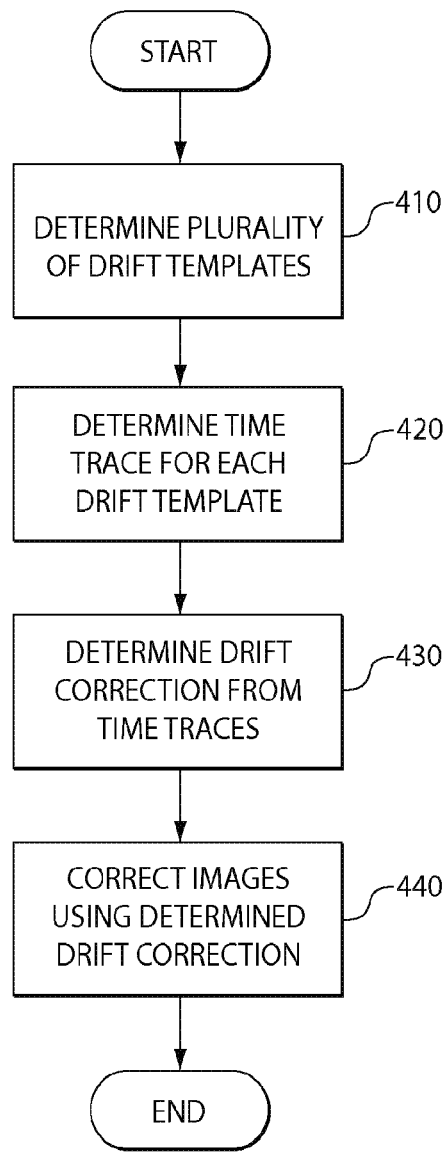
FIG. 15 illustrates a process for performing drift correction corresponding to stage 240 of FIG. 13.

FIG. 15 illustrates a process for performing drift correction corresponding to stage 240 of FIG. 2. In act 410, a plurality of drift correction templates are identified from a 2-D histogram of localizations pooled across all frames of the movie. To distinguish the drift templates from the drift markers used in the third stage, an extra upper-bound threshold in histogram count may be incorporated in addition to the range of selection criteria as mentioned above. After the drift templates have been identified, the process proceeds to act 420, where the time trace of each drift template is determined. Because the docking sites are designed to be well separated in the templates, several non-overlapping time traces from individual docking sites may be isolated from each time trace of a full drift template. This identification and separation step may be carried out in a similar manner as the identification of drift markers from the entire image. For example, a combination of local histogram thresholding and filtering on standard deviation of the individual time traces for each drift template may be used.

After the time trace for each drift template has been determined, the process proceeds to act 430, where the combination of time traces is used to determine a drift correction for this stage. In some embodiments, this is accomplished by computing relative time traces for each time trace, and the relative time traces are used, at least in part, to determine the drift correction. The relative time traces may be used in any suitable way to determine the drift correction. For example, in some embodiments, a weighted average of all the time traces of individual docking sites may be averaged to produce the final drift correction. The weight factors may be determined in any suitable way. For example, the weight factors may be based on the quality of each individual site, or the quality of each individual localization in the time trace. After determining the drift correction, the process proceeds to act 440 where the image is corrected using the determined drift correction.

Depending on the imaging quality, this stage of drift correction may result in a resolution of the final image being close to the best possible resolution. That is, if the precision of each individual localization supports a resolution of ~5 nm, performing template drift correction in accordance with the techniques described herein may achieve a resolution close to ~6 nm. In some embodiments, for the <10 nm resolution achieved after the third stage, a DNA nanostructure with 12 docking sites arranged in a 4×3 grid of lattice spacing 20 nm may be used as the drift correction template. Template-based drift correction using the techniques described in this section may enable the achievement of 6-7 nm resolution after this stage.

Fifth Stage Drift Correction

A fifth stage of drift correction (e.g., act 250 in FIG. 13) performs smoothing of the drift correction trace, and the smoothed drift correction trace may be used to perform drift correction. For example, after determining a drift correction for one or more of the second, third and fourth stages discussed above, the resultant drift correction may be smoothed using any suitable technique to produce the final drift correction result. Smoothing effectively increases the number of drift markers or drift templates in each frame, by taking the localizations in neighboring frames into account. Smoothing may be performed in any suitable manner using any suitable window period. For example, in some embodiments, smoothing is performed with a robust local regression method that operates over a window period determined by the characteristic drift time scale. A non-limiting example of a smoothing window period may be 10-30 s.

Extension to 3D Imaging

All stages described above can be directly applied to correct a 3D image (e.g., super-resolution image) as well. In 3D super-resolution imaging, for example, an astigmatism lens may be introduced in the imaging path and the ellipticity of the resulting Gaussian emission profile may be used to determine a z-position of a molecule. The above-described origami drift marker structures (e.g., geometric-constrained templates) may be used in a one-to-one fashion to perform the stages of drift correction. For the template-based drift correction stage, a DNA origami structure with a defined 3D shape (e.g., a tetrahedron) may be used.

Figure 16A:
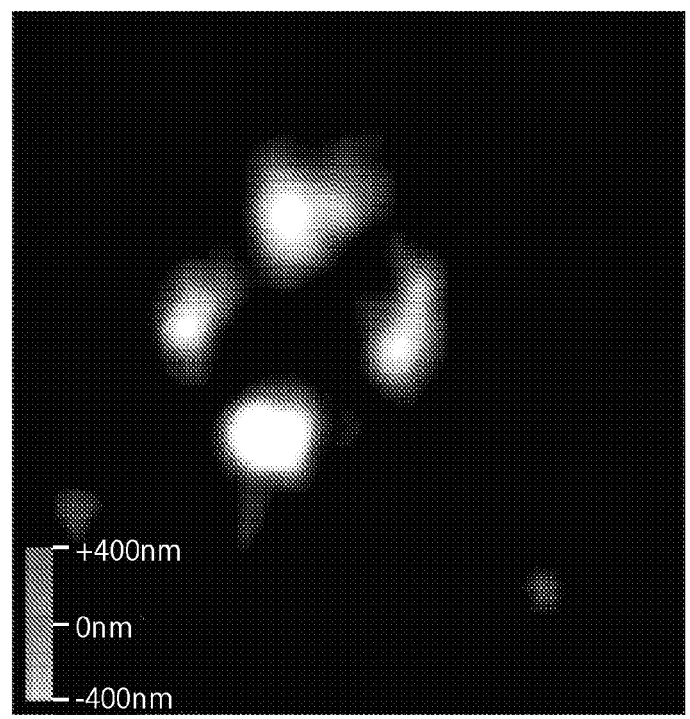
FIGS. 16A-16B illustrate 3D tetrahedrons used as templates for 3D drift correction. The four corners are labeled with docking sites.
Figure 16B:
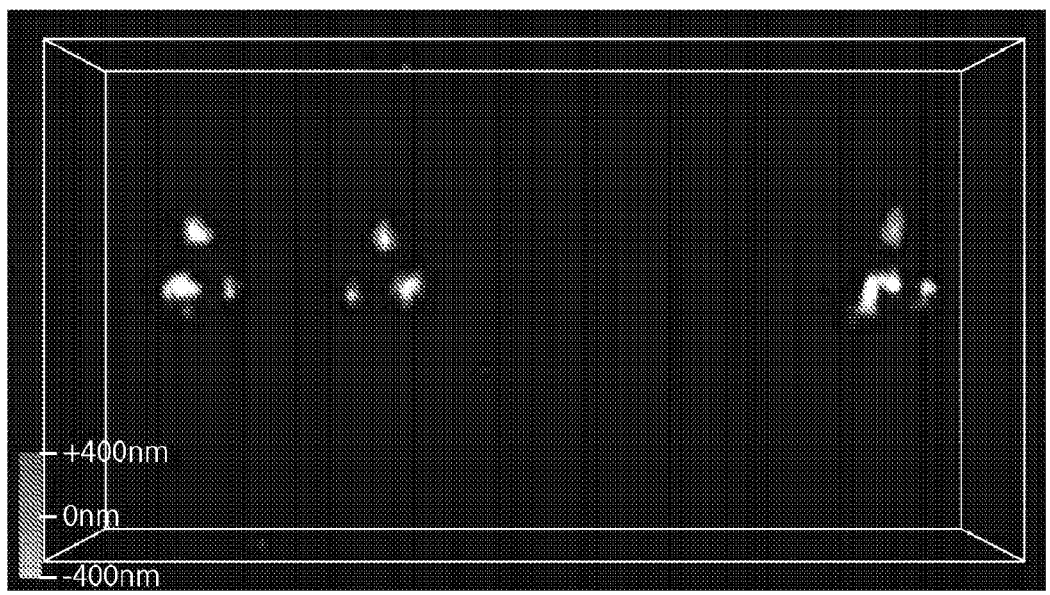

FIGS. 16A-16B illustrate 3D tetrahedrons used as templates for 3D drift correction. The four corners are labeled with docking sites. FIG. 16A shows that the four corners are clearly resolved. FIG. 16B illustrates the X-Z projection of the structures with a height of ~85 nm.

Extension to Multicolor Imaging

The above-described techniques for correcting drift in a plurality of time sequence images is described with respect to imaging a transient event identified using a single color in the images. However, it should be appreciated that these techniques may be extended to multicolor imaging in which different transient events (e.g., binding of different nucleic acid drift markers with docking sites) are labeled with different colors that can be identified in the same image. When multicolor imaging is used, the geometric templates discussed above for template-based drift correction may include information describing a particular known geometry for the different transient events that correspond to the different colors. For example, rather than just a single binding event occurring at a single docking site in a 3×4 grid, multiple binding events color-coded using different colors in the same geometric template may be represented, and the drift correction may be performed using information from the multiple binding events. Other processes for extending the techniques described herein to multicolor imaging are also contemplated, and embodiments are not limited in this respect.

Exemplary Computer System

Figure 17:
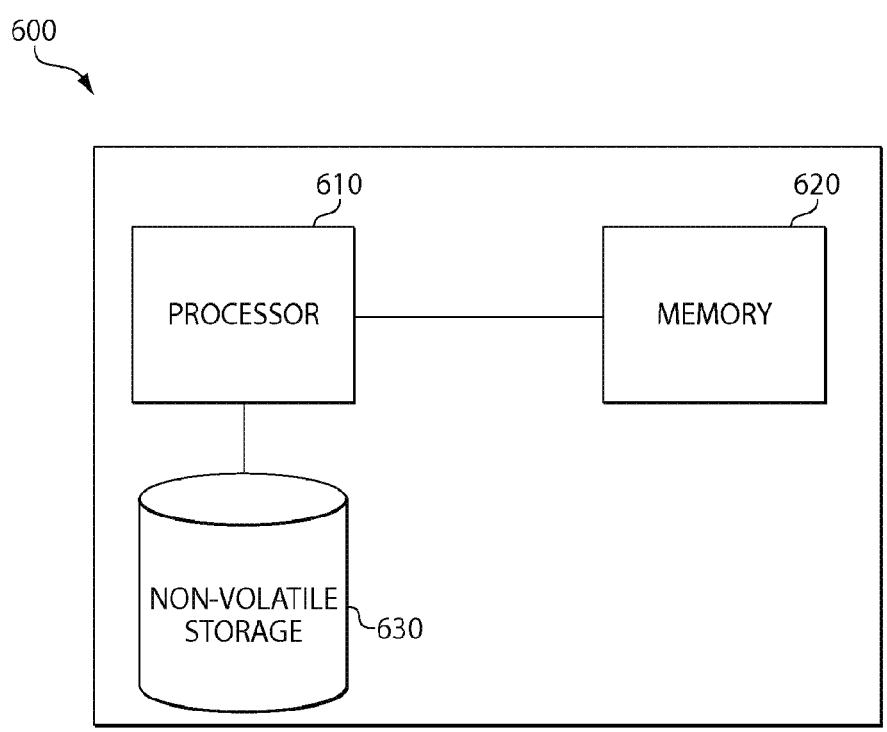
FIG. 17 shows an illustrative implementation of computer system 600 that may be used in connection with any of the embodiments of the present disclosure described herein.

An illustrative implementation of a computer system 600 that may be used in connection with any of the embodiments of the present disclosure described herein is shown in FIG. 17. The computer system 600 may include one or more processors 610 and one or more computer-readable non-transitory storage media (e.g., memory 620 and one or more non-volatile storage media 630). The processor 610 may control writing data to and reading data from the memory 620 and the non-volatile storage device 630 in any suitable manner, as the aspects of the present disclosure described herein are not limited in this respect. To perform any of the functionality described herein, the processor 610 may execute one or more instructions stored in one or more computer-readable storage media (e.g., the memory 620), which may serve as non-transitory computer-readable storage media storing instructions for execution by the processor 610.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the present disclosure comprises at least one non-transitory computer-readable storage medium (e.g., a computer memory, a floppy disk, a compact disk, a tape, etc.) encoded with a computer program (i.e., a plurality of instructions), which, when executed on a processor, performs the above-discussed functions of the embodiments of the present disclosure. The computer-readable storage medium can be transportable such that the program stored thereon can be loaded onto any computer resource to implement the aspects of the present disclosure discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present disclosure.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

Example 1: Cellular Imaging

Multiplexed super-resolution imaging of intra-cellular components in fixed cells was achieved by linking docking strands to antibodies (FIG. 2). These antibody-DNA conjugates were formed by first reacting biotinylated docking strands with streptavidin, and then incubating with a biotinylated antibody against the protein of interest. Fixed HeLa cells were then immunostained using a preassembled antibody-DNA conjugate against beta-tubulin. Prior to imaging, ATT0655-labeled imager strands were introduced to the sample in hybridization buffer (1×PBS supplemented with 500 mM NaCl), and single-molecule imaging was carried out using oblique illumination (9). The resulting super-resolution images show a clear increase in spatial resolution in contrast to the diffraction-limited representation (FIGS. 3a-3c). A cross-sectional profile taken at position <i> in FIG. 3B yields a distance of ≈79 nm between two adjacent microtubules with an apparent width of ≈47 and ≈44 nm for each of the microtubules, which is in agreement with earlier reports for immunostained microtubules (13). The antibody-DNA conjugation approach of the present disclosure yields a high labeling density, and little to no non-specific binding of imager strands to non-labeled cellular components occurs.

To demonstrate the multicolor extension of the labeling scheme of the present disclosure, where orthogonal imager strand sequences are coupled to spectrally distinct dyes, the microtubule network in a fixed HeLa cell was labeled with a preassembled antibody-DNA conjugate carrying a docking sequence for Cy3b-labeled strands, and mitochondria were stained using a second antibody linked to an orthogonal sequence for ATT0655 imager sequences. While both Cy3b- and ATT0655-labeled imager strands were present in solution at the same time, imaging was carried out sequentially in the Cy3b and ATT0655 channels and the resulting super-resolution images showed a clear increase in spatial resolution as compared to the diffraction-limited representation (FIGS. 3d-3f). As in the single-color case, little-to-no non-specific binding of the imager strands to non-labeled components in the cellular environment was observed. In addition, similar to the in vitro case, no crosstalk between the two colors was observed, indicating a sequence-specific interaction of the imager strands.

Example 2: Multiplexing

Assuming fixed localization accuracy, one can trivially obtain a direct two-fold increase in imaging resolution. This can be realized by spacing imaging spots with the same docking strand sequence (e.g., docking sites a in FIG. 4) farther apart than the actual current resolution limit, thus clearly identifying these sites as single spots in the super-resolved image. As all obtained localizations can now be assigned to a specific site, the obtainable imaging resolution is no longer the full width at half maximum (FWHM) of the reconstructed spots, but rather the standard deviation (≈2.35-times smaller than the FWHM). This is depicted in FIG. 4B1, wherein a set of seven points with 10 nm spacing was imaged with ≈14 nm resolution, leaving individual points unresolvable. Cross-sectional histogram data showed a broad peak (bottom). In FIGS. 4B2 and 4B3, imaging every other site at a time permitted the localization of individual spots. These localizations were then combined to form the final composite image with increased resolution.

FIG. 5A shows a single DNA nanostructure, displaying four distinct sets of DNA sequences, designed to resemble the digits from 0 to 3, respectively. Imaging was performed sequentially using a simple flow chamber setup, first flushing in imager strands complementary to the docking strands of the number 0, and then exchanging the solution for imager strands with a sequence complementary to docking strands of the number 1 and so forth. The resulting images were pseudo-colored to represent the respective imaging rounds. The demonstration using DNA origami structures showed the high imaging efficiency as well as no crosstalk between consecutive imaging runs.

Figure 5B:
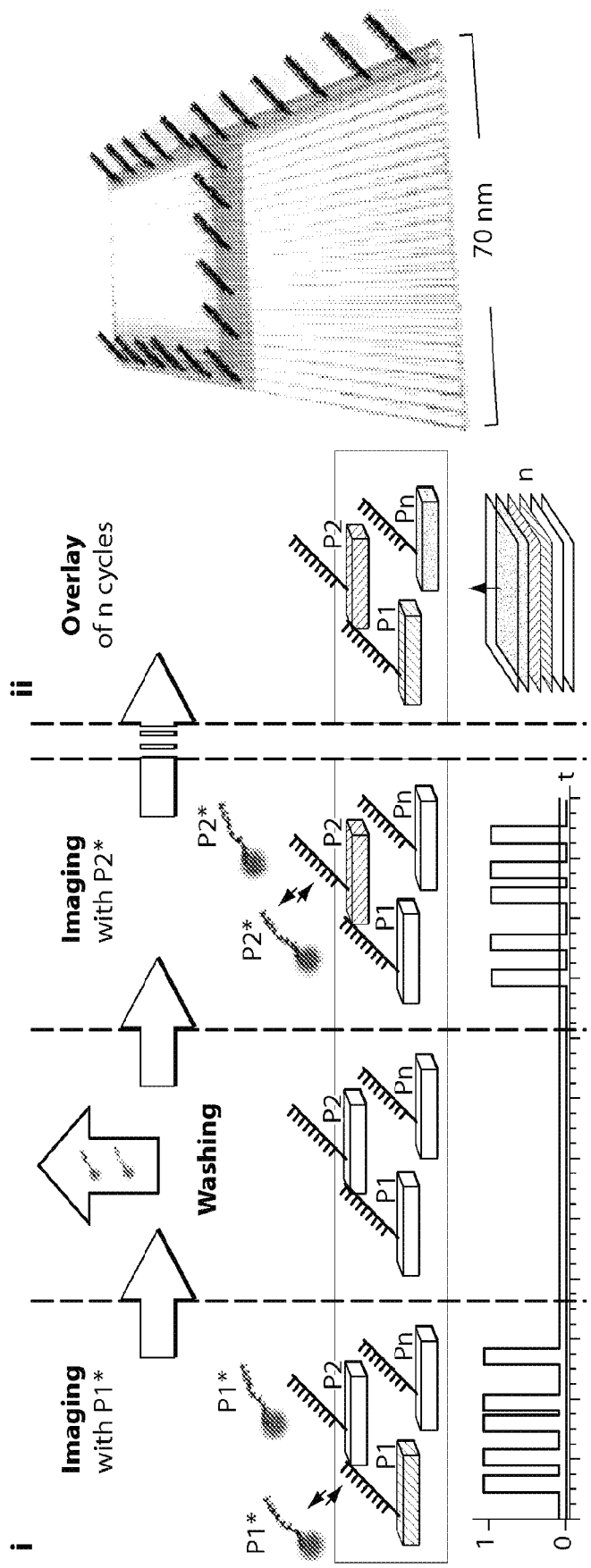
FIGS. 5B(i)-(v) show another embodiment of the present disclosure using DNA origami structures with different species of docking strands at designated positions resembling numbers 0-9 (0, 1, 2, 3, 4, 5, 6, 7, 8 and 9).
Figure 5B:
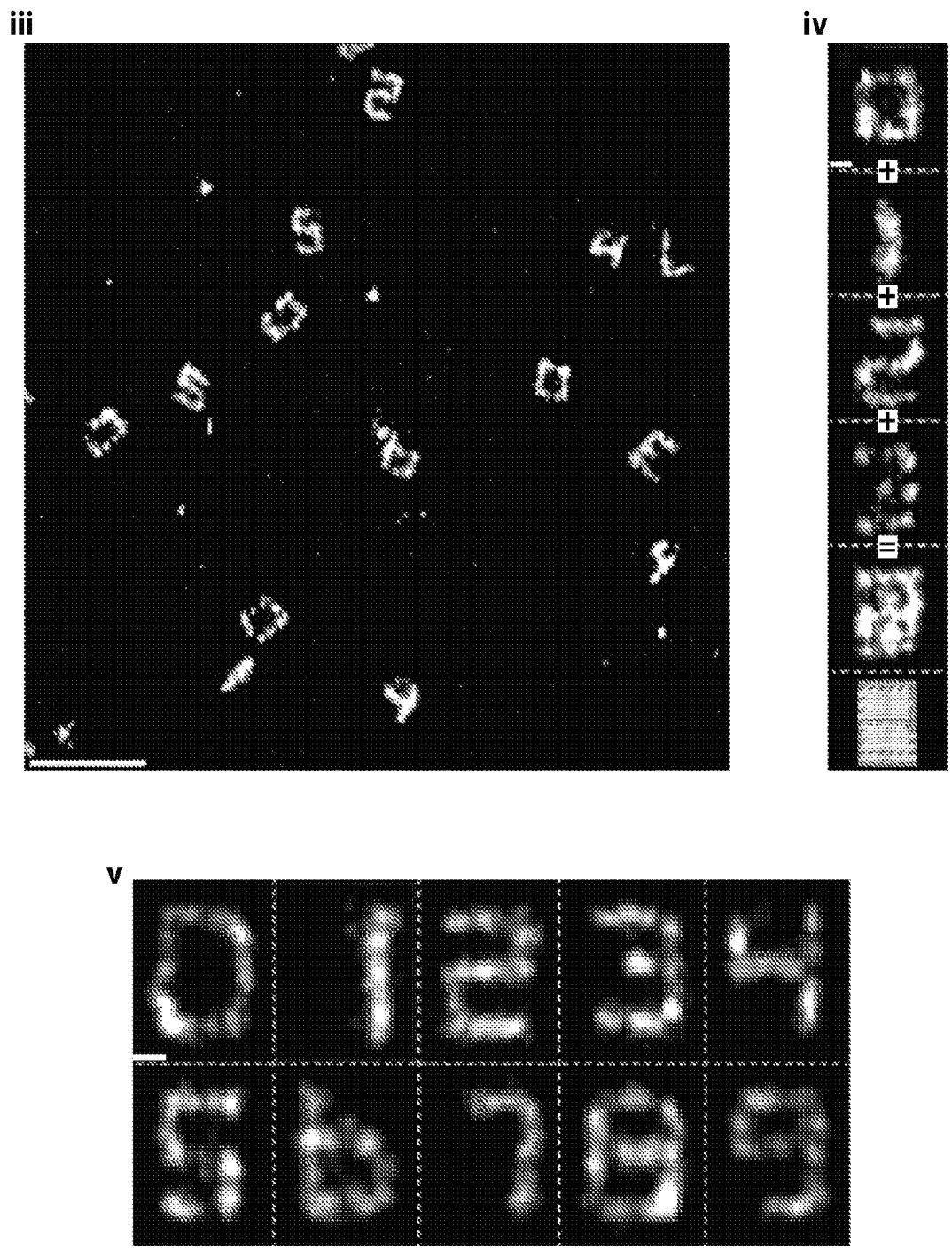

To demonstrate ten-"color" super-resolution imaging of DNA structures using Exchange-PAINT, ten unique rectangular DNA origami structures were designed, each displaying a distinct pattern of orthogonal docking strands that resembles a digit between 0 and 9 (see FIG. 5B(ii) for pattern "4"). After surface immobilization of all ten structures, sequential imaging was performed using a custom made fluidic chamber (FIG. 23A) for easy liquid handling. Ten orthogonal imager strands (P1* to P10*), all labeled with Cy3b, were used to perform Exchange-PAINT. The resulting digits from all ten imaging rounds are shown in FIG. 5B(v). Each target is resolved with high spatial resolution. Cross-sectional histograms along the bars of the digits show sub-10 nm FWHM of the distributions (data not shown). Note that high resolution is maintained for all digits, as the same optimized dye (Cy3b) and imaging conditions are used in each cycle.

FIG. 5B(iii) shows a combined image of all ten rounds, demonstrating specific interaction of imager strands with respective targets with no observable crosstalk between cycles. Digits 8 and 9 are not present in the selected area. An apparent "green" digit 5 instead of 2 was observed (<i> in FIG. 5B(iii)). This is likely not a falsely imaged digit 5 from crosstalk, but rather a "mirrored" digit 2. A mirrored image likely results from an origami immobilized upside-down, with docking strands trapped underneath, yet still accessible to imager strands.

The fluidic setup is designed to minimize sample movement by "decoupling" the fluid reservoir and syringe from the actual flow chamber via flexible tubing. To avoid sample distortion, special care was taken to ensure gentle fluid flow during washing steps. To verify that the sample indeed exhibited little movement and little-to-no distortion, a ten-round Exchange-PAINT experiment was performed. The DNA origami was imaged for digit 4 in the first round and reimaged after ten rounds of buffer exchange. The total sample movement (physical movement of the fluidic chamber with respect to the objective) was less than 2 µm, which could easily be corrected using fiducial markers. Normalized cross-correlation analysis for select structures produced a correlation coefficient 0.92, demonstrating almost no sample distortion (also see the discussion in the cellular imaging section).

Finally, using Exchange-PAINT, four different digit patterns were successfully imaged on the same DNA origami structure (FIG. 5B(iv)). Thus Exchange-PAINT is not limited to spatially separate species and can resolve sub-diffraction patterns on the same structure with no observable crosstalk or sample distortion. Aligning images from different Exchange-PAINT rounds is straightforward using DNA origami-based drift markers. Additionally, because imaging is performed using the same dye, no chromatic aberration needs to be corrected between imaging rounds.

The applicability of the methods of the present disclosure in a cellular environment was shown by targeting microtubules and mitochondria in fixed HeLa cells, similar to FIG. 3, but only using a single color fluorophore, or spectrally indistinct imager strands. Imaging was performed sequentially using imager strands labeled with the same dye (two rounds, FIG. 6).

Example 3: Quantitative Imaging

Figure 7C:
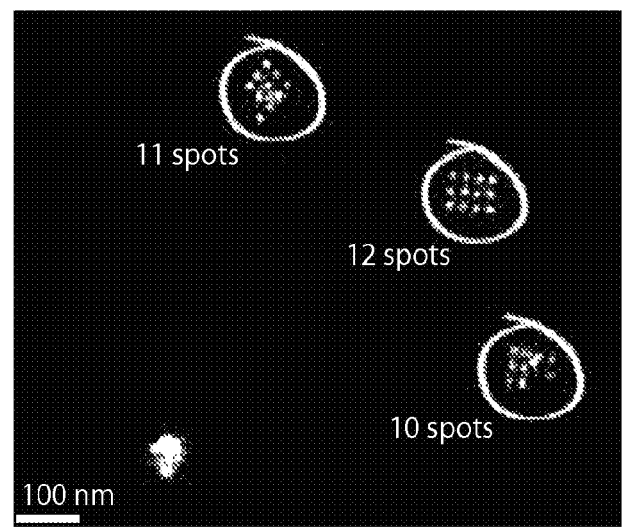
FIG. 7C shows a super-resolution image of DNA origami structures designed to display 13 binding sites as a proof-of-concept platform. The incorporation efficiency for docking sites is not 100% leading to a distribution of actually incorporated sites (FIG. 7D(1)). The structures serve as an ideal test system, as the number of displayed docking sites can be determined visually by counting the number of spots (direct counting) and comparing it with the corresponding number of sites calculated using the proposed binding kinetic analysis.

To demonstrate the feasibility of the quantitative methods of the present disclosure, a DNA origami nanostructure with 13 binding sites in a grid-like arrangement was used (FIG. 7C). The incorporation efficiency for docking sites was not 100%, leading to a distribution of actually incorporated sites (FIGS. 7C and 7D1). Nonetheless, the structures were an ideal test system because the number of available sites could be determined visually by counting the number of spots ("direct") and comparing it with the corresponding number of sites calculated using the proposed binding kinetic analysis ("kinetics"). FIG. 7D1 shows the binding site distribution for 377 origami structures obtained by direct counting. The binding site distribution for the same structures obtained by binding kinetic analysis is shown in FIG. 7D2. Finally, as a benchmark, the "offset" between direct and kinetic counting was calculated for each structure. The counting "error" or uncertainty for the method was less than 7% (determined by the coefficient of variation of the Gaussian distribution) with an imaging time of ~25 min.

Example 4: Kinetic Barcoding

Figure 8C:
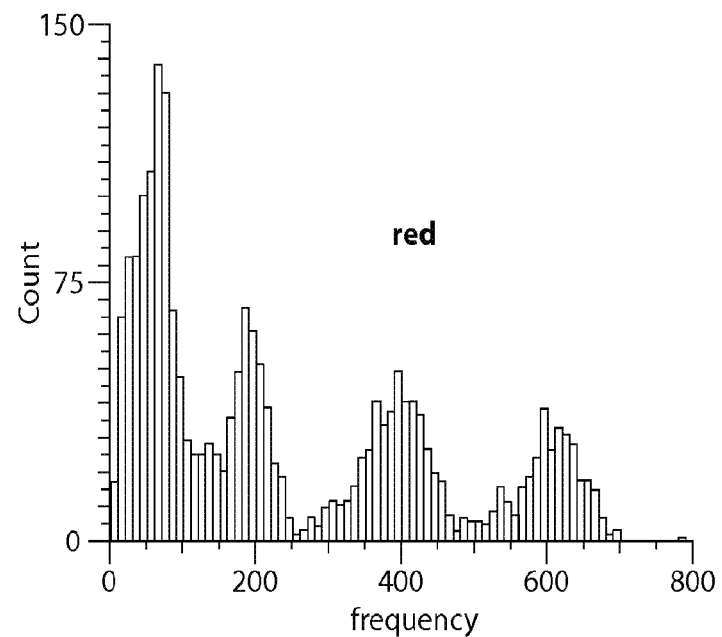
FIG. 8C shows an in vitro proof-of-principle experiment on DNA origami structures displaying 3, 9, 22 and 44 binding sites for each of the red, green, and blue imager strands, respectively (color rendering not shown). The different binding levels are clearly distinguishable for each color, suggesting 4 possible "frequency levels" per color, yielding up to 124 different possible combinations for barcoding, e.g., mRNA molecules inside cells. The barcoding space can be increased by using the fluorescence ON-time as an additional coding entity.
Figure 8C:
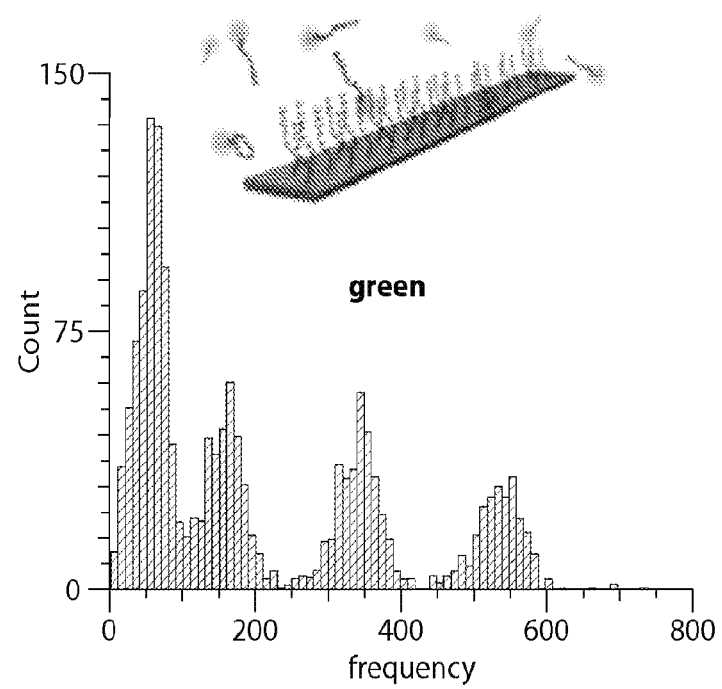
Figure 8C:
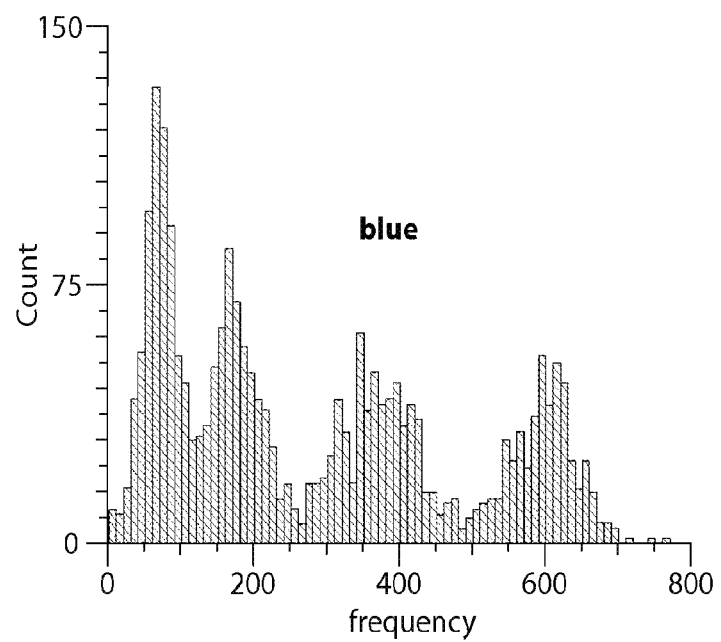

Highly multiplexed super-resolution barcoding was obtained by binding frequency analysis rather than geometrical or spectral encoding. Binding frequencies of BP-NA conjugates, or docking strands, to a molecule of interest is linearly dependent on the number of binding sites on this molecule. Given a certain concentration of fluorescently-labeled imager strands and association rate, binding frequency scales linearly with the number of binding sites, and can thus be used for identification. For example, 124 distinct dynamic "blinking signatures" were created using 3 colors and 4 levels of binding frequency per color (FIG. 8). Compared to geometrical encoding, this approach features much more compact, unstructured probes. Compared to spectral encoding (14) the method of the present disclosure is more cost effective, scalable, and easier to implement. Only 3 fluorescently-labeled imager strands are required in this frequency encoding method, making it very cost-efficient for high-throughput screening experiments. In vitro tests on a DNA origami test structure are shown in FIG. 8C.

Figure 9:
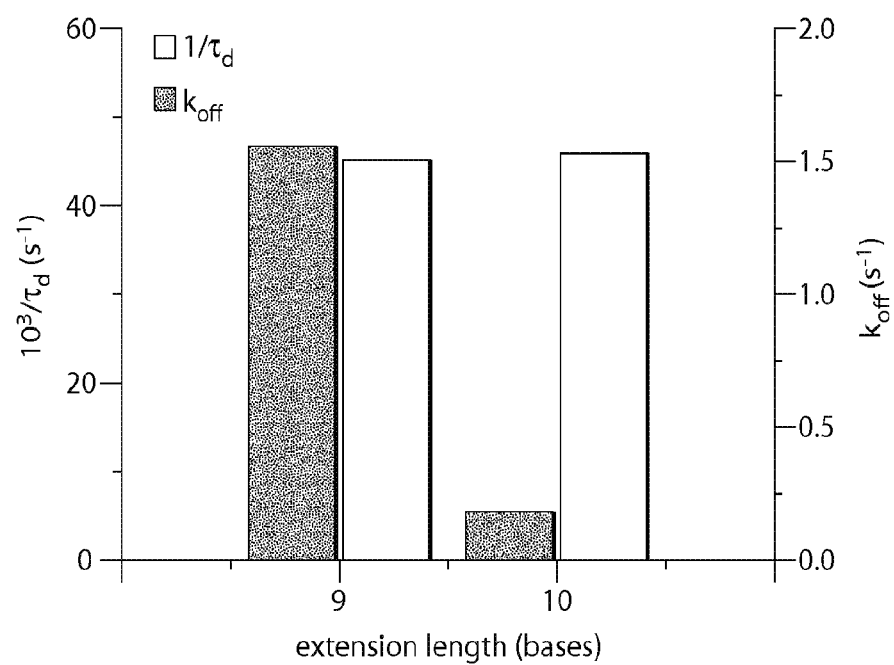
FIG. 9 shows a graph demonstrating that the fluorescence ON-time (related to the dissociation rate $k_{off}$) can be tuned independently of the fluorescence OFF-time (related to the association rate $k_{on}$). Extending the imaging/docking duplex from 9 to 10 nucleotides (nt) by adding a single CG base pair, the kinetic OFF-rate is reduced by almost one order of magnitude (8).

In addition to using the inter-event lifetime rd or binding frequency to determine the number of available binding sites and to barcode molecules, the fluorescence ON-time or $\tau_b$ and thus the dissociation constant $k_{off}$ can also be used to encode information. $k_{off}$ can be precisely tuned by the base-composition and/or length of the duplex of docking and imager strand. The feasibility of this approach is illustrated in FIG. 9: $1/\tau_d$ and $1/\tau_b$ are plotted vs. the length of the docking/imaging duplex. $1/\tau_d$, and thus $k_{on}$, is independent of the duplex stability. However, extending the imaging/docking duplex from 9 to 10 nt by adding a single CG base pair reduces the kinetic OFF-rate by almost one order of magnitude.

Figure 10A:
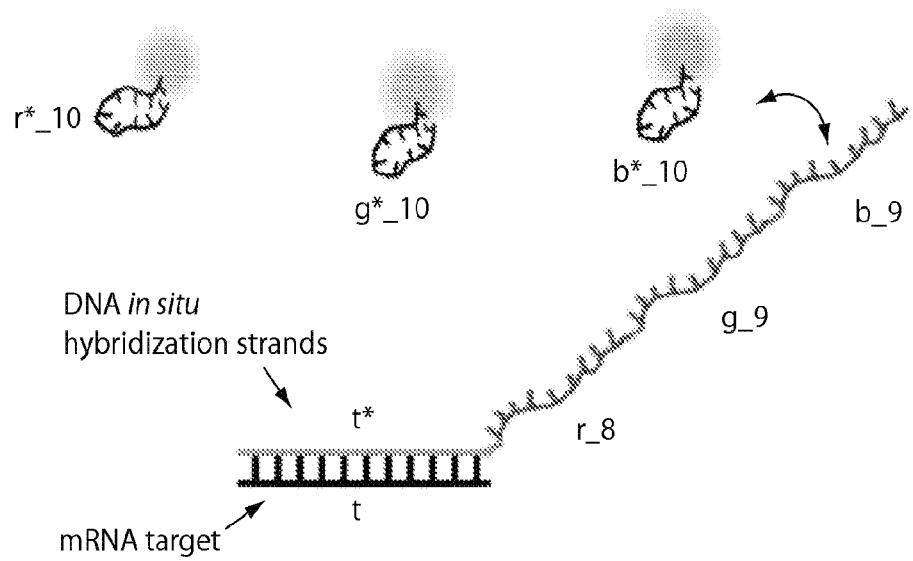
FIG. 10A shows a barcode probe that is roughly 50 nucleotide (nt) in length and can tag a biomolecule using a 21 nt target detection domain t* followed by an approximately 30 nt long "barcode" region with a combination of 8, 9, or 10 nt long binding domain for red, green, or blue imager strands. Here, 8, 9 or 10 nt long docking strands are displayed for three colors with a $k_{off}$ of 10, 1 and 0.1 per second, respectively (color rendering not shown).
Figure 10B:
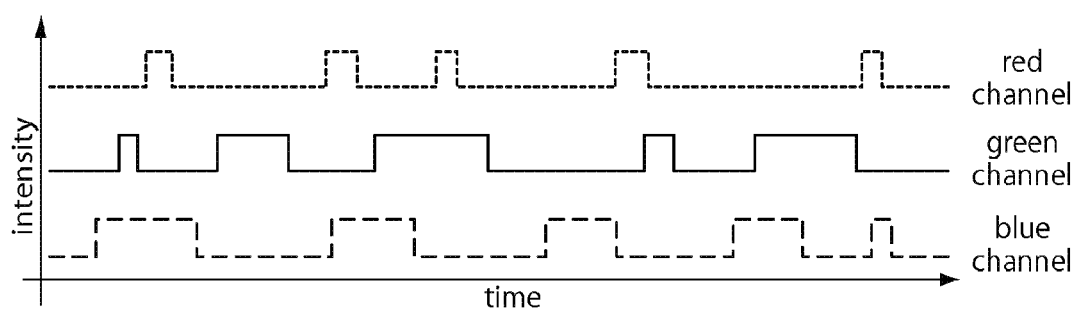
FIG. 10B shows characteristic intensity vs. time traces with increased fluorescence ON-times r for the 9 nt interaction domain compared to the 8 nt interaction domain.
Figure 10C:
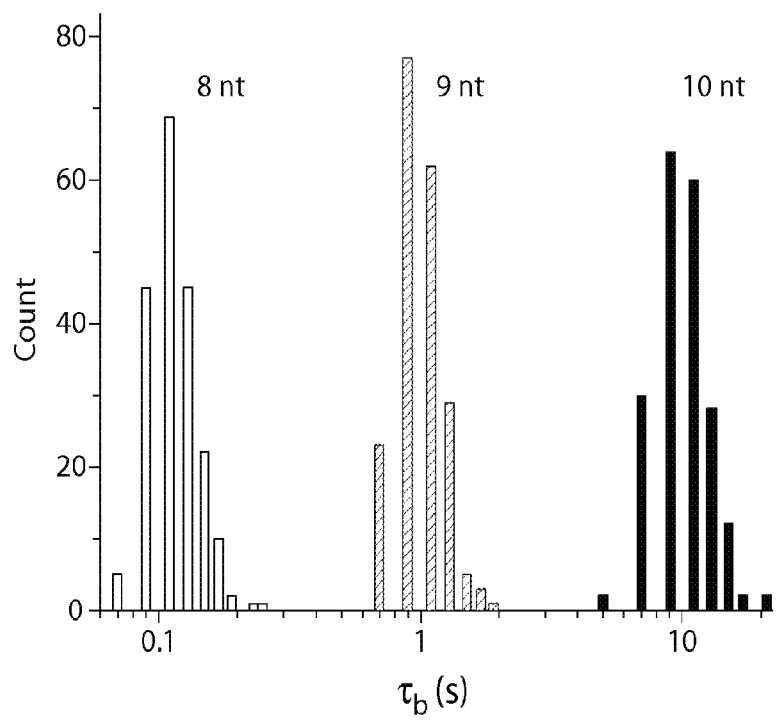
FIG. 10C shows stochastic simulations demonstrating that $k_{off}$ values of 10, 1 and 0.1 per second can be distinguished.

Finally, a "microbarcode," a minimal barcode that uses our ability to detect differences in thermodynamic stability of the imager/docking duplex was produced to identify a large number of molecules using a short, economical and unstructured probe. The barcode contains only of a single DNA molecule, roughly 50 nt in length, which is used to tag a molecule of interest using a 21 nt target detection domain t* (FIG. 10A) followed by a ~30 nt long "barcode" region with a combination of 8, 9, or 10 nt long binding domain for red, green, or blue imager strands. Despite being only 30 nt in length, it can be used to present $3^3=27$ different barcodes with only three spectrally distinct colors and three thermodynamically distinct sequence lengths. FIG. 10 illustrates a 8, 9, or 10 nt long docking strands for three colors with a $k_{off}$ of 10, 1 and 0.1 per second, respectively. FIG. 10A shows an example barcode consisting of an 8 nt long binding domain for a red imager strand, two 9 nt long binding domains for the green, and blue imager strand, respectively. This produces characteristic intensity vs. time traces with increased fluorescence ON-times $\tau_b$ for the 9 nt interaction domain compared to the 8 nt interaction domain (FIG. 10B). Stochastic simulations show that it is clearly possible to distinguish between $k_{off}$ values of 10, 1 and 0.1 per second, respectively (FIG. 10C).

Example 5: Genetically Encoded Live-Cell Super-Resolution Imaging

A significant advantage of fluorescence imaging lies in its potential to visualize biomolecular processes in living cells. There are however challenges in demonstrating live cell super-resolution imaging (ref. 22-22). One such challenge is in the delivery of a sufficient concentration of synthetic imaging probes to living cells in a biocompatible manner while also allowing for proper imaging conditions. Another challenge is the extent of background fluorescence for unbound probes in the context of a live cell environment where macromolecular crowding may be more of a significant factor compared to fixed cell environments, and "live" helicases may influence binding kinetics.

This disclosure addresses these and other challenges by utilizing a genetically encoded RNA probe that can specifically bind to a target molecule in a living cell, and only then start to fluoresce and blink to enable super-resolution imaging of the specific target.

This conditional "blinking" probe is a small single-stranded RNA (<100 nt) with a target binding domain (TBD) and a conditional blinking domain (CBD). The CBD is under mechanical control of the TBD and is dark when the TBD is not bound to a target T. The binding of TBD with target "T" results in a reconfiguration of the CBD and enables it to blink with an intensity and frequency suitable for the super-resolution imaging of T.

The blinking RNA probe is based on the Spinach aptamer system (ref. 19), a fluorescent RNA mimic of GFP (FIG. 19). Spinach can turn on the fluorescence of an initially dark small molecule DFHBI (similar to DMHBI), which is non-toxic and cell-permeable. By tagging Spinach to a target RNA, the expression of the target RNA in bacteria and mammalian cells can be imaged (ref. 19).

As the small molecule DFHBI binds and unbinds Spinach, it will alternate between a fluorescence ON- and OFF-state. The resulting blinking behavior is used to perform super-resolution fluorescence microscopy, which is referred to herein as "Spinach-PAINT" (FIG. 20). Unlike most live cell super-resolution imaging techniques, Spinach-PAINT needs no special imaging conditions such as special buffer systems or external photoswitching or activation. More importantly, DFHBI is a small, cell-permeable molecule and has been shown to provide non-toxic imaging for living cells. The necessary "blinking" behavior for super-resolution imaging can be obtained by altering the fluorescence ON- and OFF-times by adjusting the DFHBI concentration in solution and modifying/mutating Spinach to enhance/weaken the binding of DFHBI to it in the same spirit as one would tune the DNA-DNA binding interaction of an imaging strand with its partner. It is possible to characterize and optimize the binding kinetics of DFHBI to surface-immobilized Spinach based on single-molecule measurements (FIG. 20). The binding kinetics are checked for compatibility with super-resolution microscopy based on transient binding.

Generate Spinach Variants with Optimized Blinking Properties for Super-Resolution Imaging:

Based on DNA-PAINT, a starting point is to obtain Spinach variants that show ON-times of at least 50 ms, occurring at a rate of ≈2 Hz. It has been found that Spinach exhibits a $k_{off}$ of 0.02 s$^{-1}$, resulting in a residence time of ≈50 s. This is markedly longer than needed for super-resolution imaging. To identify Spinach variants with a $k_{off}$ between 1-20 s$^{-1}$, a "doped" library of Spinach variants will be prepared, using a dNTP mixture containing the dNTP that is found in Spinach for each position and the other three dNTPs in a 2:1:1:1 ratio. This approach is typically used to optimize aptamer sequences (SELEX) (ref. 23). The Spinach variants will then be screened for variants with shorter DFHBI residence times. After 5-10 rounds of SELEX, clones will be individually characterized. A first step is to confirm that all the Spinach variants still exhibit Spinach-like fluorescence with comparable quantum yield and extinction coefficient upon binding DFHBI. It is generally easy to weaken rather than to strengthen the binding interaction between an aptamer and a small molecule.

A second step involves measuring the binding and unbinding rate constants of these Spinach variants by single-molecule imaging. Spinach variants that exhibit binding durations that provide sufficient photon counts for obtaining precise super-resolution imaging will be chosen.

To optimize the blinking frequency, we will titrate with DFHBI, as the rate of RNA-fluorophore complex formation is determined by both $k_{on}$ and the DFHBI concentration, and will identify the concentration that produces a blinking rate of 5-10 Hz. Finally, we will have identified a set of Spinach variants that exhibit optimized blinking needed for super-resolution imaging.

As a testing platform, we will optimize the super-resolution ability of Spinach-PAINT by in vitro "imaging" of a DNA-based nanostructure (e.g., a nanostructure made by DNA origami). The DNA origami substrate has the advantage of providing a programmable environment for placing multiple Spinach molecules in a defined distance and geometry. This nanoscopic ruler system will enable us to precisely quantify the obtainable resolution of this super-resolution imaging technique (FIG. 21).

RNAs that Exhibit Blinking Upon Binding Tubulin for Super-Resolution Imaging of Cytoskeleton Proteins:

Spinach-based sensors that are activated by metabolites (ref. 24) and by proteins (ref. 25) have been generated. The approach of this disclosure will be used to generate Spinach-based sensors that are activated by binding tubulin, using tubulin-binding aptamers and the blinking Spinach variants described herein.

The allosteric form of Spinach is compromised of the modified Spinach aptamer domain fused to a "control" or "sensing" module consisting of an aptamer that binds a target of interest (ref. 24). Binding of the target results in the allosteric folding of the modified Spinach aptamer into an "active" conformation, enabling DFHBI binding and fluorescence (FIG. 22). Several tubulin-binding DNA aptamers have been described (ref. 26). This disclosure provides for the evolution of control modules for Spinach capable of sensing tubulin using previously established protocols. Briefly, candidate aptamers will be fused to Spinach to obtain tubulin-dependent Spinach fluorescence, and Spinach activation only in the presence of tubulin (which will be Cy5 labeled and polymerized in vitro) will be verified.

Using the conditional Spinach probe generated above and based on the super-resolution conditions tested for in vitro imaging, Spinach-PAINT can be used for, for example, super-resolution imaging of microtubules in live mammalian cells.

Example 6: Flow Chamber

FIG. 23A shows an example of an experimental setup used for in vitro DNA origami experiments, as provided herein. The sample is immobilized on a glass coverslip in a PDMS channel. Imaging and washing buffers are added to a reservoir and pulled through the channel by a syringe. Reservoirs and syringes are connected to the PDMS channel via flexible tubing and are, thus, mechanically decoupled. FIG. 23B shows an experimental setup used for in situ cell imaging. Cells are imaged in a Lab-Tek II chamber. One syringe supplies new buffer solution, the second one removes the previous buffer.

An exemplary protocol for Exchange-PAINT imaging using a flow chamber, for example, as depicted in FIGS. 23A and 23B, is as follow:

PDMS flow chamber volume: 40 µl
Rinse flow chamber with 100 µl 1 M KOH
Rinse flow chamber with 100 µl buffer A twice
Incubate for 5 min
Rinse flow chamber with 100 µl buffer A
Rinse flow chamber with 50 µl 1 mg/ml BSA-Biotin in buffer A
Incubate for 2 min
Rinse flow chamber with 50 µl 1 mg/ml BSA-Biotin in buffer A
Incubate for 2 min
Rinse flow chamber with 100 µl buffer A twice
Rinse flow chamber with 50 µl 0.5 mg/ml Streptavidin in buffer A
Incubate for 2 min
Rinse flow chamber with 50 µl 0.5 mg/ml Streptavidin in buffer A
Incubate for 2 min
Rinse flow chamber with 100 µl buffer A twice
Rinse flow chamber with 100 µl buffer B twice
Incubate for 30 min
Rinse flow chamber with 100 µl buffer B twice
Rinse flow chamber with 50 µl 1 nM origami in buffer B
Incubate for 10 min
Rinse flow chamber with 100 µl buffer B twice
Attach tubing
Operate in buffer B.

Additional Materials and Methods

Materials.

Unmodified DNA oligonucleotides were purchased from Integrated DNA Technologies. Fluorescently modified DNA oligonucleotides were purchased from Biosynthesis. Biotinylated monoclonal antibodies against β-tubulin (9F3; Catalog number: 6181) and COX IV (3E11; Catalog number: 6014) were purchased from Cell Signaling. Anti-PMP70 (Catalog number: ab28499) was purchased from Abcam. Anti-TGN46 (Catalog number: NBP1-49643B) was purchased from VWR. Streptavidin was purchased from Invitrogen (Catalog number: S-888). Bovine serum albumin (BSA), and BSA-biotin was obtained from Sigma Aldrich (Catalog Number: A8549). Glass slides and coverslips were purchased from VWR. Lab-Tek II chambered cover glass were purchased from Thermo Fisher Scientific. M13mp18 scaffold was obtained from New England Biolabs. p8064 scaffold for microtubule-like DNA origami structures was prepared as described 19. 'Freeze N Squeeze' columns were ordered from Bio-Rad. TetraSpeck Beads were purchased from Life Technologies. Paraformaldehyde, glutaraldehyde and TEM grids (FORMVAR 400 Mesh Copper Grids) were obtained from Electron Microscopy Sciences. Three buffers were used for sample preparation and imaging: Buffer A (10 mM Tris-HCl, 100 mM NaCl, 0.05% Tween-20, pH 7.5), buffer B (5 mM Tris-HCl, 10 mM MgCl2, 1 mM EDTA, 0.05% Tween-20, pH 8), and buffer C (1×PBS, 500 mM NaCl, pH 8).

Optical Setup.

Fluorescence imaging was carried out on an inverted Nikon Eclipse Ti microscope (Nikon Instruments) with the Perfect Focus System, applying an objective-type TIRF configuration using a Nikon TIRF illuminator with an oil-immersion objective (CFI Apo TIRF 100×, NA 1.49, Oil). For 2D imaging an additional 1.5 magnification was used to obtain a final magnification of ≈150-fold, corresponding to a pixel size of 107 nm. Three lasers were used for excitation: 488 nm (200 mW nominal, Coherent Sapphire), 561 nm (200 mW nominal, Coherent Sapphire) and 647 nm (300 mW nominal, MBP Communications). The laser beam was passed through cleanup filters (ZT488/10, ZET561/10, and ZET640/20, Chroma Technology) and coupled into the microscope objective using a multi-band beam splitter (ZT488rdc/ZT561rdc/ZT640rdc, Chroma Technology). Fluorescence light was spectrally filtered with emission filters (ET525/50m, ET600/50m, and ET700/75m, Chroma Technology) and imaged on an EMCCD camera (iXon X3 DU-897, Andor Technologies).

DNA Origami Self-Assembly.

The microtubule-like DNA origami structures were formed in a one-pot reaction with 40 µl total volume containing 10 nM scaffold strand (p8064), 500 nM folding staples and biotin handles, 750 nM biotin anti-handles and 1.1 µM DNA-PAINT docking strands in folding buffer (1×TAE Buffer with 20 mM $MgCl_2$). The solution was annealed using a thermal ramp13 cooling from 80° C. to 14° C. over the course of 15 h. After self-assembly, monomeric structures were purified by agarose gel electrophoresis (1.5% agarose, 0.5×TBE, 10 mM $MgCl_2$, 1×SybrSafe) at 4.5 V/cm for 1.5 h. Gel bands were cut, crushed and filled into a 'Freeze 'N Squeeze' column and spun for 5 min at 1000×g at 4° C. Polymerization was carried out at 30° C. for 48 h with a 5-fold excess of polymerization staples in folding buffer. Polymerized structures were used for imaging without further purification. DNA origami drift markers were self-assembled in a one-pot reaction (40 µl total volume, 20 nM M13mp18 scaffold, 100 nM biotinylated staples, 530 nM staples with DNA-PAINT docking sites, 1×TAE with 12.5 mM MgCl2). Self-assembled structures were purified as described before. DNA origami structures for the 4-"color" in vitro Exchange-PAINT demonstration were self-assembled in a one-pot reaction (40 µl total volume, 30 nM M13mp18 scaffold, 470 nM biotinylated staples, 400 nM staples with docking sites for number imaging, 370 nM core structure staples, 1×TAE with 12.5 mM MgCl2). Self-assembled structures were purified as described before. DNA origami structures for the 10-"color" in vitro Exchange-PAINT demonstration were self-assembled in a one-pot reaction (40 µl total volume, 30 nM M13mp18 scaffold, 36 nM biotinylated staples, 750 nM staples with docking sites for number imaging, 300 nM core structure staples, 1×TAE with 12.5 mM MgCl2). Structures were not purified. Excessive staples are washed out of the sample after immobilization of the structure on the surface. DNA strand sequences for the microtubule-like DNA origami structures can be found in Table 1. DNA strand sequences for DNA origami drift markers can be found in Table 2. DNA strand sequences for DNA origami structures for 10-"color" in vitro Exchange-PAINT demonstration can be found in Tables 3 and 4 for odd and even digits, respectively. DNA strand sequences for DNA origami structures for in vitro Exchange-PAINT demonstration (digits 0 to 3) can be found in Table 5. The scaffold sequence for p8064 and M13mp18 correspond to SEQ ID NO: 882 and 883, respectively. DNA-PAINT imager and docking sequences as well as sequences for surface attachment via Biotin are listed in Table 6.

Antibody-DNA conjugates. Antibody-DNA conjugates used to specifically label proteins of interest with DNA-PAINT docking sites were preassembled in two steps: First, 3.2 µl of 1 mg/ml streptavidin (dissolved in buffer A) was reacted with 0.5 µl biotinylated DNA-PAINT docking strands at 100 µM and an additional 5.3 µl of buffer A for 30 min at room temperature (RT) while gently shaking. The solution was then incubated in a second step with 1 µl of monoclonal biotinylated antibodies at 1 mg/ml against the protein of interest for 30 min at RT. Filter columns (Amicon 100 kDa, Millipore) were used to purify the preassembled conjugates from unreacted streptavidin-oligo conjugates.

Cell Immunostaining.

HeLa and DLD1 cells were cultured with Eagle's minimum essential medium fortified with 10% FBS with penicillin and streptomycin and were incubated at 37° C. with 5% CO2. Approximately 30% confluence cells per well were seeded into Lab-Tek II chambered cover glass 24 h before fixation. Microtubules, mitochondria, Golgi complex, and peroxisomes were immunostained using the following procedure: washing in PBS; fixation in a mixture of 3% paraformaldehyde and 0.1% glutaraldehyde in PBS for 10 min; 3-times washing with PBS; reduction with ≈1 mg/ml NaBH4 for 7 min; 3-times washing with PBS; permeabilization with 0.25% (v/v) Triton X-100 in PBS for 10 min; 3-times washing with PBS; blocking with 3% (w/v) bovine serum albumin for 30 min and staining over night with the preassembled antibody-DNA conjugates against β-tubulin, COX IV, PMP70, or TGN46 (conjugates were diluted to 10m/ml in 5% BSA); 3-times washing with PBS; post-fixation in a mixture of 3% paraformaldehyde and 0.1% glutaraldehyde in PBS for 10 min; and 3-times washing with PBS.

Super-Resolution DNA-PAINT Imaging of Microtubule-Like DNA Origami Structures.

For sample preparation, a piece of coverslip (No. 1.5, 18×18 mm2, ≈0.17 mm thick) and a glass slide (3×1 inch2, 1 mm thick) were sandwiched together by two strips of double-sided tape to form a flow chamber with inner volume of ≈20 µl. First, 20 µl of biotin-labeled bovine albumin (1 mg/ml, dissolved in buffer A) was flown into the chamber and incubated for 2 min. The chamber was then washed using 40 µl of buffer A. 20 µl of streptavidin (0.5 mg/ml, dissolved in buffer A) was then flown through the chamber and allowed to bind for 2 min. After washing with 40 µl of buffer A and subsequently with 40 µl of buffer B, 20 µl of biotin-labeled microtubule-like DNA structures (≈300 pM monomer concentration) and DNA origami drift markers (≈100 pM) in buffer B were finally flown into the chamber and incubated for 5 min. The chamber was washed using 40 µl of buffer B. The final imaging buffer solution contained 1.5 nM Cy3b-labeled imager strands in buffer B. The chamber was sealed with epoxy before subsequent imaging. The CCD readout bandwidth was set to 1 MHz at 16 bit and 5.1 pre-amp gain. No EM gain was used. Imaging was performed using TIR illumination with an excitation intensity of 294 W/cm2 at 561 nm.

Super-Resolution Exchange-PAINT Imaging of DNA Nanostructures.

For fluid exchange, a custom flow chamber was constructed. A detailed preparation protocol can be found in Example 6. Prior to functionalizing the imaging channel with BSA-biotin, it was rinsed with 1 M KOH for cleaning. Binding of the origami structures to the surface of the flow chamber was performed as described before. Each image acquisition step was followed with a brief ~1-2 min washing step consisting of at least three washes using 200 µl of buffer B each. Then the next imager strand solution was introduced. The surface was monitored throughout the washing procedure to ensure complete exchange of imager solutions. Acquisition and washing steps were repeated until all ten targets were imaged. The CCD readout bandwidth was set to 3 MHz at 14 bit and 5.1 pre-amp gain. No EM gain was used. Imaging was performed using TIR illumination with an excitation intensity of 166 W/cm2 at 561 nm (Ten-"color" Exchange-PAINT with 3 nM Cy3b-labeled imager strands in buffer B, FIG. 5B(iii) and 5B(v)) and 600 W/cm2 at 647 nm (Four-"color" Exchange-PAINT with 3 nM ATT0655-labeled imager strands in buffer B, FIG. 5B(iv)).

Super-Resolution DNA-PAINT Imaging of Cells.

All data was acquired with an EMCCD readout bandwidth of 5 MHz at 14 bit, 5.1 pre-amp gain and 255 electron-multiplying gain. Imaging was performed using HILO illumination11. The laser power densities were 283 W/cm2 at 647 nm in FIG. 3A, 142 W/cm2 at 647 nm and 19 W/cm2 at 561 nm in FIG. 3D. Imaging conditions: FIG. 3A: 700 pM ATT0655-labeled imager strands in buffer C. FIG. 3D: 600 pM Cy3b-labeled imager strands and 1.5 nM ATT0655-labeled imager strands in buffer C.

Super-resolution Exchange-PAINT imaging of cells. A Lab-Tek II chamber was adapted for fluid exchange. 2D images (FIGS. 6B and 6C) were acquired with an EMCCD readout bandwidth of 5 MHz at 14 bit, 5.1 preamp gain and 255 EM gain. 3D images (FIG. 6) were acquired with a CCD readout bandwidth of 3 MHz at 154 bit, 5.1 pre-amp gain and no EM gain. Imaging was performed using HILO illumination in both cases. Sequential imaging was done as described for the 2D origami nanostructures, but the washing steps were performed using buffer C.

3D DNA-Paint Imaging.

3D images were acquired with a cylindrical lens in the detection path (Nikon). The N-STORM analysis package for NIS Elements (Nikon) was used for data processing. Imaging was performed without additional magnification in the detection path, yielding 160 nm pixel size. 3D calibration was carried out according to the manufacturer's instructions.

Imager Strand Concentration Determination.

Optimal imager concentrations are determined empirically according to the labeling density. Generally, a high enough fluorescence OFF/ON-ratio has to be ensured in order to guarantee binding of only a single imager strand per diffraction-limited area. Additionally, a sufficient imager strand concentration (and thus sufficiently low fluorescence OFF-time) is necessary to ensure sufficient binding events and thereby robust detection of every docking strand during image acquisition.

Super-Resolution Data Processing.

Super-resolution DNA-PAINT images were reconstructed using spot-finding and 2D-Gaussian fitting algorithms programmed in LabVIEW10. A simplified version of this software is available for download at the DNA-Paint website (org suffix).

Normalized Cross-Correlation Analysis.

Normalized cross-correlation coefficients were obtained by first normalizing the respective reconstructed gray-scale super-resolution images and subsequently performing a cross-correlation analysis in MATLAB R2013b (MathWorks, Natick, Mass., USA).

Drift Correction and Channel Alignment.

Figure 6A:
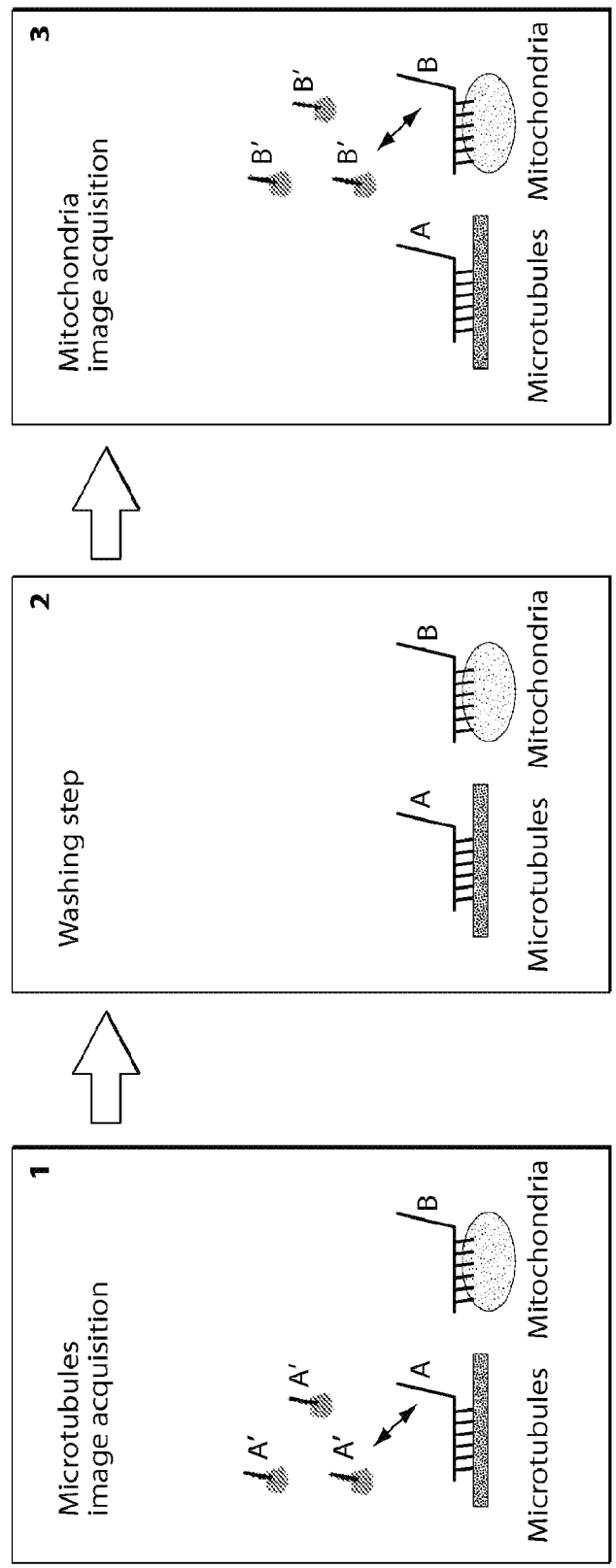
FIG. 6A shows an experimental schematic for one embodiment of the present disclosure using fixed HeLa cells, where in one round, docking strands are bound to a target, labeled imager strands are then added, an image is acquired, and the imager strands are washed away. Each round is repeated with docking strands specific for different targets along with different labeled imager strands. The docking strands may be used alone or linked to a protein-binding (e.g., antibody) or a nucleic acid-binding molecule that binds to the target of interest.
Figure 6B:
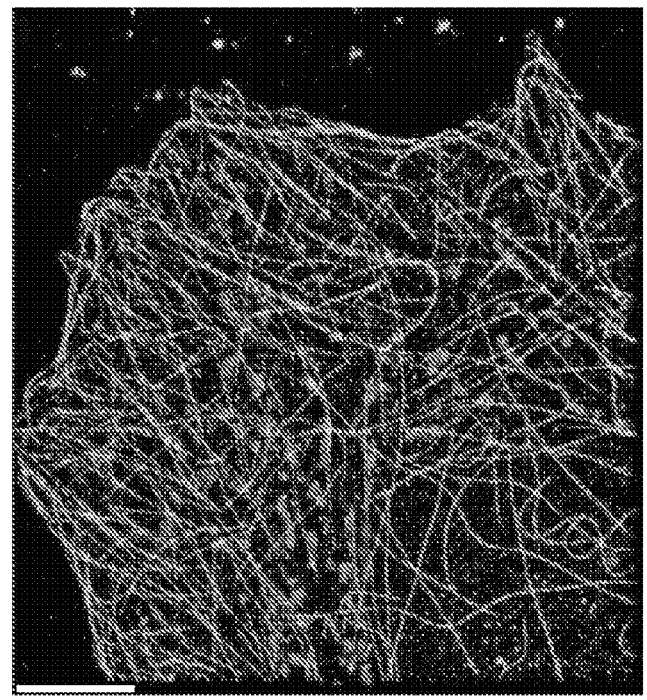
FIG. 6B shows two rounds of a method of the present disclosure using Cy3b-labeled imager strands in fixed HeLa cells. Here, microtubules (green pseudo-color; color rendering not shown) were labeled with docking sequence a and mitochondria (magenta pseudo-color; color rendering not shown) with orthogonal docking sequence b.
Figure 6C:
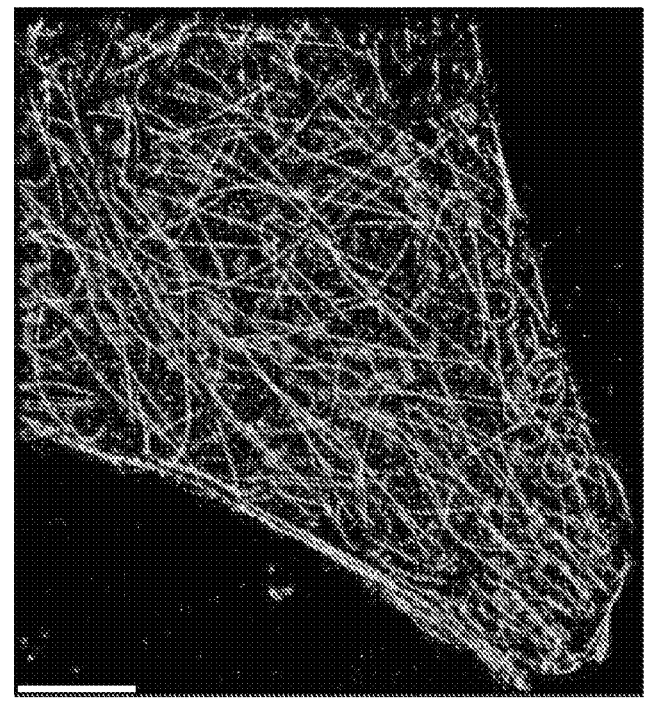
FIG. 6C shows two rounds of a method of the present disclosure using ATT0655-labeled imager strands performed in fixed HeLa cells similar to FIG. 6B. [Scale bars: 5 μm]. Note that all imager strands are labeled with the same color dye.

DNA origami structures are used for drift correction and as alignment markers in in vitro DNA-PAINT and Exchange-PAINT imaging. Drift correction was performed by tracking the position of each origami drift marker throughout the duration of each movie. The trajectories of all detected drift markers were then averaged and used to globally correct the drift in the final super-resolution reconstruction. For channel alignment between different imaging cycles in Exchange-PAINT, these structures are used as alignment points by matching their positions in each Exchange-PAINT image. For cellular imaging, 100 nm gold nanoparticles (Sigma Aldrich; 10 nM in buffer C, added before imaging) were used as drift and alignment markers. The gold nanoparticles adsorb non-specifically to the glass bottom of the imaging chambers. Drift correction and alignment is performed in a similar fashion as for the origami drift markers. Again, the apparent movement of all gold nanoparticles in a field of view is tracked throughout the movie. The obtained trajectories are then averaged and used for global drift correction of the final super-resolution image. For the dual-color image of mitochondria and microtubules in FIG. 3D-3F, the gold particles are visible in both color channels. The same gold nanoparticles are also used for drift-correction and re-alignment of the different imaging rounds in the in situ Exchange-PAINT experiments (FIG. 6).

Transmission Electron Microscopy Imaging.

For imaging, 3.5 μl of undiluted microtubules-like DNA structures were adsorbed for 2 minutes onto glow-discharged, carbon-coated TEM grids. The grids were then stained for 10 seconds using a 2% aqueous ultra-filtrated (0.2 μm filter) uranyl formate solution containing 25 mM NaOH. Imaging was performed using a JEOL JEM-1400 operated at 80 kV.

Atomic Force Microscopy Imaging.

Imaging was performed using tapping mode on a Multimode VIII atomic force microscope (AFM) with an E-scanner (Bruker). Imaging was performed in TAE/Mg2+ buffer solution with DNP-S oxide-sharpened silicon nitride cantilevers and SNL sharp nitride levers (Bruker Probes) using resonance frequencies between 7-9 kHz of the narrow 100 μm, 0.38 N/m force constant cantilever. After self-assembly of the origami structure ≈20 μl of TAE/Mg2+ buffer solution was deposited onto a freshly cleaved mica surface (Ted Pella) glued to a metal puck (Ted Pella). After 30 s the mica surface was dried using a gentle stream of N2 and 5 μl of the origami solution was deposited onto the mica surface. After another 30 s, 30 μl of additional buffer solution was added to the sample. Imaging parameters were optimized for best image quality while maintaining the highest possible setpoint to minimize damage to the samples. Images were post-processed by subtracting a 1st order polynomial from each scan line. Drive amplitudes were approximately 0.11 V, integral gains ≈2, and proportional gains ≈4.

In Tables 1-5 below, each oligonucleotide position in a described structure is set forth. Each oligonucleotide position (e.g., n[n]n[n]) in the first column is separated by a comma and corresponds respectively to a sequence identification number in the second column within the same row. Each sequence identification number identifies a corresponding oligonucleotide sequence in the attached sequence listing, incorporated by reference herein. For example, in Table 1, position 0[39]21[39] corresponds to the oligonucleotide represented by SEQ ID NO: 1; position 0[79]1[79] corresponds to the oligonucleotide represented by SEQ ID NO: 2, and so forth.

TABLE 1

Staple sequences for microtubule analog DNA structure.

| Position* | Sequence Identifiers | Description |
|---|---|---|
| 0[39]21[39], 0[79]1[79], 0[167]22[168], 0[199]2[200], 0[239]21[231], 1[24]18[24], 1[96]17[95], 1[120]1[151], 1 [152]19[167], 2[39]23[55], 2[79]23[71], 2[103]3[119], 2[127]31[143], 2[199]23[207], 2[231]5[231], 3[16]31[31], 3[56]19[55], 3[80]2[80], 3[120]24[128], 3[168]5[175], 4[71]5[87], 4[135]22[120], 4[207]6[184], 5[16]22[16], 5[32]25[31], 5[52]3[55], 5[88]23[103], 5[152]4[136], 5[176]22[184], 6[95]4[72], 6[127]8[120], 6[151]22[144], 6[159]26[160], 6[183]2[184], 6[207]4[208], 6[231]24[208], 7[16]4[16], 7[48]5[51], 7[80]25[95], 7[112]6[96], 7[176]25[191], 8[39]11[31], 8[95]12[80], 8[159]10[160], 8[191]8[160], 9[48]25[63], 9[104]24[112], 9[120]10[136], 9[136]24[144], 9[176]11[191], 9[208]25[223], 10[31]27[23], | SEQ ID NO: 1-<br>SEQ ID NO: 178 | Structure<br>Strand |

TABLE 1-continued

Staple sequences for microtubule analog DNA structure.

| Position* | Sequence Identifiers | Description |
|---|---|---|
| 10[55]8[40], 10[95]27[95], 10[135]26[112], 10[159]27[159], 10[183]27[191], 10[215]10[184], 11[192]26[208], 12[31]29[23], 12[55]28[32], 12[79]11[63], 12[119]16[120], 12[183]29[191], 12[215]27[215], 13[40]27[55], 13[72]30[80], 13[104]9[103], 13[144]17[159], 13[168]25[183], 13[216]14[224], 14[55]16[40], 14[87]28[72], 14[119]15[135], 14[223]30[208], 15[32]29[55], 15[80]18[80], 15[96]28[104], 15[160]28[168], 16[119]31[111], 16[143]30[120], 16[191]14[160], 16[207]19[207] 16[239]29[231], 17[24]14[24], 17[40]18[56], 17[64]14[56], 17[160]31[175], 17[224]31[239], 18[55]2[40], 18[79]21[79], 18[111]0[96], 18[183]30[160], 18[239]2[232], 19[56]30[64], 19[96]30[96], 19[168]3[167], 19[192]30[184], 19[208]30[224], 20[159]21[135], 20[223]21[199], 21[16]1[23], 21[40]4[32], 21[80]22[96], 21[136]2[128], 21[200]1[215], 21[232]6[232], 22[95]3[79], 22[119]2[104], 22[143]21[159], 22[167]7[175], 22[183]18[184], 22[207]21[223], 23[56]1[55], 23[72]24[56], 23[104]5[103], 23[208]22[208], 24[79]7[79], 24[127]9[135], 24[143]5[151], 24[231]26[216], 25[64]24[80], 25[224]10[216], 26[159]12[144], 26[207]6[208], 26[239]7[247], 27[96]10[96] 27[112]14[120], 27[136]7[151], 28[191]15[183], 29[56]15[79], 29[136]27[135], 29[192]13[215], 29[232]28[216], 30[95]14[88], 30[119]29[135], 30[183]16[192], 30[207]17[223], 30[223]15[239], 31[112]1[119], 31[144]19[143], 1[56]0[40], 1[80]19[95], 1[216]0[200], 2[183]19[191], 5[104]6[128], 8[63]10[56], 9[80]8[64], 11[64]9[79], 11[216]9[239], 14[159]15[159], 15[184]16[208], 17[96]15[95], 19[128]18[112], 19[144]19[127], 24[55]7[47], 24[111]7[111], 24[183]6[160], 24[207]8[192], 25[32]9[47], 25[96]8[96], 25[192]9[207], 27[32]10[32], 27[160]9[175], 30[63]17[63], 30[79]0[80], 30[159]16[144], 31[32]15[31], 31[176]0[168], 13[136]12[120], 15[136]13[135] 27[24]13[39], 27[56]12[56], 27[216]12[216], 28[71]13[71], 28[103]13[103], 28[167]13[167], 28[215]12[184] | | |
| 1[56]0[40], 1[80]19[95], 1[216]0[200], 2[183]19[191], 5[104]6[128], 8[63]10[56], 9[80]8[64], 11[64]9[79], 11[216]9[239], 14[159]15[159], 15[184]16[208], 17[96]15[95], 19[128]18[112], 19[144]19[127], 24[55]7[47], 24[111]7[111], 24[183]6[160], 24[207]8[192], 25[32]9[47], 25[96]8[96], 25[192]9[207], 27[32]10[32], 27[160]9[175], 30[63]17[63], 30[79]0[80], 30[159]16[144], 31[32]15[31], 31[176]0[168] | SEQ ID NO: 179-<br>SEQ ID NO: 206 | DNA-PAINT, docking site |
| 2[9]2[10], 4[15]6[248], 5[232]5[15], 6[247]3[15], 7[248]24[232], 9[240]11[7], 11[8]25[23], 13[8]26[240], 14[23]16[240], 15[240]28[8], 17[8]18[240], 19[3]0[248], 22[15]21[15], 24[23]7[15], 27[237]13[7], 28[7]27[236], 30[23]17[7], 31[16]31[15], 31[240]0[240] | SEQ ID NO: 207-<br>SEQ ID NO: 225 | Connector strand |
| 13[136]12[120], 15[136]13[135], 27[24]13[39], 27[56]12[56], 27[216]12[216], 28[71]13[71], 28[103]13[103], 28[167]13[167], 28[215]12[184] | SEQ ID NO: 226-<br>SEQ ID NO: 234 | 3'-Biotin, docking site |

TABLE 2

Staple sequences for drift markers.

| Position* | Sequence Identifiers | Description |
|---|---|---|
| 0[111]1[95], 0[143]1[127], 0[175]0[144], 0[207]1[191], 0[239]1[223], 1[32]3[31], 1[96]3[95], 1[224]3[223], 2[79]0[80], 2[111]0[112], 2[143]1[159], 2[175]0[176], 2[207]0[208], 3[32]5[31], 3[96]5[95], 3[160]4[144], 3[224]5[223], 4[143]3[159], 5[32]7[31], 5[96]7[95], 5[224]7[223], 6[47]4[48], 6[79]4[80], 6[111]4[112], 6[143]5[159], 6[175]4[176], 6[207]4[208], 6[239]4[240], 6[271]4[272], 7[32]9[31], 7[96]9[95], 7[160]8[144], 7[224]9[223], 8[143]7[159], 9[32]11[31], 9[64]11[63], 9[96]11[95], 9[128]11[127], 9[192]11[191], 9[224]11 [223], 9[256]11[255], 10[47]8 [48], 10[79]8[80], 10[111]8[112], 10[143]9[159], 10[175]8[176], 10[207]8[208], 10[239]8[240], 10[271]8[272], 12[143]11[159], 13[32] 15[31], 13[64]15[63], 13[96]15[95], 13[128]15[127], 13[192]15[191], 13[224]15[223], 13[256]15[255], 14[271]12[272], 15[32]17[31], 15[96]17[95], 15[160]16[144], 15[224]17[223], 16[143]15[159], 17[32]19[31], 17[96]19[95], 17[224]19[223], 18[47]16[48], 18[79]16[80], 18[111]16[112], 18[143]17[159], 18[175]16[176], 18[207]16[208], 18[239]16[240], 18[271]16[272], 19[32]21[31], 19[96]21[95], 19[160]20[144], 19[224]21[223], 20[143]19[159], 21[96]23[95], 21[160]22[144], 21[224]23[223], 22[47]20[48], 22[79]20[80], 22[111]20[112], 22[143]21[159], 22[175]20[176], 22[207]20[208], 22[239]20[240], 22[271]20[272], 23[64]22[80], 23[96]22[112], 23[128]23[159], 23[160]22[176], 23[192]22[208], 7[56]9[63], 7[120]9[127], 7[184]9[191], 7[248]9[255], 11[32]13[31], 11[64]13[63], 11[96]13[95], 11[128]13[127], 11[160]12[144], 11[192]13[191], 11[224]13[223], 11[256]13[255], 14[47]12[48], 14[79]12[80], 14[111]12[112], 14[143]13[159], 14[175]12[176], 14[207]12[208], 14[239]12[240], 21[120]23[127], 21[184]23[191], | SEQ ID NO: 235-<br>SEQ ID NO: 402 | DNA-PAINT, docking site |

TABLE 2-continued

Staple sequences for drift markers.

| Position* | Sequence Identifiers | Description |
|---|---|---|
| 1[160]2[144], 4[47]2[48], 4[79]2[80], 4[111]2[112], 4[175]2[176], 4[207]2[208], 4[239]2[240], 4[271]2[272], 5[160]6[144], 8[47]6[48], 8[79]6[80], 8[111]6[112], 8[175]6[176], 8[207]6[208], 8[239]6[240], 8[271]6[272], 9[160]10[144], 12[47]10[48], 12[79]10[80], 12[111]10[112], 12[175]10[176], 12[207]10[208], 12[239]10[240], 12[271]10[272], 13[160]14[144], 16[47]14[48], 16[79]14[80], 16[111]14[112], 16[175]14[176], 16[207]14[208], 16[239]14[240], 16[271]14[272], 17[160]18[144], 20[47]18[48], 20[79]18[80], 20[111]18[112], 20[175]18[176], 20[207]18[208], 20[239]18[240], 20[271]18[272], 0[47]1[31], 0[79]1[63], 0[271]1[255], 2[47]0[48], 2[239]0[240], 2[271]0[272], 21[32]23[31], 21[56]23[63], 21[248]23[255], 23[32]22[48], 23[224]22[240], 23[256]22[272] | | |
| 4[63]6[56], 4[127]6[120], 4[191]6[184], 4[255]6[248], 18[63]20[56], 18[127]20[120], 18[191]20[184], 18 [255]20[248] | SEQ ID NO: 403-<br>SEQ ID NO: 410 | 5'-Biotin modification |
| 1[64]4[64], 1[128]4[128], 1[192]4[192], 1[256]4[256], 15[64]18[64], 15[128]18[128], 15[192]18[192], 15[256]18[256], | SEQ ID NO: 411-<br>SEQ ID NO: 418 | Structure strand |

TABLE 3

Staple sequences for DNA origami structures for 10-"color" in vitro Exchange-PAINT demonstration (odd digits).

| Position* | Sequence Identifiers | Description (number) |
|---|---|---|
| 0[111]1[95], 0[143]1[127], 0[175]0[144], 0[79]1[63], 1[160]2[144], 2[47]0[48], 3[160]4[144], 5[160]6[144], 7[160]8[144] | SEQ ID NO: 419-<br>SEQ ID NO: 427 | 5, 9 |
| 10[271]8[272], 11[160]12[144], 12[271]10[272], 13[160]14[144], 14[271]12[272], 15[160]16[144], 16[271]14[272], 17[160]18[144], 18[271]16[272], 19[160]20[144], 2[271]0[272], 20[271]18[272], 21[160]22[144], 22[271]20[272], 4[271]2[272], 6[271]4[272], 8[271]6[272], 9[160]10[144] | SEQ ID NO: 428-<br>SEQ ID NO: 445 | 3, 5, 9 |
| 0[47]1[31], 1[32]3[31], 11[32]13[31], 13[32]15[31], 15[32]17[31], 17[32]19[31], 19[32]21[31], 3[32]5[31], 5[32]7[31], 7[32]9[31], 9[32]11[31] | SEQ ID NO: 446-<br>SEQ ID NO: 456 | 3, 5, 7, 9 |
| 21[120]23[127], 21[56]23[63], 21[96]23[95], 23[32]22[48], 23[64]22[80], 23[96]22[112] | SEQ ID NO: 457-<br>SEQ ID NO: 462 | 1, 3, 7, 9 |
| 21[184]23[191], 21[224]23[223], 21[248]23[255], 21[32]23[31], 23[128]23[159], 23[160]22[176], 23[192]22[208], 23[224]22[240], 23[256]22[272] | SEQ ID NO: 463-<br>SEQ ID NO: 471 | 1, 3, 5, 7, 9 |
| 2[111]0[112], 2[79]0[80] | SEQ ID NO: 472-<br>SEQ ID NO: 473 | 9 |
| 0[207]1[191], 0[239]1[223], 0[271]1[255], 1[128]4[128], 1[192]4[192], 1[224]3[223], 1[256]4[256], 1[64]4[64], 1[96]3[95], 10[111]8[112], 10[143]9[159], 10[175]8[176], 10[207]8[208], 10[239]8[240], 10[47]8[48], 10[79]8[80], 11[128]13[127], 11[192]13[191], 11[224]13[223], 11[256]13[255], 11[64]13[63], 11[96]13[95], 12[111]10[112], 12[143]11[159], 12[175]10[176], 12[207]10[208], 12[239]10[240], 12[47]10[48], 12[79]10[80], 13[128]15[127], 13[192]15[191], 13[224]15[223], 13[256]15[255], 13[64]15[63], 13[96]15[95], 14[111]12[112], 14[143]13[159], 14[175]12[176], 14[207]12[208], 14[239]12[240], 14[47]12[48], 14[79]12[80], 15[128]18[128], 15[192]18[192], 15[224]17[223], 15[256]18[256], 15[64]18[64], 15[96]17[95], 16[111]14[112], 16[143]15[159], 16[175]14[176], 16[207]14[208], 16[239]14[240], 16[47]14[48], 16[79]14[80], 17[224]19[223], 17[96]19[95], 18[111]16[112], 18[143]17[159], 18[175]16[176], 18[207]16[208], 18[239]16[240], 18[47]16[48], 18[79]16[80], 19[224]21[223], 19[96]21[95], 2[143]1[159], 2[175]0[176], 2[207]0[208], 2[239]0[240], 20[111]18[112], 20[143]19[159], 20[175]18[176], 20[207]18[208], 20[239]18[240], 20[47]18[48], 20[79]18[80], 22[111]20[112], 22[143]21[159], 22[175]20[176], 22[207]20[208], 22[239]20[240], 22[47]20[48], 22[79]20[80], 3[224]5[223], 3[96]5[95], 4[111]2[112], 4[143]3[159], 4[175]2[176], 4[207]2[208], 4[239]2[240], 4[47]2[48], 4[79]2[80], 5[224]7[223], 5[96]7[95], 6[111]4[112], 6[143]5[159], 6[175]4[176], 6[207]4[208], 6[239]4[240], 6[47]4[48], 6[79]4[80], 7[120]9[127], 7[184]9[191], 7[224]9[223], 7[248]9[255], 7[56]9[63], 7[96]9[95], 8[111]6[112], 8[143]7[159], 8[175]6[176], 8[207]6[208], 8[239]6[240], 8[47]6[48], 8[79]6[80], 9[128]11[127], 9[192]11[191], 9[224]11[223], 9[256]11[255], 9[64]11[63], 9[96]11[95] | SEQ ID NO: 474-<br>SEQ ID NO: 594 | Structure staple |
| 4[63]6[56], 4[127]6[120], 4[191]6[184], 4[255]6[248], 18[63]20[56], 18[127]20[120], 18[191]20[184], 18[255]20[248] | SEQ ID NO: 595-<br>SEQ ID NO: 602 | 5'-Biotin |

TABLE 4

Staple sequences for DNA origami structure for 10-"color" in vitro Exchange-PAINT demonstrate (even digits).

| Position* | Sequence Identifiers | Description (number) |
|---|---|---|
| 1[160]2[144], 11[160]12[144], 13[160]14[144], 15[160]16[144], 17[160]18[144], 19[160]20[144], 21[160]22[144], 3[160]4[144], 5[160]6[144], 7[160]8[144], 9[160]10[144] | SEQ ID NO: 603-SEQ ID NO: 613 | 2, 4, 6, 8 |
| 21[224]23[223], 21[248]23[255] | SEQ ID NO: 614-SEQ ID NO: 615 | 0, 4, 8 |
| 0[111]1[95], 0[143]1[127], 0[79]1[63], 2[111]0[112], 2[47]0[48], 2[79]0[80], 21[184]23[191], 23[160]22[176], 23[192]22[208], 23[224]22[240] | SEQ ID NO: 606-SEQ ID NO: 625 | 0, 4, 6, 8 |
| 1[32]3[31], 11[32]13[31], 13[32]15[31], 15[32]17[31], 17[32]19[31], 19[32]21[31], 3[32]5[31], 5[32]7[31], 7[32]9[31], 9[32]11[31] | SEQ ID NO: 626-SEQ ID NO: 635 | 0, 2, 8 |
| 0[207]1[191], 0[239]1[223], 0[271]1[255], 10[271]8[272], 12[271]10[272], 14[271]12[272], 16[271]14[272], 18[271]16[272], 2[175]0[176], 2[207]0[208], 2[239]0[240], 2[271]0[272], 20[271]18[272], 22[271]20[272], 4[271]2[272], 6[271]4[272], 8[271]6[272] | SEQ ID NO: 636-SEQ ID NO: 652 | 0, 2, 6, 8 |
| 21[32]23[31], 21[56]23[63], 21[96]23[95], 23[32]22[48], 23[64]22[80], 23[96]22[112] | SEQ ID NO: 653-SEQ ID NO: 658 | 0, 2, 4, 8 |
| 0[175]0[144], 0[47]1[31], 23[128]23[159], 23[256]22[272] | SEQ ID NO: 659-SEQ ID NO: 662 | 0, 2, 4, 6, 8 |
| 21[120]23[127] | SEQ ID NO: 663 | 0, 2, 4 |
| 1[128]4[128], 1[192]4[192], 1[224]3[223], 1[256]4[256], 1[64]4[64], 1[96]3[95], 10[111]8[112], 10[143]9[159], 10[175]8[176], 10[207]8[208], 10[239]8[240], 10[47]8[48], 10[79]8[80], 11[128]13[127], 11[192]13[191], 11[224]13[223], 11[256]13[255], 11[64]13[63], 11[96]13[95], 12[111]10[112], 12[143]11[159], 12[175]10[176], 12[207]10[208], 12[239]10[240], 12[47]10[48], 12[79]10[80], 13[128]15[127], 13[192]15[191], 13[224]15[223], 13[256]15[255], 13[64]15[63], 13[96]15[95], 14[111]12[112], 14[143]13[159], 14[175]12[176], 14[207]12[208], 14[239]12[240], 14[47]12[48], 14[79]12[80], 15[128]18[128], 15[192]18[192], 15[224]17[223], 15[256]18[256], 15[64]18[64], 15[96]17[95], 16[111]14[112], 16[143]15[159], 16[175]14[176], 16[207]14[208], 16[239]14[240], 16[47]14[48], 16[79]14[80], 17[224]19[223], 17[96]19[95], 18[111]16[112], 18[143]17[159], 18[175]16[176], 18[207]16[208], 18[239]16[240], 18[47]16[48], 18[79]16[80], 19[224]21[223], 19[96]21[95], 2[143]1[159], 20[111]18[112], 20[143]19[159], 20[175]18[176], 20[207]18[208], 20[239]18[240], 20[47]18[48], 20[79]18[80], 22[111]20[112], 22[143]21[159], 22[175]20[176], 22[207]20[208], 22[239]20[240], 22[47]20[48], 22[79]20[80], 3[224]5[223], 3[96]5[95], 4[111]2[112], 4[143]3[159], 4[175]2[176], 4[207]2[208], 4[239]2[240], 4[47]2[48], 4[79]2[80], 5[224]7[223], 5[96]7[95], 6[111]4[112], 6[143]5[159], 6[175]4[176], 6[207]4[208], 6[239]4[240], 6[47]4[48], 6[79]4[80], 7[120]9[127], 7[184]9[191], 7[224]9[223], 7[248]9[255], 7[56]9[63], 7[96]9[95], 8[111]6[112], 8[143]7[159], 8[175]6[176], 8[207]6[208], 8[239]6[240], 8[47]6[48], 8[79]6[80], 9[128]11[127], 9[192]11[191], 9[224]11[223], 9[256]11[255], 9[64]11[63], 9[96]11[95] | SEQ ID NO: 664-SEQ ID NO: 778 | Structure Staple |
| 4[63]6[56], 4[255]6[248], 4[191]6[184], 4[127]6[120], 18[63]20[56], 18[255]20[248], 18[191]20[184], 18[127]20[120], | SEQ ID NO: 779-SEQ ID NO: 786 | 5'-Biotin |

TABLE 5

Staple sequences for DNA origami structures for in vitro Exchange-PAINT demonstration (digits 0 to 3)

| Position* | Sequence Identifiers | Description (number) |
|---|---|---|
| 2[47]0[48], 2[79]0[80], 2[111]0[112], 2[143]1[159], 2[175]0[176], 2[207]0[208], 2[239]0[240], 6[47]4[48], 6[239]4[240], 10[47]8[48], 10[239]8[240], 14[47]12[48], 14[239]12[240], 18[47]16[48], 18[239]16[240], 22[47]20[48], 22[79]20[80], 22[111]20[112], 22[143]21[159], 22[175]20[176], 22[207]20[208], 22[239]20[240] | SEQ ID NO: 787-SEQ ID NO: 808 | 0 |
| 9[64]11[63], 9[96]11[95], 9[128]11[127], 9[192]11[191], 9[224]11[223], 9[256]11[255], 11[64]13[63], 11[96]13[95], 11[128]13[127], 11[160]12[144], 11[192]13[191], 11[224]13[223], 11[256]13[255], 12[47]10[48], 12[79]10[80], 12[111]10[112], 12[175]10[176], 12[207]10[208], 12[239]10[240], 13[160]14[144], 14[79]12[80], 14[111] 12[112], 14[175]12[176], 14[207]12[208] | SEQ ID NO: 809-SEQ ID NO: 832 | 1 |
| 0[175]0[144], 0[207]1[191], 0[239]1[223], 0[271]1[255], 1[32]3[31], 4[143]3[159], 4[271]2[272], 5[32]7[31], 8[143]7[159], 8[271]6[272], 9[32]11[31], 12[143]11[159], 12[271]10[272], 13[32]15[31], 16[143]15[159], 16[271]14[272], 17[32]19[31], 20[143]19[159], 20[271]18[272], 21[32]23[31], 21[56]23[63], 21[96]23[95], 21[120]23[127], 21[160]22[144], 23[256]22[272] | SEQ ID NO: 833-SEQ ID NO: 857 | 2 |
| 0[47]1[31], 2[271]0[272], 3[32]5[31], 6[143]5[159], 6[271]4[272], 7[32]9[31], 10[143]9[159], 10[271]8[272], 11[32]13[31], 14[143]13[159], 14[271]12[272], | SEQ ID NO: 858-SEQ ID NO: 881 | 3 |

TABLE 5-continued

Staple sequences for DNA origami structures for in vitro Exchange-PAINT demonstration (digits 0 to 3)

| Position* | Sequence Identifiers | Description (number) |
| --- | --- | --- |
| 15[32]17[31], 18[143]17[159], 18[271]16[272], 19[32]21[31], 19[160]20[144], 22[271]20[272], 23[32]22[48], 23[64]22[80], 23[96]22[112], 23[128]23[159], 23[160]22[176], 23[192]22[208], 23[224]22[240] | | |

TABLE 6

DNA-PAINT docking and imager sequences and biotin docking sequence

| Description | SEQ ID NO: | Sequence |
| --- | --- | --- |
| Imager P1* | 884 | 5'-CTAGATGTAT-dye |
| Imager P2* | 885 | 5'-TATGTAGATC-dye |
| Imager P3* | 886 | 5'-GTAATGAAGA-dye |
| Imager P4* | 887 | 5'-GTAGATTCAT-dye |
| Imager P5* | 888 | 5'-CTTTACCTAA-dye |
| Imager P6* | 889 | 5'-GTACTCAATT-dye |
| Imager P7* | 890 | 5'-CATCCTAATT-dye |
| Imager P8* | 891 | 5'-GATCCATTAT-dye |
| Imager P9* | 892 | 5'-CACCTTATTA-dye |
| Imager P10* | 893 | 5'-CCTTCTCTAT-dye |
| Imager P11* | 894 | 5'-GTATCATCAA-dye |
| Imager P12* | 895 | 5'-GAATCACTAT-dye |
| 9 nt P1 docking site | 896 | Strand-TTATACATCTA-3' |
| 9 nt P2 docking site | 897 | Strand-TTATCTACATA-3' |
| 10 nt P2 docking site | 898 | Strand-TTGATCTACATA-3' |
| 9 nt P3 docking site | 899 | Strand-TTTCTTCATTA-3' |
| 9 nt P4 docking site | 900 | Strand-TTATGAATCTA-3' |
| 9 nt P5 docking site | 901 | Strand-TTTTAGGTAAA-3' |
| 9 nt P6 docking site | 902 | Strand-TTAATTGAGTA-3' |
| 9 nt P7 docking site | 903 | Strand-TTAATTAGGAT-3' |
| 9 nt P8 docking site | 904 | Strand-TTATAATGGAT-3' |
| 9 nt P9 docking site | 905 | Strand-TTTAATAAGGT-3' |
| 9 nt P10 docking site | 906 | Strand-TTATAGAGAAG-3' |
| 9 nt P11 docking site | 907 | Strand-TTTTGATGATA-3' |
| 9 nt P12 docking site | 908 | Strand-TTATAGTGATT-3' |
| Biotinylated P1 docking site for antibody coupling | 909 | Biotin-TTATACATCTA-3' |
| Biotinylated P2 docking site for antibody coupling | 910 | Biotin-TTATCTACATA-3' |
| Biotinylated P3 docking site for antibody coupling | 911 | Biotin-TTTCTTCATTA-3' |
| Biotinylated P4 docking site for antibody coupling | 912 | Biotin-TTATGAATCTA-3' |
| Biotinylated docking site for microtubule-like structure | 913 | Biotin-GAATCGGTCACAGTACAACCG-3' |

REFERENCES

1. Rust, M. J., Bates, M. & Zhuang, X. Sub-diffraction-limit imaging by stochastic optical reconstruction microscopy (STORM). Nat Methods 3, 793-5 (2006).
2. Hell, S. W. Microscopy and its focal switch. Nature methods 6, 24-32 (2009).
3. Hell, S. W. & Wichmann, J. Breaking the diffraction resolution limit by stimulated emission: stimulated-emission-depletion fluorescence microscopy. Opt Lett 19, 780-2 (1994).
4. Betzig, E., Patterson, G. H., Sougrat, R., Lindwasser, O. W., Olenych, S., Bonifacino, J. S., Davidson, M. W., Lippincott-Schwartz, J. & Hess, H. F. Imaging intracellular fluorescent proteins at nanometer resolution. Science 313, 1642-5 (2006).
5. Sharonov, A. & Hochstrasser, R. M. Wide-field subdiffraction imaging by accumulated binding of diffusing probes. Proceedings of the National Academy of Sciences of the United States of America 103, 18911-18916 (2006).
6. Giannone, G., Hosy, E., Levet, F., Constals, A., Schulze, K., Sobolevsky, A. I., Rosconi, M. P., Gouaux, E., Tampe, R., Choquet, D. & Cognet, L. Dynamic superresolution imaging of endogenous proteins on living cells at ultra-high density. Biophys J 99, 1303-10 (2010).
7. Lew, M. D., Lee, S. F., Ptacin, J. L., Lee, M. K., Twieg, R. J., Shapiro, L. & Moerner, W. E. Three-dimensional superresolution colocalization of intracellular protein superstructures and the cell surface in live *Caulobacter crescentus*. Proc Natl Acad Sci USA 108, E1102-10 (2011).
8. Jungmann, R., Steinhauer, C., Scheible, M., Kuzyk, A., Tinnefeld, P. & Simmel, F. C. Single-Molecule Kinetics and Super-Resolution Microscopy by Fluorescence Imaging of Transient Binding on DNA Origami. Nano Letters 10, 4756-4761 (2010).
9. Tokunaga, M., Imamoto, N. & Sakata-Sogawa, K. Highly inclined thin illumination enables clear single-molecule imaging in cells. Nature Methods 5, 159-161 (2008).
10. Lin, C., Jungmann, R., Leifer, A. M., Li, C., Levner, D., Church, G. M., Shih, W. M. & Yin, P. Submicrometre geometrically encoded fluorescent barcodes self-assembled from DNA. Nat Chem 4, 832-9 (2012).
11. Derr, N. D., Goodman, B. S., Jungmann, R., Leschziner, A. E., Shih, W. M. & Reck-Peterson, S. L. Tug-of-war in motor protein ensembles revealed with a programmable DNA origami scaffold. Science 338, 662-5 (2012).
12. Johnson-Buck, A., Nangreave, J., Kim, D. N., Bathe, M., Yan, H. & Walter, N. G. Super-resolution fingerprinting detects chemical reactions and idiosyncrasies of single DNA pegboards. Nano Lett 13, 728-33 (2013).
13. Ries, J., Kaplan, C., Platonova, E., Eghlidi, H. & Ewers, H. A simple, versatile method for GFP-based super-resolution microscopy via nanobodies. Nat Methods 9, 582-4 (2012).
14. Lubeck, E. & Cai, L. Single-cell systems biology by super-resolution imaging and combinatorial labeling. Nat Methods 9, 743-8 (2012).
15. Wei, B., Dai, M. & Yin, P. Complex shapes self-assembled from single-stranded DNA tiles. Nature 485, 623-6 (2012).
16. Aitken, C. E., Marshall, R. A. & Puglisi, J. D. An oxygen scavenging system for improvement of dye stability in single-molecule fluorescence experiments. Biophys J 94, 1826-35 (2008).
17. Rasnik, I., McKinney, S. A. & Ha, T. Nonblinking and long-lasting single-molecule fluorescence imaging. Nat Methods 3, 891-3 (2006).
18. Huang, B., Wang, W., Bates, M. & Zhuang, X. Three-dimensional super-resolution imaging by stochastic optical reconstruction microscopy. Science 319, 810-3 (2008).
19. Paige, J. S., Wu, K. Y. & Jaffrey, S. R. RNA mimics of green fluorescent protein. Science 333, 642-6 (2011).
20. Hein, B., Willig, K. I. & Hell, S. W. Stimulated emission depletion (STED) nanoscopy of a fluorescent protein-labeled organelle inside a living cell. *Proc Natl Acad Sci USA* 105, 14271-6 (2008).
21. Jones, S. A., Shim, S. H., He, J. & Zhuang, X. Fast, three-dimensional super-resolution imaging of live cells. *Nature methods* 8, 499-508 (2011).
22. Willig, K. I. et al. Nanoscale resolution in GFP-based microscopy. *Nat Methods* 3, 721-3 (2006).
23. Stoltenburg, R., Reinemann, C. & Strehlitz, B. SELEX—a (r)evolutionary method to generate high-affinity nucleic acid ligands. *Biomol Eng* 24, 381-403 (2007).
24. Paige, J. S., Nguyen-Duc, T., Song, W. & Jaffrey, S. R. Fluorescence imaging of cellular metabolites with RNA. *Science* 335, 1194 (2012).
25. Jaffrey, S. R. Personal Communication. *Personal Communication* (2013).
26. Fukusaki, E. et al. SELEX for tubulin affords specific T-rich DNA aptamers. Systematic evolution of ligands by exponential enrichment. *Bioorg Med Chem Lett* 11, 2927-30 (2001).

---

What is claimed is:

1. A method of detecting a target in a sample, the method comprising:
contacting the sample with (a) at least one antibody-DNA conjugate that comprises an antibody linked to a docking strand, and (b) at least one fluorescently-labeled imager strand that is complementary to the docking strand of the at least one antibody-DNA conjugate, wherein the at least one fluorescently-labeled imager strand is capable of transiently binding to the docking strand for about 0.1 to about 10 seconds at room temperature; and
imaging fluorescence blinking produced by the binding of the at least one fluorescently-labeled imager strand to the docking strand of the at least one antibody-DNA conjugate, thereby determining whether the at least one antibody-DNA conjugate binds to the target in the sample.

2. The method of claim 1, wherein the antibody is a monoclonal antibody.

3. The method of claim 1, wherein the sample is contacted with at least two fluorescently-labeled imager strands, wherein the docking strand comprises at least two domains, and wherein each domain is complementary to an imager strand.

4. The method of claim 1, comprising:
contacting the sample with (a) at least two different antibody-DNA conjugates, each comprising an antibody linked to a docking strand, and (b) at least two labeled imager strands that are complementary to respective docking strands of the at least two different antibody-DNA conjugates; and
imaging fluorescence blinking produced by the binding of the at least one fluorescently-labeled imager strand to the docking strand of the at least one antibody-DNA conjugate, thereby determining whether the at least two antibody-DNA conjugates bind to at least two targets in the sample.

5. The method of claim 4, wherein the sample is contacted sequentially with the at least two labeled imager strands of (b).

6. The method of claim 5, comprising, in the following ordered steps:
contacting the sample with a first antibody-DNA conjugate and at least one other antibody-DNA conjugate;
contacting the sample with a first labeled imager strand that is complementary to the docking strand of the first antibody-DNA conjugate;
imaging the sample to obtain a first image;
removing the first labeled imager strand;
contacting the sample with at least one other labeled imager strand that is complementary to the docking strand of the at least one other antibody-DNA conjugate; and
imaging the sample to obtain at least one other image.

7. The method of claim 5, comprising, in the following ordered steps:
contacting the sample with a first antibody-DNA conjugate;
contacting the sample with a first labeled imager strand that is complementary to the docking strand of the first antibody-DNA conjugate;
imaging the sample to obtain a first image;
removing the first labeled imager strand;
contacting the sample with at least one other antibody-DNA conjugate;
contacting the sample with at least one other labeled imager strand that is complementary to the docking strand of the at least one other antibody-DNA conjugate; and
imaging the sample to obtain at least one other image.

8. The method of claim 1, wherein the fluorescently-labeled imager strand is 4 to 30 nucleotides in length.

9. The method of claim 1, wherein the fluorescently-labeled imager strand is 8 to 10 nucleotides in length.

10. The method of claim 1, wherein the target is a protein.

11. The method of claim 3, wherein the at least two fluorescently-labeled imager strands are spectrally distinct from one another.

12. The method of claim 4, wherein the at least two fluorescently-labeled imager strands are spectrally distinct from one another.

13. The method of claim 1, wherein the at least one fluorescently-labeled imager strand transiently binds to the docking strand for about 0.1 second to about 5 seconds.

14. The method of claim 1, wherein the at least one antibody-DNA conjugate comprises a biotinylated antibody linked to a biotinylated docking strand through a streptavidin linker.

15. The method of claim 4, wherein each of the at least two different antibody-DNA conjugates comprises a biotinylated antibody linked to a biotinylated docking strand through a streptavidin linker.

16. The method of claim 1, wherein the fluorescently-labeled imager strand is 4 to 9 nucleotides in length.

17. The method of claim 1, wherein the fluorescently-labeled imager strand is 8 or 9 nucleotides in length.

* * * * *

UNITED STATES PATENT AND TRADEMARK OFFICE
CERTIFICATE OF CORRECTION

| | | |
|---|---|---|
| PATENT NO. | : 11,536,715 B2 | Page 1 of 1 |
| APPLICATION NO. | : 16/559490 | |
| DATED | : December 27, 2022 | |
| INVENTOR(S) | : Ralf Jungmann et al. | |

It is certified that error appears in the above-identified patent and that said Letters Patent is hereby corrected as shown below:

In the Specification

At Column 1, Lines 17-18, please insert the following section:
--GOVERNMENT SUPPORT
This invention was made with government support under EB018659, OD007292, and HD072481 awarded by the National Institutes of Health, N00014-13-1-0593, N00014-10-1-0827, and N00014-11-1-0914 awarded by the Office of Naval Research, and 1162459, and 1054898 awarded by the National Science Foundation. The government has certain rights in the invention.--

Signed and Sealed this
Sixth Day of August, 2024

*Katherine Kelly Vidal*

Katherine Kelly Vidal
*Director of the United States Patent and Trademark Office*

SEQUENCE LISTING

<160> NUMBER OF SEQ ID NOS: 913

<210> SEQ ID NO 1
<211> LENGTH: 32
<212> TYPE: DNA
<213> ORGANISM: Artificial
<220> FEATURE:
<223> OTHER INFORMATION: Synthetic Polynucleotide

<400> SEQUENCE: 1
aggccacctc accagttcaa cagtggcgtt tt          32

<210> SEQ ID NO 2
<211> LENGTH: 32
<212> TYPE: DNA

```
<213> ORGANISM: Artificial
<220> FEATURE:
<223> OTHER INFORMATION: Synthetic Polynucleotide

<400> SEQUENCE: 2
cgtcaaaggg cgaaaacatt ctggccatcc ac                                    32

<210> SEQ ID NO 3
<211> LENGTH: 48
<212> TYPE: DNA
<213> ORGANISM: Artificial
<220> FEATURE:
<223> OTHER INFORMATION: Synthetic Polynucleotide

<400> SEQUENCE: 3
agaatgcgca gcgcagtact tatagctcac acattcaact tcataacc                   48

<210> SEQ ID NO 4
<211> LENGTH: 32
<212> TYPE: DNA
<213> ORGANISM: Artificial
<220> FEATURE:
<223> OTHER INFORMATION: Synthetic Polynucleotide

<400> SEQUENCE: 4
ccttacacag caaatcgttt gggtggtaaa ac                                    32

<210> SEQ ID NO 5
<211> LENGTH: 40
<212> TYPE: DNA
<213> ORGANISM: Artificial
<220> FEATURE:
<223> OTHER INFORMATION: Synthetic Polynucleotide

<400> SEQUENCE: 5
aattcgcgtc tggcctagct ttcacaggtc agtaccttta                            40

<210> SEQ ID NO 6
<211> LENGTH: 48
<212> TYPE: DNA
<213> ORGANISM: Artificial
<220> FEATURE:
<223> OTHER INFORMATION: Synthetic Polynucleotide

<400> SEQUENCE: 6
tggcagatga gtaaaaaatc gccatatttta actgtaattt aggacaac                  48

<210> SEQ ID NO 7
<211> LENGTH: 48
<212> TYPE: DNA
<213> ORGANISM: Artificial
<220> FEATURE:
<223> OTHER INFORMATION: Synthetic Polynucleotide

<400> SEQUENCE: 7
cacgctggtt aaacgggtaa acaatttggg aaggcttgca catcggaa                   48

<210> SEQ ID NO 8
<211> LENGTH: 32
<212> TYPE: DNA
<213> ORGANISM: Artificial
<220> FEATURE:
<223> OTHER INFORMATION: Synthetic Polynucleotide

<400> SEQUENCE: 8
acgggcaaca gctgggtttc tgccagcact ca                                    32
```

<210> SEQ ID NO 9
<211> LENGTH: 29
<212> TYPE: DNA
<213> ORGANISM: Artificial
<220> FEATURE:
<223> OTHER INFORMATION: Synthetic Polynucleotide

<400> SEQUENCE: 9
gacgatcgcg ggcctgggaa gaaaaatct                              29

<210> SEQ ID NO 10
<211> LENGTH: 48
<212> TYPE: DNA
<213> ORGANISM: Artificial
<220> FEATURE:
<223> OTHER INFORMATION: Synthetic Polynucleotide

<400> SEQUENCE: 10
gtctgaaaaa caggaagaag gcttcgggta ggaatcatta ccgcgccc         48

<210> SEQ ID NO 11
<211> LENGTH: 40
<212> TYPE: DNA
<213> ORGANISM: Artificial
<220> FEATURE:
<223> OTHER INFORMATION: Synthetic Polynucleotide

<400> SEQUENCE: 11
aagagacaga gatagagacc tgaaaaatca agctattttg                  40

<210> SEQ ID NO 12
<211> LENGTH: 31
<212> TYPE: DNA
<213> ORGANISM: Artificial
<220> FEATURE:
<223> OTHER INFORMATION: Synthetic Polynucleotide

<400> SEQUENCE: 12
gtttgatgaa tcggcaaaat ttgcgtattg g                           31

<210> SEQ ID NO 13
<211> LENGTH: 48
<212> TYPE: DNA
<213> ORGANISM: Artificial
<220> FEATURE:
<223> OTHER INFORMATION: Synthetic Polynucleotide

<400> SEQUENCE: 13
ttttcacccc taaaacaaag aataagcacc attacagcgt cagactgt         48

<210> SEQ ID NO 14
<211> LENGTH: 40
<212> TYPE: DNA
<213> ORGANISM: Artificial
<220> FEATURE:
<223> OTHER INFORMATION: Synthetic Polynucleotide

<400> SEQUENCE: 14
ggcatcaggg aggtgtcgag gcatatagcg agaggcttat                  40

<210> SEQ ID NO 15
<211> LENGTH: 48
<212> TYPE: DNA
<213> ORGANISM: Artificial
<220> FEATURE:

<223> OTHER INFORMATION: Synthetic Polynucleotide

<400> SEQUENCE: 15
ttaaatgtca acccgtcggc gcataaatta ttctccgtgg cggattga            48

<210> SEQ ID NO 16
<211> LENGTH: 48
<212> TYPE: DNA
<213> ORGANISM: Artificial
<220> FEATURE:
<223> OTHER INFORMATION: Synthetic Polynucleotide

<400> SEQUENCE: 16
atcacccagc cattgctgga ttatgaacgc gaagggctta gaacaaag            48

<210> SEQ ID NO 17
<211> LENGTH: 44
<212> TYPE: DNA
<213> ORGANISM: Artificial
<220> FEATURE:
<223> OTHER INFORMATION: Synthetic Polynucleotide

<400> SEQUENCE: 17
accttctacc ctactgcggg atcttaccag tataaagaaa aagc                44

<210> SEQ ID NO 18
<211> LENGTH: 32
<212> TYPE: DNA
<213> ORGANISM: Artificial
<220> FEATURE:
<223> OTHER INFORMATION: Synthetic Polynucleotide

<400> SEQUENCE: 18
gagtgttgtt ctccgagtgg tcagtttgga ac                            32

<210> SEQ ID NO 19
<211> LENGTH: 40
<212> TYPE: DNA
<213> ORGANISM: Artificial
<220> FEATURE:
<223> OTHER INFORMATION: Synthetic Polynucleotide

<400> SEQUENCE: 19
gcgccagggt ggtcgtgagg cgaagaatta tgttcaacag                    40

<210> SEQ ID NO 20
<211> LENGTH: 40
<212> TYPE: DNA
<213> ORGANISM: Artificial
<220> FEATURE:
<223> OTHER INFORMATION: Synthetic Polynucleotide

<400> SEQUENCE: 20
atcccacggc agcaaccgca agaaatgact tgtagaacgt                    40

<210> SEQ ID NO 21
<211> LENGTH: 32
<212> TYPE: DNA
<213> ORGANISM: Artificial
<220> FEATURE:
<223> OTHER INFORMATION: Synthetic Polynucleotide

<400> SEQUENCE: 21
agaatacgag cgtaaatcgt cgctattaat ta                            32

```
<210> SEQ ID NO 22
<211> LENGTH: 32
<212> TYPE: DNA
<213> ORGANISM: Artificial
<220> FEATURE:
<223> OTHER INFORMATION: Synthetic Polynucleotide

<400> SEQUENCE: 22
ccctcggcca acgcgcaact aaagtaataa tt                                  32

<210> SEQ ID NO 23
<211> LENGTH: 40
<212> TYPE: DNA
<213> ORGANISM: Artificial
<220> FEATURE:
<223> OTHER INFORMATION: Synthetic Polynucleotide

<400> SEQUENCE: 23
tatgagcatc agcggggcgc tttctaaccg tgcatctgcc                          40

<210> SEQ ID NO 24
<211> LENGTH: 48
<212> TYPE: DNA
<213> ORGANISM: Artificial
<220> FEATURE:
<223> OTHER INFORMATION: Synthetic Polynucleotide

<400> SEQUENCE: 24
atcggccttg ctggtacaat attatcaata atatccggta ttctccca                 48

<210> SEQ ID NO 25
<211> LENGTH: 48
<212> TYPE: DNA
<213> ORGANISM: Artificial
<220> FEATURE:
<223> OTHER INFORMATION: Synthetic Polynucleotide

<400> SEQUENCE: 25
atatctatta tctggtcagt tggcttatct aatctttcct taccgcac                 48

<210> SEQ ID NO 26
<211> LENGTH: 34
<212> TYPE: DNA
<213> ORGANISM: Artificial
<220> FEATURE:
<223> OTHER INFORMATION: Synthetic Polynucleotide

<400> SEQUENCE: 26
cgcgaactga ttggcacaga caatatatgg aaat                                34

<210> SEQ ID NO 27
<211> LENGTH: 32
<212> TYPE: DNA
<213> ORGANISM: Artificial
<220> FEATURE:
<223> OTHER INFORMATION: Synthetic Polynucleotide

<400> SEQUENCE: 27
attttccctc aaagaaaag gctccaaaag ga                                   32

<210> SEQ ID NO 28
<211> LENGTH: 30
<212> TYPE: DNA
<213> ORGANISM: Artificial
<220> FEATURE:
<223> OTHER INFORMATION: Synthetic Polynucleotide
```

<400> SEQUENCE: 28
cgtaatctgc caacggccac agttgaggat                              30

<210> SEQ ID NO 29
<211> LENGTH: 40
<212> TYPE: DNA
<213> ORGANISM: Artificial
<220> FEATURE:
<223> OTHER INFORMATION: Synthetic Polynucleotide

<400> SEQUENCE: 29
cagcgtggtg ctgcaggtca ttggaaacca aaagtaagag                   40

<210> SEQ ID NO 30
<211> LENGTH: 40
<212> TYPE: DNA
<213> ORGANISM: Artificial
<220> FEATURE:
<223> OTHER INFORMATION: Synthetic Polynucleotide

<400> SEQUENCE: 30
gctatatgtg agtgaaaatt tcttatagcc cgagatagta                   40

<210> SEQ ID NO 31
<211> LENGTH: 40
<212> TYPE: DNA
<213> ORGANISM: Artificial
<220> FEATURE:
<223> OTHER INFORMATION: Synthetic Polynucleotide

<400> SEQUENCE: 31
tttccagtaa tgagtgagct aactgagccg gaagcataaa                   40

<210> SEQ ID NO 32
<211> LENGTH: 38
<212> TYPE: DNA
<213> ORGANISM: Artificial
<220> FEATURE:
<223> OTHER INFORMATION: Synthetic Polynucleotide

<400> SEQUENCE: 32
tttcccgttc aactttaatc attttatgcg attgtaaa                     38

<210> SEQ ID NO 33
<211> LENGTH: 44
<212> TYPE: DNA
<213> ORGANISM: Artificial
<220> FEATURE:
<223> OTHER INFORMATION: Synthetic Polynucleotide

<400> SEQUENCE: 33
atagctggaa attggaggtt tccctcagaa cagtatatat acgc              44

<210> SEQ ID NO 34
<211> LENGTH: 48
<212> TYPE: DNA
<213> ORGANISM: Artificial
<220> FEATURE:
<223> OTHER INFORMATION: Synthetic Polynucleotide

<400> SEQUENCE: 34
agttttaaga cgataatctg gtcacaacca gcttacggct atgccggg          48

<210> SEQ ID NO 35
<211> LENGTH: 46

<212> TYPE: DNA
<213> ORGANISM: Artificial
<220> FEATURE:
<223> OTHER INFORMATION: Synthetic Polynucleotide

<400> SEQUENCE: 35
gcgcatcggc actcaatccg ccgggcaacg ggaacagcgg ttgcgg          46

<210> SEQ ID NO 36
<211> LENGTH: 39
<212> TYPE: DNA
<213> ORGANISM: Artificial
<220> FEATURE:
<223> OTHER INFORMATION: Synthetic Polynucleotide

<400> SEQUENCE: 36
ataggtcacg ttggtgggag caaagagcgg aatcgtcat                  39

<210> SEQ ID NO 37
<211> LENGTH: 32
<212> TYPE: DNA
<213> ORGANISM: Artificial
<220> FEATURE:
<223> OTHER INFORMATION: Synthetic Polynucleotide

<400> SEQUENCE: 37
gaggaaggaa atcaacgaaa ccaaccgttg cc                         32

<210> SEQ ID NO 38
<211> LENGTH: 36
<212> TYPE: DNA
<213> ORGANISM: Artificial
<220> FEATURE:
<223> OTHER INFORMATION: Synthetic Polynucleotide

<400> SEQUENCE: 38
aaattaaacg ccaccctcaa tcaatagtct ttaatg                     36

<210> SEQ ID NO 39
<211> LENGTH: 32
<212> TYPE: DNA
<213> ORGANISM: Artificial
<220> FEATURE:
<223> OTHER INFORMATION: Synthetic Polynucleotide

<400> SEQUENCE: 39
tacataaatc aattagttat cagcatcaat ag                         32

<210> SEQ ID NO 40
<211> LENGTH: 31
<212> TYPE: DNA
<213> ORGANISM: Artificial
<220> FEATURE:
<223> OTHER INFORMATION: Synthetic Polynucleotide

<400> SEQUENCE: 40
gggtgcctcg ggaaacctaa acatagcgat a                          31

<210> SEQ ID NO 41
<211> LENGTH: 32
<212> TYPE: DNA
<213> ORGANISM: Artificial
<220> FEATURE:
<223> OTHER INFORMATION: Synthetic Polynucleotide

<400> SEQUENCE: 41
tcagagggga cgacgattttt gccatagtaa aa                                    32

<210> SEQ ID NO 42
<211> LENGTH: 40
<212> TYPE: DNA
<213> ORGANISM: Artificial
<220> FEATURE:
<223> OTHER INFORMATION: Synthetic Polynucleotide

<400> SEQUENCE: 42
tgctgatctt taggagtaga taatcagagg gttttgaacc                             40

<210> SEQ ID NO 43
<211> LENGTH: 48
<212> TYPE: DNA
<213> ORGANISM: Artificial
<220> FEATURE:
<223> OTHER INFORMATION: Synthetic Polynucleotide

<400> SEQUENCE: 43
tgacctttaa ttaattcata tggtcggctt agataactat atggaatt                    48

<210> SEQ ID NO 44
<211> LENGTH: 30
<212> TYPE: DNA
<213> ORGANISM: Artificial
<220> FEATURE:
<223> OTHER INFORMATION: Synthetic Polynucleotide

<400> SEQUENCE: 44
gctcacaaaa cgcggtccgt ttaagggtaa                                        30

<210> SEQ ID NO 45
<211> LENGTH: 32
<212> TYPE: DNA
<213> ORGANISM: Artificial
<220> FEATURE:
<223> OTHER INFORMATION: Synthetic Polynucleotide

<400> SEQUENCE: 45
cggcctcagg aagcgctggc agcctccggt cc                                     32

<210> SEQ ID NO 46
<211> LENGTH: 31
<212> TYPE: DNA
<213> ORGANISM: Artificial
<220> FEATURE:
<223> OTHER INFORMATION: Synthetic Polynucleotide

<400> SEQUENCE: 46
ctagtcagag gcgaagagcc caacgctaac g                                      31

<210> SEQ ID NO 47
<211> LENGTH: 39
<212> TYPE: DNA
<213> ORGANISM: Artificial
<220> FEATURE:
<223> OTHER INFORMATION: Synthetic Polynucleotide

<400> SEQUENCE: 47
tcatatgctc atttggtgta aagagacgtt agagtgaga                              39

<210> SEQ ID NO 48
<211> LENGTH: 48
<212> TYPE: DNA
<213> ORGANISM: Artificial

```
<220> FEATURE:
<223> OTHER INFORMATION: Synthetic Polynucleotide

<400> SEQUENCE: 48
ccgccagcac cctcatgaaa cagcaaaaaa atcccgtaaa atttgtac                    48

<210> SEQ ID NO 49
<211> LENGTH: 40
<212> TYPE: DNA
<213> ORGANISM: Artificial
<220> FEATURE:
<223> OTHER INFORMATION: Synthetic Polynucleotide

<400> SEQUENCE: 49
ggttggccgt tccggcattc cacatttcgc caagtacgct                             40

<210> SEQ ID NO 50
<211> LENGTH: 32
<212> TYPE: DNA
<213> ORGANISM: Artificial
<220> FEATURE:
<223> OTHER INFORMATION: Synthetic Polynucleotide

<400> SEQUENCE: 50
cgtatcgcac tccagcggat aagtagctca aa                                     32

<210> SEQ ID NO 51
<211> LENGTH: 29
<212> TYPE: DNA
<213> ORGANISM: Artificial
<220> FEATURE:
<223> OTHER INFORMATION: Synthetic Polynucleotide

<400> SEQUENCE: 51
gagggtaaga gatccgtcca atactgaat                                         29

<210> SEQ ID NO 52
<211> LENGTH: 40
<212> TYPE: DNA
<213> ORGANISM: Artificial
<220> FEATURE:
<223> OTHER INFORMATION: Synthetic Polynucleotide

<400> SEQUENCE: 52
gaggatttag aagtatttaa atccaattga gctgagttaa                             40

<210> SEQ ID NO 53
<211> LENGTH: 48
<212> TYPE: DNA
<213> ORGANISM: Artificial
<220> FEATURE:
<223> OTHER INFORMATION: Synthetic Polynucleotide

<400> SEQUENCE: 53
gtgccacgtt tgcacgagcc taatttgccc tgaacaagca catcacct                    48

<210> SEQ ID NO 54
<211> LENGTH: 48
<212> TYPE: DNA
<213> ORGANISM: Artificial
<220> FEATURE:
<223> OTHER INFORMATION: Synthetic Polynucleotide

<400> SEQUENCE: 54
acctttttaa ccaagaaaca tctcttaaaa cgaaaagcca gcgccaaa                    48
```

<210> SEQ ID NO 55
<211> LENGTH: 40
<212> TYPE: DNA
<213> ORGANISM: Artificial
<220> FEATURE:
<223> OTHER INFORMATION: Synthetic Polynucleotide

<400> SEQUENCE: 55
atcgacatgg atcaaactta aattgagacg catttgtaac          40

<210> SEQ ID NO 56
<211> LENGTH: 46
<212> TYPE: DNA
<213> ORGANISM: Artificial
<220> FEATURE:
<223> OTHER INFORMATION: Synthetic Polynucleotide

<400> SEQUENCE: 56
agttaaacga tgctgaaaag ccgagaaccg catgtaccgt aacgga    46

<210> SEQ ID NO 57
<211> LENGTH: 40
<212> TYPE: DNA
<213> ORGANISM: Artificial
<220> FEATURE:
<223> OTHER INFORMATION: Synthetic Polynucleotide

<400> SEQUENCE: 57
cgcttctgcc aggcaagccg tcgagaaccg cctccctcag          40

<210> SEQ ID NO 58
<211> LENGTH: 31
<212> TYPE: DNA
<213> ORGANISM: Artificial
<220> FEATURE:
<223> OTHER INFORMATION: Synthetic Polynucleotide

<400> SEQUENCE: 58
tgcaaccgtt ctagctgata ctttccggca c                   31

<210> SEQ ID NO 59
<211> LENGTH: 30
<212> TYPE: DNA
<213> ORGANISM: Artificial
<220> FEATURE:
<223> OTHER INFORMATION: Synthetic Polynucleotide

<400> SEQUENCE: 59
tcaccatcaa tatgatattc gggtcaggtt                     30

<210> SEQ ID NO 60
<211> LENGTH: 40
<212> TYPE: DNA
<213> ORGANISM: Artificial
<220> FEATURE:
<223> OTHER INFORMATION: Synthetic Polynucleotide

<400> SEQUENCE: 60
ggttagcccg aacgttattt tgcgtaataa gattagagag          40

<210> SEQ ID NO 61
<211> LENGTH: 40
<212> TYPE: DNA
<213> ORGANISM: Artificial
<220> FEATURE:
<223> OTHER INFORMATION: Synthetic Polynucleotide

<400> SEQUENCE: 61
agaaataata gattttatat tatttatcca gcgcattaga                          40

<210> SEQ ID NO 62
<211> LENGTH: 46
<212> TYPE: DNA
<213> ORGANISM: Artificial
<220> FEATURE:
<223> OTHER INFORMATION: Synthetic Polynucleotide

<400> SEQUENCE: 62
attcatttca acatatcaaa gacaccacgg tctttccagt aacaaa                   46

<210> SEQ ID NO 63
<211> LENGTH: 48
<212> TYPE: DNA
<213> ORGANISM: Artificial
<220> FEATURE:
<223> OTHER INFORMATION: Synthetic Polynucleotide

<400> SEQUENCE: 63
tggtgaagag acggtctgta gcatgacaac gtcaccaatg gtacaacg                 48

<210> SEQ ID NO 64
<211> LENGTH: 40
<212> TYPE: DNA
<213> ORGANISM: Artificial
<220> FEATURE:
<223> OTHER INFORMATION: Synthetic Polynucleotide

<400> SEQUENCE: 64
attcgccagc aactgtcgcc accccaccct cagagcccat                          40

<210> SEQ ID NO 65
<211> LENGTH: 30
<212> TYPE: DNA
<213> ORGANISM: Artificial
<220> FEATURE:
<223> OTHER INFORMATION: Synthetic Polynucleotide

<400> SEQUENCE: 65
aaaaaagggt gagaatagga ttagcgggtg                                     30

<210> SEQ ID NO 66
<211> LENGTH: 32
<212> TYPE: DNA
<213> ORGANISM: Artificial
<220> FEATURE:
<223> OTHER INFORMATION: Synthetic Polynucleotide

<400> SEQUENCE: 66
ctgttgcgag aaaaatacca gttacaaaat aa                                  32

<210> SEQ ID NO 67
<211> LENGTH: 40
<212> TYPE: DNA
<213> ORGANISM: Artificial
<220> FEATURE:
<223> OTHER INFORMATION: Synthetic Polynucleotide

<400> SEQUENCE: 67
atcgcgcaga ggctaaaaca tgttgcagtc gatcaccgtc                          40

<210> SEQ ID NO 68

<211> LENGTH: 44
<212> TYPE: DNA
<213> ORGANISM: Artificial
<220> FEATURE:
<223> OTHER INFORMATION: Synthetic Polynucleotide

<400> SEQUENCE: 68
gaggcgcgga tagcctcata ggatctaaag tttatttatc aaaa                        44

<210> SEQ ID NO 69
<211> LENGTH: 45
<212> TYPE: DNA
<213> ORGANISM: Artificial
<220> FEATURE:
<223> OTHER INFORMATION: Synthetic Polynucleotide

<400> SEQUENCE: 69
aactttgatg agtttccacc gtaacagaat accggatatt cacgg                       45

<210> SEQ ID NO 70
<211> LENGTH: 48
<212> TYPE: DNA
<213> ORGANISM: Artificial
<220> FEATURE:
<223> OTHER INFORMATION: Synthetic Polynucleotide

<400> SEQUENCE: 70
gtagctgctt cagcagcacc accggagggt tgagcccgga ataggtaa                    48

<210> SEQ ID NO 71
<211> LENGTH: 50
<212> TYPE: DNA
<213> ORGANISM: Artificial
<220> FEATURE:
<223> OTHER INFORMATION: Synthetic Polynucleotide

<400> SEQUENCE: 71
ttttagaacc ctcgcaaaat taagcaatag caaggcaaag aattaatata                  50

<210> SEQ ID NO 72
<211> LENGTH: 32
<212> TYPE: DNA
<213> ORGANISM: Artificial
<220> FEATURE:
<223> OTHER INFORMATION: Synthetic Polynucleotide

<400> SEQUENCE: 72
cagtaacaca tcgggataaa taaggcgcca gt                                     32

<210> SEQ ID NO 73
<211> LENGTH: 32
<212> TYPE: DNA
<213> ORGANISM: Artificial
<220> FEATURE:
<223> OTHER INFORMATION: Synthetic Polynucleotide

<400> SEQUENCE: 73
caattgaata ccaagtctta ttacagcaaa cg                                     32

<210> SEQ ID NO 74
<211> LENGTH: 32
<212> TYPE: DNA
<213> ORGANISM: Artificial
<220> FEATURE:
<223> OTHER INFORMATION: Synthetic Polynucleotide

<400> SEQUENCE: 74
tccatgttta tttgtatcat cgcctgataa at                                            32

<210> SEQ ID NO 75
<211> LENGTH: 45
<212> TYPE: DNA
<213> ORGANISM: Artificial
<220> FEATURE:
<223> OTHER INFORMATION: Synthetic Polynucleotide

<400> SEQUENCE: 75
ttttaaatgc aatgcctgag taataagagg ctgagtaact atttc                              45

<210> SEQ ID NO 76
<211> LENGTH: 40
<212> TYPE: DNA
<213> ORGANISM: Artificial
<220> FEATURE:
<223> OTHER INFORMATION: Synthetic Polynucleotide

<400> SEQUENCE: 76
gcaattcatc attttagtac cataggacaa tccaaataag                                    40

<210> SEQ ID NO 77
<211> LENGTH: 48
<212> TYPE: DNA
<213> ORGANISM: Artificial
<220> FEATURE:
<223> OTHER INFORMATION: Synthetic Polynucleotide

<400> SEQUENCE: 77
ttgctagaaa tttaatggtt tgaacagcag cgaaagacag gggagtta                           48

<210> SEQ ID NO 78
<211> LENGTH: 36
<212> TYPE: DNA
<213> ORGANISM: Artificial
<220> FEATURE:
<223> OTHER INFORMATION: Synthetic Polynucleotide

<400> SEQUENCE: 78
aaactttttc aaataactta gcaaatattt ccacag                                        36

<210> SEQ ID NO 79
<211> LENGTH: 40
<212> TYPE: DNA
<213> ORGANISM: Artificial
<220> FEATURE:
<223> OTHER INFORMATION: Synthetic Polynucleotide

<400> SEQUENCE: 79
cgggaacgga tcagcttacg caactttgcc actcagacat                                    40

<210> SEQ ID NO 80
<211> LENGTH: 36
<212> TYPE: DNA
<213> ORGANISM: Artificial
<220> FEATURE:
<223> OTHER INFORMATION: Synthetic Polynucleotide

<400> SEQUENCE: 80
gagattttag ttaatgcaac ggaattatta gcaaaa                                        36

<210> SEQ ID NO 81
<211> LENGTH: 40
<212> TYPE: DNA

<213> ORGANISM: Artificial
<220> FEATURE:
<223> OTHER INFORMATION: Synthetic Polynucleotide

<400> SEQUENCE: 81
cttcatcatg acaagacaag tttgcctttc attagcaagg                                40

<210> SEQ ID NO 82
<211> LENGTH: 48
<212> TYPE: DNA
<213> ORGANISM: Artificial
<220> FEATURE:
<223> OTHER INFORMATION: Synthetic Polynucleotide

<400> SEQUENCE: 82
caatgtgctg caaggcgatt tcagaggtgg agtgccatct ctcaccgg                       48

<210> SEQ ID NO 83
<211> LENGTH: 46
<212> TYPE: DNA
<213> ORGANISM: Artificial
<220> FEATURE:
<223> OTHER INFORMATION: Synthetic Polynucleotide

<400> SEQUENCE: 83
acatttcgat tcccaattct gcggtacggt gtctggaaat tctgta                        46

<210> SEQ ID NO 84
<211> LENGTH: 24
<212> TYPE: DNA
<213> ORGANISM: Artificial
<220> FEATURE:
<223> OTHER INFORMATION: Synthetic Polynucleotide

<400> SEQUENCE: 84
aacatccaag gtgttagtct ctga                                                24

<210> SEQ ID NO 85
<211> LENGTH: 48
<212> TYPE: DNA
<213> ORGANISM: Artificial
<220> FEATURE:
<223> OTHER INFORMATION: Synthetic Polynucleotide

<400> SEQUENCE: 85
aataacagag gcatttaata agagaaaaac agtaatcctg attgtcaa                      48

<210> SEQ ID NO 86
<211> LENGTH: 47
<212> TYPE: DNA
<213> ORGANISM: Artificial
<220> FEATURE:
<223> OTHER INFORMATION: Synthetic Polynucleotide

<400> SEQUENCE: 86
tcgagttacg tcaaaaagga aaccgaggaa acgcaataag gaaccgg                       47

<210> SEQ ID NO 87
<211> LENGTH: 37
<212> TYPE: DNA
<213> ORGANISM: Artificial
<220> FEATURE:
<223> OTHER INFORMATION: Synthetic Polynucleotide

<400> SEQUENCE: 87
tcaccctata ccgacaagac tctaccagat gaatata                                  37

<210> SEQ ID NO 88
<211> LENGTH: 32
<212> TYPE: DNA
<213> ORGANISM: Artificial
<220> FEATURE:
<223> OTHER INFORMATION: Synthetic Polynucleotide

<400> SEQUENCE: 88
ccagtgccaa gcttaaccat agccggtcac ca                                     32

<210> SEQ ID NO 89
<211> LENGTH: 32
<212> TYPE: DNA
<213> ORGANISM: Artificial
<220> FEATURE:
<223> OTHER INFORMATION: Synthetic Polynucleotide

<400> SEQUENCE: 89
gatgcatcaa ttctactaaa gccaattcac aa                                     32

<210> SEQ ID NO 90
<211> LENGTH: 48
<212> TYPE: DNA
<213> ORGANISM: Artificial
<220> FEATURE:
<223> OTHER INFORMATION: Synthetic Polynucleotide

<400> SEQUENCE: 90
aatcataatt acaacaaacg cctagccaac gccacacgac gctcaatc                    48

<210> SEQ ID NO 91
<211> LENGTH: 48
<212> TYPE: DNA
<213> ORGANISM: Artificial
<220> FEATURE:
<223> OTHER INFORMATION: Synthetic Polynucleotide

<400> SEQUENCE: 91
aaggccgctg ccgcatgccc agttatacaa atggttttga agcgttgc                    48

<210> SEQ ID NO 92
<211> LENGTH: 45
<212> TYPE: DNA
<213> ORGANISM: Artificial
<220> FEATURE:
<223> OTHER INFORMATION: Synthetic Polynucleotide

<400> SEQUENCE: 92
aggctttgac tttttcatgt aacgcctggc cctgagagag ttgca                       45

<210> SEQ ID NO 93
<211> LENGTH: 40
<212> TYPE: DNA
<213> ORGANISM: Artificial
<220> FEATURE:
<223> OTHER INFORMATION: Synthetic Polynucleotide

<400> SEQUENCE: 93
tttcccagtc acgacgttgt aaaagcattt tccccttatt                             40

<210> SEQ ID NO 94
<211> LENGTH: 40
<212> TYPE: DNA
<213> ORGANISM: Artificial
<220> FEATURE:

<223> OTHER INFORMATION: Synthetic Polynucleotide

<400> SEQUENCE: 94
aaccagacct ctttaacgcg tcaatcatta acattttaca         40

<210> SEQ ID NO 95
<211> LENGTH: 37
<212> TYPE: DNA
<213> ORGANISM: Artificial
<220> FEATURE:
<223> OTHER INFORMATION: Synthetic Polynucleotide

<400> SEQUENCE: 95
ctgtttagta tcatattttg cgtaacggaa aactggc              37

<210> SEQ ID NO 96
<211> LENGTH: 32
<212> TYPE: DNA
<213> ORGANISM: Artificial
<220> FEATURE:
<223> OTHER INFORMATION: Synthetic Polynucleotide

<400> SEQUENCE: 96
cgcctaaaga ggatgattag agcccattaa ag                   32

<210> SEQ ID NO 97
<211> LENGTH: 48
<212> TYPE: DNA
<213> ORGANISM: Artificial
<220> FEATURE:
<223> OTHER INFORMATION: Synthetic Polynucleotide

<400> SEQUENCE: 97
acgttaattt taggaatgtc actgagccag cggtgccggt gtggtgcc  48

<210> SEQ ID NO 98
<211> LENGTH: 40
<212> TYPE: DNA
<213> ORGANISM: Artificial
<220> FEATURE:
<223> OTHER INFORMATION: Synthetic Polynucleotide

<400> SEQUENCE: 98
acaacattgt ttcatttgac aggattattc tgaaagccac          40

<210> SEQ ID NO 99
<211> LENGTH: 47
<212> TYPE: DNA
<213> ORGANISM: Artificial
<220> FEATURE:
<223> OTHER INFORMATION: Synthetic Polynucleotide

<400> SEQUENCE: 99
gctcaacatg ttttaaatgc aaacggaaat ggccttgatg aatggaa    47

<210> SEQ ID NO 100
<211> LENGTH: 39
<212> TYPE: DNA
<213> ORGANISM: Artificial
<220> FEATURE:
<223> OTHER INFORMATION: Synthetic Polynucleotide

<400> SEQUENCE: 100
ccagtcagga gcttgccctg acgagaaggc agaaagaac            39

```
<210> SEQ ID NO 101
<211> LENGTH: 39
<212> TYPE: DNA
<213> ORGANISM: Artificial
<220> FEATURE:
<223> OTHER INFORMATION: Synthetic Polynucleotide

<400> SEQUENCE: 101
gattattgct gaatataatg acaggtagaa agccaaaag                              39

<210> SEQ ID NO 102
<211> LENGTH: 24
<212> TYPE: DNA
<213> ORGANISM: Artificial
<220> FEATURE:
<223> OTHER INFORMATION: Synthetic Polynucleotide

<400> SEQUENCE: 102
taatataatt acaatatgta gcat                                             24

<210> SEQ ID NO 103
<211> LENGTH: 40
<212> TYPE: DNA
<213> ORGANISM: Artificial
<220> FEATURE:
<223> OTHER INFORMATION: Synthetic Polynucleotide

<400> SEQUENCE: 103
agcgaaccca gatataaaac gctcttttga atggccagaa                            40

<210> SEQ ID NO 104
<211> LENGTH: 46
<212> TYPE: DNA
<213> ORGANISM: Artificial
<220> FEATURE:
<223> OTHER INFORMATION: Synthetic Polynucleotide

<400> SEQUENCE: 104
gccgacaatg aatacgtaat gccactacga attgaaaatc tccaaa                     46

<210> SEQ ID NO 105
<211> LENGTH: 40
<212> TYPE: DNA
<213> ORGANISM: Artificial
<220> FEATURE:
<223> OTHER INFORMATION: Synthetic Polynucleotide

<400> SEQUENCE: 105
accagaacga gtattagcag cgtgcctgtt cttcgttttc                            40

<210> SEQ ID NO 106
<211> LENGTH: 29
<212> TYPE: DNA
<213> ORGANISM: Artificial
<220> FEATURE:
<223> OTHER INFORMATION: Synthetic Polynucleotide

<400> SEQUENCE: 106
gaatggctta gagcttgcgg ctaaaggtt                                        29

<210> SEQ ID NO 107
<211> LENGTH: 48
<212> TYPE: DNA
<213> ORGANISM: Artificial
<220> FEATURE:
<223> OTHER INFORMATION: Synthetic Polynucleotide
```

<400> SEQUENCE: 107
attagaggga ttagctcctt ttgacaaatg ctttaaagaa ttaatggg    48

<210> SEQ ID NO 108
<211> LENGTH: 32
<212> TYPE: DNA
<213> ORGANISM: Artificial
<220> FEATURE:
<223> OTHER INFORMATION: Synthetic Polynucleotide

<400> SEQUENCE: 108
aaaaacagct tgataccgat acttagcggg tt    32

<210> SEQ ID NO 109
<211> LENGTH: 31
<212> TYPE: DNA
<213> ORGANISM: Artificial
<220> FEATURE:
<223> OTHER INFORMATION: Synthetic Polynucleotide

<400> SEQUENCE: 109
ttttcacggg caccaaagtg gcgaaaatcc t    31

<210> SEQ ID NO 110
<211> LENGTH: 45
<212> TYPE: DNA
<213> ORGANISM: Artificial
<220> FEATURE:
<223> OTHER INFORMATION: Synthetic Polynucleotide

<400> SEQUENCE: 110
ttgggcttcc gtgagcctcc tagcaccgtc ggccccctag aactg    45

<210> SEQ ID NO 111
<211> LENGTH: 40
<212> TYPE: DNA
<213> ORGANISM: Artificial
<220> FEATURE:
<223> OTHER INFORMATION: Synthetic Polynucleotide

<400> SEQUENCE: 111
ctcttaccgt gaagttgtac tcagttacca gagcacatcc    40

<210> SEQ ID NO 112
<211> LENGTH: 48
<212> TYPE: DNA
<213> ORGANISM: Artificial
<220> FEATURE:
<223> OTHER INFORMATION: Synthetic Polynucleotide

<400> SEQUENCE: 112
caacactaaa tgcagataca taacgattca tcgccagcat ccaagggt    48

<210> SEQ ID NO 113
<211> LENGTH: 47
<212> TYPE: DNA
<213> ORGANISM: Artificial
<220> FEATURE:
<223> OTHER INFORMATION: Synthetic Polynucleotide

<400> SEQUENCE: 113
gcggattacc agccgggtca ctgttgagta agagcgccct aagagag    47

<210> SEQ ID NO 114
<211> LENGTH: 46

<212> TYPE: DNA
<213> ORGANISM: Artificial
<220> FEATURE:
<223> OTHER INFORMATION: Synthetic Polynucleotide

<400> SEQUENCE: 114
aatgttgatt aagcaagcaa attcccgact attttgacca gtaata            46

<210> SEQ ID NO 115
<211> LENGTH: 45
<212> TYPE: DNA
<213> ORGANISM: Artificial
<220> FEATURE:
<223> OTHER INFORMATION: Synthetic Polynucleotide

<400> SEQUENCE: 115
cacccgtgta accttgcttc tcctaaaaca taataccgtc ctgaa             45

<210> SEQ ID NO 116
<211> LENGTH: 46
<212> TYPE: DNA
<213> ORGANISM: Artificial
<220> FEATURE:
<223> OTHER INFORMATION: Synthetic Polynucleotide

<400> SEQUENCE: 116
gccttagaaa ggaacgggga gaggcggtcc cttataaatt agaatc            46

<210> SEQ ID NO 117
<211> LENGTH: 30
<212> TYPE: DNA
<213> ORGANISM: Artificial
<220> FEATURE:
<223> OTHER INFORMATION: Synthetic Polynucleotide

<400> SEQUENCE: 117
tcattgaatc ccccttaaga ggtcattttt                              30

<210> SEQ ID NO 118
<211> LENGTH: 32
<212> TYPE: DNA
<213> ORGANISM: Artificial
<220> FEATURE:
<223> OTHER INFORMATION: Synthetic Polynucleotide

<400> SEQUENCE: 118
gagagctaca attttaaacg aaccaccagc ag                           32

<210> SEQ ID NO 119
<211> LENGTH: 40
<212> TYPE: DNA
<213> ORGANISM: Artificial
<220> FEATURE:
<223> OTHER INFORMATION: Synthetic Polynucleotide

<400> SEQUENCE: 119
tttcagcggt aaatgaattt tctggagcca ccagttgggc                   40

<210> SEQ ID NO 120
<211> LENGTH: 40
<212> TYPE: DNA
<213> ORGANISM: Artificial
<220> FEATURE:
<223> OTHER INFORMATION: Synthetic Polynucleotide

<400> SEQUENCE: 120
aaacaactgt ttaatttgcg ctcagtaccg agctcgaatt                         40

<210> SEQ ID NO 121
<211> LENGTH: 48
<212> TYPE: DNA
<213> ORGANISM: Artificial
<220> FEATURE:
<223> OTHER INFORMATION: Synthetic Polynucleotide

<400> SEQUENCE: 121
cagaaaacca agagaagtaa tcgtaaattt tggctatact taacggggg              48

<210> SEQ ID NO 122
<211> LENGTH: 32
<212> TYPE: DNA
<213> ORGANISM: Artificial
<220> FEATURE:
<223> OTHER INFORMATION: Synthetic Polynucleotide

<400> SEQUENCE: 122
agcgaataag tttattttgt cacattgctt tc                                32

<210> SEQ ID NO 123
<211> LENGTH: 40
<212> TYPE: DNA
<213> ORGANISM: Artificial
<220> FEATURE:
<223> OTHER INFORMATION: Synthetic Polynucleotide

<400> SEQUENCE: 123
gaccataaat aagtttagca tgtcgaccct gtaatacttt                        40

<210> SEQ ID NO 124
<211> LENGTH: 29
<212> TYPE: DNA
<213> ORGANISM: Artificial
<220> FEATURE:
<223> OTHER INFORMATION: Synthetic Polynucleotide

<400> SEQUENCE: 124
caccctccac aggcttacca gtcccggaa                                    29

<210> SEQ ID NO 125
<211> LENGTH: 46
<212> TYPE: DNA
<213> ORGANISM: Artificial
<220> FEATURE:
<223> OTHER INFORMATION: Synthetic Polynucleotide

<400> SEQUENCE: 125
ttgctcagct ggatagtaca aaggattgcc tgagagtctt agatgg                 46

<210> SEQ ID NO 126
<211> LENGTH: 40
<212> TYPE: DNA
<213> ORGANISM: Artificial
<220> FEATURE:
<223> OTHER INFORMATION: Synthetic Polynucleotide

<400> SEQUENCE: 126
tactggtaat caaaaacccg aacgtcgata aaaacaggaa                        40

<210> SEQ ID NO 127
<211> LENGTH: 46
<212> TYPE: DNA
<213> ORGANISM: Artificial

```
<220> FEATURE:
<223> OTHER INFORMATION: Synthetic Polynucleotide

<400> SEQUENCE: 127
gacaagcctc tgttatgttg gcacggaaaa atcggtctga gagact                    46

<210> SEQ ID NO 128
<211> LENGTH: 40
<212> TYPE: DNA
<213> ORGANISM: Artificial
<220> FEATURE:
<223> OTHER INFORMATION: Synthetic Polynucleotide

<400> SEQUENCE: 128
ttagccaggg atagcaacaa cgccaatcat aacgacctgc                           40

<210> SEQ ID NO 129
<211> LENGTH: 48
<212> TYPE: DNA
<213> ORGANISM: Artificial
<220> FEATURE:
<223> OTHER INFORMATION: Synthetic Polynucleotide

<400> SEQUENCE: 129
aggaacccca ccctcatatg ggatcaacat accacattaa ttgtgtgt                  48

<210> SEQ ID NO 130
<211> LENGTH: 40
<212> TYPE: DNA
<213> ORGANISM: Artificial
<220> FEATURE:
<223> OTHER INFORMATION: Synthetic Polynucleotide

<400> SEQUENCE: 130
ctcagaactg ggaaggcggg cctcttcgct atggcgaaag                           40

<210> SEQ ID NO 131
<211> LENGTH: 38
<212> TYPE: DNA
<213> ORGANISM: Artificial
<220> FEATURE:
<223> OTHER INFORMATION: Synthetic Polynucleotide

<400> SEQUENCE: 131
aaacgattcg tgtgagaaac aataacggat tcgcctga                             38

<210> SEQ ID NO 132
<211> LENGTH: 32
<212> TYPE: DNA
<213> ORGANISM: Artificial
<220> FEATURE:
<223> OTHER INFORMATION: Synthetic Polynucleotide

<400> SEQUENCE: 132
gatagcaggt caccagtaca aactagccca at                                   32

<210> SEQ ID NO 133
<211> LENGTH: 39
<212> TYPE: DNA
<213> ORGANISM: Artificial
<220> FEATURE:
<223> OTHER INFORMATION: Synthetic Polynucleotide

<400> SEQUENCE: 133
gaaagtattg tcggtggcga tgtaggtaaa gattcaaat                            39
```

<210> SEQ ID NO 134
<211> LENGTH: 32
<212> TYPE: DNA
<213> ORGANISM: Artificial
<220> FEATURE:
<223> OTHER INFORMATION: Synthetic Polynucleotide

<400> SEQUENCE: 134
atttaccgcg tcatacatgt gcccgtataa ac            32

<210> SEQ ID NO 135
<211> LENGTH: 40
<212> TYPE: DNA
<213> ORGANISM: Artificial
<220> FEATURE:
<223> OTHER INFORMATION: Synthetic Polynucleotide

<400> SEQUENCE: 135
gtgaattatt gagggaggga aggtcggtcc aatcgcaaga            40

<210> SEQ ID NO 136
<211> LENGTH: 48
<212> TYPE: DNA
<213> ORGANISM: Artificial
<220> FEATURE:
<223> OTHER INFORMATION: Synthetic Polynucleotide

<400> SEQUENCE: 136
ccggaggact aataccaagc gcgaaacaat ctagagtaaa aaaccatc            48

<210> SEQ ID NO 137
<211> LENGTH: 40
<212> TYPE: DNA
<213> ORGANISM: Artificial
<220> FEATURE:
<223> OTHER INFORMATION: Synthetic Polynucleotide

<400> SEQUENCE: 137
cagaaccagt tgggtaacgc ctataacagt tgcaaatggt            40

<210> SEQ ID NO 138
<211> LENGTH: 47
<212> TYPE: DNA
<213> ORGANISM: Artificial
<220> FEATURE:
<223> OTHER INFORMATION: Synthetic Polynucleotide

<400> SEQUENCE: 138
ggaacctagg ttgaggcagg tcagacgatt gcaactaaaa acgagta            47

<210> SEQ ID NO 139
<211> LENGTH: 48
<212> TYPE: DNA
<213> ORGANISM: Artificial
<220> FEATURE:
<223> OTHER INFORMATION: Synthetic Polynucleotide

<400> SEQUENCE: 139
agccctgctg cccgcagttt gaccggggcg cgagctgaaa ataaatca            48

<210> SEQ ID NO 140
<211> LENGTH: 38
<212> TYPE: DNA
<213> ORGANISM: Artificial
<220> FEATURE:
<223> OTHER INFORMATION: Synthetic Polynucleotide

```
<400> SEQUENCE: 140
tcaccagtca caggaagttt ccatttgccc cagcagag                              38

<210> SEQ ID NO 141
<211> LENGTH: 46
<212> TYPE: DNA
<213> ORGANISM: Artificial
<220> FEATURE:
<223> OTHER INFORMATION: Synthetic Polynucleotide

<400> SEQUENCE: 141
agcgcgtttt catcgcgatt acccaaatca acgtaacatt cagtga                    46

<210> SEQ ID NO 142
<211> LENGTH: 30
<212> TYPE: DNA
<213> ORGANISM: Artificial
<220> FEATURE:
<223> OTHER INFORMATION: Synthetic Polynucleotide

<400> SEQUENCE: 142
aaagggaacc gtctatcatt ataatcagtg                                       30

<210> SEQ ID NO 143
<211> LENGTH: 32
<212> TYPE: DNA
<213> ORGANISM: Artificial
<220> FEATURE:
<223> OTHER INFORMATION: Synthetic Polynucleotide

<400> SEQUENCE: 143
tattaaagaa ccggtcgcaa ggtgtattcg gt                                    32

<210> SEQ ID NO 144
<211> LENGTH: 31
<212> TYPE: DNA
<213> ORGANISM: Artificial
<220> FEATURE:
<223> OTHER INFORMATION: Synthetic Polynucleotide

<400> SEQUENCE: 144
tcttagcctc ctgttgctcg tcataaacat c                                     31

<210> SEQ ID NO 145
<211> LENGTH: 40
<212> TYPE: DNA
<213> ORGANISM: Artificial
<220> FEATURE:
<223> OTHER INFORMATION: Synthetic Polynucleotide

<400> SEQUENCE: 145
ttacctgccg cgcctgtgct gttctggtga ctctaacgga                            40

<210> SEQ ID NO 146
<211> LENGTH: 39
<212> TYPE: DNA
<213> ORGANISM: Artificial
<220> FEATURE:
<223> OTHER INFORMATION: Synthetic Polynucleotide

<400> SEQUENCE: 146
cttgagtcgt gccagctgca ttaatgaacg gctgcccgc                             39

<210> SEQ ID NO 147
```

```
<211> LENGTH: 37
<212> TYPE: DNA
<213> ORGANISM: Artificial
<220> FEATURE:
<223> OTHER INFORMATION: Synthetic Polynucleotide

<400> SEQUENCE: 147
agaggtgtat taacacctac atttaatgcc tgcaaca                              37

<210> SEQ ID NO 148
<211> LENGTH: 32
<212> TYPE: DNA
<213> ORGANISM: Artificial
<220> FEATURE:
<223> OTHER INFORMATION: Synthetic Polynucleotide

<400> SEQUENCE: 148
ttcatttgtt taatggaaac agaagataaa ac                                   32

<210> SEQ ID NO 149
<211> LENGTH: 32
<212> TYPE: DNA
<213> ORGANISM: Artificial
<220> FEATURE:
<223> OTHER INFORMATION: Synthetic Polynucleotide

<400> SEQUENCE: 149
agaagatgat gaaacaaaac aaaattaaca at                                   32

<210> SEQ ID NO 150
<211> LENGTH: 40
<212> TYPE: DNA
<213> ORGANISM: Artificial
<220> FEATURE:
<223> OTHER INFORMATION: Synthetic Polynucleotide

<400> SEQUENCE: 150
agaagccttt attagctaaa tcggaacatt ataatcatat                           40

<210> SEQ ID NO 151
<211> LENGTH: 30
<212> TYPE: DNA
<213> ORGANISM: Artificial
<220> FEATURE:
<223> OTHER INFORMATION: Synthetic Polynucleotide

<400> SEQUENCE: 151
aaacaggaca gatgagacca ggcgcatcca                                      30

<210> SEQ ID NO 152
<211> LENGTH: 38
<212> TYPE: DNA
<213> ORGANISM: Artificial
<220> FEATURE:
<223> OTHER INFORMATION: Synthetic Polynucleotide

<400> SEQUENCE: 152
ggggataacc tgtttagcta tattttcatt tattagat                             38

<210> SEQ ID NO 153
<211> LENGTH: 32
<212> TYPE: DNA
<213> ORGANISM: Artificial
<220> FEATURE:
<223> OTHER INFORMATION: Synthetic Polynucleotide

<400> SEQUENCE: 153
```
cgagggtatt catcttctga cctaacgcga ga                              32

<210> SEQ ID NO 154
<211> LENGTH: 32
<212> TYPE: DNA
<213> ORGANISM: Artificial
<220> FEATURE:
<223> OTHER INFORMATION: Synthetic Polynucleotide

<400> SEQUENCE: 154
tctgctcaaa gctttgaccc ccagcgattc ag                              32

<210> SEQ ID NO 155
<211> LENGTH: 48
<212> TYPE: DNA
<213> ORGANISM: Artificial
<220> FEATURE:
<223> OTHER INFORMATION: Synthetic Polynucleotide

<400> SEQUENCE: 155
ataagcgtgt tttcacggtc ataccgggat tgcccttcac aacactca              48

<210> SEQ ID NO 156
<211> LENGTH: 40
<212> TYPE: DNA
<213> ORGANISM: Artificial
<220> FEATURE:
<223> OTHER INFORMATION: Synthetic Polynucleotide

<400> SEQUENCE: 156
tcttacgttt ttattttcat cctgaataac ctcaaatatc                      40

<210> SEQ ID NO 157
<211> LENGTH: 30
<212> TYPE: DNA
<213> ORGANISM: Artificial
<220> FEATURE:
<223> OTHER INFORMATION: Synthetic Polynucleotide

<400> SEQUENCE: 157
attaattgta tcggtattaa gacgctgatg                                 30

<210> SEQ ID NO 158
<211> LENGTH: 40
<212> TYPE: DNA
<213> ORGANISM: Artificial
<220> FEATURE:
<223> OTHER INFORMATION: Synthetic Polynucleotide

<400> SEQUENCE: 158
gagggggtgt atcacctacc agaccggaac gtgccgggtc                      40

<210> SEQ ID NO 159
<211> LENGTH: 32
<212> TYPE: DNA
<213> ORGANISM: Artificial
<220> FEATURE:
<223> OTHER INFORMATION: Synthetic Polynucleotide

<400> SEQUENCE: 159
aaatttgcaa aagaagcaga ggtcctatct at                              32

<210> SEQ ID NO 160
<211> LENGTH: 32
<212> TYPE: DNA

<213> ORGANISM: Artificial
<220> FEATURE:
<223> OTHER INFORMATION: Synthetic Polynucleotide

<400> SEQUENCE: 160
tcatcgagaa caaagtacag caaatgaaaa at                                32

<210> SEQ ID NO 161
<211> LENGTH: 30
<212> TYPE: DNA
<213> ORGANISM: Artificial
<220> FEATURE:
<223> OTHER INFORMATION: Synthetic Polynucleotide

<400> SEQUENCE: 161
aaatgtcgtc tttccccgaa gagtcaatag                                   30

<210> SEQ ID NO 162
<211> LENGTH: 32
<212> TYPE: DNA
<213> ORGANISM: Artificial
<220> FEATURE:
<223> OTHER INFORMATION: Synthetic Polynucleotide

<400> SEQUENCE: 162
tgtttagata ccaggccaga attaatgccg ga                                32

<210> SEQ ID NO 163
<211> LENGTH: 48
<212> TYPE: DNA
<213> ORGANISM: Artificial
<220> FEATURE:
<223> OTHER INFORMATION: Synthetic Polynucleotide

<400> SEQUENCE: 163
aactgaacaa tggaagtacc atatcaaaat tactgagagc cagcattt               48

<210> SEQ ID NO 164
<211> LENGTH: 48
<212> TYPE: DNA
<213> ORGANISM: Artificial
<220> FEATURE:
<223> OTHER INFORMATION: Synthetic Polynucleotide

<400> SEQUENCE: 164
accagagccg ccatgtggcc tttagtggga aagtgccatg tttcgtct               48

<210> SEQ ID NO 165
<211> LENGTH: 32
<212> TYPE: DNA
<213> ORGANISM: Artificial
<220> FEATURE:
<223> OTHER INFORMATION: Synthetic Polynucleotide

<400> SEQUENCE: 165
atgatttttt gtttaaaata agaataaact cg                                32

<210> SEQ ID NO 166
<211> LENGTH: 48
<212> TYPE: DNA
<213> ORGANISM: Artificial
<220> FEATURE:
<223> OTHER INFORMATION: Synthetic Polynucleotide

<400> SEQUENCE: 166
accaaaagta cccgacttga gccacaacca tcaaccgata gactccaa               48

<210> SEQ ID NO 167
<211> LENGTH: 31
<212> TYPE: DNA
<213> ORGANISM: Artificial
<220> FEATURE:
<223> OTHER INFORMATION: Synthetic Polynucleotide

<400> SEQUENCE: 167
agctagcgat caggttccga ggctggctga c                           31

<210> SEQ ID NO 168
<211> LENGTH: 48
<212> TYPE: DNA
<213> ORGANISM: Artificial
<220> FEATURE:
<223> OTHER INFORMATION: Synthetic Polynucleotide

<400> SEQUENCE: 168
ttaccagaat gaaatagca gcctaataac ataatataaa agatgatg           48

<210> SEQ ID NO 169
<211> LENGTH: 40
<212> TYPE: DNA
<213> ORGANISM: Artificial
<220> FEATURE:
<223> OTHER INFORMATION: Synthetic Polynucleotide

<400> SEQUENCE: 169
gagccgccag ttgagaaaaa cgaactgtgg tgctgcggcc                  40

<210> SEQ ID NO 170
<211> LENGTH: 32
<212> TYPE: DNA
<213> ORGANISM: Artificial
<220> FEATURE:
<223> OTHER INFORMATION: Synthetic Polynucleotide

<400> SEQUENCE: 170
aactgacctt tgtgagagat agactttctc cg                          32

<210> SEQ ID NO 171
<211> LENGTH: 32
<212> TYPE: DNA
<213> ORGANISM: Artificial
<220> FEATURE:
<223> OTHER INFORMATION: Synthetic Polynucleotide

<400> SEQUENCE: 171
tgtgtacaac ggtgtcgaaa tccggggaac cg                          32

<210> SEQ ID NO 172
<211> LENGTH: 32
<212> TYPE: DNA
<213> ORGANISM: Artificial
<220> FEATURE:
<223> OTHER INFORMATION: Synthetic Polynucleotide

<400> SEQUENCE: 172
gccgaattcg ggacaagaat tggattatac tt                          32

<210> SEQ ID NO 173
<211> LENGTH: 30
<212> TYPE: DNA
<213> ORGANISM: Artificial
<220> FEATURE:

```
<223> OTHER INFORMATION: Synthetic Polynucleotide

<400> SEQUENCE: 173
acaacataaa ggtggcaatt acctgagaac                                    30

<210> SEQ ID NO 174
<211> LENGTH: 32
<212> TYPE: DNA
<213> ORGANISM: Artificial
<220> FEATURE:
<223> OTHER INFORMATION: Synthetic Polynucleotide

<400> SEQUENCE: 174
ccttgagtaa caggcttaat caacgcaagg at                                 32

<210> SEQ ID NO 175
<211> LENGTH: 30
<212> TYPE: DNA
<213> ORGANISM: Artificial
<220> FEATURE:
<223> OTHER INFORMATION: Synthetic Polynucleotide

<400> SEQUENCE: 175
tagaaaatac atgcccaggt ttaacgtaaa                                    30

<210> SEQ ID NO 176
<211> LENGTH: 32
<212> TYPE: DNA
<213> ORGANISM: Artificial
<220> FEATURE:
<223> OTHER INFORMATION: Synthetic Polynucleotide

<400> SEQUENCE: 176 acaagggcg acattcatgc tgatgcaaaa ac                                  32

<210> SEQ ID NO 177
<211> LENGTH: 30
<212> TYPE: DNA
<213> ORGANISM: Artificial
<220> FEATURE:
<223> OTHER INFORMATION: Synthetic Polynucleotide

<400> SEQUENCE: 177
aatcaaaatc accacaagaa tcggcgaaac                                    30

<210> SEQ ID NO 178
<211> LENGTH: 47
<212> TYPE: DNA
<213> ORGANISM: Artificial
<220> FEATURE:
<223> OTHER INFORMATION: Synthetic Polynucleotide

<400> SEQUENCE: 178
agtactcctc aagagaagcc accagccgga taggccggag acaggcc                 47

<210> SEQ ID NO 179
<211> LENGTH: 30
<212> TYPE: DNA
<213> ORGANISM: Artificial
<220> FEATURE:
<223> OTHER INFORMATION: Synthetic Polynucleotide

<400> SEQUENCE: 179
aaagggaacc gtctatcatt ataatcagtg                                    30
```

```
<210> SEQ ID NO 180
<211> LENGTH: 32
<212> TYPE: DNA
<213> ORGANISM: Artificial
<220> FEATURE:
<223> OTHER INFORMATION: Synthetic Polynucleotide

<400> SEQUENCE: 180
tattaaagaa ccggtcgcaa ggtgtattcg gt                                32

<210> SEQ ID NO 181
<211> LENGTH: 31
<212> TYPE: DNA
<213> ORGANISM: Artificial
<220> FEATURE:
<223> OTHER INFORMATION: Synthetic Polynucleotide

<400> SEQUENCE: 181
tcttagcctc ctgttgctcg tcataaacat c                                 31

<210> SEQ ID NO 182
<211> LENGTH: 40
<212> TYPE: DNA
<213> ORGANISM: Artificial
<220> FEATURE:
<223> OTHER INFORMATION: Synthetic Polynucleotide

<400> SEQUENCE: 182
ttacctgccg cgcctgtgct gttctggtga ctctaacgga                        40

<210> SEQ ID NO 183
<211> LENGTH: 39
<212> TYPE: DNA
<213> ORGANISM: Artificial
<220> FEATURE:
<223> OTHER INFORMATION: Synthetic Polynucleotide

<400> SEQUENCE: 183
cttgagtcgt gccagctgca ttaatgaacg gctgcccgc                         39

<210> SEQ ID NO 184
<211> LENGTH: 37
<212> TYPE: DNA
<213> ORGANISM: Artificial
<220> FEATURE:
<223> OTHER INFORMATION: Synthetic Polynucleotide

<400> SEQUENCE: 184
agaggtgtat taacacctac atttaatgcc tgcaaca                           37

<210> SEQ ID NO 185
<211> LENGTH: 32
<212> TYPE: DNA
<213> ORGANISM: Artificial
<220> FEATURE:
<223> OTHER INFORMATION: Synthetic Polynucleotide

<400> SEQUENCE: 185
ttcatttgtt taatggaaac agaagataaa ac                                32

<210> SEQ ID NO 186
<211> LENGTH: 32
<212> TYPE: DNA
<213> ORGANISM: Artificial
<220> FEATURE:
<223> OTHER INFORMATION: Synthetic Polynucleotide
```

<400> SEQUENCE: 186
agaagatgat gaaacaaaac aaaattaaca at    32

<210> SEQ ID NO 187
<211> LENGTH: 40
<212> TYPE: DNA
<213> ORGANISM: Artificial
<220> FEATURE:
<223> OTHER INFORMATION: Synthetic Polynucleotide

<400> SEQUENCE: 187
agaagccttt attagctaaa tcggaacatt ataatcatat    40

<210> SEQ ID NO 188
<211> LENGTH: 30
<212> TYPE: DNA
<213> ORGANISM: Artificial
<220> FEATURE:
<223> OTHER INFORMATION: Synthetic Polynucleotide

<400> SEQUENCE: 188
aaacaggaca gatgagacca ggcgcatcca    30

<210> SEQ ID NO 189
<211> LENGTH: 38
<212> TYPE: DNA
<213> ORGANISM: Artificial
<220> FEATURE:
<223> OTHER INFORMATION: Synthetic Polynucleotide

<400> SEQUENCE: 189
ggggataacc tgtttagcta tattttcatt tattagat    38

<210> SEQ ID NO 190
<211> LENGTH: 32
<212> TYPE: DNA
<213> ORGANISM: Artificial
<220> FEATURE:
<223> OTHER INFORMATION: Synthetic Polynucleotide

<400> SEQUENCE: 190
cgagggtatt catcttctga cctaacgcga ga    32

<210> SEQ ID NO 191
<211> LENGTH: 32
<212> TYPE: DNA
<213> ORGANISM: Artificial
<220> FEATURE:
<223> OTHER INFORMATION: Synthetic Polynucleotide

<400> SEQUENCE: 191
tctgctcaaa gctttgaccc ccagcgattc ag    32

<210> SEQ ID NO 192
<211> LENGTH: 48
<212> TYPE: DNA
<213> ORGANISM: Artificial
<220> FEATURE:
<223> OTHER INFORMATION: Synthetic Polynucleotide

<400> SEQUENCE: 192
ataagcgtgt tttcacggtc ataccgggat tgcccttcac aacactca    48

<210> SEQ ID NO 193
<211> LENGTH: 40

```
<212> TYPE: DNA
<213> ORGANISM: Artificial
<220> FEATURE:
<223> OTHER INFORMATION: Synthetic Polynucleotide

<400> SEQUENCE: 193
tcttacgttt ttattttcat cctgaataac ctcaaatatc                        40

<210> SEQ ID NO 194
<211> LENGTH: 30
<212> TYPE: DNA
<213> ORGANISM: Artificial
<220> FEATURE:
<223> OTHER INFORMATION: Synthetic Polynucleotide

<400> SEQUENCE: 194
attaattgta tcggtattaa gacgctgatg                                   30

<210> SEQ ID NO 195
<211> LENGTH: 40
<212> TYPE: DNA
<213> ORGANISM: Artificial
<220> FEATURE:
<223> OTHER INFORMATION: Synthetic Polynucleotide

<400> SEQUENCE: 195 gaggggtgt atcacctacc agaccggaac gtgccgggtc                         40

<210> SEQ ID NO 196
<211> LENGTH: 32
<212> TYPE: DNA
<213> ORGANISM: Artificial
<220> FEATURE:
<223> OTHER INFORMATION: Synthetic Polynucleotide

<400> SEQUENCE: 196
aaatttgcaa aagaagcaga ggtcctatct at                                32

<210> SEQ ID NO 197
<211> LENGTH: 32
<212> TYPE: DNA
<213> ORGANISM: Artificial
<220> FEATURE:
<223> OTHER INFORMATION: Synthetic Polynucleotide

<400> SEQUENCE: 197
tcatcgagaa caaagtacag caaatgaaaa at                                32

<210> SEQ ID NO 198
<211> LENGTH: 30
<212> TYPE: DNA
<213> ORGANISM: Artificial
<220> FEATURE:
<223> OTHER INFORMATION: Synthetic Polynucleotide

<400> SEQUENCE: 198
aaatgtcgtc tttccccgaa gagtcaatag                                   30

<210> SEQ ID NO 199
<211> LENGTH: 32
<212> TYPE: DNA
<213> ORGANISM: Artificial
<220> FEATURE:
<223> OTHER INFORMATION: Synthetic Polynucleotide

<400> SEQUENCE: 199
```
tgtttagata ccaggccaga attaatgccg ga                                    32

<210> SEQ ID NO 200
<211> LENGTH: 48
<212> TYPE: DNA
<213> ORGANISM: Artificial
<220> FEATURE:
<223> OTHER INFORMATION: Synthetic Polynucleotide

<400> SEQUENCE: 200
aactgaacaa tggaagtacc atatcaaaat tactgagagc cagcattt                   48

<210> SEQ ID NO 201
<211> LENGTH: 48
<212> TYPE: DNA
<213> ORGANISM: Artificial
<220> FEATURE:
<223> OTHER INFORMATION: Synthetic Polynucleotide

<400> SEQUENCE: 201
accagagccg ccatgtggcc tttagtggga aagtgccatg tttcgtct                   48

<210> SEQ ID NO 202
<211> LENGTH: 32
<212> TYPE: DNA
<213> ORGANISM: Artificial
<220> FEATURE:
<223> OTHER INFORMATION: Synthetic Polynucleotide

<400> SEQUENCE: 202
atgatttttt gtttaaaata agaataaact cg                                    32

<210> SEQ ID NO 203
<211> LENGTH: 48
<212> TYPE: DNA
<213> ORGANISM: Artificial
<220> FEATURE:
<223> OTHER INFORMATION: Synthetic Polynucleotide

<400> SEQUENCE: 203
accaaaagta cccgacttga gccacaacca tcaaccgata gactccaa                   48

<210> SEQ ID NO 204
<211> LENGTH: 31
<212> TYPE: DNA
<213> ORGANISM: Artificial
<220> FEATURE:
<223> OTHER INFORMATION: Synthetic Polynucleotide

<400> SEQUENCE: 204
agctagcgat caggttccga ggctggctga c                                     31

<210> SEQ ID NO 205
<211> LENGTH: 48
<212> TYPE: DNA
<213> ORGANISM: Artificial
<220> FEATURE:
<223> OTHER INFORMATION: Synthetic Polynucleotide

<400> SEQUENCE: 205
ttaccagaat gaaaatagca gcctaataac ataatataaa agatgatg                   48

<210> SEQ ID NO 206
<211> LENGTH: 40
<212> TYPE: DNA
<213> ORGANISM: Artificial

<220> FEATURE:
<223> OTHER INFORMATION: Synthetic Polynucleotide

<400> SEQUENCE: 206
gagccgccag ttgagaaaaa cgaactgtgg tgctgcggcc        40

<210> SEQ ID NO 207
<211> LENGTH: 42
<212> TYPE: DNA
<213> ORGANISM: Artificial
<220> FEATURE:
<223> OTHER INFORMATION: Synthetic Polynucleotide

<400> SEQUENCE: 207
ttgattaaat cagctccaat aggaacgaat taaccgtctt ct        42

<210> SEQ ID NO 208
<211> LENGTH: 38
<212> TYPE: DNA
<213> ORGANISM: Artificial
<220> FEATURE:
<223> OTHER INFORMATION: Synthetic Polynucleotide

<400> SEQUENCE: 208
tgagtagaag atagatcgag catgtaagtt gaatataa        38

<210> SEQ ID NO 209
<211> LENGTH: 29
<212> TYPE: DNA
<213> ORGANISM: Artificial
<220> FEATURE:
<223> OTHER INFORMATION: Synthetic Polynucleotide

<400> SEQUENCE: 209
ccgtaaattg taaacgttaa actcaaact        29

<210> SEQ ID NO 210
<211> LENGTH: 45
<212> TYPE: DNA
<213> ORGANISM: Artificial
<220> FEATURE:
<223> OTHER INFORMATION: Synthetic Polynucleotide

<400> SEQUENCE: 210
gcaaatatgc aaagcgtttt gttataaatt tttgttagta ataac        45

<210> SEQ ID NO 211
<211> LENGTH: 42
<212> TYPE: DNA
<213> ORGANISM: Artificial
<220> FEATURE:
<223> OTHER INFORMATION: Synthetic Polynucleotide

<400> SEQUENCE: 211
gattgtaatc agaaaagctc aggtcttatt atagtcacag tt        42

<210> SEQ ID NO 212
<211> LENGTH: 39
<212> TYPE: DNA
<213> ORGANISM: Artificial
<220> FEATURE:
<223> OTHER INFORMATION: Synthetic Polynucleotide

<400> SEQUENCE: 212
gtaccccggt tgatacaaac accaaattgt aattcgaca        39

<210> SEQ ID NO 213
<211> LENGTH: 45
<212> TYPE: DNA
<213> ORGANISM: Artificial
<220> FEATURE:
<223> OTHER INFORMATION: Synthetic Polynucleotide

<400> SEQUENCE: 213
actcgtatag acttgattag agccgtcaac actaacaaaa ccaag                45

<210> SEQ ID NO 214
<211> LENGTH: 41
<212> TYPE: DNA
<213> ORGANISM: Artificial
<220> FEATURE:
<223> OTHER INFORMATION: Synthetic Polynucleotide

<400> SEQUENCE: 214
cattatcatt aattcaagaa tgctaatatc agagaggagt g                    41

<210> SEQ ID NO 215
<211> LENGTH: 44
<212> TYPE: DNA
<213> ORGANISM: Artificial
<220> FEATURE:
<223> OTHER INFORMATION: Synthetic Polynucleotide

<400> SEQUENCE: 215
agaaaccatg attatcgtac cgacaaaagg taaagtgtag catt                 44

<210> SEQ ID NO 216
<211> LENGTH: 41
<212> TYPE: DNA
<213> ORGANISM: Artificial
<220> FEATURE:
<223> OTHER INFORMATION: Synthetic Polynucleotide

<400> SEQUENCE: 216
tacagttatc atcatattcc ccagaagagc tatcgcaaga a                    41

<210> SEQ ID NO 217
<211> LENGTH: 43
<212> TYPE: DNA
<213> ORGANISM: Artificial
<220> FEATURE:
<223> OTHER INFORMATION: Synthetic Polynucleotide

<400> SEQUENCE: 217
tgtccagaag ccctttttaa tcctcattaa tagtatcaaa gcg                  43

<210> SEQ ID NO 218
<211> LENGTH: 41
<212> TYPE: DNA
<213> ORGANISM: Artificial
<220> FEATURE:
<223> OTHER INFORMATION: Synthetic Polynucleotide

<400> SEQUENCE: 218
gcgcctgttt atcaacagag gagtctgtcc atcacgcacc a                    41

<210> SEQ ID NO 219
<211> LENGTH: 42
<212> TYPE: DNA
<213> ORGANISM: Artificial
<220> FEATURE:
<223> OTHER INFORMATION: Synthetic Polynucleotide

```
<400> SEQUENCE: 219
tcctaattta tgcatcaaaa aaagcccgaa agacaagaaa aa                          42

<210> SEQ ID NO 220
<211> LENGTH: 46
<212> TYPE: DNA
<213> ORGANISM: Artificial
<220> FEATURE:
<223> OTHER INFORMATION: Synthetic Polynucleotide

<400> SEQUENCE: 220
tatcattcca agaacctgac ttaccgggta ttactaataa ggaatt                      46

<210> SEQ ID NO 221
<211> LENGTH: 42
<212> TYPE: DNA
<213> ORGANISM: Artificial
<220> FEATURE:
<223> OTHER INFORMATION: Synthetic Polynucleotide

<400> SEQUENCE: 221
tgatacaggt aagttccaat agcaatgagc ggaattgagt aa                          42

<210> SEQ ID NO 222
<211> LENGTH: 42
<212> TYPE: DNA
<213> ORGANISM: Artificial
<220> FEATURE:
<223> OTHER INFORMATION: Synthetic Polynucleotide

<400> SEQUENCE: 222
acaatgaaat aacccattaa aagtaagcct cagagcattt ga                          42

<210> SEQ ID NO 223
<211> LENGTH: 41
<212> TYPE: DNA
<213> ORGANISM: Artificial
<220> FEATURE:
<223> OTHER INFORMATION: Synthetic Polynucleotide

<400> SEQUENCE: 223
ttacaccgac gacgacatgt tcagctaatg cagaacaatt c                           41

<210> SEQ ID NO 224
<211> LENGTH: 41
<212> TYPE: DNA
<213> ORGANISM: Artificial
<220> FEATURE:
<223> OTHER INFORMATION: Synthetic Polynucleotide

<400> SEQUENCE: 224
agatagccat tatagataag tcctgaacta gaaaagtaag c                           41

<210> SEQ ID NO 225
<211> LENGTH: 32
<212> TYPE: DNA
<213> ORGANISM: Artificial
<220> FEATURE:
<223> OTHER INFORMATION: Synthetic Polynucleotide

<400> SEQUENCE: 225
acaaataatc aaatatttcg agcttcaaaa at                                     32

<210> SEQ ID NO 226
```

<210> SEQ ID NO 226
<211> LENGTH: 53
<212> TYPE: DNA
<213> ORGANISM: Artificial
<220> FEATURE:
<223> OTHER INFORMATION: Synthetic Polynucleotide

<400> SEQUENCE: 226
aactgacctt tgtgagagat agactttctc cgcggttgta ctgtgaccga ttc    53

<210> SEQ ID NO 227
<211> LENGTH: 53
<212> TYPE: DNA
<213> ORGANISM: Artificial
<220> FEATURE:
<223> OTHER INFORMATION: Synthetic Polynucleotide

<400> SEQUENCE: 227
tgtgtacaac ggtgtcgaaa tccggggaac cgcggttgta ctgtgaccga ttc    53

<210> SEQ ID NO 228
<211> LENGTH: 53
<212> TYPE: DNA
<213> ORGANISM: Artificial
<220> FEATURE:
<223> OTHER INFORMATION: Synthetic Polynucleotide

<400> SEQUENCE: 228
gccgaattcg ggacaagaat tggattatac ttcggttgta ctgtgaccga ttc    53

<210> SEQ ID NO 229
<211> LENGTH: 51
<212> TYPE: DNA
<213> ORGANISM: Artificial
<220> FEATURE:
<223> OTHER INFORMATION: Synthetic Polynucleotide

<400> SEQUENCE: 229
acaacataaa ggtggcaatt acctgagaac cggttgtact gtgaccgatt c    51

<210> SEQ ID NO 230
<211> LENGTH: 53
<212> TYPE: DNA
<213> ORGANISM: Artificial
<220> FEATURE:
<223> OTHER INFORMATION: Synthetic Polynucleotide

<400> SEQUENCE: 230
ccttgagtaa caggcttaat caacgcaagg atcggttgta ctgtgaccga ttc    53

<210> SEQ ID NO 231
<211> LENGTH: 51
<212> TYPE: DNA
<213> ORGANISM: Artificial
<220> FEATURE:
<223> OTHER INFORMATION: Synthetic Polynucleotide

<400> SEQUENCE: 231
tagaaaatac atgcccaggt ttaacgtaaa cggttgtact gtgaccgatt c    51

<210> SEQ ID NO 232
<211> LENGTH: 53
<212> TYPE: DNA
<213> ORGANISM: Artificial
<220> FEATURE:
<223> OTHER INFORMATION: Synthetic Polynucleotide

<400> SEQUENCE: 232
acaaagggcg acattcatgc tgatgcaaaa accggttgta ctgtgaccga ttc            53

<210> SEQ ID NO 233
<211> LENGTH: 51
<212> TYPE: DNA
<213> ORGANISM: Artificial
<220> FEATURE:
<223> OTHER INFORMATION: Synthetic Polynucleotide

<400> SEQUENCE: 233
aatcaaaatc accacaagaa tcggcgaaac cggttgtact gtgaccgatt c              51

<210> SEQ ID NO 234
<211> LENGTH: 68
<212> TYPE: DNA
<213> ORGANISM: Artificial
<220> FEATURE:
<223> OTHER INFORMATION: Synthetic Polynucleotide

<400> SEQUENCE: 234
agtactcctc aagagaagcc accagccgga taggccggag acaggcccgg ttgtactgtg     60
accgattc                                                              68

<210> SEQ ID NO 235
<211> LENGTH: 44
<212> TYPE: DNA
<213> ORGANISM: Artificial
<220> FEATURE:
<223> OTHER INFORMATION: Synthetic Polynucleotide

<400> SEQUENCE: 235
taaatgaatt ttctgtatgg gattaatttc ttttgatcta cata                      44

<210> SEQ ID NO 236
<211> LENGTH: 43
<212> TYPE: DNA
<213> ORGANISM: Artificial
<220> FEATURE:
<223> OTHER INFORMATION: Synthetic Polynucleotide

<400> SEQUENCE: 236
tctaaagttt tgtcgtcttt ccagccgaca attgatctac ata                       43

<210> SEQ ID NO 237
<211> LENGTH: 44
<212> TYPE: DNA
<213> ORGANISM: Artificial
<220> FEATURE:
<223> OTHER INFORMATION: Synthetic Polynucleotide

<400> SEQUENCE: 237
tccacagaca gccctcatag ttagcgtaac gattgatcta cata                      44

<210> SEQ ID NO 238
<211> LENGTH: 44
<212> TYPE: DNA
<213> ORGANISM: Artificial
<220> FEATURE:
<223> OTHER INFORMATION: Synthetic Polynucleotide

<400> SEQUENCE: 238
tcaccagtac aaactacaac gcctagtacc agttgatcta cata                      44

<210> SEQ ID NO 239

```
<211> LENGTH: 43
<212> TYPE: DNA
<213> ORGANISM: Artificial
<220> FEATURE:
<223> OTHER INFORMATION: Synthetic Polynucleotide

<400> SEQUENCE: 239
aggaacccat gtaccgtaac acttgatata attgatctac ata                    43

<210> SEQ ID NO 240
<211> LENGTH: 42
<212> TYPE: DNA
<213> ORGANISM: Artificial
<220> FEATURE:
<223> OTHER INFORMATION: Synthetic Polynucleotide

<400> SEQUENCE: 240
aggctccaga ggctttgagg acacgggtaa ttgatctaca ta                     42

<210> SEQ ID NO 241
<211> LENGTH: 44
<212> TYPE: DNA
<213> ORGANISM: Artificial
<220> FEATURE:
<223> OTHER INFORMATION: Synthetic Polynucleotide

<400> SEQUENCE: 241
aaacagcttt ttgcgggatc gtcaacacta aattgatcta cata                   44

<210> SEQ ID NO 242
<211> LENGTH: 42
<212> TYPE: DNA
<213> ORGANISM: Artificial
<220> FEATURE:
<223> OTHER INFORMATION: Synthetic Polynucleotide

<400> SEQUENCE: 242
gtatagcaaa cagttaatgc ccaatcctca ttgatctaca ta                     42

<210> SEQ ID NO 243
<211> LENGTH: 42
<212> TYPE: DNA
<213> ORGANISM: Artificial
<220> FEATURE:
<223> OTHER INFORMATION: Synthetic Polynucleotide

<400> SEQUENCE: 243
cagcgaaact tgctttcgag gtgttgctaa ttgatctaca ta                     42

<210> SEQ ID NO 244
<211> LENGTH: 44
<212> TYPE: DNA
<213> ORGANISM: Artificial
<220> FEATURE:
<223> OTHER INFORMATION: Synthetic Polynucleotide

<400> SEQUENCE: 244
aaggccgctg ataccgatag ttgcgacgtt agttgatcta cata                   44

<210> SEQ ID NO 245
<211> LENGTH: 44
<212> TYPE: DNA
<213> ORGANISM: Artificial
<220> FEATURE:
<223> OTHER INFORMATION: Synthetic Polynucleotide

<400> SEQUENCE: 245
```

```
atattcggaa ccatcgccca cgcagagaag gattgatcta cata          44

<210> SEQ ID NO 246
<211> LENGTH: 42
<212> TYPE: DNA
<213> ORGANISM: Artificial
<220> FEATURE:
<223> OTHER INFORMATION: Synthetic Polynucleotide

<400> SEQUENCE: 246
tattaagaag cggggttttg ctcgtagcat ttgatctaca ta            42

<210> SEQ ID NO 247
<211> LENGTH: 44
<212> TYPE: DNA
<213> ORGANISM: Artificial
<220> FEATURE:
<223> OTHER INFORMATION: Synthetic Polynucleotide

<400> SEQUENCE: 247
tttcggaagt gccgtcgaga gggtgagttt cgttgatcta cata          44

<210> SEQ ID NO 248
<211> LENGTH: 42
<212> TYPE: DNA
<213> ORGANISM: Artificial
<220> FEATURE:
<223> OTHER INFORMATION: Synthetic Polynucleotide

<400> SEQUENCE: 248
aatacgtttg aaagaggaca gactgacctt ttgatctaca ta            42

<210> SEQ ID NO 249
<211> LENGTH: 44
<212> TYPE: DNA
<213> ORGANISM: Artificial
<220> FEATURE:
<223> OTHER INFORMATION: Synthetic Polynucleotide

<400> SEQUENCE: 249
acactcatcc atgttactta gccgaaagct gcttgatcta cata          44

<210> SEQ ID NO 250
<211> LENGTH: 44
<212> TYPE: DNA
<213> ORGANISM: Artificial
<220> FEATURE:
<223> OTHER INFORMATION: Synthetic Polynucleotide

<400> SEQUENCE: 250
ttgacaggcc accaccagag ccgcgatttg tattgatcta cata          44

<210> SEQ ID NO 251
<211> LENGTH: 42
<212> TYPE: DNA
<213> ORGANISM: Artificial
<220> FEATURE:
<223> OTHER INFORMATION: Synthetic Polynucleotide

<400> SEQUENCE: 251
ttaaagccag agccgccacc ctcgacagaa ttgatctaca ta            42

<210> SEQ ID NO 252
<211> LENGTH: 44
<212> TYPE: DNA
```

<213> ORGANISM: Artificial
<220> FEATURE:
<223> OTHER INFORMATION: Synthetic Polynucleotide

<400> SEQUENCE: 252
tcatcgccaa caaagtacaa cggacgccag cattgatcta cata          44

<210> SEQ ID NO 253
<211> LENGTH: 42
<212> TYPE: DNA
<213> ORGANISM: Artificial
<220> FEATURE:
<223> OTHER INFORMATION: Synthetic Polynucleotide

<400> SEQUENCE: 253
catcaagtaa acgaactaa cgagttgaga ttgatctaca ta          42

<210> SEQ ID NO 254
<211> LENGTH: 44
<212> TYPE: DNA
<213> ORGANISM: Artificial
<220> FEATURE:
<223> OTHER INFORMATION: Synthetic Polynucleotide

<400> SEQUENCE: 254
tcattcagat gcgattttaa gaacaggcat agttgatcta cata          44

<210> SEQ ID NO 255
<211> LENGTH: 42
<212> TYPE: DNA
<213> ORGANISM: Artificial
<220> FEATURE:
<223> OTHER INFORMATION: Synthetic Polynucleotide

<400> SEQUENCE: 255
tcaagtttca ttaaaggtga atataaaaga ttgatctaca ta          42

<210> SEQ ID NO 256
<211> LENGTH: 44
<212> TYPE: DNA
<213> ORGANISM: Artificial
<220> FEATURE:
<223> OTHER INFORMATION: Synthetic Polynucleotide

<400> SEQUENCE: 256
tacgttaaag taatcttgac aagaaccgaa ctttgatcta cata          44

<210> SEQ ID NO 257
<211> LENGTH: 42
<212> TYPE: DNA
<213> ORGANISM: Artificial
<220> FEATURE:
<223> OTHER INFORMATION: Synthetic Polynucleotide

<400> SEQUENCE: 257
ttataccacc aaatcaacgt aacgaacgag ttgatctaca ta          42

<210> SEQ ID NO 258
<211> LENGTH: 44
<212> TYPE: DNA
<213> ORGANISM: Artificial
<220> FEATURE:
<223> OTHER INFORMATION: Synthetic Polynucleotide

<400> SEQUENCE: 258
attacctttg aataaggctt gcccaaatcc gcttgatcta cata          44

<210> SEQ ID NO 259
<211> LENGTH: 44
<212> TYPE: DNA
<213> ORGANISM: Artificial
<220> FEATURE:
<223> OTHER INFORMATION: Synthetic Polynucleotide

<400> SEQUENCE: 259
gatggtttga acgagtagta aatttaccat tattgatcta cata                    44

<210> SEQ ID NO 260
<211> LENGTH: 42
<212> TYPE: DNA
<213> ORGANISM: Artificial
<220> FEATURE:
<223> OTHER INFORMATION: Synthetic Polynucleotide

<400> SEQUENCE: 260
cagcaaaagg aaacgtcacc aatgagccgc ttgatctaca ta                      42

<210> SEQ ID NO 261
<211> LENGTH: 44
<212> TYPE: DNA
<213> ORGANISM: Artificial
<220> FEATURE:
<223> OTHER INFORMATION: Synthetic Polynucleotide

<400> SEQUENCE: 261
tcaccgacgc accgtaatca gtagcagaac cgttgatcta cata                    44

<210> SEQ ID NO 262
<211> LENGTH: 44
<212> TYPE: DNA
<213> ORGANISM: Artificial
<220> FEATURE:
<223> OTHER INFORMATION: Synthetic Polynucleotide

<400> SEQUENCE: 262
gaaattattg cctttagcgt cagaccggaa ccttgatcta cata                    44

<210> SEQ ID NO 263
<211> LENGTH: 42
<212> TYPE: DNA
<213> ORGANISM: Artificial
<220> FEATURE:
<223> OTHER INFORMATION: Synthetic Polynucleotide

<400> SEQUENCE: 263
accgattgtc ggcattttcg gtcataatca ttgatctaca ta                      42

<210> SEQ ID NO 264
<211> LENGTH: 42
<212> TYPE: DNA
<213> ORGANISM: Artificial
<220> FEATURE:
<223> OTHER INFORMATION: Synthetic Polynucleotide

<400> SEQUENCE: 264
tttaggacaa atgctttaaa caatcaggtc ttgatctaca ta                      42

<210> SEQ ID NO 265
<211> LENGTH: 44
<212> TYPE: DNA
<213> ORGANISM: Artificial
<220> FEATURE:

```
<223> OTHER INFORMATION: Synthetic Polynucleotide

<400> SEQUENCE: 265
taagagcaaa tgtttagact ggataggaag ccttgatcta cata                    44

<210> SEQ ID NO 266
<211> LENGTH: 44
<212> TYPE: DNA
<213> ORGANISM: Artificial
<220> FEATURE:
<223> OTHER INFORMATION: Synthetic Polynucleotide

<400> SEQUENCE: 266
ttattacgaa gaactggcat gattgcgaga ggttgatcta cata                    44

<210> SEQ ID NO 267
<211> LENGTH: 42
<212> TYPE: DNA
<213> ORGANISM: Artificial
<220> FEATURE:
<223> OTHER INFORMATION: Synthetic Polynucleotide

<400> SEQUENCE: 267
aacgcaaaga tagccgaaca aaccctgaac ttgatctaca ta                      42

<210> SEQ ID NO 268
<211> LENGTH: 44
<212> TYPE: DNA
<213> ORGANISM: Artificial
<220> FEATURE:
<223> OTHER INFORMATION: Synthetic Polynucleotide

<400> SEQUENCE: 268
cttttgcaga taaaaaccaa aataaagact ccttgatcta cata                    44

<210> SEQ ID NO 269
<211> LENGTH: 42
<212> TYPE: DNA
<213> ORGANISM: Artificial
<220> FEATURE:
<223> OTHER INFORMATION: Synthetic Polynucleotide

<400> SEQUENCE: 269
tttaccccaa catgttttaa atttccatat ttgatctaca ta                      42

<210> SEQ ID NO 270
<211> LENGTH: 44
<212> TYPE: DNA
<213> ORGANISM: Artificial
<220> FEATURE:
<223> OTHER INFORMATION: Synthetic Polynucleotide

<400> SEQUENCE: 270
cggattgcag agcttaattg ctgaaacgag tattgatcta cata                    44

<210> SEQ ID NO 271
<211> LENGTH: 44
<212> TYPE: DNA
<213> ORGANISM: Artificial
<220> FEATURE:
<223> OTHER INFORMATION: Synthetic Polynucleotide

<400> SEQUENCE: 271
cgaaagactt tgataagagg tcatatttcg cattgatcta cata                    44
```

```
<210> SEQ ID NO 272
<211> LENGTH: 42
<212> TYPE: DNA
<213> ORGANISM: Artificial
<220> FEATURE:
<223> OTHER INFORMATION: Synthetic Polynucleotide

<400> SEQUENCE: 272
gcttcaatca ggattagaga gttattttca ttgatctaca ta                      42

<210> SEQ ID NO 273
<211> LENGTH: 44
<212> TYPE: DNA
<213> ORGANISM: Artificial
<220> FEATURE:
<223> OTHER INFORMATION: Synthetic Polynucleotide

<400> SEQUENCE: 273
ttagacggcc aaataagaaa cgatagaagg ctttgatcta cata                    44

<210> SEQ ID NO 274
<211> LENGTH: 42
<212> TYPE: DNA
<213> ORGANISM: Artificial
<220> FEATURE:
<223> OTHER INFORMATION: Synthetic Polynucleotide

<400> SEQUENCE: 274
aaagtcacaa aataaacagc cagcgtttta ttgatctaca ta                      42

<210> SEQ ID NO 275
<211> LENGTH: 44
<212> TYPE: DNA
<213> ORGANISM: Artificial
<220> FEATURE:
<223> OTHER INFORMATION: Synthetic Polynucleotide

<400> SEQUENCE: 275
gagagataga gcgtctttcc agaggttttg aattgatcta cata                    44

<210> SEQ ID NO 276
<211> LENGTH: 44
<212> TYPE: DNA
<213> ORGANISM: Artificial
<220> FEATURE:
<223> OTHER INFORMATION: Synthetic Polynucleotide

<400> SEQUENCE: 276
ctgtagcttg actattatag tcagttcatt gattgatcta cata                    44

<210> SEQ ID NO 277
<211> LENGTH: 42
<212> TYPE: DNA
<213> ORGANISM: Artificial
<220> FEATURE:
<223> OTHER INFORMATION: Synthetic Polynucleotide

<400> SEQUENCE: 277
gatggcttat caaaaagatt aagagcgtcc ttgatctaca ta                      42

<210> SEQ ID NO 278
<211> LENGTH: 44
<212> TYPE: DNA
<213> ORGANISM: Artificial
<220> FEATURE:
<223> OTHER INFORMATION: Synthetic Polynucleotide
```

-continued

<400> SEQUENCE: 278
ttgctccttt caaatatcgc gtttgagggg gtttgatcta cata                         44

<210> SEQ ID NO 279
<211> LENGTH: 44
<212> TYPE: DNA
<213> ORGANISM: Artificial
<220> FEATURE:
<223> OTHER INFORMATION: Synthetic Polynucleotide

<400> SEQUENCE: 279
ccaacaggag cgaaccagac cggagccttt acttgatcta cata                         44

<210> SEQ ID NO 280
<211> LENGTH: 42
<212> TYPE: DNA
<213> ORGANISM: Artificial
<220> FEATURE:
<223> OTHER INFORMATION: Synthetic Polynucleotide

<400> SEQUENCE: 280
ttaacgtcta acataaaaac aggtaacgga ttgatctaca ta                           42

<210> SEQ ID NO 281
<211> LENGTH: 44
<212> TYPE: DNA
<213> ORGANISM: Artificial
<220> FEATURE:
<223> OTHER INFORMATION: Synthetic Polynucleotide

<400> SEQUENCE: 281
atcccaatga gaattaactg aacagttacc agttgatcta cata                         44

<210> SEQ ID NO 282
<211> LENGTH: 44
<212> TYPE: DNA
<213> ORGANISM: Artificial
<220> FEATURE:
<223> OTHER INFORMATION: Synthetic Polynucleotide

<400> SEQUENCE: 282
gccagttaga gggtaattga gcgctttaag aattgatcta cata                         44

<210> SEQ ID NO 283
<211> LENGTH: 42
<212> TYPE: DNA
<213> ORGANISM: Artificial
<220> FEATURE:
<223> OTHER INFORMATION: Synthetic Polynucleotide

<400> SEQUENCE: 283
acgctaacac ccacaagaat tgaaaatagc ttgatctaca ta                           42

<210> SEQ ID NO 284
<211> LENGTH: 44
<212> TYPE: DNA
<213> ORGANISM: Artificial
<220> FEATURE:
<223> OTHER INFORMATION: Synthetic Polynucleotide

<400> SEQUENCE: 284
ttctactacg cgagctgaaa aggttaccgc gcttgatcta cata                         44

<210> SEQ ID NO 285
<211> LENGTH: 42

```
<212> TYPE: DNA
<213> ORGANISM: Artificial
<220> FEATURE:
<223> OTHER INFORMATION: Synthetic Polynucleotide

<400> SEQUENCE: 285
aacgcaaaat cgatgaacgg taccggttga ttgatctaca ta                            42

<210> SEQ ID NO 286
<211> LENGTH: 44
<212> TYPE: DNA
<213> ORGANISM: Artificial
<220> FEATURE:
<223> OTHER INFORMATION: Synthetic Polynucleotide

<400> SEQUENCE: 286
tatattttgt cattgcctga gagtggaaga ttttgatcta cata                          44

<210> SEQ ID NO 287
<211> LENGTH: 44
<212> TYPE: DNA
<213> ORGANISM: Artificial
<220> FEATURE:
<223> OTHER INFORMATION: Synthetic Polynucleotide

<400> SEQUENCE: 287
taggtaaact atttttgaga gatcaaacgt tattgatcta cata                          44

<210> SEQ ID NO 288
<211> LENGTH: 42
<212> TYPE: DNA
<213> ORGANISM: Artificial
<220> FEATURE:
<223> OTHER INFORMATION: Synthetic Polynucleotide

<400> SEQUENCE: 288
gagacagcta gctgataaat taattttgt ttgatctaca ta                             42

<210> SEQ ID NO 289
<211> LENGTH: 44
<212> TYPE: DNA
<213> ORGANISM: Artificial
<220> FEATURE:
<223> OTHER INFORMATION: Synthetic Polynucleotide

<400> SEQUENCE: 289
gtaaagtaat cgccatattt aacaaaactt ttttgatcta cata                          44

<210> SEQ ID NO 290
<211> LENGTH: 42
<212> TYPE: DNA
<213> ORGANISM: Artificial
<220> FEATURE:
<223> OTHER INFORMATION: Synthetic Polynucleotide

<400> SEQUENCE: 290
acaacatgcc aacgctcaac agtcttctga ttgatctaca ta                            42

<210> SEQ ID NO 291
<211> LENGTH: 44
<212> TYPE: DNA
<213> ORGANISM: Artificial
<220> FEATURE:
<223> OTHER INFORMATION: Synthetic Polynucleotide

<400> SEQUENCE: 291
```
gtttatcaat atgcgttata caaaccgacc gtttgatcta cata    44

<210> SEQ ID NO 292
<211> LENGTH: 42
<212> TYPE: DNA
<213> ORGANISM: Artificial
<220> FEATURE:
<223> OTHER INFORMATION: Synthetic Polynucleotide

<400> SEQUENCE: 292
ttagtatcac aatagataag tccacgagca ttgatctaca ta    42

<210> SEQ ID NO 293
<211> LENGTH: 42
<212> TYPE: DNA
<213> ORGANISM: Artificial
<220> FEATURE:
<223> OTHER INFORMATION: Synthetic Polynucleotide

<400> SEQUENCE: 293
taatcagcgg attgaccgta atcgtaaccg ttgatctaca ta    42

<210> SEQ ID NO 294
<211> LENGTH: 44
<212> TYPE: DNA
<213> ORGANISM: Artificial
<220> FEATURE:
<223> OTHER INFORMATION: Synthetic Polynucleotide

<400> SEQUENCE: 294
atattttggc tttcatcaac attatccagc cattgatcta cata    44

<210> SEQ ID NO 295
<211> LENGTH: 44
<212> TYPE: DNA
<213> ORGANISM: Artificial
<220> FEATURE:
<223> OTHER INFORMATION: Synthetic Polynucleotide

<400> SEQUENCE: 295
atcgcaagta tgtaaatgct gatgatagga acttgatcta cata    44

<210> SEQ ID NO 296
<211> LENGTH: 42
<212> TYPE: DNA
<213> ORGANISM: Artificial
<220> FEATURE:
<223> OTHER INFORMATION: Synthetic Polynucleotide

<400> SEQUENCE: 296
cctaaatcaa aatcataggt ctaaacagta ttgatctaca ta    42

<210> SEQ ID NO 297
<211> LENGTH: 44
<212> TYPE: DNA
<213> ORGANISM: Artificial
<220> FEATURE:
<223> OTHER INFORMATION: Synthetic Polynucleotide

<400> SEQUENCE: 297
gccatcaagc tcattttta accacaaatc cattgatcta cata    44

<210> SEQ ID NO 298
<211> LENGTH: 42
<212> TYPE: DNA
<213> ORGANISM: Artificial

```
<220> FEATURE:
<223> OTHER INFORMATION: Synthetic Polynucleotide

<400> SEQUENCE: 298
tgcatctttc ccagtcacga cggcctgcag ttgatctaca ta         42

<210> SEQ ID NO 299
<211> LENGTH: 44
<212> TYPE: DNA
<213> ORGANISM: Artificial
<220> FEATURE:
<223> OTHER INFORMATION: Synthetic Polynucleotide

<400> SEQUENCE: 299
gctttccgat tacgccagct ggcggctgtt tcttgatcta cata       44

<210> SEQ ID NO 300
<211> LENGTH: 42
<212> TYPE: DNA
<213> ORGANISM: Artificial
<220> FEATURE:
<223> OTHER INFORMATION: Synthetic Polynucleotide

<400> SEQUENCE: 300
cataaatctt tgaataccaa gtgttagaac ttgatctaca ta         42

<210> SEQ ID NO 301
<211> LENGTH: 44
<212> TYPE: DNA
<213> ORGANISM: Artificial
<220> FEATURE:
<223> OTHER INFORMATION: Synthetic Polynucleotide

<400> SEQUENCE: 301
ccagggttgc cagtttgagg ggacccgtgg gattgatcta cata       44

<210> SEQ ID NO 302
<211> LENGTH: 42
<212> TYPE: DNA
<213> ORGANISM: Artificial
<220> FEATURE:
<223> OTHER INFORMATION: Synthetic Polynucleotide

<400> SEQUENCE: 302
gatgtgcttc aggaagatcg cacaatgtga ttgatctaca ta         42

<210> SEQ ID NO 303
<211> LENGTH: 44
<212> TYPE: DNA
<213> ORGANISM: Artificial
<220> FEATURE:
<223> OTHER INFORMATION: Synthetic Polynucleotide

<400> SEQUENCE: 303
tcttcgctgc accgcttctg gtgcggcctt ccttgatcta cata       44

<210> SEQ ID NO 304
<211> LENGTH: 44
<212> TYPE: DNA
<213> ORGANISM: Artificial
<220> FEATURE:
<223> OTHER INFORMATION: Synthetic Polynucleotide

<400> SEQUENCE: 304
caactgttgc gccattcgcc attcaaacat cattgatcta cata       44
```

<210> SEQ ID NO 305
<211> LENGTH: 42
<212> TYPE: DNA
<213> ORGANISM: Artificial
<220> FEATURE:
<223> OTHER INFORMATION: Synthetic Polynucleotide

<400> SEQUENCE: 305
ctgagcaaaa attaattaca ttttgggtta ttgatctaca ta                42

<210> SEQ ID NO 306
<211> LENGTH: 44
<212> TYPE: DNA
<213> ORGANISM: Artificial
<220> FEATURE:
<223> OTHER INFORMATION: Synthetic Polynucleotide

<400> SEQUENCE: 306
cgcgcagatt acctttttta atgggagaga ctttgatcta cata              44

<210> SEQ ID NO 307
<211> LENGTH: 44
<212> TYPE: DNA
<213> ORGANISM: Artificial
<220> FEATURE:
<223> OTHER INFORMATION: Synthetic Polynucleotide

<400> SEQUENCE: 307
cctgattgca atatatgtga gtgatcaata gtttgatcta cata              44

<210> SEQ ID NO 308
<211> LENGTH: 42
<212> TYPE: DNA
<213> ORGANISM: Artificial
<220> FEATURE:
<223> OTHER INFORMATION: Synthetic Polynucleotide

<400> SEQUENCE: 308
cttttacaaa atcgtcgcta ttagcgatag ttgatctaca ta                42

<210> SEQ ID NO 309
<211> LENGTH: 42
<212> TYPE: DNA
<213> ORGANISM: Artificial
<220> FEATURE:
<223> OTHER INFORMATION: Synthetic Polynucleotide

<400> SEQUENCE: 309
gtcgacttcg gccaacgcgc ggggtttttc ttgatctaca ta                42

<210> SEQ ID NO 310
<211> LENGTH: 44
<212> TYPE: DNA
<213> ORGANISM: Artificial
<220> FEATURE:
<223> OTHER INFORMATION: Synthetic Polynucleotide

<400> SEQUENCE: 310
ctgtgtgatt gcgttgcgct cactagagtt gcttgatcta cata              44

<210> SEQ ID NO 311
<211> LENGTH: 44
<212> TYPE: DNA
<213> ORGANISM: Artificial
<220> FEATURE:
<223> OTHER INFORMATION: Synthetic Polynucleotide

<400> SEQUENCE: 311
gcaattcaca tattcctgat tatcaaagtg tattgatcta cata    44

<210> SEQ ID NO 312
<211> LENGTH: 42
<212> TYPE: DNA
<213> ORGANISM: Artificial
<220> FEATURE:
<223> OTHER INFORMATION: Synthetic Polynucleotide

<400> SEQUENCE: 312
ctaccatagt ttgagtaaca tttaaaatat ttgatctaca ta    42

<210> SEQ ID NO 313
<211> LENGTH: 44
<212> TYPE: DNA
<213> ORGANISM: Artificial
<220> FEATURE:
<223> OTHER INFORMATION: Synthetic Polynucleotide

<400> SEQUENCE: 313
aagcctggta cgagccggaa gcatagatga tgttgatcta cata    44

<210> SEQ ID NO 314
<211> LENGTH: 44
<212> TYPE: DNA
<213> ORGANISM: Artificial
<220> FEATURE:
<223> OTHER INFORMATION: Synthetic Polynucleotide

<400> SEQUENCE: 314
agcaagcgta gggttgagtg ttgtagggag ccttgatcta cata    44

<210> SEQ ID NO 315
<211> LENGTH: 44
<212> TYPE: DNA
<213> ORGANISM: Artificial
<220> FEATURE:
<223> OTHER INFORMATION: Synthetic Polynucleotide

<400> SEQUENCE: 315
tcaatatcga acctcaaata tcaattccga aattgatcta cata    44

<210> SEQ ID NO 316
<211> LENGTH: 42
<212> TYPE: DNA
<213> ORGANISM: Artificial
<220> FEATURE:
<223> OTHER INFORMATION: Synthetic Polynucleotide

<400> SEQUENCE: 316
ctttagggcc tgcaacagtg ccaatacgtg ttgatctaca ta    42

<210> SEQ ID NO 317
<211> LENGTH: 44
<212> TYPE: DNA
<213> ORGANISM: Artificial
<220> FEATURE:
<223> OTHER INFORMATION: Synthetic Polynucleotide

<400> SEQUENCE: 317
ctccaacgca gtgagacggg caaccagctg cattgatcta cata    44

<210> SEQ ID NO 318

```
<211> LENGTH: 42
<212> TYPE: DNA
<213> ORGANISM: Artificial
<220> FEATURE:
<223> OTHER INFORMATION: Synthetic Polynucleotide

<400> SEQUENCE: 318
tggaacaacc gcctggccct gaggcccgct tgatctaca ta                          42

<210> SEQ ID NO 319
<211> LENGTH: 44
<212> TYPE: DNA
<213> ORGANISM: Artificial
<220> FEATURE:
<223> OTHER INFORMATION: Synthetic Polynucleotide

<400> SEQUENCE: 319
gcccgagagt ccacgctggt ttgcagctaa ctttgatcta cata                       44

<210> SEQ ID NO 320
<211> LENGTH: 44
<212> TYPE: DNA
<213> ORGANISM: Artificial
<220> FEATURE:
<223> OTHER INFORMATION: Synthetic Polynucleotide

<400> SEQUENCE: 320
tcggcaaatc ctgtttgatg gtggaccctc aattgatcta cata                       44

<210> SEQ ID NO 321
<211> LENGTH: 42
<212> TYPE: DNA
<213> ORGANISM: Artificial
<220> FEATURE:
<223> OTHER INFORMATION: Synthetic Polynucleotide

<400> SEQUENCE: 321
accttgcttg gtcagttggc aaagagcgga ttgatctaca ta                         42

<210> SEQ ID NO 322
<211> LENGTH: 44
<212> TYPE: DNA
<213> ORGANISM: Artificial
<220> FEATURE:
<223> OTHER INFORMATION: Synthetic Polynucleotide

<400> SEQUENCE: 322
agccagcaat tgaggaaggt tatcatcatt ttttgatcta cata                       44

<210> SEQ ID NO 323
<211> LENGTH: 44
<212> TYPE: DNA
<213> ORGANISM: Artificial
<220> FEATURE:
<223> OTHER INFORMATION: Synthetic Polynucleotide

<400> SEQUENCE: 323
ttaacaccag cactaacaac taatcgttat tattgatcta cata                       44

<210> SEQ ID NO 324
<211> LENGTH: 42
<212> TYPE: DNA
<213> ORGANISM: Artificial
<220> FEATURE:
<223> OTHER INFORMATION: Synthetic Polynucleotide

<400> SEQUENCE: 324
```
cagaagatta gataatacat tgtcgacaa ttgatctaca ta            42

<210> SEQ ID NO 325
<211> LENGTH: 42
<212> TYPE: DNA
<213> ORGANISM: Artificial
<220> FEATURE:
<223> OTHER INFORMATION: Synthetic Polynucleotide

<400> SEQUENCE: 325
aaagcactaa atcggaaccc taatccagtt ttgatctaca ta            42

<210> SEQ ID NO 326
<211> LENGTH: 44
<212> TYPE: DNA
<213> ORGANISM: Artificial
<220> FEATURE:
<223> OTHER INFORMATION: Synthetic Polynucleotide

<400> SEQUENCE: 326
cccgatttag agcttgacgg ggaaaaagaa tattgatcta cata            44

<210> SEQ ID NO 327
<211> LENGTH: 43
<212> TYPE: DNA
<213> ORGANISM: Artificial
<220> FEATURE:
<223> OTHER INFORMATION: Synthetic Polynucleotide

<400> SEQUENCE: 327
aacgtggcga gaaaggaagg gaaaccagta attgatctac ata            43

<210> SEQ ID NO 328
<211> LENGTH: 42
<212> TYPE: DNA
<213> ORGANISM: Artificial
<220> FEATURE:
<223> OTHER INFORMATION: Synthetic Polynucleotide

<400> SEQUENCE: 328
taaaagggac attctggcca acaaagcatc ttgatctaca ta            42

<210> SEQ ID NO 329
<211> LENGTH: 44
<212> TYPE: DNA
<213> ORGANISM: Artificial
<220> FEATURE:
<223> OTHER INFORMATION: Synthetic Polynucleotide

<400> SEQUENCE: 329
acccttctga cctgaaagcg taagacgctg agttgatcta cata            44

<210> SEQ ID NO 330
<211> LENGTH: 52
<212> TYPE: DNA
<213> ORGANISM: Artificial
<220> FEATURE:
<223> OTHER INFORMATION: Synthetic Polynucleotide

<400> SEQUENCE: 330
atgcagatac ataacgggaa tcgtcataaa taaagcaaag ttgatctaca ta            52

<210> SEQ ID NO 331
<211> LENGTH: 50
<212> TYPE: DNA

<213> ORGANISM: Artificial
<220> FEATURE:
<223> OTHER INFORMATION: Synthetic Polynucleotide

<400> SEQUENCE: 331
cgtttaccag acgacaaaga agttttgcca taattcgatt gatctacata         50

<210> SEQ ID NO 332
<211> LENGTH: 52
<212> TYPE: DNA
<213> ORGANISM: Artificial
<220> FEATURE:
<223> OTHER INFORMATION: Synthetic Polynucleotide

<400> SEQUENCE: 332
cgtagaaaat acataccgag gaaacgcaat aagaagcgca ttgatctaca ta       52

<210> SEQ ID NO 333
<211> LENGTH: 52
<212> TYPE: DNA
<213> ORGANISM: Artificial
<220> FEATURE:
<223> OTHER INFORMATION: Synthetic Polynucleotide

<400> SEQUENCE: 333
gtttattttg tcacaatctt accgaagccc tttaatatca ttgatctaca ta       52

<210> SEQ ID NO 334
<211> LENGTH: 42
<212> TYPE: DNA
<213> ORGANISM: Artificial
<220> FEATURE:
<223> OTHER INFORMATION: Synthetic Polynucleotide

<400> SEQUENCE: 334
aacagttttg taccaaaaac attttatttc ttgatctaca ta                 42

<210> SEQ ID NO 335
<211> LENGTH: 44
<212> TYPE: DNA
<213> ORGANISM: Artificial
<220> FEATURE:
<223> OTHER INFORMATION: Synthetic Polynucleotide

<400> SEQUENCE: 335
gatttagtca ataaagcctc agagaaccct cattgatcta cata               44

<210> SEQ ID NO 336
<211> LENGTH: 44
<212> TYPE: DNA
<213> ORGANISM: Artificial
<220> FEATURE:
<223> OTHER INFORMATION: Synthetic Polynucleotide

<400> SEQUENCE: 336
aatggtcaac aggcaaggca aagagtaatg tgttgatcta cata               44

<210> SEQ ID NO 337
<211> LENGTH: 42
<212> TYPE: DNA
<213> ORGANISM: Artificial
<220> FEATURE:
<223> OTHER INFORMATION: Synthetic Polynucleotide

<400> SEQUENCE: 337
tttggggata gtagtagcat taaaaggccg ttgatctaca ta                 42

<210> SEQ ID NO 338
<211> LENGTH: 44
<212> TYPE: DNA
<213> ORGANISM: Artificial
<220> FEATURE:
<223> OTHER INFORMATION: Synthetic Polynucleotide

<400> SEQUENCE: 338
ccaatagctc atcgtaggaa tcatggcatc aattgatcta cata                44

<210> SEQ ID NO 339
<211> LENGTH: 44
<212> TYPE: DNA
<213> ORGANISM: Artificial
<220> FEATURE:
<223> OTHER INFORMATION: Synthetic Polynucleotide

<400> SEQUENCE: 339
tatccggtct catcgagaac aagcgacaaa agttgatcta cata                44

<210> SEQ ID NO 340
<211> LENGTH: 42
<212> TYPE: DNA
<213> ORGANISM: Artificial
<220> FEATURE:
<223> OTHER INFORMATION: Synthetic Polynucleotide

<400> SEQUENCE: 340
gcgaacctcc aagaacgggt atgacaataa ttgatctaca ta                  42

<210> SEQ ID NO 341
<211> LENGTH: 44
<212> TYPE: DNA
<213> ORGANISM: Artificial
<220> FEATURE:
<223> OTHER INFORMATION: Synthetic Polynucleotide

<400> SEQUENCE: 341
gccttaaacc aatcaataat cggcacgcgc ctttgatcta cata                44

<210> SEQ ID NO 342
<211> LENGTH: 44
<212> TYPE: DNA
<213> ORGANISM: Artificial
<220> FEATURE:
<223> OTHER INFORMATION: Synthetic Polynucleotide

<400> SEQUENCE: 342
aacaagaggg ataaaaattt ttagcataaa gcttgatcta cata                44

<210> SEQ ID NO 343
<211> LENGTH: 42
<212> TYPE: DNA
<213> ORGANISM: Artificial
<220> FEATURE:
<223> OTHER INFORMATION: Synthetic Polynucleotide

<400> SEQUENCE: 343
gctatcagaa atgcaatgcc tgaattagca ttgatctaca ta                  42

<210> SEQ ID NO 344
<211> LENGTH: 44
<212> TYPE: DNA
<213> ORGANISM: Artificial
<220> FEATURE:

<223> OTHER INFORMATION: Synthetic Polynucleotide

<400> SEQUENCE: 344
gagggtagga ttcaaaaggg tgagacatcc aattgatcta cata        44

<210> SEQ ID NO 345
<211> LENGTH: 44
<212> TYPE: DNA
<213> ORGANISM: Artificial
<220> FEATURE:
<223> OTHER INFORMATION: Synthetic Polynucleotide

<400> SEQUENCE: 345
caaccgtttc aaatcaccat caattcgagc cattgatcta cata        44

<210> SEQ ID NO 346
<211> LENGTH: 42
<212> TYPE: DNA
<213> ORGANISM: Artificial
<220> FEATURE:
<223> OTHER INFORMATION: Synthetic Polynucleotide

<400> SEQUENCE: 346
catgtaatag aatataaagt accaagccgt ttgatctaca ta        42

<210> SEQ ID NO 347
<211> LENGTH: 44
<212> TYPE: DNA
<213> ORGANISM: Artificial
<220> FEATURE:
<223> OTHER INFORMATION: Synthetic Polynucleotide

<400> SEQUENCE: 347
aattgagaat tctgtccaga cgactaaacc aattgatcta cata        44

<210> SEQ ID NO 348
<211> LENGTH: 44
<212> TYPE: DNA
<213> ORGANISM: Artificial
<220> FEATURE:
<223> OTHER INFORMATION: Synthetic Polynucleotide

<400> SEQUENCE: 348
agtataaagt tcagctaatg cagatgtctt tcttgatcta cata        44

<210> SEQ ID NO 349
<211> LENGTH: 50
<212> TYPE: DNA
<213> ORGANISM: Artificial
<220> FEATURE:
<223> OTHER INFORMATION: Synthetic Polynucleotide

<400> SEQUENCE: 349
cccagcaggc gaaaatccc ttataaatca agccggcgtt gatctacata        50

<210> SEQ ID NO 350
<211> LENGTH: 52
<212> TYPE: DNA
<213> ORGANISM: Artificial
<220> FEATURE:
<223> OTHER INFORMATION: Synthetic Polynucleotide

<400> SEQUENCE: 350
tcaacagttg aaaggagcaa atgaaaaatc tagagataga ttgatctaca ta        52

```
<210> SEQ ID NO 351
<211> LENGTH: 44
<212> TYPE: DNA
<213> ORGANISM: Artificial
<220> FEATURE:
<223> OTHER INFORMATION: Synthetic Polynucleotide

<400> SEQUENCE: 351
ttaggattgg ctgagactcc tcaataaccg atttgatcta cata            44

<210> SEQ ID NO 352
<211> LENGTH: 44
<212> TYPE: DNA
<213> ORGANISM: Artificial
<220> FEATURE:
<223> OTHER INFORMATION: Synthetic Polynucleotide

<400> SEQUENCE: 352
gaccaactaa tgccactacg aagggggtag cattgatcta cata            44

<210> SEQ ID NO 353
<211> LENGTH: 42
<212> TYPE: DNA
<213> ORGANISM: Artificial
<220> FEATURE:
<223> OTHER INFORMATION: Synthetic Polynucleotide

<400> SEQUENCE: 353
gcgcagacaa gaggcaaaag aatccctcag ttgatctaca ta              42

<210> SEQ ID NO 354
<211> LENGTH: 44
<212> TYPE: DNA
<213> ORGANISM: Artificial
<220> FEATURE:
<223> OTHER INFORMATION: Synthetic Polynucleotide

<400> SEQUENCE: 354
gacctgctct ttgaccccca gcgagggagt tattgatcta cata            44

<210> SEQ ID NO 355
<211> LENGTH: 42
<212> TYPE: DNA
<213> ORGANISM: Artificial
<220> FEATURE:
<223> OTHER INFORMATION: Synthetic Polynucleotide

<400> SEQUENCE: 355
caccagaaag gttgaggcag gtcatgaaag ttgatctaca ta              42

<210> SEQ ID NO 356
<211> LENGTH: 44
<212> TYPE: DNA
<213> ORGANISM: Artificial
<220> FEATURE:
<223> OTHER INFORMATION: Synthetic Polynucleotide

<400> SEQUENCE: 356
ccaccctcta ttcacaaaca aatacctgcc tattgatcta cata            44

<210> SEQ ID NO 357
<211> LENGTH: 44
<212> TYPE: DNA
<213> ORGANISM: Artificial
<220> FEATURE:
<223> OTHER INFORMATION: Synthetic Polynucleotide
```

<400> SEQUENCE: 357
gcctccctca gaatggaaag cgcagtaaca gtttgatcta cata         44

<210> SEQ ID NO 358
<211> LENGTH: 42
<212> TYPE: DNA
<213> ORGANISM: Artificial
<220> FEATURE:
<223> OTHER INFORMATION: Synthetic Polynucleotide

<400> SEQUENCE: 358
aaatcacctt ccagtaagcg tcagtaataa ttgatctaca ta         42

<210> SEQ ID NO 359
<211> LENGTH: 44
<212> TYPE: DNA
<213> ORGANISM: Artificial
<220> FEATURE:
<223> OTHER INFORMATION: Synthetic Polynucleotide

<400> SEQUENCE: 359
gcaaggcctc accagtagca ccatgggctt gattgatcta cata         44

<210> SEQ ID NO 360
<211> LENGTH: 44
<212> TYPE: DNA
<213> ORGANISM: Artificial
<220> FEATURE:
<223> OTHER INFORMATION: Synthetic Polynucleotide

<400> SEQUENCE: 360 atcccctat accacattca actagaaaaa tcttgatcta cata         44

<210> SEQ ID NO 361
<211> LENGTH: 42
<212> TYPE: DNA
<213> ORGANISM: Artificial
<220> FEATURE:
<223> OTHER INFORMATION: Synthetic Polynucleotide

<400> SEQUENCE: 361
aatactgccc aaaaggaatt acgtggctca ttgatctaca ta         42

<210> SEQ ID NO 362
<211> LENGTH: 44
<212> TYPE: DNA
<213> ORGANISM: Artificial
<220> FEATURE:
<223> OTHER INFORMATION: Synthetic Polynucleotide

<400> SEQUENCE: 362
aatagtaaac actatcataa ccctcattgt gattgatcta cata         44

<210> SEQ ID NO 363
<211> LENGTH: 42
<212> TYPE: DNA
<213> ORGANISM: Artificial
<220> FEATURE:
<223> OTHER INFORMATION: Synthetic Polynucleotide

<400> SEQUENCE: 363
atacccaaca gtatgttagc aaattagagc ttgatctaca ta         42

<210> SEQ ID NO 364
<211> LENGTH: 44

```
<212> TYPE: DNA
<213> ORGANISM: Artificial
<220> FEATURE:
<223> OTHER INFORMATION: Synthetic Polynucleotide

<400> SEQUENCE: 364
aaggaaacat aaaggtggca acattatcac cgttgatcta cata            44

<210> SEQ ID NO 365
<211> LENGTH: 44
<212> TYPE: DNA
<213> ORGANISM: Artificial
<220> FEATURE:
<223> OTHER INFORMATION: Synthetic Polynucleotide

<400> SEQUENCE: 365
aagtaagcag acaccacgga ataatattga cgttgatcta cata            44

<210> SEQ ID NO 366
<211> LENGTH: 42
<212> TYPE: DNA
<213> ORGANISM: Artificial
<220> FEATURE:
<223> OTHER INFORMATION: Synthetic Polynucleotide

<400> SEQUENCE: 366
aatagctatc aatagaaaat tcaacattca ttgatctaca ta              42

<210> SEQ ID NO 367
<211> LENGTH: 44
<212> TYPE: DNA
<213> ORGANISM: Artificial
<220> FEATURE:
<223> OTHER INFORMATION: Synthetic Polynucleotide

<400> SEQUENCE: 367
agagagaaaa aaatgaaaat agcaagcaaa ctttgatcta cata            44

<210> SEQ ID NO 368
<211> LENGTH: 44
<212> TYPE: DNA
<213> ORGANISM: Artificial
<220> FEATURE:
<223> OTHER INFORMATION: Synthetic Polynucleotide

<400> SEQUENCE: 368
taaatcggga ttcccaattc tgcgatataa tgttgatcta cata            44

<210> SEQ ID NO 369
<211> LENGTH: 42
<212> TYPE: DNA
<213> ORGANISM: Artificial
<220> FEATURE:
<223> OTHER INFORMATION: Synthetic Polynucleotide

<400> SEQUENCE: 369
aaattaagtt gaccattaga tacttttgcg ttgatctaca ta              42

<210> SEQ ID NO 370
<211> LENGTH: 44
<212> TYPE: DNA
<213> ORGANISM: Artificial
<220> FEATURE:
<223> OTHER INFORMATION: Synthetic Polynucleotide

<400> SEQUENCE: 370
```

```
taaatcatat aacctgttta gctaacctt  aattgatcta cata                    44
```

<210> SEQ ID NO 371
<211> LENGTH: 42
<212> TYPE: DNA
<213> ORGANISM: Artificial
<220> FEATURE:
<223> OTHER INFORMATION: Synthetic Polynucleotide

<400> SEQUENCE: 371

```
ttttatttaa gcaaatcaga tattttttgt tgatctaca ta                       42
```

<210> SEQ ID NO 372
<211> LENGTH: 44
<212> TYPE: DNA
<213> ORGANISM: Artificial
<220> FEATURE:
<223> OTHER INFORMATION: Synthetic Polynucleotide

<400> SEQUENCE: 372

```
gtaccgcaat tctaagaacg cgagtattat ttttgatcta cata                    44
```

<210> SEQ ID NO 373
<211> LENGTH: 44
<212> TYPE: DNA
<213> ORGANISM: Artificial
<220> FEATURE:
<223> OTHER INFORMATION: Synthetic Polynucleotide

<400> SEQUENCE: 373

```
cttatcattc ccgacttgcg ggagcctaat ttttgatcta cata                    44
```

<210> SEQ ID NO 374
<211> LENGTH: 42
<212> TYPE: DNA
<213> ORGANISM: Artificial
<220> FEATURE:
<223> OTHER INFORMATION: Synthetic Polynucleotide

<400> SEQUENCE: 374

```
tgtagaaatc aagattagtt gctcttacca ttgatctaca ta                      42
```

<210> SEQ ID NO 375
<211> LENGTH: 44
<212> TYPE: DNA
<213> ORGANISM: Artificial
<220> FEATURE:
<223> OTHER INFORMATION: Synthetic Polynucleotide

<400> SEQUENCE: 375

```
gtaataagtt aggcagaggc atttatgata ttttgatcta cata                    44
```

<210> SEQ ID NO 376
<211> LENGTH: 44
<212> TYPE: DNA
<213> ORGANISM: Artificial
<220> FEATURE:
<223> OTHER INFORMATION: Synthetic Polynucleotide

<400> SEQUENCE: 376

```
acaaacggaa aagcccccaaa aacactggag cattgatcta cata                   44
```

<210> SEQ ID NO 377
<211> LENGTH: 42
<212> TYPE: DNA
<213> ORGANISM: Artificial

```
<220> FEATURE:
<223> OTHER INFORMATION: Synthetic Polynucleotide

<400> SEQUENCE: 377
gcgagtaaaa atatttaaat tgttacaaag ttgatctaca ta                   42

<210> SEQ ID NO 378
<211> LENGTH: 44
<212> TYPE: DNA
<213> ORGANISM: Artificial
<220> FEATURE:
<223> OTHER INFORMATION: Synthetic Polynucleotide

<400> SEQUENCE: 378
tgtagccatt aaaattcgca ttaaatgccg gattgatcta cata                 44

<210> SEQ ID NO 379
<211> LENGTH: 42
<212> TYPE: DNA
<213> ORGANISM: Artificial
<220> FEATURE:
<223> OTHER INFORMATION: Synthetic Polynucleotide

<400> SEQUENCE: 379
tataactaac aaagaacgcg agaacgccaa ttgatctaca ta                   42

<210> SEQ ID NO 380
<211> LENGTH: 44
<212> TYPE: DNA
<213> ORGANISM: Artificial
<220> FEATURE:
<223> OTHER INFORMATION: Synthetic Polynucleotide

<400> SEQUENCE: 380
acctttttat tttagttaat ttcatagggc ttttgatcta cata                 44

<210> SEQ ID NO 381
<211> LENGTH: 44
<212> TYPE: DNA
<213> ORGANISM: Artificial
<220> FEATURE:
<223> OTHER INFORMATION: Synthetic Polynucleotide

<400> SEQUENCE: 381
gaatttattt aatggtttga aatattctta ccttgatcta cata                 44

<210> SEQ ID NO 382
<211> LENGTH: 42
<212> TYPE: DNA
<213> ORGANISM: Artificial
<220> FEATURE:
<223> OTHER INFORMATION: Synthetic Polynucleotide

<400> SEQUENCE: 382
cttagattta aggcgttaaa taaagcctgt ttgatctaca ta                   42

<210> SEQ ID NO 383
<211> LENGTH: 44
<212> TYPE: DNA
<213> ORGANISM: Artificial
<220> FEATURE:
<223> OTHER INFORMATION: Synthetic Polynucleotide

<400> SEQUENCE: 383
agaaaacaaa gaagatgatg aaacaggctg cgttgatcta cata                 44
```

<210> SEQ ID NO 384
<211> LENGTH: 44
<212> TYPE: DNA
<213> ORGANISM: Artificial
<220> FEATURE:
<223> OTHER INFORMATION: Synthetic Polynucleotide

<400> SEQUENCE: 384
ttaatgaact agaggatccc cgggggtaa cgttgatcta cata                              44

<210> SEQ ID NO 385
<211> LENGTH: 42
<212> TYPE: DNA
<213> ORGANISM: Artificial
<220> FEATURE:
<223> OTHER INFORMATION: Synthetic Polynucleotide

<400> SEQUENCE: 385
ttccagtcgt aatcatggtc ataaaagggg ttgatctaca ta                               42

<210> SEQ ID NO 386
<211> LENGTH: 44
<212> TYPE: DNA
<213> ORGANISM: Artificial
<220> FEATURE:
<223> OTHER INFORMATION: Synthetic Polynucleotide

<400> SEQUENCE: 386
cacattaaaa ttgttatccg ctcatgcggg ccttgatcta cata                             44

<210> SEQ ID NO 387
<211> LENGTH: 42
<212> TYPE: DNA
<213> ORGANISM: Artificial
<220> FEATURE:
<223> OTHER INFORMATION: Synthetic Polynucleotide

<400> SEQUENCE: 387
attatcattc aatataatcc tgacaattac ttgatctaca ta                               42

<210> SEQ ID NO 388
<211> LENGTH: 44
<212> TYPE: DNA
<213> ORGANISM: Artificial
<220> FEATURE:
<223> OTHER INFORMATION: Synthetic Polynucleotide

<400> SEQUENCE: 388
gcggaacatc tgaataatgg aaggtacaaa atttgatcta cata                             44

<210> SEQ ID NO 389
<211> LENGTH: 44
<212> TYPE: DNA
<213> ORGANISM: Artificial
<220> FEATURE:
<223> OTHER INFORMATION: Synthetic Polynucleotide

<400> SEQUENCE: 389
attttaaaat caaaattatt tgcacggatt cgttgatcta cata                             44

<210> SEQ ID NO 390
<211> LENGTH: 42
<212> TYPE: DNA
<213> ORGANISM: Artificial
<220> FEATURE:
<223> OTHER INFORMATION: Synthetic Polynucleotide

<400> SEQUENCE: 390
ctcgtattag aaattgcgta gatacagtac ttgatctaca ta                                  42

<210> SEQ ID NO 391
<211> LENGTH: 43
<212> TYPE: DNA
<213> ORGANISM: Artificial
<220> FEATURE:
<223> OTHER INFORMATION: Synthetic Polynucleotide

<400> SEQUENCE: 391
agaaaggaac aactaaagga attcaaaaaa attgatctac ata                                 43

<210> SEQ ID NO 392
<211> LENGTH: 44
<212> TYPE: DNA
<213> ORGANISM: Artificial
<220> FEATURE:
<223> OTHER INFORMATION: Synthetic Polynucleotide

<400> SEQUENCE: 392
acaactttca acagtttcag cggatgtatc ggttgatcta cata                               44

<210> SEQ ID NO 393
<211> LENGTH: 44
<212> TYPE: DNA
<213> ORGANISM: Artificial
<220> FEATURE:
<223> OTHER INFORMATION: Synthetic Polynucleotide

<400> SEQUENCE: 393
ccaccctcat tttcagggat agcaaccgta ctttgatcta cata                               44

<210> SEQ ID NO 394
<211> LENGTH: 44
<212> TYPE: DNA
<213> ORGANISM: Artificial
<220> FEATURE:
<223> OTHER INFORMATION: Synthetic Polynucleotide

<400> SEQUENCE: 394
acggctacaa aaggagcctt taatgtgaga atttgatcta cata                               44

<210> SEQ ID NO 395
<211> LENGTH: 44
<212> TYPE: DNA
<213> ORGANISM: Artificial
<220> FEATURE:
<223> OTHER INFORMATION: Synthetic Polynucleotide

<400> SEQUENCE: 395
gcccgtatcc ggaataggtg tatcagccca atttgatcta cata                               44

<210> SEQ ID NO 396
<211> LENGTH: 42
<212> TYPE: DNA
<213> ORGANISM: Artificial
<220> FEATURE:
<223> OTHER INFORMATION: Synthetic Polynucleotide

<400> SEQUENCE: 396
gttttaactt agtaccgcca cccagagcca ttgatctaca ta                                  42

<210> SEQ ID NO 397

```
<210> SEQ ID NO 397
<211> LENGTH: 42
<212> TYPE: DNA
<213> ORGANISM: Artificial
<220> FEATURE:
<223> OTHER INFORMATION: Synthetic Polynucleotide

<400> SEQUENCE: 397
ttttcactca aagggcgaaa aaccatcacc ttgatctaca ta                           42

<210> SEQ ID NO 398
<211> LENGTH: 52
<212> TYPE: DNA
<213> ORGANISM: Artificial
<220> FEATURE:
<223> OTHER INFORMATION: Synthetic Polynucleotide

<400> SEQUENCE: 398
agctgattgc ccttcagagt ccactattaa agggtgccgt ttgatctaca ta               52

<210> SEQ ID NO 399
<211> LENGTH: 52
<212> TYPE: DNA
<213> ORGANISM: Artificial
<220> FEATURE:
<223> OTHER INFORMATION: Synthetic Polynucleotide

<400> SEQUENCE: 399
agattagagc cgtcaaaaaa cagaggtgag gcctattagt ttgatctaca ta               52

<210> SEQ ID NO 400
<211> LENGTH: 43
<212> TYPE: DNA
<213> ORGANISM: Artificial
<220> FEATURE:
<223> OTHER INFORMATION: Synthetic Polynucleotide

<400> SEQUENCE: 400
caaatcaagt tttttggggt cgaaacgtgg attgatctac ata                         43

<210> SEQ ID NO 401
<211> LENGTH: 43
<212> TYPE: DNA
<213> ORGANISM: Artificial
<220> FEATURE:
<223> OTHER INFORMATION: Synthetic Polynucleotide

<400> SEQUENCE: 401
gcacagacaa tatttttgaa tggggtcagt attgatctac ata                         43

<210> SEQ ID NO 402
<211> LENGTH: 42
<212> TYPE: DNA
<213> ORGANISM: Artificial
<220> FEATURE:
<223> OTHER INFORMATION: Synthetic Polynucleotide

<400> SEQUENCE: 402
ctttaatgcg cgaactgata gccccaccag ttgatctaca ta                          42

<210> SEQ ID NO 403
<211> LENGTH: 40
<212> TYPE: DNA
<213> ORGANISM: Artificial
<220> FEATURE:
<223> OTHER INFORMATION: Synthetic Polynucleotide

<400> SEQUENCE: 403
```
ataagggaac cggatattca ttacgtcagg acgttgggaa                                40

<210> SEQ ID NO 404
<211> LENGTH: 38
<212> TYPE: DNA
<213> ORGANISM: Artificial
<220> FEATURE:
<223> OTHER INFORMATION: Synthetic Polynucleotide

<400> SEQUENCE: 404
ttgtgtcgtg acgagaaaca ccaaatttca actttaat                                  38

<210> SEQ ID NO 405
<211> LENGTH: 40
<212> TYPE: DNA
<213> ORGANISM: Artificial
<220> FEATURE:
<223> OTHER INFORMATION: Synthetic Polynucleotide

<400> SEQUENCE: 405
caccctcaga aaccatcgat agcattgagc catttgggaa                                40

<210> SEQ ID NO 406
<211> LENGTH: 40
<212> TYPE: DNA
<213> ORGANISM: Artificial
<220> FEATURE:
<223> OTHER INFORMATION: Synthetic Polynucleotide

<400> SEQUENCE: 406
agccaccact gtagcgcgtt ttcaagggag ggaaggtaaa                                40

<210> SEQ ID NO 407
<211> LENGTH: 40
<212> TYPE: DNA
<213> ORGANISM: Artificial
<220> FEATURE:
<223> OTHER INFORMATION: Synthetic Polynucleotide

<400> SEQUENCE: 407
attaagttta ccgagctcga attcgggaaa cctgtcgtgc                                40

<210> SEQ ID NO 408
<211> LENGTH: 38
<212> TYPE: DNA
<213> ORGANISM: Artificial
<220> FEATURE:
<223> OTHER INFORMATION: Synthetic Polynucleotide

<400> SEQUENCE: 408
gcgatcggca attccacaca acaggtgcct aatgagtg                                  38

<210> SEQ ID NO 409
<211> LENGTH: 40
<212> TYPE: DNA
<213> ORGANISM: Artificial
<220> FEATURE:
<223> OTHER INFORMATION: Synthetic Polynucleotide

<400> SEQUENCE: 409
attcattttt gtttggatta tactaagaaa ccaccagaag                                40

<210> SEQ ID NO 410
<211> LENGTH: 40
<212> TYPE: DNA

```
<213> ORGANISM: Artificial
<220> FEATURE:
<223> OTHER INFORMATION: Synthetic Polynucleotide

<400> SEQUENCE: 410
aacaataacg taaaacagaa ataaaaatcc tttgcccgaa                    40

<210> SEQ ID NO 411
<211> LENGTH: 48
<212> TYPE: DNA
<213> ORGANISM: Artificial
<220> FEATURE:
<223> OTHER INFORMATION: Synthetic Polynucleotide

<400> SEQUENCE: 411
tttatcagga cagcatcgga acgacaccaa cctaaaacga ggtcaatc           48

<210> SEQ ID NO 412
<211> LENGTH: 44
<212> TYPE: DNA
<213> ORGANISM: Artificial
<220> FEATURE:
<223> OTHER INFORMATION: Synthetic Polynucleotide

<400> SEQUENCE: 412
tgacaactcg ctgaggcttg cattatacca agcgcgatga taaa               44

<210> SEQ ID NO 413
<211> LENGTH: 48
<212> TYPE: DNA
<213> ORGANISM: Artificial
<220> FEATURE:
<223> OTHER INFORMATION: Synthetic Polynucleotide

<400> SEQUENCE: 413
gcggataacc tattattctg aaacagacga ttggccttga agagccac           48

<210> SEQ ID NO 414
<211> LENGTH: 48
<212> TYPE: DNA
<213> ORGANISM: Artificial
<220> FEATURE:
<223> OTHER INFORMATION: Synthetic Polynucleotide

<400> SEQUENCE: 414
caggaggtgg ggtcagtgcc ttgagtctct gaatttaccg ggaaccag           48

<210> SEQ ID NO 415
<211> LENGTH: 48
<212> TYPE: DNA
<213> ORGANISM: Artificial
<220> FEATURE:
<223> OTHER INFORMATION: Synthetic Polynucleotide

<400> SEQUENCE: 415
gtataagcca acccgtcgga ttctgacgac agtatcggcc gcaaggcg           48

<210> SEQ ID NO 416
<211> LENGTH: 44
<212> TYPE: DNA
<213> ORGANISM: Artificial
<220> FEATURE:
<223> OTHER INFORMATION: Synthetic Polynucleotide

<400> SEQUENCE: 416
taaatcaaaa taattcgcgt ctcggaaacc aggcaaaggg aagg               44
```

```
<210> SEQ ID NO 417
<211> LENGTH: 48
<212> TYPE: DNA
<213> ORGANISM: Artificial
<220> FEATURE:
<223> OTHER INFORMATION: Synthetic Polynucleotide

<400> SEQUENCE: 417
tcaaatataa cctccggctt aggtaacaat ttcatttgaa ggcgaatt                  48

<210> SEQ ID NO 418
<211> LENGTH: 48
<212> TYPE: DNA
<213> ORGANISM: Artificial
<220> FEATURE:
<223> OTHER INFORMATION: Synthetic Polynucleotide

<400> SEQUENCE: 418
gtgataaaaa gacgctgaga agagataacc ttgcttctgt tcgggaga                  48

<210> SEQ ID NO 419
<211> LENGTH: 32
<212> TYPE: DNA
<213> ORGANISM: Artificial
<220> FEATURE:
<223> OTHER INFORMATION: Synthetic Polynucleotide

<400> SEQUENCE: 419
aaggaattgc gaataataat ttttgtcgct ga                                    32

<210> SEQ ID NO 420
<211> LENGTH: 31
<212> TYPE: DNA
<213> ORGANISM: Artificial
<220> FEATURE:
<223> OTHER INFORMATION: Synthetic Polynucleotide

<400> SEQUENCE: 420
tcagcggagt gagaatagaa aggttttgcg g                                     31

<210> SEQ ID NO 421
<211> LENGTH: 32
<212> TYPE: DNA
<213> ORGANISM: Artificial
<220> FEATURE:
<223> OTHER INFORMATION: Synthetic Polynucleotide

<400> SEQUENCE: 421
tatgggattt tgctaaacaa ctttcaacag tt                                    32

<210> SEQ ID NO 422
<211> LENGTH: 32
<212> TYPE: DNA
<213> ORGANISM: Artificial
<220> FEATURE:
<223> OTHER INFORMATION: Synthetic Polynucleotide

<400> SEQUENCE: 422
gaaaatctcc aaaaaaaagg ctccaaccat cg                                    32

<210> SEQ ID NO 423
<211> LENGTH: 32
<212> TYPE: DNA
<213> ORGANISM: Artificial
<220> FEATURE:
```

<223> OTHER INFORMATION: Synthetic Polynucleotide

<400> SEQUENCE: 423
ggtgtatctt gatataagta tagcgacagc at                          32

<210> SEQ ID NO 424
<211> LENGTH: 32
<212> TYPE: DNA
<213> ORGANISM: Artificial
<220> FEATURE:
<223> OTHER INFORMATION: Synthetic Polynucleotide

<400> SEQUENCE: 424
tacgaaggcg ccgacaatga caacaaaagg ag                          32

<210> SEQ ID NO 425
<211> LENGTH: 32
<212> TYPE: DNA
<213> ORGANISM: Artificial
<220> FEATURE:
<223> OTHER INFORMATION: Synthetic Polynucleotide

<400> SEQUENCE: 425
aaagcgcaaa atcctcatta aagcggtcaa tc                          32

<210> SEQ ID NO 426
<211> LENGTH: 32
<212> TYPE: DNA
<213> ORGANISM: Artificial
<220> FEATURE:
<223> OTHER INFORMATION: Synthetic Polynucleotide

<400> SEQUENCE: 426
gcgtcagagc gacagaatca agttgtcagg ac                          32

<210> SEQ ID NO 427
<211> LENGTH: 32
<212> TYPE: DNA
<213> ORGANISM: Artificial
<220> FEATURE:
<223> OTHER INFORMATION: Synthetic Polynucleotide

<400> SEQUENCE: 427
cggaataata taaagaaac gcaaggaatc gt                           32

<210> SEQ ID NO 428
<211> LENGTH: 30
<212> TYPE: DNA
<213> ORGANISM: Artificial
<220> FEATURE:
<223> OTHER INFORMATION: Synthetic Polynucleotide

<400> SEQUENCE: 428
agaaacgatt taagaaaagt aagcgaggaa                             30

<210> SEQ ID NO 429
<211> LENGTH: 32
<212> TYPE: DNA
<213> ORGANISM: Artificial
<220> FEATURE:
<223> OTHER INFORMATION: Synthetic Polynucleotide

<400> SEQUENCE: 429
tgcgggaggg cgttttagcg aacccaataa ag                          32

```
<210> SEQ ID NO 430
<211> LENGTH: 30
<212> TYPE: DNA
<213> ORGANISM: Artificial
<220> FEATURE:
<223> OTHER INFORMATION: Synthetic Polynucleotide

<400> SEQUENCE: 430
agaacaagcc taatttgcca gttccaaata                                          30

<210> SEQ ID NO 431
<211> LENGTH: 32
<212> TYPE: DNA
<213> ORGANISM: Artificial
<220> FEATURE:
<223> OTHER INFORMATION: Synthetic Polynucleotide

<400> SEQUENCE: 431
aatgcagacg acaataaaca acatgtcatt gc                                       32

<210> SEQ ID NO 432
<211> LENGTH: 30
<212> TYPE: DNA
<213> ORGANISM: Artificial
<220> FEATURE:
<223> OTHER INFORMATION: Synthetic Polynucleotide

<400> SEQUENCE: 432
tatttaactg tctttcctta tcactcatcg                                          30

<210> SEQ ID NO 433
<211> LENGTH: 32
<212> TYPE: DNA
<213> ORGANISM: Artificial
<220> FEATURE:
<223> OTHER INFORMATION: Synthetic Polynucleotide

<400> SEQUENCE: 433
ttgaaataat cttctgacct aaatcaaccc gt                                       32

<210> SEQ ID NO 434
<211> LENGTH: 30
<212> TYPE: DNA
<213> ORGANISM: Artificial
<220> FEATURE:
<223> OTHER INFORMATION: Synthetic Polynucleotide

<400> SEQUENCE: 434
ggcttaggtt cttaccagta taaatcgcca                                          30

<210> SEQ ID NO 435
<211> LENGTH: 32
<212> TYPE: DNA
<213> ORGANISM: Artificial
<220> FEATURE:
<223> OTHER INFORMATION: Synthetic Polynucleotide

<400> SEQUENCE: 435
gtgagtgaga aacagtacat aaatgcaagg cg                                       32

<210> SEQ ID NO 436
<211> LENGTH: 30
<212> TYPE: DNA
<213> ORGANISM: Artificial
<220> FEATURE:
<223> OTHER INFORMATION: Synthetic Polynucleotide
```

```
<400> SEQUENCE: 436
tattcatttc aatagtgaat ttaaacctcc                                    30

<210> SEQ ID NO 437
<211> LENGTH: 32
<212> TYPE: DNA
<213> ORGANISM: Artificial
<220> FEATURE:
<223> OTHER INFORMATION: Synthetic Polynucleotide

<400> SEQUENCE: 437
tatttgcagg ttagaaccta ccatgggaaa cc                                 32

<210> SEQ ID NO 438
<211> LENGTH: 30
<212> TYPE: DNA
<213> ORGANISM: Artificial
<220> FEATURE:
<223> OTHER INFORMATION: Synthetic Polynucleotide

<400> SEQUENCE: 438
ttctgaaaag cccaatagga accacaaact                                    30

<210> SEQ ID NO 439
<211> LENGTH: 30
<212> TYPE: DNA
<213> ORGANISM: Artificial
<220> FEATURE:
<223> OTHER INFORMATION: Synthetic Polynucleotide

<400> SEQUENCE: 439
caccagaacg gattcgcctg attggcgaat                                    30

<210> SEQ ID NO 440
<211> LENGTH: 32
<212> TYPE: DNA
<213> ORGANISM: Artificial
<220> FEATURE:
<223> OTHER INFORMATION: Synthetic Polynucleotide

<400> SEQUENCE: 440
caactaatct aaaatatctt tagggagtcc ac                                 32

<210> SEQ ID NO 441
<211> LENGTH: 30
<212> TYPE: DNA
<213> ORGANISM: Artificial
<220> FEATURE:
<223> OTHER INFORMATION: Synthetic Polynucleotide

<400> SEQUENCE: 441
aaaaatctcg ttattaattt taaaagaaac                                    30

<210> SEQ ID NO 442
<211> LENGTH: 30
<212> TYPE: DNA
<213> ORGANISM: Artificial
<220> FEATURE:
<223> OTHER INFORMATION: Synthetic Polynucleotide

<400> SEQUENCE: 442
ccaccctcgt aacagtgccc gtacctatta                                    30

<210> SEQ ID NO 443
<211> LENGTH: 30
```

```
<212> TYPE: DNA
<213> ORGANISM: Artificial
<220> FEATURE:
<223> OTHER INFORMATION: Synthetic Polynucleotide

<400> SEQUENCE: 443
atttgggacc ggaaccgcct cccagagcca                                      30

<210> SEQ ID NO 444
<211> LENGTH: 30
<212> TYPE: DNA
<213> ORGANISM: Artificial
<220> FEATURE:
<223> OTHER INFORMATION: Synthetic Polynucleotide

<400> SEQUENCE: 444
acgcaatata ttgacggaaa ttattgagcc                                      30

<210> SEQ ID NO 445
<211> LENGTH: 32
<212> TYPE: DNA
<213> ORGANISM: Artificial
<220> FEATURE:
<223> OTHER INFORMATION: Synthetic Polynucleotide

<400> SEQUENCE: 445
ttgagcgcac cctgaacaaa gtcaagagct ta                                   32

<210> SEQ ID NO 446
<211> LENGTH: 31
<212> TYPE: DNA
<213> ORGANISM: Artificial
<220> FEATURE:
<223> OTHER INFORMATION: Synthetic Polynucleotide

<400> SEQUENCE: 446
cctttaattg tatcggttta tcatgatacc g                                    31

<210> SEQ ID NO 447
<211> LENGTH: 30
<212> TYPE: DNA
<213> ORGANISM: Artificial
<220> FEATURE:
<223> OTHER INFORMATION: Synthetic Polynucleotide

<400> SEQUENCE: 447
atagttgcac caacctaaaa cgctttgacc                                      30

<210> SEQ ID NO 448
<211> LENGTH: 30
<212> TYPE: DNA
<213> ORGANISM: Artificial
<220> FEATURE:
<223> OTHER INFORMATION: Synthetic Polynucleotide

<400> SEQUENCE: 448
tttagctaac cctcatatat ttgattcaaa                                      30

<210> SEQ ID NO 449
<211> LENGTH: 30
<212> TYPE: DNA
<213> ORGANISM: Artificial
<220> FEATURE:
<223> OTHER INFORMATION: Synthetic Polynucleotide

<400> SEQUENCE: 449
```

```
agggtgagga agattgtata agttaaaatt                                           30

<210> SEQ ID NO 450
<211> LENGTH: 30
<212> TYPE: DNA
<213> ORGANISM: Artificial
<220> FEATURE:
<223> OTHER INFORMATION: Synthetic Polynucleotide

<400> SEQUENCE: 450
cgcattagac gacagtatcg gcgcaccgct                                           30

<210> SEQ ID NO 451
<211> LENGTH: 30
<212> TYPE: DNA
<213> ORGANISM: Artificial
<220> FEATURE:
<223> OTHER INFORMATION: Synthetic Polynucleotide

<400> SEQUENCE: 451
tctggtgtac cgagctcgaa ttaattgtta                                           30

<210> SEQ ID NO 452
<211> LENGTH: 30
<212> TYPE: DNA
<213> ORGANISM: Artificial
<220> FEATURE:
<223> OTHER INFORMATION: Synthetic Polynucleotide

<400> SEQUENCE: 452
tccgctcagc tgattgccct tcgtccacgc                                           30

<210> SEQ ID NO 453
<211> LENGTH: 30
<212> TYPE: DNA
<213> ORGANISM: Artificial
<220> FEATURE:
<223> OTHER INFORMATION: Synthetic Polynucleotide

<400> SEQUENCE: 453
cccagcgacc ggatattcat tatgaataag                                           30

<210> SEQ ID NO 454
<211> LENGTH: 30
<212> TYPE: DNA
<213> ORGANISM: Artificial
<220> FEATURE:
<223> OTHER INFORMATION: Synthetic Polynucleotide

<400> SEQUENCE: 454
gcttgccatg cagatacata acacactatc                                           30

<210> SEQ ID NO 455
<211> LENGTH: 30
<212> TYPE: DNA
<213> ORGANISM: Artificial
<220> FEATURE:
<223> OTHER INFORMATION: Synthetic Polynucleotide

<400> SEQUENCE: 455
ataacccaag caaagcggat tgttcaaata                                           30

<210> SEQ ID NO 456
<211> LENGTH: 30
<212> TYPE: DNA
<213> ORGANISM: Artificial
```

```
<220> FEATURE:
<223> OTHER INFORMATION: Synthetic Polynucleotide

<400> SEQUENCE: 456
tcgcgttaac gagtagattt agataacctg                                      30

<210> SEQ ID NO 457
<211> LENGTH: 38
<212> TYPE: DNA
<213> ORGANISM: Artificial
<220> FEATURE:
<223> OTHER INFORMATION: Synthetic Polynucleotide

<400> SEQUENCE: 457
tagggttgag tgttgaacgt ggactccaac gacctgaa                             38

<210> SEQ ID NO 458
<211> LENGTH: 40
<212> TYPE: DNA
<213> ORGANISM: Artificial
<220> FEATURE:
<223> OTHER INFORMATION: Synthetic Polynucleotide

<400> SEQUENCE: 458
tcctgtttga tggtggacca tcacccaaat cacgagaaag                           40

<210> SEQ ID NO 459
<211> LENGTH: 32
<212> TYPE: DNA
<213> ORGANISM: Artificial
<220> FEATURE:
<223> OTHER INFORMATION: Synthetic Polynucleotide

<400> SEQUENCE: 459
ataaatcacc gtctatcagg gcgagacatt ct                                   32

<210> SEQ ID NO 460
<211> LENGTH: 31
<212> TYPE: DNA
<213> ORGANISM: Artificial
<220> FEATURE:
<223> OTHER INFORMATION: Synthetic Polynucleotide

<400> SEQUENCE: 460
acggggaaag ccggcgaacg tggagttttt t                                    31

<210> SEQ ID NO 461
<211> LENGTH: 30
<212> TYPE: DNA
<213> ORGANISM: Artificial
<220> FEATURE:
<223> OTHER INFORMATION: Synthetic Polynucleotide

<400> SEQUENCE: 461
gaagggaaac cagtaataaa aggtggccca                                      30

<210> SEQ ID NO 462
<211> LENGTH: 32
<212> TYPE: DNA
<213> ORGANISM: Artificial
<220> FEATURE:
<223> OTHER INFORMATION: Synthetic Polynucleotide

<400> SEQUENCE: 462
ggccaacaga gatagaaccc ttctgtcaaa gg                                   32
```

<210> SEQ ID NO 463
<211> LENGTH: 40
<212> TYPE: DNA
<213> ORGANISM: Artificial
<220> FEATURE:
<223> OTHER INFORMATION: Synthetic Polynucleotide

<400> SEQUENCE: 463
atagataata catttgtcaa cagttgaaag gagcgcgaac					40

<210> SEQ ID NO 464
<211> LENGTH: 30
<212> TYPE: DNA
<213> ORGANISM: Artificial
<220> FEATURE:
<223> OTHER INFORMATION: Synthetic Polynucleotide

<400> SEQUENCE: 464
caaacaaacc ctcaatcaat ataaaaatac					30

<210> SEQ ID NO 465
<211> LENGTH: 40
<212> TYPE: DNA
<213> ORGANISM: Artificial
<220> FEATURE:
<223> OTHER INFORMATION: Synthetic Polynucleotide

<400> SEQUENCE: 465
aaatcctttg cccgaaaaag catcaccttg ctaaaacaga					40

<210> SEQ ID NO 466
<211> LENGTH: 30
<212> TYPE: DNA
<213> ORGANISM: Artificial
<220> FEATURE:
<223> OTHER INFORMATION: Synthetic Polynucleotide

<400> SEQUENCE: 466
tggtttgggt gccgtaaagc acagagcttg					30

<210> SEQ ID NO 467
<211> LENGTH: 31
<212> TYPE: DNA
<213> ORGANISM: Artificial
<220> FEATURE:
<223> OTHER INFORMATION: Synthetic Polynucleotide

<400> SEQUENCE: 467
agcgtaagaa tacgtggcac agacaatatt t					31

<210> SEQ ID NO 468
<211> LENGTH: 30
<212> TYPE: DNA
<213> ORGANISM: Artificial
<220> FEATURE:
<223> OTHER INFORMATION: Synthetic Polynucleotide

<400> SEQUENCE: 468
ttgaatggct attagtcttt aatattgagg					30

<210> SEQ ID NO 469
<211> LENGTH: 32
<212> TYPE: DNA
<213> ORGANISM: Artificial
<220> FEATURE:
<223> OTHER INFORMATION: Synthetic Polynucleotide

<400> SEQUENCE: 469
tgatagccct aaaacatcgc cattctggtc ag                          32

<210> SEQ ID NO 470
<211> LENGTH: 31
<212> TYPE: DNA
<213> ORGANISM: Artificial
<220> FEATURE:
<223> OTHER INFORMATION: Synthetic Polynucleotide

<400> SEQUENCE: 470
cgaacgaacc accagcagaa gatgaacctc a                           31

<210> SEQ ID NO 471
<211> LENGTH: 30
<212> TYPE: DNA
<213> ORGANISM: Artificial
<220> FEATURE:
<223> OTHER INFORMATION: Synthetic Polynucleotide

<400> SEQUENCE: 471
ggtgaggcgg tcagtattaa cacgcaaatg                             30

<210> SEQ ID NO 472
<211> LENGTH: 32
<212> TYPE: DNA
<213> ORGANISM: Artificial
<220> FEATURE:
<223> OTHER INFORMATION: Synthetic Polynucleotide

<400> SEQUENCE: 472
ttgaggacgg gagttaaagg ccgcaacaac ta                          32

<210> SEQ ID NO 473
<211> LENGTH: 30
<212> TYPE: DNA
<213> ORGANISM: Artificial
<220> FEATURE:
<223> OTHER INFORMATION: Synthetic Polynucleotide

<400> SEQUENCE: 473
ttccattata accgatatat tcgtcacgtt                             30

<210> SEQ ID NO 474
<211> LENGTH: 32
<212> TYPE: DNA
<213> ORGANISM: Artificial
<220> FEATURE:
<223> OTHER INFORMATION: Synthetic Polynucleotide

<400> SEQUENCE: 474
tctttccaga cgttagtaaa tgaatttagt ac                          32

<210> SEQ ID NO 475
<211> LENGTH: 31
<212> TYPE: DNA
<213> ORGANISM: Artificial
<220> FEATURE:
<223> OTHER INFORMATION: Synthetic Polynucleotide

<400> SEQUENCE: 475
atagttagcg taacgatcta aagcagaacc g                           31

<210> SEQ ID NO 476

```
<211> LENGTH: 32
<212> TYPE: DNA
<213> ORGANISM: Artificial
<220> FEATURE:
<223> OTHER INFORMATION: Synthetic Polynucleotide

<400> SEQUENCE: 476
acaacgcctg tagcattcca cagaattttc ag                              32

<210> SEQ ID NO 477
<211> LENGTH: 44
<212> TYPE: DNA
<213> ORGANISM: Artificial
<220> FEATURE:
<223> OTHER INFORMATION: Synthetic Polynucleotide

<400> SEQUENCE: 477
gatcgtcggg tagcaacggc taccatgtta cttagccacc gaac                 44

<210> SEQ ID NO 478
<211> LENGTH: 48
<212> TYPE: DNA
<213> ORGANISM: Artificial
<220> FEATURE:
<223> OTHER INFORMATION: Synthetic Polynucleotide

<400> SEQUENCE: 478
cgccacccag taccaggcgg ataagttcca gtaagcgtca agacgatt             48

<210> SEQ ID NO 479
<211> LENGTH: 30
<212> TYPE: DNA
<213> ORGANISM: Artificial
<220> FEATURE:
<223> OTHER INFORMATION: Synthetic Polynucleotide

<400> SEQUENCE: 479
ccaccctgag aaggattagg atatacagga                                 30

<210> SEQ ID NO 480
<211> LENGTH: 48
<212> TYPE: DNA
<213> ORGANISM: Artificial
<220> FEATURE:
<223> OTHER INFORMATION: Synthetic Polynucleotide

<400> SEQUENCE: 480
ggatagcaca tgaaagtatt aagaggggtc agtgccttga agagccgc             48

<210> SEQ ID NO 481
<211> LENGTH: 48
<212> TYPE: DNA
<213> ORGANISM: Artificial
<220> FEATURE:
<223> OTHER INFORMATION: Synthetic Polynucleotide

<400> SEQUENCE: 481
cccacgcaaa cgggtaaaat acgtaacaaa gtacaacgga gctgacct             48

<210> SEQ ID NO 482
<211> LENGTH: 32
<212> TYPE: DNA
<213> ORGANISM: Artificial
<220> FEATURE:
<223> OTHER INFORMATION: Synthetic Polynucleotide

<400> SEQUENCE: 482
```
ggcttgcata aagactttt catgctgata aa        32

<210> SEQ ID NO 483
<211> LENGTH: 32
<212> TYPE: DNA
<213> ORGANISM: Artificial
<220> FEATURE:
<223> OTHER INFORMATION: Synthetic Polynucleotide

<400> SEQUENCE: 483
ttttaaatac ctttaattgc tccttcaaat gc        32

<210> SEQ ID NO 484
<211> LENGTH: 32
<212> TYPE: DNA
<213> ORGANISM: Artificial
<220> FEATURE:
<223> OTHER INFORMATION: Synthetic Polynucleotide

<400> SEQUENCE: 484
attgctgatt tttgcggatg gcttgagggt aa        32

<210> SEQ ID NO 485
<211> LENGTH: 30
<212> TYPE: DNA
<213> ORGANISM: Artificial
<220> FEATURE:
<223> OTHER INFORMATION: Synthetic Polynucleotide

<400> SEQUENCE: 485
aactgaacta atatcagaga gatataaagg        30

<210> SEQ ID NO 486
<211> LENGTH: 32
<212> TYPE: DNA
<213> ORGANISM: Artificial
<220> FEATURE:
<223> OTHER INFORMATION: Synthetic Polynucleotide

<400> SEQUENCE: 486
aaaacagggt taagcccaat aatagcagta tg        32

<210> SEQ ID NO 487
<211> LENGTH: 32
<212> TYPE: DNA
<213> ORGANISM: Artificial
<220> FEATURE:
<223> OTHER INFORMATION: Synthetic Polynucleotide

<400> SEQUENCE: 487
aaatagcaga aatagcaata gctaaagaac tg        32

<210> SEQ ID NO 488
<211> LENGTH: 32
<212> TYPE: DNA
<213> ORGANISM: Artificial
<220> FEATURE:
<223> OTHER INFORMATION: Synthetic Polynucleotide

<400> SEQUENCE: 488
attctgcgtt aattcgagct tcaatgacta tt        32

<210> SEQ ID NO 489
<211> LENGTH: 30
<212> TYPE: DNA

```
<213> ORGANISM: Artificial
<220> FEATURE:
<223> OTHER INFORMATION: Synthetic Polynucleotide

<400> SEQUENCE: 489
gaagtttcag caaactccaa cagtgaccat                                      30

<210> SEQ ID NO 490
<211> LENGTH: 30
<212> TYPE: DNA
<213> ORGANISM: Artificial
<220> FEATURE:
<223> OTHER INFORMATION: Synthetic Polynucleotide

<400> SEQUENCE: 490
ggcaaagcat aaagctaaat cgctattttt                                      30

<210> SEQ ID NO 491
<211> LENGTH: 32
<212> TYPE: DNA
<213> ORGANISM: Artificial
<220> FEATURE:
<223> OTHER INFORMATION: Synthetic Polynucleotide

<400> SEQUENCE: 491
tagttgctag aaggcttatc cggtaacaat ag                                   32

<210> SEQ ID NO 492
<211> LENGTH: 30
<212> TYPE: DNA
<213> ORGANISM: Artificial
<220> FEATURE:
<223> OTHER INFORMATION: Synthetic Polynucleotide

<400> SEQUENCE: 492
tcctgaatac cgcgcccaat agtatcccat                                      30

<210> SEQ ID NO 493
<211> LENGTH: 32
<212> TYPE: DNA
<213> ORGANISM: Artificial
<220> FEATURE:
<223> OTHER INFORMATION: Synthetic Polynucleotide

<400> SEQUENCE: 493
ttccagagca agccgttttt atttccaatc aa                                   32

<210> SEQ ID NO 494
<211> LENGTH: 32
<212> TYPE: DNA
<213> ORGANISM: Artificial
<220> FEATURE:
<223> OTHER INFORMATION: Synthetic Polynucleotide

<400> SEQUENCE: 494
gaaaaggtct ttatttcaac gcaatcaaat ca                                   32

<210> SEQ ID NO 495
<211> LENGTH: 32
<212> TYPE: DNA
<213> ORGANISM: Artificial
<220> FEATURE:
<223> OTHER INFORMATION: Synthetic Polynucleotide

<400> SEQUENCE: 495
tagcattata tgaccctgta atactctagc tg                                   32
```

<210> SEQ ID NO 496
<211> LENGTH: 32
<212> TYPE: DNA
<213> ORGANISM: Artificial
<220> FEATURE:
<223> OTHER INFORMATION: Synthetic Polynucleotide

<400> SEQUENCE: 496
aaaaacatac atccaataaa tcattcaaca tg                                    32

<210> SEQ ID NO 497
<211> LENGTH: 32
<212> TYPE: DNA
<213> ORGANISM: Artificial
<220> FEATURE:
<223> OTHER INFORMATION: Synthetic Polynucleotide

<400> SEQUENCE: 497
cctcagagaa ttagcaaaat taagtcccga ct                                    32

<210> SEQ ID NO 498
<211> LENGTH: 30
<212> TYPE: DNA
<213> ORGANISM: Artificial
<220> FEATURE:
<223> OTHER INFORMATION: Synthetic Polynucleotide

<400> SEQUENCE: 498
gaacgcgagt tttgaagcct taagagaatt                                       30

<210> SEQ ID NO 499
<211> LENGTH: 32
<212> TYPE: DNA
<213> ORGANISM: Artificial
<220> FEATURE:
<223> OTHER INFORMATION: Synthetic Polynucleotide

<400> SEQUENCE: 499
tcagatatat tttgcaccca gctaataaca ta                                    32

<210> SEQ ID NO 500
<211> LENGTH: 32
<212> TYPE: DNA
<213> ORGANISM: Artificial
<220> FEATURE:
<223> OTHER INFORMATION: Synthetic Polynucleotide

<400> SEQUENCE: 500
ggaatcattc ttaccaacgc taacaaaaat ga                                    32

<210> SEQ ID NO 501
<211> LENGTH: 32
<212> TYPE: DNA
<213> ORGANISM: Artificial
<220> FEATURE:
<223> OTHER INFORMATION: Synthetic Polynucleotide

<400> SEQUENCE: 501
atttttagat attttcattt gggggattcc ca                                    32

<210> SEQ ID NO 502
<211> LENGTH: 30
<212> TYPE: DNA
<213> ORGANISM: Artificial
<220> FEATURE:

<223> OTHER INFORMATION: Synthetic Polynucleotide

<400> SEQUENCE: 502
ggagaagcgg catcaattct actgtgtctg            30

<210> SEQ ID NO 503
<211> LENGTH: 30
<212> TYPE: DNA
<213> ORGANISM: Artificial
<220> FEATURE:
<223> OTHER INFORMATION: Synthetic Polynucleotide

<400> SEQUENCE: 503
gagagatctg gagcaaacaa gagctttcat            30

<210> SEQ ID NO 504
<211> LENGTH: 32
<212> TYPE: DNA
<213> ORGANISM: Artificial
<220> FEATURE:
<223> OTHER INFORMATION: Synthetic Polynucleotide

<400> SEQUENCE: 504
ataagtccga caaaaggtaa agtaataagg cg          32

<210> SEQ ID NO 505
<211> LENGTH: 30
<212> TYPE: DNA
<213> ORGANISM: Artificial
<220> FEATURE:
<223> OTHER INFORMATION: Synthetic Polynucleotide

<400> SEQUENCE: 505
cctaatttcg agccagtaat aacataatta            30

<210> SEQ ID NO 506
<211> LENGTH: 32
<212> TYPE: DNA
<213> ORGANISM: Artificial
<220> FEATURE:
<223> OTHER INFORMATION: Synthetic Polynucleotide

<400> SEQUENCE: 506
taatcggcaa cgccaacatg taatatatgc gt          32

<210> SEQ ID NO 507
<211> LENGTH: 32
<212> TYPE: DNA
<213> ORGANISM: Artificial
<220> FEATURE:
<223> OTHER INFORMATION: Synthetic Polynucleotide

<400> SEQUENCE: 507
ccatcaatcc cggttgataa tcaggctcat tt          32

<210> SEQ ID NO 508
<211> LENGTH: 32
<212> TYPE: DNA
<213> ORGANISM: Artificial
<220> FEATURE:
<223> OTHER INFORMATION: Synthetic Polynucleotide

<400> SEQUENCE: 508
ataaattaat cgtaaaacta gcataaaata at          32

<210> SEQ ID NO 509
<211> LENGTH: 32
<212> TYPE: DNA
<213> ORGANISM: Artificial
<220> FEATURE:
<223> OTHER INFORMATION: Synthetic Polynucleotide

<400> SEQUENCE: 509
gaacggtaat gccggagagg gtaggttgta cc        32

<210> SEQ ID NO 510
<211> LENGTH: 32
<212> TYPE: DNA
<213> ORGANISM: Artificial
<220> FEATURE:
<223> OTHER INFORMATION: Synthetic Polynucleotide

<400> SEQUENCE: 510
ctgagagtct acaaaggcta tcaggttcag ct        32

<210> SEQ ID NO 511
<211> LENGTH: 30
<212> TYPE: DNA
<213> ORGANISM: Artificial
<220> FEATURE:
<223> OTHER INFORMATION: Synthetic Polynucleotide

<400> SEQUENCE: 511
ccagacgaac gcgcctgttt atcattctaa        30

<210> SEQ ID NO 512
<211> LENGTH: 32
<212> TYPE: DNA
<213> ORGANISM: Artificial
<220> FEATURE:
<223> OTHER INFORMATION: Synthetic Polynucleotide

<400> SEQUENCE: 512
aaagtacctg aacaagaaaa ataacaagca aa        32

<210> SEQ ID NO 513
<211> LENGTH: 32
<212> TYPE: DNA
<213> ORGANISM: Artificial
<220> FEATURE:
<223> OTHER INFORMATION: Synthetic Polynucleotide

<400> SEQUENCE: 513
aggcatttta cgagcatgta gaaatcatcg ta        32

<210> SEQ ID NO 514
<211> LENGTH: 32
<212> TYPE: DNA
<213> ORGANISM: Artificial
<220> FEATURE:
<223> OTHER INFORMATION: Synthetic Polynucleotide

<400> SEQUENCE: 514
caaaaacaga aaggccggag acagggataa aa        32

<210> SEQ ID NO 515
<211> LENGTH: 30
<212> TYPE: DNA
<213> ORGANISM: Artificial
<220> FEATURE:
<223> OTHER INFORMATION: Synthetic Polynucleotide

```
<400> SEQUENCE: 515
atatgtacat gatattcaac cgtttttgcg                                    30

<210> SEQ ID NO 516
<211> LENGTH: 44
<212> TYPE: DNA
<213> ORGANISM: Artificial
<220> FEATURE:
<223> OTHER INFORMATION: Synthetic Polynucleotide

<400> SEQUENCE: 516
caacattccg tgggaacaaa cgattacgcc agctggcggg taac                    44

<210> SEQ ID NO 517
<211> LENGTH: 48
<212> TYPE: DNA
<213> ORGANISM: Artificial
<220> FEATURE:
<223> OTHER INFORMATION: Synthetic Polynucleotide

<400> SEQUENCE: 517
ttaaataaaa acttttcaa atattaaatc gtcgctatta aacaattt                 48

<210> SEQ ID NO 518
<211> LENGTH: 30
<212> TYPE: DNA
<213> ORGANISM: Artificial
<220> FEATURE:
<223> OTHER INFORMATION: Synthetic Polynucleotide

<400> SEQUENCE: 518
ctagaaacaa atccaatcgc aaaatccttg                                    30

<210> SEQ ID NO 519
<211> LENGTH: 48
<212> TYPE: DNA
<213> ORGANISM: Artificial
<220> FEATURE:
<223> OTHER INFORMATION: Synthetic Polynucleotide

<400> SEQUENCE: 519
tatacaaatt gggttatata actaaagacg ctgagaagag tcaattac                48

<210> SEQ ID NO 520
<211> LENGTH: 48
<212> TYPE: DNA
<213> ORGANISM: Artificial
<220> FEATURE:
<223> OTHER INFORMATION: Synthetic Polynucleotide

<400> SEQUENCE: 520
tttaaccatc gtaaccgtgc atctgcgcca ttcgccattc tgcctgca                48

<210> SEQ ID NO 521
<211> LENGTH: 32
<212> TYPE: DNA
<213> ORGANISM: Artificial
<220> FEATURE:
<223> OTHER INFORMATION: Synthetic Polynucleotide

<400> SEQUENCE: 521
tcgcgtctgg gataggtcac gttgtgggaa gg                                 32

<210> SEQ ID NO 522
<211> LENGTH: 32
```

```
<212> TYPE: DNA
<213> ORGANISM: Artificial
<220> FEATURE:
<223> OTHER INFORMATION: Synthetic Polynucleotide

<400> SEQUENCE: 522
accgtaatgg ccttcctgta gccagaatcg at                                 32

<210> SEQ ID NO 523
<211> LENGTH: 32
<212> TYPE: DNA
<213> ORGANISM: Artificial
<220> FEATURE:
<223> OTHER INFORMATION: Synthetic Polynucleotide

<400> SEQUENCE: 523
cggattctaa atgtgagcga gtaattaatg gt                                 32

<210> SEQ ID NO 524
<211> LENGTH: 30
<212> TYPE: DNA
<213> ORGANISM: Artificial
<220> FEATURE:
<223> OTHER INFORMATION: Synthetic Polynucleotide

<400> SEQUENCE: 524
ttaatttccc gaccgtgtga taaattctgt                                    30

<210> SEQ ID NO 525
<211> LENGTH: 32
<212> TYPE: DNA
<213> ORGANISM: Artificial
<220> FEATURE:
<223> OTHER INFORMATION: Synthetic Polynucleotide

<400> SEQUENCE: 525
acgcgagaga ataaacaccg gaatgagaat at                                 32

<210> SEQ ID NO 526
<211> LENGTH: 32
<212> TYPE: DNA
<213> ORGANISM: Artificial
<220> FEATURE:
<223> OTHER INFORMATION: Synthetic Polynucleotide

<400> SEQUENCE: 526
tgctgatgaa gcctgtttag tatcttaggc ag                                 32

<210> SEQ ID NO 527
<211> LENGTH: 32
<212> TYPE: DNA
<213> ORGANISM: Artificial
<220> FEATURE:
<223> OTHER INFORMATION: Synthetic Polynucleotide

<400> SEQUENCE: 527
gaggggacaa tttttgttaa atcaaaaagc cc                                 32

<210> SEQ ID NO 528
<211> LENGTH: 30
<212> TYPE: DNA
<213> ORGANISM: Artificial
<220> FEATURE:
<223> OTHER INFORMATION: Synthetic Polynucleotide

<400> SEQUENCE: 528
```
tgggcgcaat aggaacgcca tcagtcaatc                                                30

<210> SEQ ID NO 529
<211> LENGTH: 30
<212> TYPE: DNA
<213> ORGANISM: Artificial
<220> FEATURE:
<223> OTHER INFORMATION: Synthetic Polynucleotide

<400> SEQUENCE: 529
aaaacataaa catcaagaaa acagatgaat                                                30

<210> SEQ ID NO 530
<211> LENGTH: 32
<212> TYPE: DNA
<213> ORGANISM: Artificial
<220> FEATURE:
<223> OTHER INFORMATION: Synthetic Polynucleotide

<400> SEQUENCE: 530
gcgatcggtt gtaaaacgac ggccgggtgc ct                                             32

<210> SEQ ID NO 531
<211> LENGTH: 32
<212> TYPE: DNA
<213> ORGANISM: Artificial
<220> FEATURE:
<223> OTHER INFORMATION: Synthetic Polynucleotide

<400> SEQUENCE: 531
tcacgacgtg cgggcctctt cgctgcggat tg                                             32

<210> SEQ ID NO 532
<211> LENGTH: 32
<212> TYPE: DNA
<213> ORGANISM: Artificial
<220> FEATURE:
<223> OTHER INFORMATION: Synthetic Polynucleotide

<400> SEQUENCE: 532
attaagttga aaggggatg tgctcaatat at                                              32

<210> SEQ ID NO 533
<211> LENGTH: 30
<212> TYPE: DNA
<213> ORGANISM: Artificial
<220> FEATURE:
<223> OTHER INFORMATION: Synthetic Polynucleotide

<400> SEQUENCE: 533
ttttaatgat aaccttgctt ctgattttag                                                30

<210> SEQ ID NO 534
<211> LENGTH: 32
<212> TYPE: DNA
<213> ORGANISM: Artificial
<220> FEATURE:
<223> OTHER INFORMATION: Synthetic Polynucleotide

<400> SEQUENCE: 534
ttacatttat taattttccc ttaggacaaa ga                                             32

<210> SEQ ID NO 535
<211> LENGTH: 32
<212> TYPE: DNA
<213> ORGANISM: Artificial

<220> FEATURE:
<223> OTHER INFORMATION: Synthetic Polynucleotide

<400> SEQUENCE: 535
gatgaaacag cgatagctta gatttatgta aa        32

<210> SEQ ID NO 536
<211> LENGTH: 32
<212> TYPE: DNA
<213> ORGANISM: Artificial
<220> FEATURE:
<223> OTHER INFORMATION: Synthetic Polynucleotide

<400> SEQUENCE: 536
tccccgggcc ggaaaccagg caaagccagt tt        32

<210> SEQ ID NO 537
<211> LENGTH: 30
<212> TYPE: DNA
<213> ORGANISM: Artificial
<220> FEATURE:
<223> OTHER INFORMATION: Synthetic Polynucleotide

<400> SEQUENCE: 537
agcttgcaag gctgcgcaac tgtgtgtaga        30

<210> SEQ ID NO 538
<211> LENGTH: 30
<212> TYPE: DNA
<213> ORGANISM: Artificial
<220> FEATURE:
<223> OTHER INFORMATION: Synthetic Polynucleotide

<400> SEQUENCE: 538
atacagtaga tgatggcaat tcagacttta        30

<210> SEQ ID NO 539
<211> LENGTH: 32
<212> TYPE: DNA
<213> ORGANISM: Artificial
<220> FEATURE:
<223> OTHER INFORMATION: Synthetic Polynucleotide

<400> SEQUENCE: 539
aatgagtggg agaggcggtt tgcgaatccc tt        32

<210> SEQ ID NO 540
<211> LENGTH: 32
<212> TYPE: DNA
<213> ORGANISM: Artificial
<220> FEATURE:
<223> OTHER INFORMATION: Synthetic Polynucleotide

<400> SEQUENCE: 540
cggaacgaac cctcagcagc gaaaccggaa ta        32

<210> SEQ ID NO 541
<211> LENGTH: 30
<212> TYPE: DNA
<213> ORGANISM: Artificial
<220> FEATURE:
<223> OTHER INFORMATION: Synthetic Polynucleotide

<400> SEQUENCE: 541
cgagagggac cgtactcagg aggttttctg        30

<210> SEQ ID NO 542
<211> LENGTH: 32
<212> TYPE: DNA
<213> ORGANISM: Artificial
<220> FEATURE:
<223> OTHER INFORMATION: Synthetic Polynucleotide

<400> SEQUENCE: 542
ttttgctctc agaaccgcca ccctttttgt cg                      32

<210> SEQ ID NO 543
<211> LENGTH: 32
<212> TYPE: DNA
<213> ORGANISM: Artificial
<220> FEATURE:
<223> OTHER INFORMATION: Synthetic Polynucleotide

<400> SEQUENCE: 543
ctcctcaaca gagccaccac cctccagccc tc                      32

<210> SEQ ID NO 544
<211> LENGTH: 32
<212> TYPE: DNA
<213> ORGANISM: Artificial
<220> FEATURE:
<223> OTHER INFORMATION: Synthetic Polynucleotide

<400> SEQUENCE: 544
acgcgcggag ctaactcaca ttaatttccc ag                      32

<210> SEQ ID NO 545
<211> LENGTH: 32
<212> TYPE: DNA
<213> ORGANISM: Artificial
<220> FEATURE:
<223> OTHER INFORMATION: Synthetic Polynucleotide

<400> SEQUENCE: 545
tgtcgtgctg cccgctttcc agtcatcaaa at                      32

<210> SEQ ID NO 546
<211> LENGTH: 30
<212> TYPE: DNA
<213> ORGANISM: Artificial
<220> FEATURE:
<223> OTHER INFORMATION: Synthetic Polynucleotide

<400> SEQUENCE: 546
aatggaagcg taaaacagaa atattacctt                         30

<210> SEQ ID NO 547
<211> LENGTH: 32
<212> TYPE: DNA
<213> ORGANISM: Artificial
<220> FEATURE:
<223> OTHER INFORMATION: Synthetic Polynucleotide

<400> SEQUENCE: 547
aatcctgatt tcaggtttaa cgtcaaaatt aa                      32

<210> SEQ ID NO 548
<211> LENGTH: 32
<212> TYPE: DNA
<213> ORGANISM: Artificial
<220> FEATURE:
<223> OTHER INFORMATION: Synthetic Polynucleotide

<400> SEQUENCE: 548
tgattatcaa cagtaccttt tacaaagaag at    32

<210> SEQ ID NO 549
<211> LENGTH: 32
<212> TYPE: DNA
<213> ORGANISM: Artificial
<220> FEATURE:
<223> OTHER INFORMATION: Synthetic Polynucleotide

<400> SEQUENCE: 549
cgggcaacac aattccacac aacactagag ga    32

<210> SEQ ID NO 550
<211> LENGTH: 30
<212> TYPE: DNA
<213> ORGANISM: Artificial
<220> FEATURE:
<223> OTHER INFORMATION: Synthetic Polynucleotide

<400> SEQUENCE: 550
cgccagggaa agtgtaaagc ctgagtgcca    30

<210> SEQ ID NO 551
<211> LENGTH: 32
<212> TYPE: DNA
<213> ORGANISM: Artificial
<220> FEATURE:
<223> OTHER INFORMATION: Synthetic Polynucleotide

<400> SEQUENCE: 551
gcgaaaaaaa agaatagccc gagaatcggc ca    32

<210> SEQ ID NO 552
<211> LENGTH: 32
<212> TYPE: DNA
<213> ORGANISM: Artificial
<220> FEATURE:
<223> OTHER INFORMATION: Synthetic Polynucleotide

<400> SEQUENCE: 552
tattaaagtt ccagtttgga acaaagcact aa    32

<210> SEQ ID NO 553
<211> LENGTH: 30
<212> TYPE: DNA
<213> ORGANISM: Artificial
<220> FEATURE:
<223> OTHER INFORMATION: Synthetic Polynucleotide

<400> SEQUENCE: 553
aaggttatag attagagccg tcatctgaat    30

<210> SEQ ID NO 554
<211> LENGTH: 32
<212> TYPE: DNA
<213> ORGANISM: Artificial
<220> FEATURE:
<223> OTHER INFORMATION: Synthetic Polynucleotide

<400> SEQUENCE: 554
ttggcaaaag gatttagaag tattatcaat at    32

<210> SEQ ID NO 555

```
<211> LENGTH: 32
<212> TYPE: DNA
<213> ORGANISM: Artificial
<220> FEATURE:
<223> OTHER INFORMATION: Synthetic Polynucleotide

<400> SEQUENCE: 555
aatatcaatt cgacaactcg tattcatatt cc                                  32

<210> SEQ ID NO 556
<211> LENGTH: 32
<212> TYPE: DNA
<213> ORGANISM: Artificial
<220> FEATURE:
<223> OTHER INFORMATION: Synthetic Polynucleotide

<400> SEQUENCE: 556
ggggtcgacc ccagcaggcg aaaacagtga ga                                  32

<210> SEQ ID NO 557
<211> LENGTH: 30
<212> TYPE: DNA
<213> ORGANISM: Artificial
<220> FEATURE:
<223> OTHER INFORMATION: Synthetic Polynucleotide

<400> SEQUENCE: 557
ctacgtgatt ccgaaatcgg caatattggg                                     30

<210> SEQ ID NO 558
<211> LENGTH: 30
<212> TYPE: DNA
<213> ORGANISM: Artificial
<220> FEATURE:
<223> OTHER INFORMATION: Synthetic Polynucleotide

<400> SEQUENCE: 558
gtgtactcgc cagcattgac agcgtttgcc                                     30

<210> SEQ ID NO 559
<211> LENGTH: 32
<212> TYPE: DNA
<213> ORGANISM: Artificial
<220> FEATURE:
<223> OTHER INFORMATION: Synthetic Polynucleotide

<400> SEQUENCE: 559
ttgtgtcgtg aacggtgtac agactaattt ca                                  32

<210> SEQ ID NO 560
<211> LENGTH: 32
<212> TYPE: DNA
<213> ORGANISM: Artificial
<220> FEATURE:
<223> OTHER INFORMATION: Synthetic Polynucleotide

<400> SEQUENCE: 560
aggacagaaa atccgcgacc tgctcagagg ct                                  32

<210> SEQ ID NO 561
<211> LENGTH: 32
<212> TYPE: DNA
<213> ORGANISM: Artificial
<220> FEATURE:
<223> OTHER INFORMATION: Synthetic Polynucleotide

<400> SEQUENCE: 561
```
ataagggagg aacgaggcgc agaccagaat gg                                    32

<210> SEQ ID NO 562
<211> LENGTH: 30
<212> TYPE: DNA
<213> ORGANISM: Artificial
<220> FEATURE:
<223> OTHER INFORMATION: Synthetic Polynucleotide

<400> SEQUENCE: 562
aaacaaatgt ctctgaattt accgtgccgt                                       30

<210> SEQ ID NO 563
<211> LENGTH: 32
<212> TYPE: DNA
<213> ORGANISM: Artificial
<220> FEATURE:
<223> OTHER INFORMATION: Synthetic Polynucleotide

<400> SEQUENCE: 563
ggcaggtcta catggctttt gatgtagcgg gg                                    32

<210> SEQ ID NO 564
<211> LENGTH: 32
<212> TYPE: DNA
<213> ORGANISM: Artificial
<220> FEATURE:
<223> OTHER INFORMATION: Synthetic Polynucleotide

<400> SEQUENCE: 564
agagccgcgg taataagttt taacggctga ga                                    32

<210> SEQ ID NO 565
<211> LENGTH: 32
<212> TYPE: DNA
<213> ORGANISM: Artificial
<220> FEATURE:
<223> OTHER INFORMATION: Synthetic Polynucleotide

<400> SEQUENCE: 565
tgacaagaat tataccaagc gcgaaatgcc ac                                    32

<210> SEQ ID NO 566
<211> LENGTH: 30
<212> TYPE: DNA
<213> ORGANISM: Artificial
<220> FEATURE:
<223> OTHER INFORMATION: Synthetic Polynucleotide

<400> SEQUENCE: 566
ataggctgga tttgtatcat cgcaggaagt                                       30

<210> SEQ ID NO 567
<211> LENGTH: 30
<212> TYPE: DNA
<213> ORGANISM: Artificial
<220> FEATURE:
<223> OTHER INFORMATION: Synthetic Polynucleotide

<400> SEQUENCE: 567 atcttttac cattagcaag gccaaagaca                                        30

<210> SEQ ID NO 568
<211> LENGTH: 32
<212> TYPE: DNA

-continued

```
<213> ORGANISM: Artificial
<220> FEATURE:
<223> OTHER INFORMATION: Synthetic Polynucleotide

<400> SEQUENCE: 568
actttaatga acaacattat tacaaaaaga ag                                      32

<210> SEQ ID NO 569
<211> LENGTH: 32
<212> TYPE: DNA
<213> ORGANISM: Artificial
<220> FEATURE:
<223> OTHER INFORMATION: Synthetic Polynucleotide

<400> SEQUENCE: 569
aactaacgca ttgtgaatta ccttttttgaa ag                                     32

<210> SEQ ID NO 570
<211> LENGTH: 32
<212> TYPE: DNA
<213> ORGANISM: Artificial
<220> FEATURE:
<223> OTHER INFORMATION: Synthetic Polynucleotide

<400> SEQUENCE: 570
gttgggaact ggctcattat accatgcctt ta                                      32

<210> SEQ ID NO 571
<211> LENGTH: 30
<212> TYPE: DNA
<213> ORGANISM: Artificial
<220> FEATURE:
<223> OTHER INFORMATION: Synthetic Polynucleotide

<400> SEQUENCE: 571
aatcagtact gtagcgcgtt ttctattcac                                         30

<210> SEQ ID NO 572
<211> LENGTH: 32
<212> TYPE: DNA
<213> ORGANISM: Artificial
<220> FEATURE:
<223> OTHER INFORMATION: Synthetic Polynucleotide

<400> SEQUENCE: 572
tcaccaatat agcccccctta ttaggaggtt ga                                     32

<210> SEQ ID NO 573
<211> LENGTH: 32
<212> TYPE: DNA
<213> ORGANISM: Artificial
<220> FEATURE:
<223> OTHER INFORMATION: Synthetic Polynucleotide

<400> SEQUENCE: 573
agcaccatca taatcaaaat caccccacca cc                                      32

<210> SEQ ID NO 574
<211> LENGTH: 32
<212> TYPE: DNA
<213> ORGANISM: Artificial
<220> FEATURE:
<223> OTHER INFORMATION: Synthetic Polynucleotide

<400> SEQUENCE: 574
ttcaactact gacgagaaac accaagtaat ct                                      32
```

<210> SEQ ID NO 575
<211> LENGTH: 30
<212> TYPE: DNA
<213> ORGANISM: Artificial
<220> FEATURE:
<223> OTHER INFORMATION: Synthetic Polynucleotide

<400> SEQUENCE: 575
agattcatgg gcttgagatg gttcaggcgc                                        30

<210> SEQ ID NO 576
<211> LENGTH: 38
<212> TYPE: DNA
<213> ORGANISM: Artificial
<220> FEATURE:
<223> OTHER INFORMATION: Synthetic Polynucleotide

<400> SEQUENCE: 576
aatgtttaga ctggattcat tgaatccccc tttgataa                               38

<210> SEQ ID NO 577
<211> LENGTH: 40
<212> TYPE: DNA
<213> ORGANISM: Artificial
<220> FEATURE:
<223> OTHER INFORMATION: Synthetic Polynucleotide

<400> SEQUENCE: 577
atcaatagaa aattcacgta gaaaatacat acaacccaca                             40

<210> SEQ ID NO 578
<211> LENGTH: 30
<212> TYPE: DNA
<213> ORGANISM: Artificial
<220> FEATURE:
<223> OTHER INFORMATION: Synthetic Polynucleotide

<400> SEQUENCE: 578
aaagggcaag actccttatt acagagcaag                                        30

<210> SEQ ID NO 579
<211> LENGTH: 40
<212> TYPE: DNA
<213> ORGANISM: Artificial
<220> FEATURE:
<223> OTHER INFORMATION: Synthetic Polynucleotide

<400> SEQUENCE: 579
agggagggaa ggtaaaataa cggaatacccc aatcttaccg                            40

<210> SEQ ID NO 580
<211> LENGTH: 40
<212> TYPE: DNA
<213> ORGANISM: Artificial
<220> FEATURE:
<223> OTHER INFORMATION: Synthetic Polynucleotide

<400> SEQUENCE: 580
gataaaaacc aaaataaatc aggtctttac ccagcgaacc                             40

<210> SEQ ID NO 581
<211> LENGTH: 32
<212> TYPE: DNA
<213> ORGANISM: Artificial
<220> FEATURE:

<223> OTHER INFORMATION: Synthetic Polynucleotide

<400> SEQUENCE: 581
ttttgccagt tcagaaaacg agaagtcagg at                          32

<210> SEQ ID NO 582
<211> LENGTH: 32
<212> TYPE: DNA
<213> ORGANISM: Artificial
<220> FEATURE:
<223> OTHER INFORMATION: Synthetic Polynucleotide

<400> SEQUENCE: 582
tttaaacaga gggggtaata gtaaataaaa cg                          32

<210> SEQ ID NO 583
<211> LENGTH: 32
<212> TYPE: DNA
<213> ORGANISM: Artificial
<220> FEATURE:
<223> OTHER INFORMATION: Synthetic Polynucleotide

<400> SEQUENCE: 583
cataaatata gcgtccaata ctgcagacac ca                          32

<210> SEQ ID NO 584
<211> LENGTH: 30
<212> TYPE: DNA
<213> ORGANISM: Artificial
<220> FEATURE:
<223> OTHER INFORMATION: Synthetic Polynucleotide

<400> SEQUENCE: 584
tggcaacagt ttattttgtc acagcaccgt                             30

<210> SEQ ID NO 585
<211> LENGTH: 32
<212> TYPE: DNA
<213> ORGANISM: Artificial
<220> FEATURE:
<223> OTHER INFORMATION: Synthetic Polynucleotide

<400> SEQUENCE: 585
ttagcaaata tggtttacca gcgccggaaa cg                          32

<210> SEQ ID NO 586
<211> LENGTH: 32
<212> TYPE: DNA
<213> ORGANISM: Artificial
<220> FEATURE:
<223> OTHER INFORMATION: Synthetic Polynucleotide

<400> SEQUENCE: 586
gcatgattga cattcaaccg attgtcacca gt                          32

<210> SEQ ID NO 587
<211> LENGTH: 32
<212> TYPE: DNA
<213> ORGANISM: Artificial
<220> FEATURE:
<223> OTHER INFORMATION: Synthetic Polynucleotide

<400> SEQUENCE: 587
atagtcagtc gtttaccaga cgacatacca ca                          32

```
<210> SEQ ID NO 588
<211> LENGTH: 30
<212> TYPE: DNA
<213> ORGANISM: Artificial
<220> FEATURE:
<223> OTHER INFORMATION: Synthetic Polynucleotide

<400> SEQUENCE: 588
aaatcaaagc gagaggcttt tgcggtagaa                                    30

<210> SEQ ID NO 589
<211> LENGTH: 30
<212> TYPE: DNA
<213> ORGANISM: Artificial
<220> FEATURE:
<223> OTHER INFORMATION: Synthetic Polynucleotide

<400> SEQUENCE: 589
gaggtcaata taatgctgta gcacaggcaa                                    30

<210> SEQ ID NO 590
<211> LENGTH: 32
<212> TYPE: DNA
<213> ORGANISM: Artificial
<220> FEATURE:
<223> OTHER INFORMATION: Synthetic Polynucleotide

<400> SEQUENCE: 590
agaattgaga agcgcattag acggatcaag at                                 32

<210> SEQ ID NO 591
<211> LENGTH: 30
<212> TYPE: DNA
<213> ORGANISM: Artificial
<220> FEATURE:
<223> OTHER INFORMATION: Synthetic Polynucleotide

<400> SEQUENCE: 591
aaacaatgcc tttacagaga gacaattta                                     30

<210> SEQ ID NO 592
<211> LENGTH: 32
<212> TYPE: DNA
<213> ORGANISM: Artificial
<220> FEATURE:
<223> OTHER INFORMATION: Synthetic Polynucleotide

<400> SEQUENCE: 592
aagccctttt ttttgtttaa cgtcgagcgt ct                                 32

<210> SEQ ID NO 593
<211> LENGTH: 32
<212> TYPE: DNA
<213> ORGANISM: Artificial
<220> FEATURE:
<223> OTHER INFORMATION: Synthetic Polynucleotide

<400> SEQUENCE: 593
agaccggaat tccatataac agttcgcgag ct                                 32

<210> SEQ ID NO 594
<211> LENGTH: 32
<212> TYPE: DNA
<213> ORGANISM: Artificial
<220> FEATURE:
<223> OTHER INFORMATION: Synthetic Polynucleotide
```

<400> SEQUENCE: 594
tagagagtat gcaactaaag tacgaatagt ag                32

<210> SEQ ID NO 595
<211> LENGTH: 40
<212> TYPE: DNA
<213> ORGANISM: Artificial
<220> FEATURE:
<223> OTHER INFORMATION: Synthetic Polynucleotide

<400> SEQUENCE: 595
ataagggaac cggatattca ttacgtcagg acgttgggaa        40

<210> SEQ ID NO 596
<211> LENGTH: 38
<212> TYPE: DNA
<213> ORGANISM: Artificial
<220> FEATURE:
<223> OTHER INFORMATION: Synthetic Polynucleotide

<400> SEQUENCE: 596
ttgtgtcgtg acgagaaaca ccaaatttca actttaat          38

<210> SEQ ID NO 597
<211> LENGTH: 40
<212> TYPE: DNA
<213> ORGANISM: Artificial
<220> FEATURE:
<223> OTHER INFORMATION: Synthetic Polynucleotide

<400> SEQUENCE: 597
caccctcaga aaccatcgat agcattgagc catttgggaa        40

<210> SEQ ID NO 598
<211> LENGTH: 40
<212> TYPE: DNA
<213> ORGANISM: Artificial
<220> FEATURE:
<223> OTHER INFORMATION: Synthetic Polynucleotide

<400> SEQUENCE: 598
agccaccact gtagcgcgtt ttcaagggag ggaaggtaaa        40

<210> SEQ ID NO 599
<211> LENGTH: 40
<212> TYPE: DNA
<213> ORGANISM: Artificial
<220> FEATURE:
<223> OTHER INFORMATION: Synthetic Polynucleotide

<400> SEQUENCE: 599
attaagttta ccgagctcga attcgggaaa cctgtcgtgc        40

<210> SEQ ID NO 600
<211> LENGTH: 38
<212> TYPE: DNA
<213> ORGANISM: Artificial
<220> FEATURE:
<223> OTHER INFORMATION: Synthetic Polynucleotide

<400> SEQUENCE: 600
gcgatcggca attccacaca acaggtgcct aatgagtg          38

<210> SEQ ID NO 601
<211> LENGTH: 40

<212> TYPE: DNA
<213> ORGANISM: Artificial
<220> FEATURE:
<223> OTHER INFORMATION: Synthetic Polynucleotide

<400> SEQUENCE: 601
attcattttt gtttggatta tactaagaaa ccaccagaag                    40

<210> SEQ ID NO 602
<211> LENGTH: 40
<212> TYPE: DNA
<213> ORGANISM: Artificial
<220> FEATURE:
<223> OTHER INFORMATION: Synthetic Polynucleotide

<400> SEQUENCE: 602
aacaataacg taaaacagaa ataaaaatcc tttgcccgaa                    40

<210> SEQ ID NO 603
<211> LENGTH: 32
<212> TYPE: DNA
<213> ORGANISM: Artificial
<220> FEATURE:
<223> OTHER INFORMATION: Synthetic Polynucleotide

<400> SEQUENCE: 603
ggtgtatctt gatataagta tagcgacagc at                            32

<210> SEQ ID NO 604
<211> LENGTH: 32
<212> TYPE: DNA
<213> ORGANISM: Artificial
<220> FEATURE:
<223> OTHER INFORMATION: Synthetic Polynucleotide

<400> SEQUENCE: 604
tgcgggaggg cgttttagcg aacccaataa ag                            32

<210> SEQ ID NO 605
<211> LENGTH: 32
<212> TYPE: DNA
<213> ORGANISM: Artificial
<220> FEATURE:
<223> OTHER INFORMATION: Synthetic Polynucleotide

<400> SEQUENCE: 605
aatgcagacg acaataaaca acatgtcatt gc                            32

<210> SEQ ID NO 606
<211> LENGTH: 32
<212> TYPE: DNA
<213> ORGANISM: Artificial
<220> FEATURE:
<223> OTHER INFORMATION: Synthetic Polynucleotide

<400> SEQUENCE: 606
ttgaaataat cttctgacct aaatcaaccc gt                            32

<210> SEQ ID NO 607
<211> LENGTH: 32
<212> TYPE: DNA
<213> ORGANISM: Artificial
<220> FEATURE:
<223> OTHER INFORMATION: Synthetic Polynucleotide

<400> SEQUENCE: 607

-continued gtgagtgaga acagtacat aaatgcaagg cg    32

<210> SEQ ID NO 608
<211> LENGTH: 32
<212> TYPE: DNA
<213> ORGANISM: Artificial
<220> FEATURE:
<223> OTHER INFORMATION: Synthetic Polynucleotide

<400> SEQUENCE: 608
tatttgcagg ttagaaccta ccatgggaaa cc    32

<210> SEQ ID NO 609
<211> LENGTH: 32
<212> TYPE: DNA
<213> ORGANISM: Artificial
<220> FEATURE:
<223> OTHER INFORMATION: Synthetic Polynucleotide

<400> SEQUENCE: 609
caactaatct aaaatatctt tagggagtcc ac    32

<210> SEQ ID NO 610
<211> LENGTH: 32
<212> TYPE: DNA
<213> ORGANISM: Artificial
<220> FEATURE:
<223> OTHER INFORMATION: Synthetic Polynucleotide

<400> SEQUENCE: 610
aaagcgcaaa atcctcatta aagcggtcaa tc    32

<210> SEQ ID NO 611
<211> LENGTH: 32
<212> TYPE: DNA
<213> ORGANISM: Artificial
<220> FEATURE:
<223> OTHER INFORMATION: Synthetic Polynucleotide

<400> SEQUENCE: 611
gcgtcagagc gacagaatca agttgtcagg ac    32

<210> SEQ ID NO 612
<211> LENGTH: 32
<212> TYPE: DNA
<213> ORGANISM: Artificial
<220> FEATURE:
<223> OTHER INFORMATION: Synthetic Polynucleotide

<400> SEQUENCE: 612
cggaataata taaagaaac gcaaggaatc gt    32

<210> SEQ ID NO 613
<211> LENGTH: 32
<212> TYPE: DNA
<213> ORGANISM: Artificial
<220> FEATURE:
<223> OTHER INFORMATION: Synthetic Polynucleotide

<400> SEQUENCE: 613
ttgagcgcac cctgaacaaa gtcaagagct ta    32

<210> SEQ ID NO 614
<211> LENGTH: 30
<212> TYPE: DNA
<213> ORGANISM: Artificial

```
<220> FEATURE:
<223> OTHER INFORMATION: Synthetic Polynucleotide

<400> SEQUENCE: 614
caaacaaacc ctcaatcaat ataaaaatac                                    30

<210> SEQ ID NO 615
<211> LENGTH: 40
<212> TYPE: DNA
<213> ORGANISM: Artificial
<220> FEATURE:
<223> OTHER INFORMATION: Synthetic Polynucleotide

<400> SEQUENCE: 615
aaatcctttg cccgaaaaag catcaccttg ctaaaacaga                         40

<210> SEQ ID NO 616
<211> LENGTH: 32
<212> TYPE: DNA
<213> ORGANISM: Artificial
<220> FEATURE:
<223> OTHER INFORMATION: Synthetic Polynucleotide

<400> SEQUENCE: 616
aaggaattgc gaataataat ttttgtcgct ga                                 32

<210> SEQ ID NO 617
<211> LENGTH: 31
<212> TYPE: DNA
<213> ORGANISM: Artificial
<220> FEATURE:
<223> OTHER INFORMATION: Synthetic Polynucleotide

<400> SEQUENCE: 617
tcagcggagt gagaatagaa aggttttgcg g                                  31

<210> SEQ ID NO 618
<211> LENGTH: 32
<212> TYPE: DNA
<213> ORGANISM: Artificial
<220> FEATURE:
<223> OTHER INFORMATION: Synthetic Polynucleotide

<400> SEQUENCE: 618
gaaaatctcc aaaaaaaagg ctccaaccat cg                                 32

<210> SEQ ID NO 619
<211> LENGTH: 32
<212> TYPE: DNA
<213> ORGANISM: Artificial
<220> FEATURE:
<223> OTHER INFORMATION: Synthetic Polynucleotide

<400> SEQUENCE: 619
ttgaggacgg gagttaaagg ccgcaacaac ta                                 32

<210> SEQ ID NO 620
<211> LENGTH: 32
<212> TYPE: DNA
<213> ORGANISM: Artificial
<220> FEATURE:
<223> OTHER INFORMATION: Synthetic Polynucleotide

<400> SEQUENCE: 620
tacgaaggcg ccgacaatga caacaaaagg ag                                 32
```

<210> SEQ ID NO 621
<211> LENGTH: 30
<212> TYPE: DNA
<213> ORGANISM: Artificial
<220> FEATURE:
<223> OTHER INFORMATION: Synthetic Polynucleotide

<400> SEQUENCE: 621
ttccattata accgatatat tcgtcacgtt                                       30

<210> SEQ ID NO 622
<211> LENGTH: 40
<212> TYPE: DNA
<213> ORGANISM: Artificial
<220> FEATURE:
<223> OTHER INFORMATION: Synthetic Polynucleotide

<400> SEQUENCE: 622
atagataata catttgtcaa cagttgaaag gagcgcgaac                            40

<210> SEQ ID NO 623
<211> LENGTH: 30
<212> TYPE: DNA
<213> ORGANISM: Artificial
<220> FEATURE:
<223> OTHER INFORMATION: Synthetic Polynucleotide

<400> SEQUENCE: 623
ttgaatggct attagtcttt aatattgagg                                       30

<210> SEQ ID NO 624
<211> LENGTH: 32
<212> TYPE: DNA
<213> ORGANISM: Artificial
<220> FEATURE:
<223> OTHER INFORMATION: Synthetic Polynucleotide

<400> SEQUENCE: 624
tgatagccct aaaacatcgc cattctggtc ag                                    32

<210> SEQ ID NO 625
<211> LENGTH: 31
<212> TYPE: DNA
<213> ORGANISM: Artificial
<220> FEATURE:
<223> OTHER INFORMATION: Synthetic Polynucleotide

<400> SEQUENCE: 625
cgaacgaacc accagcagaa gatgaacctc a                                     31

<210> SEQ ID NO 626
<211> LENGTH: 30
<212> TYPE: DNA
<213> ORGANISM: Artificial
<220> FEATURE:
<223> OTHER INFORMATION: Synthetic Polynucleotide

<400> SEQUENCE: 626
atagttgcac caacctaaaa cgctttgacc                                       30

<210> SEQ ID NO 627
<211> LENGTH: 30
<212> TYPE: DNA
<213> ORGANISM: Artificial
<220> FEATURE:
<223> OTHER INFORMATION: Synthetic Polynucleotide

```
<400> SEQUENCE: 627
tttagctaac cctcatatat ttgattcaaa                                30

<210> SEQ ID NO 628
<211> LENGTH: 30
<212> TYPE: DNA
<213> ORGANISM: Artificial
<220> FEATURE:
<223> OTHER INFORMATION: Synthetic Polynucleotide

<400> SEQUENCE: 628
agggtgagga agattgtata agttaaaatt                                30

<210> SEQ ID NO 629
<211> LENGTH: 30
<212> TYPE: DNA
<213> ORGANISM: Artificial
<220> FEATURE:
<223> OTHER INFORMATION: Synthetic Polynucleotide

<400> SEQUENCE: 629
cgcattagac gacagtatcg gcgcaccgct                                30

<210> SEQ ID NO 630
<211> LENGTH: 30
<212> TYPE: DNA
<213> ORGANISM: Artificial
<220> FEATURE:
<223> OTHER INFORMATION: Synthetic Polynucleotide

<400> SEQUENCE: 630
tctggtgtac cgagctcgaa ttaattgtta                                30

<210> SEQ ID NO 631
<211> LENGTH: 30
<212> TYPE: DNA
<213> ORGANISM: Artificial
<220> FEATURE:
<223> OTHER INFORMATION: Synthetic Polynucleotide

<400> SEQUENCE: 631
tccgctcagc tgattgccct tcgtccacgc                                30

<210> SEQ ID NO 632
<211> LENGTH: 30
<212> TYPE: DNA
<213> ORGANISM: Artificial
<220> FEATURE:
<223> OTHER INFORMATION: Synthetic Polynucleotide

<400> SEQUENCE: 632
cccagcgacc ggatattcat tatgaataag                                30

<210> SEQ ID NO 633
<211> LENGTH: 30
<212> TYPE: DNA
<213> ORGANISM: Artificial
<220> FEATURE:
<223> OTHER INFORMATION: Synthetic Polynucleotide

<400> SEQUENCE: 633
gcttgccatg cagatacata acacactatc                                30

<210> SEQ ID NO 634
```

```
<211> LENGTH: 30
<212> TYPE: DNA
<213> ORGANISM: Artificial
<220> FEATURE:
<223> OTHER INFORMATION: Synthetic Polynucleotide

<400> SEQUENCE: 634
ataacccaag caaagcggat tgttcaaata                                        30

<210> SEQ ID NO 635
<211> LENGTH: 30
<212> TYPE: DNA
<213> ORGANISM: Artificial
<220> FEATURE:
<223> OTHER INFORMATION: Synthetic Polynucleotide

<400> SEQUENCE: 635
tcgcgttaac gagtagattt agataacctg                                        30

<210> SEQ ID NO 636
<211> LENGTH: 32
<212> TYPE: DNA
<213> ORGANISM: Artificial
<220> FEATURE:
<223> OTHER INFORMATION: Synthetic Polynucleotide

<400> SEQUENCE: 636
tctttccaga cgttagtaaa tgaatttagt ac                                     32

<210> SEQ ID NO 637
<211> LENGTH: 31
<212> TYPE: DNA
<213> ORGANISM: Artificial
<220> FEATURE:
<223> OTHER INFORMATION: Synthetic Polynucleotide

<400> SEQUENCE: 637
atagttagcg taacgatcta aagcagaacc g                                      31

<210> SEQ ID NO 638
<211> LENGTH: 32
<212> TYPE: DNA
<213> ORGANISM: Artificial
<220> FEATURE:
<223> OTHER INFORMATION: Synthetic Polynucleotide

<400> SEQUENCE: 638
acaacgcctg tagcattcca cagaattttc ag                                     32

<210> SEQ ID NO 639
<211> LENGTH: 30
<212> TYPE: DNA
<213> ORGANISM: Artificial
<220> FEATURE:
<223> OTHER INFORMATION: Synthetic Polynucleotide

<400> SEQUENCE: 639
agaaacgatt taagaaaagt aagcgaggaa                                        30

<210> SEQ ID NO 640
<211> LENGTH: 30
<212> TYPE: DNA
<213> ORGANISM: Artificial
<220> FEATURE:
<223> OTHER INFORMATION: Synthetic Polynucleotide

<400> SEQUENCE: 640
```
agaacaagcc taatttgcca gttccaaata                                              30

<210> SEQ ID NO 641
<211> LENGTH: 30
<212> TYPE: DNA
<213> ORGANISM: Artificial
<220> FEATURE:
<223> OTHER INFORMATION: Synthetic Polynucleotide

<400> SEQUENCE: 641
tatttaactg tctttcctta tcactcatcg                                              30

<210> SEQ ID NO 642
<211> LENGTH: 30
<212> TYPE: DNA
<213> ORGANISM: Artificial
<220> FEATURE:
<223> OTHER INFORMATION: Synthetic Polynucleotide

<400> SEQUENCE: 642
ggcttaggtt cttaccagta taaatcgcca                                              30

<210> SEQ ID NO 643
<211> LENGTH: 30
<212> TYPE: DNA
<213> ORGANISM: Artificial
<220> FEATURE:
<223> OTHER INFORMATION: Synthetic Polynucleotide

<400> SEQUENCE: 643
tattcatttc aatagtgaat ttaaacctcc                                              30

<210> SEQ ID NO 644
<211> LENGTH: 30
<212> TYPE: DNA
<213> ORGANISM: Artificial
<220> FEATURE:
<223> OTHER INFORMATION: Synthetic Polynucleotide

<400> SEQUENCE: 644
cgagagggac cgtactcagg aggttttctg                                              30

<210> SEQ ID NO 645
<211> LENGTH: 32
<212> TYPE: DNA
<213> ORGANISM: Artificial
<220> FEATURE:
<223> OTHER INFORMATION: Synthetic Polynucleotide

<400> SEQUENCE: 645
ttttgctctc agaaccgcca ccctttttgt cg                                           32

<210> SEQ ID NO 646
<211> LENGTH: 32
<212> TYPE: DNA
<213> ORGANISM: Artificial
<220> FEATURE:
<223> OTHER INFORMATION: Synthetic Polynucleotide

<400> SEQUENCE: 646
ctcctcaaca gagccaccac cctccagccc tc                                           32

<210> SEQ ID NO 647
<211> LENGTH: 30
<212> TYPE: DNA

```
<213> ORGANISM: Artificial
<220> FEATURE:
<223> OTHER INFORMATION: Synthetic Polynucleotide

<400> SEQUENCE: 647
ttctgaaaag cccaatagga accacaaact                              30

<210> SEQ ID NO 648
<211> LENGTH: 30
<212> TYPE: DNA
<213> ORGANISM: Artificial
<220> FEATURE:
<223> OTHER INFORMATION: Synthetic Polynucleotide

<400> SEQUENCE: 648
caccagaacg gattcgcctg attggcgaat                              30

<210> SEQ ID NO 649
<211> LENGTH: 30
<212> TYPE: DNA
<213> ORGANISM: Artificial
<220> FEATURE:
<223> OTHER INFORMATION: Synthetic Polynucleotide

<400> SEQUENCE: 649
aaaaatctcg ttattaattt taaaagaaac                              30

<210> SEQ ID NO 650
<211> LENGTH: 30
<212> TYPE: DNA
<213> ORGANISM: Artificial
<220> FEATURE:
<223> OTHER INFORMATION: Synthetic Polynucleotide

<400> SEQUENCE: 650
ccaccctcgt aacagtgccc gtacctatta                              30

<210> SEQ ID NO 651
<211> LENGTH: 30
<212> TYPE: DNA
<213> ORGANISM: Artificial
<220> FEATURE:
<223> OTHER INFORMATION: Synthetic Polynucleotide

<400> SEQUENCE: 651
atttgggacc ggaaccgcct cccagagcca                              30

<210> SEQ ID NO 652
<211> LENGTH: 30
<212> TYPE: DNA
<213> ORGANISM: Artificial
<220> FEATURE:
<223> OTHER INFORMATION: Synthetic Polynucleotide

<400> SEQUENCE: 652
acgcaatata ttgacggaaa ttattgagcc                              30

<210> SEQ ID NO 653
<211> LENGTH: 30
<212> TYPE: DNA
<213> ORGANISM: Artificial
<220> FEATURE:
<223> OTHER INFORMATION: Synthetic Polynucleotide

<400> SEQUENCE: 653
tggtttgggt gccgtaaagc acagagcttg                              30
```

<210> SEQ ID NO 654
<211> LENGTH: 40
<212> TYPE: DNA
<213> ORGANISM: Artificial
<220> FEATURE:
<223> OTHER INFORMATION: Synthetic Polynucleotide

<400> SEQUENCE: 654
tcctgtttga tggtggacca tcacccaaat cacgagaaag                          40

<210> SEQ ID NO 655
<211> LENGTH: 32
<212> TYPE: DNA
<213> ORGANISM: Artificial
<220> FEATURE:
<223> OTHER INFORMATION: Synthetic Polynucleotide

<400> SEQUENCE: 655
ataaatcacc gtctatcagg gcgagacatt ct                                  32

<210> SEQ ID NO 656
<211> LENGTH: 31
<212> TYPE: DNA
<213> ORGANISM: Artificial
<220> FEATURE:
<223> OTHER INFORMATION: Synthetic Polynucleotide

<400> SEQUENCE: 656
acggggaaag ccggcgaacg tggagttttt t                                   31

<210> SEQ ID NO 657
<211> LENGTH: 30
<212> TYPE: DNA
<213> ORGANISM: Artificial
<220> FEATURE:
<223> OTHER INFORMATION: Synthetic Polynucleotide

<400> SEQUENCE: 657
gaagggaaac cagtaataaa aggtggccca                                     30

<210> SEQ ID NO 658
<211> LENGTH: 32
<212> TYPE: DNA
<213> ORGANISM: Artificial
<220> FEATURE:
<223> OTHER INFORMATION: Synthetic Polynucleotide

<400> SEQUENCE: 658
ggccaacaga gatagaaccc ttctgtcaaa gg                                  32

<210> SEQ ID NO 659
<211> LENGTH: 32
<212> TYPE: DNA
<213> ORGANISM: Artificial
<220> FEATURE:
<223> OTHER INFORMATION: Synthetic Polynucleotide

<400> SEQUENCE: 659
tatgggattt tgctaaacaa ctttcaacag tt                                  32

<210> SEQ ID NO 660
<211> LENGTH: 31
<212> TYPE: DNA
<213> ORGANISM: Artificial
<220> FEATURE:

```
<223> OTHER INFORMATION: Synthetic Polynucleotide

<400> SEQUENCE: 660
cctttaattg tatcggttta tcatgatacc g                              31

<210> SEQ ID NO 661
<211> LENGTH: 31
<212> TYPE: DNA
<213> ORGANISM: Artificial
<220> FEATURE:
<223> OTHER INFORMATION: Synthetic Polynucleotide

<400> SEQUENCE: 661
agcgtaagaa tacgtggcac agacaatatt t                              31

<210> SEQ ID NO 662
<211> LENGTH: 30
<212> TYPE: DNA
<213> ORGANISM: Artificial
<220> FEATURE:
<223> OTHER INFORMATION: Synthetic Polynucleotide

<400> SEQUENCE: 662
ggtgaggcgg tcagtattaa cacgcaaatg                                30

<210> SEQ ID NO 663
<211> LENGTH: 38
<212> TYPE: DNA
<213> ORGANISM: Artificial
<220> FEATURE:
<223> OTHER INFORMATION: Synthetic Polynucleotide

<400> SEQUENCE: 663
tagggttgag tgttgaacgt ggactccaac gacctgaa                       38

<210> SEQ ID NO 664
<211> LENGTH: 44
<212> TYPE: DNA
<213> ORGANISM: Artificial
<220> FEATURE:
<223> OTHER INFORMATION: Synthetic Polynucleotide

<400> SEQUENCE: 664
gatcgtcggg tagcaacggc taccatgtta cttagccacc gaac                44

<210> SEQ ID NO 665
<211> LENGTH: 48
<212> TYPE: DNA
<213> ORGANISM: Artificial
<220> FEATURE:
<223> OTHER INFORMATION: Synthetic Polynucleotide

<400> SEQUENCE: 665
cgccacccag taccaggcgg ataagttcca gtaagcgtca agacgatt            48

<210> SEQ ID NO 666
<211> LENGTH: 30
<212> TYPE: DNA
<213> ORGANISM: Artificial
<220> FEATURE:
<223> OTHER INFORMATION: Synthetic Polynucleotide

<400> SEQUENCE: 666
ccaccctgag aaggattagg atatacagga                                30
```

```
<210> SEQ ID NO 667
<211> LENGTH: 48
<212> TYPE: DNA
<213> ORGANISM: Artificial
<220> FEATURE:
<223> OTHER INFORMATION: Synthetic Polynucleotide

<400> SEQUENCE: 667
ggatagcaca tgaaagtatt aagaggggtc agtgccttga agagccgc              48

<210> SEQ ID NO 668
<211> LENGTH: 48
<212> TYPE: DNA
<213> ORGANISM: Artificial
<220> FEATURE:
<223> OTHER INFORMATION: Synthetic Polynucleotide

<400> SEQUENCE: 668
cccacgcaaa cgggtaaaat acgtaacaaa gtacaacgga gctgacct              48

<210> SEQ ID NO 669
<211> LENGTH: 32
<212> TYPE: DNA
<213> ORGANISM: Artificial
<220> FEATURE:
<223> OTHER INFORMATION: Synthetic Polynucleotide

<400> SEQUENCE: 669
ggcttgcata aagactttt catgctgata aa                                32

<210> SEQ ID NO 670
<211> LENGTH: 32
<212> TYPE: DNA
<213> ORGANISM: Artificial
<220> FEATURE:
<223> OTHER INFORMATION: Synthetic Polynucleotide

<400> SEQUENCE: 670
ttttaaatac ctttaattgc tccttcaaat gc                               32

<210> SEQ ID NO 671
<211> LENGTH: 32
<212> TYPE: DNA
<213> ORGANISM: Artificial
<220> FEATURE:
<223> OTHER INFORMATION: Synthetic Polynucleotide

<400> SEQUENCE: 671
attgctgatt tttgcggatg gcttgagggt aa                               32

<210> SEQ ID NO 672
<211> LENGTH: 30
<212> TYPE: DNA
<213> ORGANISM: Artificial
<220> FEATURE:
<223> OTHER INFORMATION: Synthetic Polynucleotide

<400> SEQUENCE: 672
aactgaacta atatcagaga gatataaagg                                  30

<210> SEQ ID NO 673
<211> LENGTH: 32
<212> TYPE: DNA
<213> ORGANISM: Artificial
<220> FEATURE:
<223> OTHER INFORMATION: Synthetic Polynucleotide
```

<400> SEQUENCE: 673
aaaacagggt taagcccaat aatagcagta tg                                32

<210> SEQ ID NO 674
<211> LENGTH: 32
<212> TYPE: DNA
<213> ORGANISM: Artificial
<220> FEATURE:
<223> OTHER INFORMATION: Synthetic Polynucleotide

<400> SEQUENCE: 674
aaatagcaga aatagcaata gctaaagaac tg                                32

<210> SEQ ID NO 675
<211> LENGTH: 32
<212> TYPE: DNA
<213> ORGANISM: Artificial
<220> FEATURE:
<223> OTHER INFORMATION: Synthetic Polynucleotide

<400> SEQUENCE: 675
attctgcgtt aattcgagct tcaatgacta tt                                32

<210> SEQ ID NO 676
<211> LENGTH: 30
<212> TYPE: DNA
<213> ORGANISM: Artificial
<220> FEATURE:
<223> OTHER INFORMATION: Synthetic Polynucleotide

<400> SEQUENCE: 676
gaagtttcag caaactccaa cagtgaccat                                   30

<210> SEQ ID NO 677
<211> LENGTH: 30
<212> TYPE: DNA
<213> ORGANISM: Artificial
<220> FEATURE:
<223> OTHER INFORMATION: Synthetic Polynucleotide

<400> SEQUENCE: 677
ggcaaagcat aaagctaaat cgctattttt                                   30

<210> SEQ ID NO 678
<211> LENGTH: 32
<212> TYPE: DNA
<213> ORGANISM: Artificial
<220> FEATURE:
<223> OTHER INFORMATION: Synthetic Polynucleotide

<400> SEQUENCE: 678
tagttgctag aaggcttatc cggtaacaat ag                                32

<210> SEQ ID NO 679
<211> LENGTH: 30
<212> TYPE: DNA
<213> ORGANISM: Artificial
<220> FEATURE:
<223> OTHER INFORMATION: Synthetic Polynucleotide

<400> SEQUENCE: 679
tcctgaatac cgcgcccaat agtatcccat                                   30

<210> SEQ ID NO 680
<211> LENGTH: 32

```
<212> TYPE: DNA
<213> ORGANISM: Artificial
<220> FEATURE:
<223> OTHER INFORMATION: Synthetic Polynucleotide

<400> SEQUENCE: 680
ttccagagca agccgttttt atttccaatc aa                                 32

<210> SEQ ID NO 681
<211> LENGTH: 32
<212> TYPE: DNA
<213> ORGANISM: Artificial
<220> FEATURE:
<223> OTHER INFORMATION: Synthetic Polynucleotide

<400> SEQUENCE: 681
gaaaaggtct ttatttcaac gcaatcaaat ca                                 32

<210> SEQ ID NO 682
<211> LENGTH: 32
<212> TYPE: DNA
<213> ORGANISM: Artificial
<220> FEATURE:
<223> OTHER INFORMATION: Synthetic Polynucleotide

<400> SEQUENCE: 682
tagcattata tgaccctgta atactctagc tg                                 32

<210> SEQ ID NO 683
<211> LENGTH: 32
<212> TYPE: DNA
<213> ORGANISM: Artificial
<220> FEATURE:
<223> OTHER INFORMATION: Synthetic Polynucleotide

<400> SEQUENCE: 683
aaaaacatac atccaataaa tcattcaaca tg                                 32

<210> SEQ ID NO 684
<211> LENGTH: 32
<212> TYPE: DNA
<213> ORGANISM: Artificial
<220> FEATURE:
<223> OTHER INFORMATION: Synthetic Polynucleotide

<400> SEQUENCE: 684
cctcagagaa ttagcaaaat taagtcccga ct                                 32

<210> SEQ ID NO 685
<211> LENGTH: 30
<212> TYPE: DNA
<213> ORGANISM: Artificial
<220> FEATURE:
<223> OTHER INFORMATION: Synthetic Polynucleotide

<400> SEQUENCE: 685
gaacgcgagt tttgaagcct taagagaatt                                    30

<210> SEQ ID NO 686
<211> LENGTH: 32
<212> TYPE: DNA
<213> ORGANISM: Artificial
<220> FEATURE:
<223> OTHER INFORMATION: Synthetic Polynucleotide

<400> SEQUENCE: 686
```
tcagatatat tttgcaccca gctaataaca ta                32

<210> SEQ ID NO 687
<211> LENGTH: 32
<212> TYPE: DNA
<213> ORGANISM: Artificial
<220> FEATURE:
<223> OTHER INFORMATION: Synthetic Polynucleotide

<400> SEQUENCE: 687
ggaatcattc ttaccaacgc taacaaaaat ga                32

<210> SEQ ID NO 688
<211> LENGTH: 32
<212> TYPE: DNA
<213> ORGANISM: Artificial
<220> FEATURE:
<223> OTHER INFORMATION: Synthetic Polynucleotide

<400> SEQUENCE: 688
atttttagat attttcattt gggggattcc ca                32

<210> SEQ ID NO 689
<211> LENGTH: 30
<212> TYPE: DNA
<213> ORGANISM: Artificial
<220> FEATURE:
<223> OTHER INFORMATION: Synthetic Polynucleotide

<400> SEQUENCE: 689
ggagaagcgg catcaattct actgtgtctg                30

<210> SEQ ID NO 690
<211> LENGTH: 30
<212> TYPE: DNA
<213> ORGANISM: Artificial
<220> FEATURE:
<223> OTHER INFORMATION: Synthetic Polynucleotide

<400> SEQUENCE: 690
gagagatctg gagcaaacaa gagctttcat                30

<210> SEQ ID NO 691
<211> LENGTH: 32
<212> TYPE: DNA
<213> ORGANISM: Artificial
<220> FEATURE:
<223> OTHER INFORMATION: Synthetic Polynucleotide

<400> SEQUENCE: 691
ataagtccga caaaggtaa agtaataagg cg                32

<210> SEQ ID NO 692
<211> LENGTH: 30
<212> TYPE: DNA
<213> ORGANISM: Artificial
<220> FEATURE:
<223> OTHER INFORMATION: Synthetic Polynucleotide

<400> SEQUENCE: 692
cctaatttcg agccagtaat aacataatta                30

<210> SEQ ID NO 693
<211> LENGTH: 32
<212> TYPE: DNA
<213> ORGANISM: Artificial

```
<220> FEATURE:
<223> OTHER INFORMATION: Synthetic Polynucleotide

<400> SEQUENCE: 693
taatcggcaa cgccaacatg taatatatgc gt                                  32

<210> SEQ ID NO 694
<211> LENGTH: 32
<212> TYPE: DNA
<213> ORGANISM: Artificial
<220> FEATURE:
<223> OTHER INFORMATION: Synthetic Polynucleotide

<400> SEQUENCE: 694
ccatcaatcc cggttgataa tcaggctcat tt                                  32

<210> SEQ ID NO 695
<211> LENGTH: 32
<212> TYPE: DNA
<213> ORGANISM: Artificial
<220> FEATURE:
<223> OTHER INFORMATION: Synthetic Polynucleotide

<400> SEQUENCE: 695
ataaattaat cgtaaaacta gcataaaata at                                  32

<210> SEQ ID NO 696
<211> LENGTH: 32
<212> TYPE: DNA
<213> ORGANISM: Artificial
<220> FEATURE:
<223> OTHER INFORMATION: Synthetic Polynucleotide

<400> SEQUENCE: 696
gaacggtaat gccggagagg gtaggttgta cc                                  32

<210> SEQ ID NO 697
<211> LENGTH: 32
<212> TYPE: DNA
<213> ORGANISM: Artificial
<220> FEATURE:
<223> OTHER INFORMATION: Synthetic Polynucleotide

<400> SEQUENCE: 697
ctgagagtct acaaaggcta tcaggttcag ct                                  32

<210> SEQ ID NO 698
<211> LENGTH: 30
<212> TYPE: DNA
<213> ORGANISM: Artificial
<220> FEATURE:
<223> OTHER INFORMATION: Synthetic Polynucleotide

<400> SEQUENCE: 698
ccagacgaac gcgcctgttt atcattctaa                                     30

<210> SEQ ID NO 699
<211> LENGTH: 32
<212> TYPE: DNA
<213> ORGANISM: Artificial
<220> FEATURE:
<223> OTHER INFORMATION: Synthetic Polynucleotide

<400> SEQUENCE: 699
aaagtacctg aacaagaaaa ataacaagca aa                                  32
```

<210> SEQ ID NO 700
<211> LENGTH: 32
<212> TYPE: DNA
<213> ORGANISM: Artificial
<220> FEATURE:
<223> OTHER INFORMATION: Synthetic Polynucleotide

<400> SEQUENCE: 700
aggcatttta cgagcatgta gaaatcatcg ta                          32

<210> SEQ ID NO 701
<211> LENGTH: 32
<212> TYPE: DNA
<213> ORGANISM: Artificial
<220> FEATURE:
<223> OTHER INFORMATION: Synthetic Polynucleotide

<400> SEQUENCE: 701
caaaaacaga aaggccggag acagggataa aa                          32

<210> SEQ ID NO 702
<211> LENGTH: 30
<212> TYPE: DNA
<213> ORGANISM: Artificial
<220> FEATURE:
<223> OTHER INFORMATION: Synthetic Polynucleotide

<400> SEQUENCE: 702
atatgtacat gatattcaac cgttttttgcg                            30

<210> SEQ ID NO 703
<211> LENGTH: 44
<212> TYPE: DNA
<213> ORGANISM: Artificial
<220> FEATURE:
<223> OTHER INFORMATION: Synthetic Polynucleotide

<400> SEQUENCE: 703
caacattccg tgggaacaaa cgattacgcc agctggcggg taac              44

<210> SEQ ID NO 704
<211> LENGTH: 48
<212> TYPE: DNA
<213> ORGANISM: Artificial
<220> FEATURE:
<223> OTHER INFORMATION: Synthetic Polynucleotide

<400> SEQUENCE: 704
ttaaataaaa acttttttcaa atattaaatc gtcgctatta aacaattt          48

<210> SEQ ID NO 705
<211> LENGTH: 30
<212> TYPE: DNA
<213> ORGANISM: Artificial
<220> FEATURE:
<223> OTHER INFORMATION: Synthetic Polynucleotide

<400> SEQUENCE: 705
ctagaaacaa atccaatcgc aaaatccttg                             30

<210> SEQ ID NO 706
<211> LENGTH: 48
<212> TYPE: DNA
<213> ORGANISM: Artificial
<220> FEATURE:
<223> OTHER INFORMATION: Synthetic Polynucleotide

```
<400> SEQUENCE: 706
tatacaaatt gggttatata actaaagacg ctgagaagag tcaattac                48

<210> SEQ ID NO 707
<211> LENGTH: 48
<212> TYPE: DNA
<213> ORGANISM: Artificial
<220> FEATURE:
<223> OTHER INFORMATION: Synthetic Polynucleotide

<400> SEQUENCE: 707
tttaaccatc gtaaccgtgc atctgcgcca ttcgccattc tgcctgca                48

<210> SEQ ID NO 708
<211> LENGTH: 32
<212> TYPE: DNA
<213> ORGANISM: Artificial
<220> FEATURE:
<223> OTHER INFORMATION: Synthetic Polynucleotide

<400> SEQUENCE: 708
tcgcgtctgg gataggtcac gttgtgggaa gg                                 32

<210> SEQ ID NO 709
<211> LENGTH: 32
<212> TYPE: DNA
<213> ORGANISM: Artificial
<220> FEATURE:
<223> OTHER INFORMATION: Synthetic Polynucleotide

<400> SEQUENCE: 709
accgtaatgg ccttcctgta gccagaatcg at                                 32

<210> SEQ ID NO 710
<211> LENGTH: 32
<212> TYPE: DNA
<213> ORGANISM: Artificial
<220> FEATURE:
<223> OTHER INFORMATION: Synthetic Polynucleotide

<400> SEQUENCE: 710
cggattctaa atgtgagcga gtaattaatg gt                                 32

<210> SEQ ID NO 711
<211> LENGTH: 30
<212> TYPE: DNA
<213> ORGANISM: Artificial
<220> FEATURE:
<223> OTHER INFORMATION: Synthetic Polynucleotide

<400> SEQUENCE: 711
ttaatttccc gaccgtgtga taaattctgt                                    30

<210> SEQ ID NO 712
<211> LENGTH: 32
<212> TYPE: DNA
<213> ORGANISM: Artificial
<220> FEATURE:
<223> OTHER INFORMATION: Synthetic Polynucleotide

<400> SEQUENCE: 712
acgcgagaga ataaacaccg gaatgagaat at                                 32

<210> SEQ ID NO 713
```

```
<211> LENGTH: 32
<212> TYPE: DNA
<213> ORGANISM: Artificial
<220> FEATURE:
<223> OTHER INFORMATION: Synthetic Polynucleotide

<400> SEQUENCE: 713
tgctgatgaa gcctgtttag tatcttaggc ag                                    32

<210> SEQ ID NO 714
<211> LENGTH: 32
<212> TYPE: DNA
<213> ORGANISM: Artificial
<220> FEATURE:
<223> OTHER INFORMATION: Synthetic Polynucleotide

<400> SEQUENCE: 714
gaggggacaa tttttgttaa atcaaaaagc cc                                    32

<210> SEQ ID NO 715
<211> LENGTH: 30
<212> TYPE: DNA
<213> ORGANISM: Artificial
<220> FEATURE:
<223> OTHER INFORMATION: Synthetic Polynucleotide

<400> SEQUENCE: 715
tgggcgcaat aggaacgcca tcagtcaatc                                       30

<210> SEQ ID NO 716
<211> LENGTH: 30
<212> TYPE: DNA
<213> ORGANISM: Artificial
<220> FEATURE:
<223> OTHER INFORMATION: Synthetic Polynucleotide

<400> SEQUENCE: 716
aaaacataaa catcaagaaa acagatgaat                                       30

<210> SEQ ID NO 717
<211> LENGTH: 32
<212> TYPE: DNA
<213> ORGANISM: Artificial
<220> FEATURE:
<223> OTHER INFORMATION: Synthetic Polynucleotide

<400> SEQUENCE: 717
gcgatcggtt gtaaaacgac ggccgggtgc ct                                    32

<210> SEQ ID NO 718
<211> LENGTH: 32
<212> TYPE: DNA
<213> ORGANISM: Artificial
<220> FEATURE:
<223> OTHER INFORMATION: Synthetic Polynucleotide

<400> SEQUENCE: 718
tcacgacgtg cgggcctctt cgctgcggat tg                                    32

<210> SEQ ID NO 719
<211> LENGTH: 32
<212> TYPE: DNA
<213> ORGANISM: Artificial
<220> FEATURE:
<223> OTHER INFORMATION: Synthetic Polynucleotide

<400> SEQUENCE: 719
```

```
attaagttga aaggggatg tgctcaatat at                              32

<210> SEQ ID NO 720
<211> LENGTH: 30
<212> TYPE: DNA
<213> ORGANISM: Artificial
<220> FEATURE:
<223> OTHER INFORMATION: Synthetic Polynucleotide

<400> SEQUENCE: 720
ttttaatgat aaccttgctt ctgattttag                                30

<210> SEQ ID NO 721
<211> LENGTH: 32
<212> TYPE: DNA
<213> ORGANISM: Artificial
<220> FEATURE:
<223> OTHER INFORMATION: Synthetic Polynucleotide

<400> SEQUENCE: 721
ttacatttat taattttccc ttaggacaaa ga                             32

<210> SEQ ID NO 722
<211> LENGTH: 32
<212> TYPE: DNA
<213> ORGANISM: Artificial
<220> FEATURE:
<223> OTHER INFORMATION: Synthetic Polynucleotide

<400> SEQUENCE: 722
gatgaaacag cgatagctta gatttatgta aa                             32

<210> SEQ ID NO 723
<211> LENGTH: 32
<212> TYPE: DNA
<213> ORGANISM: Artificial
<220> FEATURE:
<223> OTHER INFORMATION: Synthetic Polynucleotide

<400> SEQUENCE: 723
tccccgggcc ggaaaccagg caaagccagt tt                             32

<210> SEQ ID NO 724
<211> LENGTH: 30
<212> TYPE: DNA
<213> ORGANISM: Artificial
<220> FEATURE:
<223> OTHER INFORMATION: Synthetic Polynucleotide

<400> SEQUENCE: 724
agcttgcaag gctgcgcaac tgtgtgtaga                                30

<210> SEQ ID NO 725
<211> LENGTH: 30
<212> TYPE: DNA
<213> ORGANISM: Artificial
<220> FEATURE:
<223> OTHER INFORMATION: Synthetic Polynucleotide

<400> SEQUENCE: 725
atacagtaga tgatggcaat tcagacttta                                30

<210> SEQ ID NO 726
<211> LENGTH: 32
<212> TYPE: DNA
```

```
<213> ORGANISM: Artificial
<220> FEATURE:
<223> OTHER INFORMATION: Synthetic Polynucleotide

<400> SEQUENCE: 726
aatgagtggg agaggcggtt tgcgaatccc tt                                32

<210> SEQ ID NO 727
<211> LENGTH: 32
<212> TYPE: DNA
<213> ORGANISM: Artificial
<220> FEATURE:
<223> OTHER INFORMATION: Synthetic Polynucleotide

<400> SEQUENCE: 727
cggaacgaac cctcagcagc gaaaccggaa ta                                32

<210> SEQ ID NO 728
<211> LENGTH: 32
<212> TYPE: DNA
<213> ORGANISM: Artificial
<220> FEATURE:
<223> OTHER INFORMATION: Synthetic Polynucleotide

<400> SEQUENCE: 728
acgcgcggag ctaactcaca ttaatttccc ag                                32

<210> SEQ ID NO 729
<211> LENGTH: 32
<212> TYPE: DNA
<213> ORGANISM: Artificial
<220> FEATURE:
<223> OTHER INFORMATION: Synthetic Polynucleotide

<400> SEQUENCE: 729
tgtcgtgctg cccgctttcc agtcatcaaa at                                32

<210> SEQ ID NO 730
<211> LENGTH: 30
<212> TYPE: DNA
<213> ORGANISM: Artificial
<220> FEATURE:
<223> OTHER INFORMATION: Synthetic Polynucleotide

<400> SEQUENCE: 730
aatggaagcg taaaacagaa atattacctt                                   30

<210> SEQ ID NO 731
<211> LENGTH: 32
<212> TYPE: DNA
<213> ORGANISM: Artificial
<220> FEATURE:
<223> OTHER INFORMATION: Synthetic Polynucleotide

<400> SEQUENCE: 731
aatcctgatt tcaggtttaa cgtcaaaatt aa                                32

<210> SEQ ID NO 732
<211> LENGTH: 32
<212> TYPE: DNA
<213> ORGANISM: Artificial
<220> FEATURE:
<223> OTHER INFORMATION: Synthetic Polynucleotide

<400> SEQUENCE: 732
tgattatcaa cagtaccttt tacaaagaag at                                32
```

<210> SEQ ID NO 733
<211> LENGTH: 32
<212> TYPE: DNA
<213> ORGANISM: Artificial
<220> FEATURE:
<223> OTHER INFORMATION: Synthetic Polynucleotide

<400> SEQUENCE: 733
cgggcaacac aattccacac aacactagag ga                                    32

<210> SEQ ID NO 734
<211> LENGTH: 30
<212> TYPE: DNA
<213> ORGANISM: Artificial
<220> FEATURE:
<223> OTHER INFORMATION: Synthetic Polynucleotide

<400> SEQUENCE: 734
cgccagggaa agtgtaaagc ctgagtgcca                                       30

<210> SEQ ID NO 735
<211> LENGTH: 32
<212> TYPE: DNA
<213> ORGANISM: Artificial
<220> FEATURE:
<223> OTHER INFORMATION: Synthetic Polynucleotide

<400> SEQUENCE: 735
gcgaaaaaaa agaatagccc gagaatcggc ca                                    32

<210> SEQ ID NO 736
<211> LENGTH: 32
<212> TYPE: DNA
<213> ORGANISM: Artificial
<220> FEATURE:
<223> OTHER INFORMATION: Synthetic Polynucleotide

<400> SEQUENCE: 736
tattaaagtt ccagtttgga acaaagcact aa                                    32

<210> SEQ ID NO 737
<211> LENGTH: 30
<212> TYPE: DNA
<213> ORGANISM: Artificial
<220> FEATURE:
<223> OTHER INFORMATION: Synthetic Polynucleotide

<400> SEQUENCE: 737
aaggttatag attagagccg tcatctgaat                                       30

<210> SEQ ID NO 738
<211> LENGTH: 32
<212> TYPE: DNA
<213> ORGANISM: Artificial
<220> FEATURE:
<223> OTHER INFORMATION: Synthetic Polynucleotide

<400> SEQUENCE: 738
ttggcaaaag gatttagaag tattatcaat at                                    32

<210> SEQ ID NO 739
<211> LENGTH: 32
<212> TYPE: DNA
<213> ORGANISM: Artificial
<220> FEATURE:

<223> OTHER INFORMATION: Synthetic Polynucleotide

<400> SEQUENCE: 739
aatatcaatt cgacaactcg tattcatatt cc                               32

<210> SEQ ID NO 740
<211> LENGTH: 32
<212> TYPE: DNA
<213> ORGANISM: Artificial
<220> FEATURE:
<223> OTHER INFORMATION: Synthetic Polynucleotide

<400> SEQUENCE: 740
ggggtcgacc ccagcaggcg aaaacagtga ga                               32

<210> SEQ ID NO 741
<211> LENGTH: 30
<212> TYPE: DNA
<213> ORGANISM: Artificial
<220> FEATURE:
<223> OTHER INFORMATION: Synthetic Polynucleotide

<400> SEQUENCE: 741
ctacgtgatt ccgaaatcgg caatattggg                                  30

<210> SEQ ID NO 742
<211> LENGTH: 30
<212> TYPE: DNA
<213> ORGANISM: Artificial
<220> FEATURE:
<223> OTHER INFORMATION: Synthetic Polynucleotide

<400> SEQUENCE: 742
gtgtactcgc cagcattgac agcgtttgcc                                  30

<210> SEQ ID NO 743
<211> LENGTH: 32
<212> TYPE: DNA
<213> ORGANISM: Artificial
<220> FEATURE:
<223> OTHER INFORMATION: Synthetic Polynucleotide

<400> SEQUENCE: 743
ttgtgtcgtg aacggtgtac agactaattt ca                               32

<210> SEQ ID NO 744
<211> LENGTH: 32
<212> TYPE: DNA
<213> ORGANISM: Artificial
<220> FEATURE:
<223> OTHER INFORMATION: Synthetic Polynucleotide

<400> SEQUENCE: 744
aggacagaaa atccgcgacc tgctcagagg ct                               32

<210> SEQ ID NO 745
<211> LENGTH: 32
<212> TYPE: DNA
<213> ORGANISM: Artificial
<220> FEATURE:
<223> OTHER INFORMATION: Synthetic Polynucleotide

<400> SEQUENCE: 745
ataagggagg aacgaggcgc agaccagaat gg                               32

```
<210> SEQ ID NO 746
<211> LENGTH: 30
<212> TYPE: DNA
<213> ORGANISM: Artificial
<220> FEATURE:
<223> OTHER INFORMATION: Synthetic Polynucleotide

<400> SEQUENCE: 746
aaacaaatgt ctctgaattt accgtgccgt                                          30

<210> SEQ ID NO 747
<211> LENGTH: 32
<212> TYPE: DNA
<213> ORGANISM: Artificial
<220> FEATURE:
<223> OTHER INFORMATION: Synthetic Polynucleotide

<400> SEQUENCE: 747
ggcaggtcta catggctttt gatgtagcgg gg                                       32

<210> SEQ ID NO 748
<211> LENGTH: 32
<212> TYPE: DNA
<213> ORGANISM: Artificial
<220> FEATURE:
<223> OTHER INFORMATION: Synthetic Polynucleotide

<400> SEQUENCE: 748
agagccgcgg taataagttt taacggctga ga                                       32

<210> SEQ ID NO 749
<211> LENGTH: 32
<212> TYPE: DNA
<213> ORGANISM: Artificial
<220> FEATURE:
<223> OTHER INFORMATION: Synthetic Polynucleotide

<400> SEQUENCE: 749
tgacaagaat tataccaagc gcgaaatgcc ac                                       32

<210> SEQ ID NO 750
<211> LENGTH: 30
<212> TYPE: DNA
<213> ORGANISM: Artificial
<220> FEATURE:
<223> OTHER INFORMATION: Synthetic Polynucleotide

<400> SEQUENCE: 750
ataggctgga tttgtatcat cgcaggaagt                                          30

<210> SEQ ID NO 751
<211> LENGTH: 30
<212> TYPE: DNA
<213> ORGANISM: Artificial
<220> FEATURE:
<223> OTHER INFORMATION: Synthetic Polynucleotide

<400> SEQUENCE: 751
atctttttac cattagcaag gccaaagaca                                          30

<210> SEQ ID NO 752
<211> LENGTH: 32
<212> TYPE: DNA
<213> ORGANISM: Artificial
<220> FEATURE:
<223> OTHER INFORMATION: Synthetic Polynucleotide
```

<400> SEQUENCE: 752
actttaatga acaacattat tacaaaaaga ag                                    32

<210> SEQ ID NO 753
<211> LENGTH: 32
<212> TYPE: DNA
<213> ORGANISM: Artificial
<220> FEATURE:
<223> OTHER INFORMATION: Synthetic Polynucleotide

<400> SEQUENCE: 753
aactaacgca ttgtgaatta ccttttttgaa ag                                   32

<210> SEQ ID NO 754
<211> LENGTH: 32
<212> TYPE: DNA
<213> ORGANISM: Artificial
<220> FEATURE:
<223> OTHER INFORMATION: Synthetic Polynucleotide

<400> SEQUENCE: 754
gttgggaact ggctcattat accatgcctt ta                                    32

<210> SEQ ID NO 755
<211> LENGTH: 30
<212> TYPE: DNA
<213> ORGANISM: Artificial
<220> FEATURE:
<223> OTHER INFORMATION: Synthetic Polynucleotide

<400> SEQUENCE: 755
aatcagtact gtagcgcgtt ttctattcac                                       30

<210> SEQ ID NO 756
<211> LENGTH: 32
<212> TYPE: DNA
<213> ORGANISM: Artificial
<220> FEATURE:
<223> OTHER INFORMATION: Synthetic Polynucleotide

<400> SEQUENCE: 756
tcaccaatat agcccccttta ttaggaggtt ga                                   32

<210> SEQ ID NO 757
<211> LENGTH: 32
<212> TYPE: DNA
<213> ORGANISM: Artificial
<220> FEATURE:
<223> OTHER INFORMATION: Synthetic Polynucleotide

<400> SEQUENCE: 757
agcaccatca taatcaaaat caccccacca cc                                    32

<210> SEQ ID NO 758
<211> LENGTH: 32
<212> TYPE: DNA
<213> ORGANISM: Artificial
<220> FEATURE:
<223> OTHER INFORMATION: Synthetic Polynucleotide

<400> SEQUENCE: 758
ttcaactact gacgagaaac accaagtaat ct                                    32

<210> SEQ ID NO 759
<211> LENGTH: 30

<212> TYPE: DNA
<213> ORGANISM: Artificial
<220> FEATURE:
<223> OTHER INFORMATION: Synthetic Polynucleotide

<400> SEQUENCE: 759
agattcatgg gcttgagatg gttcaggcgc                                    30

<210> SEQ ID NO 760
<211> LENGTH: 38
<212> TYPE: DNA
<213> ORGANISM: Artificial
<220> FEATURE:
<223> OTHER INFORMATION: Synthetic Polynucleotide

<400> SEQUENCE: 760
aatgtttaga ctggattcat tgaatccccc tttgataa                           38

<210> SEQ ID NO 761
<211> LENGTH: 40
<212> TYPE: DNA
<213> ORGANISM: Artificial
<220> FEATURE:
<223> OTHER INFORMATION: Synthetic Polynucleotide

<400> SEQUENCE: 761
atcaatagaa aattcacgta gaaaatacat acaacccaca                         40

<210> SEQ ID NO 762
<211> LENGTH: 30
<212> TYPE: DNA
<213> ORGANISM: Artificial
<220> FEATURE:
<223> OTHER INFORMATION: Synthetic Polynucleotide

<400> SEQUENCE: 762
aaagggcaag actccttatt acagagcaag                                    30

<210> SEQ ID NO 763
<211> LENGTH: 40
<212> TYPE: DNA
<213> ORGANISM: Artificial
<220> FEATURE:
<223> OTHER INFORMATION: Synthetic Polynucleotide

<400> SEQUENCE: 763
agggagggaa ggtaaaataa cggaataccc aatcttaccg                         40

<210> SEQ ID NO 764
<211> LENGTH: 40
<212> TYPE: DNA
<213> ORGANISM: Artificial
<220> FEATURE:
<223> OTHER INFORMATION: Synthetic Polynucleotide

<400> SEQUENCE: 764
gataaaaacc aaaataaatc aggtctttac ccagcgaacc                         40

<210> SEQ ID NO 765
<211> LENGTH: 32
<212> TYPE: DNA
<213> ORGANISM: Artificial
<220> FEATURE:
<223> OTHER INFORMATION: Synthetic Polynucleotide

<400> SEQUENCE: 765
ttttgccagt tcagaaaacg agaagtcagg at            32

<210> SEQ ID NO 766
<211> LENGTH: 32
<212> TYPE: DNA
<213> ORGANISM: Artificial
<220> FEATURE:
<223> OTHER INFORMATION: Synthetic Polynucleotide

<400> SEQUENCE: 766
tttaaacaga gggggtaata gtaaataaaa cg            32

<210> SEQ ID NO 767
<211> LENGTH: 32
<212> TYPE: DNA
<213> ORGANISM: Artificial
<220> FEATURE:
<223> OTHER INFORMATION: Synthetic Polynucleotide

<400> SEQUENCE: 767
cataaatata gcgtccaata ctgcagacac ca            32

<210> SEQ ID NO 768
<211> LENGTH: 30
<212> TYPE: DNA
<213> ORGANISM: Artificial
<220> FEATURE:
<223> OTHER INFORMATION: Synthetic Polynucleotide

<400> SEQUENCE: 768
tggcaacagt ttattttgtc acagcaccgt            30

<210> SEQ ID NO 769
<211> LENGTH: 32
<212> TYPE: DNA
<213> ORGANISM: Artificial
<220> FEATURE:
<223> OTHER INFORMATION: Synthetic Polynucleotide

<400> SEQUENCE: 769
ttagcaaata tggtttacca gcgccggaaa cg            32

<210> SEQ ID NO 770
<211> LENGTH: 32
<212> TYPE: DNA
<213> ORGANISM: Artificial
<220> FEATURE:
<223> OTHER INFORMATION: Synthetic Polynucleotide

<400> SEQUENCE: 770
gcatgattga cattcaaccg attgtcacca gt            32

<210> SEQ ID NO 771
<211> LENGTH: 32
<212> TYPE: DNA
<213> ORGANISM: Artificial
<220> FEATURE:
<223> OTHER INFORMATION: Synthetic Polynucleotide

<400> SEQUENCE: 771
atagtcagtc gtttaccaga cgacatacca ca            32

<210> SEQ ID NO 772
<211> LENGTH: 30
<212> TYPE: DNA
<213> ORGANISM: Artificial

<220> FEATURE:
<223> OTHER INFORMATION: Synthetic Polynucleotide

<400> SEQUENCE: 772
aaatcaaagc gagaggcttt tgcggtagaa          30

<210> SEQ ID NO 773
<211> LENGTH: 30
<212> TYPE: DNA
<213> ORGANISM: Artificial
<220> FEATURE:
<223> OTHER INFORMATION: Synthetic Polynucleotide

<400> SEQUENCE: 773
gaggtcaata taatgctgta gcacaggcaa          30

<210> SEQ ID NO 774
<211> LENGTH: 32
<212> TYPE: DNA
<213> ORGANISM: Artificial
<220> FEATURE:
<223> OTHER INFORMATION: Synthetic Polynucleotide

<400> SEQUENCE: 774
agaattgaga agcgcattag acggatcaag at          32

<210> SEQ ID NO 775
<211> LENGTH: 30
<212> TYPE: DNA
<213> ORGANISM: Artificial
<220> FEATURE:
<223> OTHER INFORMATION: Synthetic Polynucleotide

<400> SEQUENCE: 775
aaacaatgcc tttacagaga gacaattta          30

<210> SEQ ID NO 776
<211> LENGTH: 32
<212> TYPE: DNA
<213> ORGANISM: Artificial
<220> FEATURE:
<223> OTHER INFORMATION: Synthetic Polynucleotide

<400> SEQUENCE: 776
aagccctttt ttttgtttaa cgtcgagcgt ct          32

<210> SEQ ID NO 777
<211> LENGTH: 32
<212> TYPE: DNA
<213> ORGANISM: Artificial
<220> FEATURE:
<223> OTHER INFORMATION: Synthetic Polynucleotide

<400> SEQUENCE: 777
agaccggaat tccatataac agttcgcgag ct          32

<210> SEQ ID NO 778
<211> LENGTH: 32
<212> TYPE: DNA
<213> ORGANISM: Artificial
<220> FEATURE:
<223> OTHER INFORMATION: Synthetic Polynucleotide

<400> SEQUENCE: 778
tagagagtat gcaactaaag tacgaatagt ag          32

<210> SEQ ID NO 779
<211> LENGTH: 40
<212> TYPE: DNA
<213> ORGANISM: Artificial
<220> FEATURE:
<223> OTHER INFORMATION: Synthetic Polynucleotide

<400> SEQUENCE: 779
tcatcaagga acgagtagta aattcagttg agatttagga           40

<210> SEQ ID NO 780
<211> LENGTH: 40
<212> TYPE: DNA
<213> ORGANISM: Artificial
<220> FEATURE:
<223> OTHER INFORMATION: Synthetic Polynucleotide

<400> SEQUENCE: 780
caccagaagg aaccagagcc accaattaga gccagcaaaa           40

<210> SEQ ID NO 781
<211> LENGTH: 40
<212> TYPE: DNA
<213> ORGANISM: Artificial
<220> FEATURE:
<223> OTHER INFORMATION: Synthetic Polynucleotide

<400> SEQUENCE: 781
ggccttgaat cggcattttc ggtcgaaacc atcgatagca           40

<210> SEQ ID NO 782
<211> LENGTH: 38
<212> TYPE: DNA
<213> ORGANISM: Artificial
<220> FEATURE:
<223> OTHER INFORMATION: Synthetic Polynucleotide

<400> SEQUENCE: 782
tgaccaacat gcgattttaa gaagaaaat ctacgtta              38

<210> SEQ ID NO 783
<211> LENGTH: 40
<212> TYPE: DNA
<213> ORGANISM: Artificial
<220> FEATURE:
<223> OTHER INFORMATION: Synthetic Polynucleotide

<400> SEQUENCE: 783
ggtcgactta cgagccggaa gcattggttt ttcttttcac           40

<210> SEQ ID NO 784
<211> LENGTH: 40
<212> TYPE: DNA
<213> ORGANISM: Artificial
<220> FEATURE:
<223> OTHER INFORMATION: Synthetic Polynucleotide

<400> SEQUENCE: 784
ctgagcaatc gggagaaaca ataaggagcg gaattatcat           40

<210> SEQ ID NO 785
<211> LENGTH: 40
<212> TYPE: DNA
<213> ORGANISM: Artificial
<220> FEATURE:
<223> OTHER INFORMATION: Synthetic Polynucleotide -continued

<400> SEQUENCE: 785
catttgaaaa gaaattgcgt agatttgttt ggattatact                          40

<210> SEQ ID NO 786
<211> LENGTH: 38
<212> TYPE: DNA
<213> ORGANISM: Artificial
<220> FEATURE:
<223> OTHER INFORMATION: Synthetic Polynucleotide

<400> SEQUENCE: 786
gccagggttt gcgttgcgct caccagctgc attaatga                            38

<210> SEQ ID NO 787
<211> LENGTH: 43
<212> TYPE: DNA
<213> ORGANISM: Artificial
<220> FEATURE:
<223> OTHER INFORMATION: Synthetic Polynucleotide

<400> SEQUENCE: 787
acggctacaa aaggagcctt taatgtgaga atttatacat cta                      43

<210> SEQ ID NO 788
<211> LENGTH: 41
<212> TYPE: DNA
<213> ORGANISM: Artificial
<220> FEATURE:
<223> OTHER INFORMATION: Synthetic Polynucleotide

<400> SEQUENCE: 788
cagcgaaact tgctttcgag gtgttgctaa ttatacatct a                        41

<210> SEQ ID NO 789
<211> LENGTH: 43
<212> TYPE: DNA
<213> ORGANISM: Artificial
<220> FEATURE:
<223> OTHER INFORMATION: Synthetic Polynucleotide

<400> SEQUENCE: 789
aaggccgctg ataccgatag ttgcgacgtt agttatacat cta                      43

<210> SEQ ID NO 790
<211> LENGTH: 43
<212> TYPE: DNA
<213> ORGANISM: Artificial
<220> FEATURE:
<223> OTHER INFORMATION: Synthetic Polynucleotide

<400> SEQUENCE: 790
atattcggaa ccatcgccca cgcagagaag gattatacat cta                      43

<210> SEQ ID NO 791
<211> LENGTH: 41
<212> TYPE: DNA
<213> ORGANISM: Artificial
<220> FEATURE:
<223> OTHER INFORMATION: Synthetic Polynucleotide

<400> SEQUENCE: 791
tattaagaag cggggttttg ctcgtagcat ttatacatct a                        41

<210> SEQ ID NO 792

<211> LENGTH: 43
<212> TYPE: DNA
<213> ORGANISM: Artificial
<220> FEATURE:
<223> OTHER INFORMATION: Synthetic Polynucleotide

<400> SEQUENCE: 792
tttcggaagt gccgtcgaga gggtgagttt cgttatacat cta                        43

<210> SEQ ID NO 793
<211> LENGTH: 43
<212> TYPE: DNA
<213> ORGANISM: Artificial
<220> FEATURE:
<223> OTHER INFORMATION: Synthetic Polynucleotide

<400> SEQUENCE: 793
gcccgtatcc ggaataggtg tatcagccca atttatacat cta                        43

<210> SEQ ID NO 794
<211> LENGTH: 43
<212> TYPE: DNA
<213> ORGANISM: Artificial
<220> FEATURE:
<223> OTHER INFORMATION: Synthetic Polynucleotide

<400> SEQUENCE: 794
tacgttaaag taatcttgac aagaaccgaa ctttatacat cta                        43

<210> SEQ ID NO 795
<211> LENGTH: 43
<212> TYPE: DNA
<213> ORGANISM: Artificial
<220> FEATURE:
<223> OTHER INFORMATION: Synthetic Polynucleotide

<400> SEQUENCE: 795
gaaattattg cctttagcgt cagaccggaa ccttatacat cta                        43

<210> SEQ ID NO 796
<211> LENGTH: 43
<212> TYPE: DNA
<213> ORGANISM: Artificial
<220> FEATURE:
<223> OTHER INFORMATION: Synthetic Polynucleotide

<400> SEQUENCE: 796
ctgtagcttg actattatag tcagttcatt gattatacat cta                        43

<210> SEQ ID NO 797
<211> LENGTH: 43
<212> TYPE: DNA
<213> ORGANISM: Artificial
<220> FEATURE:
<223> OTHER INFORMATION: Synthetic Polynucleotide

<400> SEQUENCE: 797
gccagttaga gggtaattga gcgctttaag aattatacat cta                        43

<210> SEQ ID NO 798
<211> LENGTH: 43
<212> TYPE: DNA
<213> ORGANISM: Artificial
<220> FEATURE:
<223> OTHER INFORMATION: Synthetic Polynucleotide

<400> SEQUENCE: 798
aacaagaggg ataaaaattt ttagcataaa gcttatacat cta                         43

<210> SEQ ID NO 799
<211> LENGTH: 43
<212> TYPE: DNA
<213> ORGANISM: Artificial
<220> FEATURE:
<223> OTHER INFORMATION: Synthetic Polynucleotide

<400> SEQUENCE: 799
agtataaagt tcagctaatg cagatgtctt tcttatacat cta                         43

<210> SEQ ID NO 800
<211> LENGTH: 43
<212> TYPE: DNA
<213> ORGANISM: Artificial
<220> FEATURE:
<223> OTHER INFORMATION: Synthetic Polynucleotide

<400> SEQUENCE: 800
ccagggttgc cagtttgagg ggacccgtgg gattatacat cta                         43

<210> SEQ ID NO 801
<211> LENGTH: 43
<212> TYPE: DNA
<213> ORGANISM: Artificial
<220> FEATURE:
<223> OTHER INFORMATION: Synthetic Polynucleotide

<400> SEQUENCE: 801
cctgattgca atatatgtga gtgatcaata gtttatacat cta                         43

<210> SEQ ID NO 802
<211> LENGTH: 43
<212> TYPE: DNA
<213> ORGANISM: Artificial
<220> FEATURE:
<223> OTHER INFORMATION: Synthetic Polynucleotide

<400> SEQUENCE: 802
ctccaacgca gtgagacggg caaccagctg cattatacat cta                         43

<210> SEQ ID NO 803
<211> LENGTH: 41
<212> TYPE: DNA
<213> ORGANISM: Artificial
<220> FEATURE:
<223> OTHER INFORMATION: Synthetic Polynucleotide

<400> SEQUENCE: 803
tggaacaacc gcctggccct gaggcccgct ttatacatct a                           41

<210> SEQ ID NO 804
<211> LENGTH: 43
<212> TYPE: DNA
<213> ORGANISM: Artificial
<220> FEATURE:
<223> OTHER INFORMATION: Synthetic Polynucleotide

<400> SEQUENCE: 804
gcccgagagt ccacgctggt ttgcagctaa ctttatacat cta                         43

<210> SEQ ID NO 805
<211> LENGTH: 43
<212> TYPE: DNA

<213> ORGANISM: Artificial
<220> FEATURE:
<223> OTHER INFORMATION: Synthetic Polynucleotide

<400> SEQUENCE: 805
tcggcaaatc ctgtttgatg gtggaccctc aattatacat cta                43

<210> SEQ ID NO 806
<211> LENGTH: 41
<212> TYPE: DNA
<213> ORGANISM: Artificial
<220> FEATURE:
<223> OTHER INFORMATION: Synthetic Polynucleotide

<400> SEQUENCE: 806
accttgcttg gtcagttggc aaagagcgga ttatacatct a                  41

<210> SEQ ID NO 807
<211> LENGTH: 43
<212> TYPE: DNA
<213> ORGANISM: Artificial
<220> FEATURE:
<223> OTHER INFORMATION: Synthetic Polynucleotide

<400> SEQUENCE: 807
agccagcaat tgaggaaggt tatcatcatt ttttatacat cta                43

<210> SEQ ID NO 808
<211> LENGTH: 43
<212> TYPE: DNA
<213> ORGANISM: Artificial
<220> FEATURE:
<223> OTHER INFORMATION: Synthetic Polynucleotide

<400> SEQUENCE: 808
ttaacaccag cactaacaac taatcgttat tattatacat cta                43

<210> SEQ ID NO 809
<211> LENGTH: 43
<212> TYPE: DNA
<213> ORGANISM: Artificial
<220> FEATURE:
<223> OTHER INFORMATION: Synthetic Polynucleotide

<400> SEQUENCE: 809
cggattgcag agcttaattg ctgaaacgag tattatctac ata                43

<210> SEQ ID NO 810
<211> LENGTH: 43
<212> TYPE: DNA
<213> ORGANISM: Artificial
<220> FEATURE:
<223> OTHER INFORMATION: Synthetic Polynucleotide

<400> SEQUENCE: 810
cgaaagactt tgataagagg tcatatttcg cattatctac ata                43

<210> SEQ ID NO 811
<211> LENGTH: 41
<212> TYPE: DNA
<213> ORGANISM: Artificial
<220> FEATURE:
<223> OTHER INFORMATION: Synthetic Polynucleotide

<400> SEQUENCE: 811
gcttcaatca ggattagaga gttatttttca ttatctacat a                 41

<210> SEQ ID NO 812
<211> LENGTH: 43
<212> TYPE: DNA
<213> ORGANISM: Artificial
<220> FEATURE:
<223> OTHER INFORMATION: Synthetic Polynucleotide

<400> SEQUENCE: 812
ttagacggcc aaataagaaa cgatagaagg ctttatctac ata          43

<210> SEQ ID NO 813
<211> LENGTH: 41
<212> TYPE: DNA
<213> ORGANISM: Artificial
<220> FEATURE:
<223> OTHER INFORMATION: Synthetic Polynucleotide

<400> SEQUENCE: 813
aaagtcacaa aataaacagc cagcgtttta ttatctacat a            41

<210> SEQ ID NO 814
<211> LENGTH: 43
<212> TYPE: DNA
<213> ORGANISM: Artificial
<220> FEATURE:
<223> OTHER INFORMATION: Synthetic Polynucleotide

<400> SEQUENCE: 814
gagagataga gcgtctttcc agaggttttg aattatctac ata          43

<210> SEQ ID NO 815
<211> LENGTH: 43
<212> TYPE: DNA
<213> ORGANISM: Artificial
<220> FEATURE:
<223> OTHER INFORMATION: Synthetic Polynucleotide

<400> SEQUENCE: 815
gatttagtca ataaagcctc agagaaccct cattatctac ata          43

<210> SEQ ID NO 816
<211> LENGTH: 43
<212> TYPE: DNA
<213> ORGANISM: Artificial
<220> FEATURE:
<223> OTHER INFORMATION: Synthetic Polynucleotide

<400> SEQUENCE: 816
aatggtcaac aggcaaggca aagagtaatg tgttatctac ata          43

<210> SEQ ID NO 817
<211> LENGTH: 41
<212> TYPE: DNA
<213> ORGANISM: Artificial
<220> FEATURE:
<223> OTHER INFORMATION: Synthetic Polynucleotide

<400> SEQUENCE: 817
tttggggata gtagtagcat taaaaggccg ttatctacat a            41

<210> SEQ ID NO 818
<211> LENGTH: 43
<212> TYPE: DNA
<213> ORGANISM: Artificial
<220> FEATURE:

-continued

<223> OTHER INFORMATION: Synthetic Polynucleotide

<400> SEQUENCE: 818
ccaatagctc atcgtaggaa tcatggcatc aattatctac ata                43

<210> SEQ ID NO 819
<211> LENGTH: 43
<212> TYPE: DNA
<213> ORGANISM: Artificial
<220> FEATURE:
<223> OTHER INFORMATION: Synthetic Polynucleotide

<400> SEQUENCE: 819
tatccggtct catcgagaac aagcgacaaa agttatctac ata                43

<210> SEQ ID NO 820
<211> LENGTH: 41
<212> TYPE: DNA
<213> ORGANISM: Artificial
<220> FEATURE:
<223> OTHER INFORMATION: Synthetic Polynucleotide

<400> SEQUENCE: 820
gcgaacctcc aagaacgggt atgacaataa ttatctacat a                  41

<210> SEQ ID NO 821
<211> LENGTH: 43
<212> TYPE: DNA
<213> ORGANISM: Artificial
<220> FEATURE:
<223> OTHER INFORMATION: Synthetic Polynucleotide

<400> SEQUENCE: 821
gccttaaacc aatcaataat cggcacgcgc ctttatctac ata                43

<210> SEQ ID NO 822
<211> LENGTH: 43
<212> TYPE: DNA
<213> ORGANISM: Artificial
<220> FEATURE:
<223> OTHER INFORMATION: Synthetic Polynucleotide

<400> SEQUENCE: 822
taaatcggga ttcccaattc tgcgatataa tgttatctac ata                43

<210> SEQ ID NO 823
<211> LENGTH: 41
<212> TYPE: DNA
<213> ORGANISM: Artificial
<220> FEATURE:
<223> OTHER INFORMATION: Synthetic Polynucleotide

<400> SEQUENCE: 823
aaattaagtt gaccattaga tacttttgcg ttatctacat a                  41

<210> SEQ ID NO 824
<211> LENGTH: 43
<212> TYPE: DNA
<213> ORGANISM: Artificial
<220> FEATURE:
<223> OTHER INFORMATION: Synthetic Polynucleotide

<400> SEQUENCE: 824
taaatcatat aacctgttta gctaacccttt aattatctac ata               43

<210> SEQ ID NO 825
<211> LENGTH: 41
<212> TYPE: DNA
<213> ORGANISM: Artificial
<220> FEATURE:
<223> OTHER INFORMATION: Synthetic Polynucleotide

<400> SEQUENCE: 825
ttttatttaa gcaaatcaga tattttttgt ttatctacat a     41

<210> SEQ ID NO 826
<211> LENGTH: 43
<212> TYPE: DNA
<213> ORGANISM: Artificial
<220> FEATURE:
<223> OTHER INFORMATION: Synthetic Polynucleotide

<400> SEQUENCE: 826
gtaccgcaat tctaagaacg cgagtattat ttttatctac ata     43

<210> SEQ ID NO 827
<211> LENGTH: 43
<212> TYPE: DNA
<213> ORGANISM: Artificial
<220> FEATURE:
<223> OTHER INFORMATION: Synthetic Polynucleotide

<400> SEQUENCE: 827
cttatcattc ccgacttgcg ggagcctaat ttttatctac ata     43

<210> SEQ ID NO 828
<211> LENGTH: 43
<212> TYPE: DNA
<213> ORGANISM: Artificial
<220> FEATURE:
<223> OTHER INFORMATION: Synthetic Polynucleotide

<400> SEQUENCE: 828
gtaataagtt aggcagaggc atttatgata ttttatctac ata     43

<210> SEQ ID NO 829
<211> LENGTH: 41
<212> TYPE: DNA
<213> ORGANISM: Artificial
<220> FEATURE:
<223> OTHER INFORMATION: Synthetic Polynucleotide

<400> SEQUENCE: 829
gctatcagaa atgcaatgcc tgaattagca ttatctacat a     41

<210> SEQ ID NO 830
<211> LENGTH: 43
<212> TYPE: DNA
<213> ORGANISM: Artificial
<220> FEATURE:
<223> OTHER INFORMATION: Synthetic Polynucleotide

<400> SEQUENCE: 830
gagggtagga ttcaaaaggg tgagacatcc aattatctac ata     43

<210> SEQ ID NO 831
<211> LENGTH: 41
<212> TYPE: DNA
<213> ORGANISM: Artificial
<220> FEATURE:
<223> OTHER INFORMATION: Synthetic Polynucleotide

```
<400> SEQUENCE: 831
catgtaatag aatataaagt accaagccgt ttatctacat a                    41

<210> SEQ ID NO 832
<211> LENGTH: 43
<212> TYPE: DNA
<213> ORGANISM: Artificial
<220> FEATURE:
<223> OTHER INFORMATION: Synthetic Polynucleotide

<400> SEQUENCE: 832
aattgagaat tctgtccaga cgactaaacc aattatctac ata                  43

<210> SEQ ID NO 833
<211> LENGTH: 43
<212> TYPE: DNA
<213> ORGANISM: Artificial
<220> FEATURE:
<223> OTHER INFORMATION: Synthetic Polynucleotide

<400> SEQUENCE: 833
tccacagaca gccctcatag ttagcgtaac gatttcttca tta                  43

<210> SEQ ID NO 834
<211> LENGTH: 43
<212> TYPE: DNA
<213> ORGANISM: Artificial
<220> FEATURE:
<223> OTHER INFORMATION: Synthetic Polynucleotide

<400> SEQUENCE: 834
tcaccagtac aaactacaac gcctagtacc agtttcttca tta                  43

<210> SEQ ID NO 835
<211> LENGTH: 42
<212> TYPE: DNA
<213> ORGANISM: Artificial
<220> FEATURE:
<223> OTHER INFORMATION: Synthetic Polynucleotide

<400> SEQUENCE: 835
aggaacccat gtaccgtaac acttgatata atttcttcat ta                   42

<210> SEQ ID NO 836
<211> LENGTH: 43
<212> TYPE: DNA
<213> ORGANISM: Artificial
<220> FEATURE:
<223> OTHER INFORMATION: Synthetic Polynucleotide

<400> SEQUENCE: 836
ccaccctcat tttcagggat agcaaccgta cttttcttca tta                  43

<210> SEQ ID NO 837
<211> LENGTH: 41
<212> TYPE: DNA
<213> ORGANISM: Artificial
<220> FEATURE:
<223> OTHER INFORMATION: Synthetic Polynucleotide

<400> SEQUENCE: 837
aggctccaga ggctttgagg acacgggtaa tttcttcatt a                    41

<210> SEQ ID NO 838
<211> LENGTH: 43
```

```
<212> TYPE: DNA
<213> ORGANISM: Artificial
<220> FEATURE:
<223> OTHER INFORMATION: Synthetic Polynucleotide

<400> SEQUENCE: 838
tcatcgccaa caaagtacaa cggacgccag catttcttca tta                    43

<210> SEQ ID NO 839
<211> LENGTH: 41
<212> TYPE: DNA
<213> ORGANISM: Artificial
<220> FEATURE:
<223> OTHER INFORMATION: Synthetic Polynucleotide

<400> SEQUENCE: 839
aaatcacctt ccagtaagcg tcagtaataa tttcttcatt a                      41

<210> SEQ ID NO 840
<211> LENGTH: 41
<212> TYPE: DNA
<213> ORGANISM: Artificial
<220> FEATURE:
<223> OTHER INFORMATION: Synthetic Polynucleotide

<400> SEQUENCE: 840
catcaagtaa aacgaactaa cgagttgaga tttcttcatt a                      41

<210> SEQ ID NO 841
<211> LENGTH: 43
<212> TYPE: DNA
<213> ORGANISM: Artificial
<220> FEATURE:
<223> OTHER INFORMATION: Synthetic Polynucleotide

<400> SEQUENCE: 841
cttttgcaga taaaaaccaa aataaagact cctttcttca tta                    43

<210> SEQ ID NO 842
<211> LENGTH: 41
<212> TYPE: DNA
<213> ORGANISM: Artificial
<220> FEATURE:
<223> OTHER INFORMATION: Synthetic Polynucleotide

<400> SEQUENCE: 842
aatagctatc aatagaaaat tcaacattca tttcttcatt a                      41

<210> SEQ ID NO 843
<211> LENGTH: 41
<212> TYPE: DNA
<213> ORGANISM: Artificial
<220> FEATURE:
<223> OTHER INFORMATION: Synthetic Polynucleotide

<400> SEQUENCE: 843
tttaccccaa catgttttaa atttccatat tttcttcatt a                      41

<210> SEQ ID NO 844
<211> LENGTH: 43
<212> TYPE: DNA
<213> ORGANISM: Artificial
<220> FEATURE:
<223> OTHER INFORMATION: Synthetic Polynucleotide

<400> SEQUENCE: 844
```
ttctactacg cgagctgaaa aggttaccgc gctttcttca tta          43

<210> SEQ ID NO 845
<211> LENGTH: 41
<212> TYPE: DNA
<213> ORGANISM: Artificial
<220> FEATURE:
<223> OTHER INFORMATION: Synthetic Polynucleotide

<400> SEQUENCE: 845
tgtagaaatc aagattagtt gctcttacca tttcttcatt a          41

<210> SEQ ID NO 846
<211> LENGTH: 41
<212> TYPE: DNA
<213> ORGANISM: Artificial
<220> FEATURE:
<223> OTHER INFORMATION: Synthetic Polynucleotide

<400> SEQUENCE: 846
aacgcaaaat cgatgaacgg taccggttga tttcttcatt a          41

<210> SEQ ID NO 847
<211> LENGTH: 43
<212> TYPE: DNA
<213> ORGANISM: Artificial
<220> FEATURE:
<223> OTHER INFORMATION: Synthetic Polynucleotide

<400> SEQUENCE: 847
gccatcaagc tcatttttta accacaaatc catttcttca tta          43

<210> SEQ ID NO 848
<211> LENGTH: 41
<212> TYPE: DNA
<213> ORGANISM: Artificial
<220> FEATURE:
<223> OTHER INFORMATION: Synthetic Polynucleotide

<400> SEQUENCE: 848
cttagattta aggcgttaaa taaagcctgt tttcttcatt a          41

<210> SEQ ID NO 849
<211> LENGTH: 41
<212> TYPE: DNA
<213> ORGANISM: Artificial
<220> FEATURE:
<223> OTHER INFORMATION: Synthetic Polynucleotide

<400> SEQUENCE: 849
tgcatctttc ccagtcacga cggcctgcag tttcttcatt a          41

<210> SEQ ID NO 850
<211> LENGTH: 43
<212> TYPE: DNA
<213> ORGANISM: Artificial
<220> FEATURE:
<223> OTHER INFORMATION: Synthetic Polynucleotide

<400> SEQUENCE: 850
aagcctggta cgagccggaa gcatagatga tgtttcttca tta          43

<210> SEQ ID NO 851
<211> LENGTH: 41
<212> TYPE: DNA
<213> ORGANISM: Artificial

```
<220> FEATURE:
<223> OTHER INFORMATION: Synthetic Polynucleotide

<400> SEQUENCE: 851
ctcgtattag aaattgcgta gatacagtac tttcttcatt a                    41

<210> SEQ ID NO 852
<211> LENGTH: 41
<212> TYPE: DNA
<213> ORGANISM: Artificial
<220> FEATURE:
<223> OTHER INFORMATION: Synthetic Polynucleotide

<400> SEQUENCE: 852
ttttcactca aagggcgaaa aaccatcacc tttcttcatt a                    41

<210> SEQ ID NO 853
<211> LENGTH: 51
<212> TYPE: DNA
<213> ORGANISM: Artificial
<220> FEATURE:
<223> OTHER INFORMATION: Synthetic Polynucleotide

<400> SEQUENCE: 853
agctgattgc ccttcagagt ccactattaa agggtgccgt tttcttcatt a         51

<210> SEQ ID NO 854
<211> LENGTH: 43
<212> TYPE: DNA
<213> ORGANISM: Artificial
<220> FEATURE:
<223> OTHER INFORMATION: Synthetic Polynucleotide

<400> SEQUENCE: 854
agcaagcgta gggttgagtg ttgtagggag cctttcttca tta                  43

<210> SEQ ID NO 855
<211> LENGTH: 49
<212> TYPE: DNA
<213> ORGANISM: Artificial
<220> FEATURE:
<223> OTHER INFORMATION: Synthetic Polynucleotide

<400> SEQUENCE: 855
cccagcaggc gaaaaatccc ttataaatca agccggcgtt tcttcatta            49

<210> SEQ ID NO 856
<211> LENGTH: 43
<212> TYPE: DNA
<213> ORGANISM: Artificial
<220> FEATURE:
<223> OTHER INFORMATION: Synthetic Polynucleotide

<400> SEQUENCE: 856
tcaatatcga acctcaaata tcaattccga aatttcttca tta                  43

<210> SEQ ID NO 857
<211> LENGTH: 41
<212> TYPE: DNA
<213> ORGANISM: Artificial
<220> FEATURE:
<223> OTHER INFORMATION: Synthetic Polynucleotide

<400> SEQUENCE: 857
ctttaatgcg cgaactgata gccccaccag tttcttcatt a                    41
```

<210> SEQ ID NO 858
<211> LENGTH: 42
<212> TYPE: DNA
<213> ORGANISM: Artificial
<220> FEATURE:
<223> OTHER INFORMATION: Synthetic Polynucleotide

<400> SEQUENCE: 858
agaaaggaac aactaaagga attcaaaaaa attatgaatc ta                42

<210> SEQ ID NO 859
<211> LENGTH: 41
<212> TYPE: DNA
<213> ORGANISM: Artificial
<220> FEATURE:
<223> OTHER INFORMATION: Synthetic Polynucleotide

<400> SEQUENCE: 859
gttttaactt agtaccgcca cccagagcca ttatgaatct a                 41

<210> SEQ ID NO 860
<211> LENGTH: 41
<212> TYPE: DNA
<213> ORGANISM: Artificial
<220> FEATURE:
<223> OTHER INFORMATION: Synthetic Polynucleotide

<400> SEQUENCE: 860
aatacgtttg aaagaggaca gactgacctt ttatgaatct a                 41

<210> SEQ ID NO 861
<211> LENGTH: 43
<212> TYPE: DNA
<213> ORGANISM: Artificial
<220> FEATURE:
<223> OTHER INFORMATION: Synthetic Polynucleotide

<400> SEQUENCE: 861
gatggtttga acgagtagta aatttaccat tattatgaat cta               43

<210> SEQ ID NO 862
<211> LENGTH: 41
<212> TYPE: DNA
<213> ORGANISM: Artificial
<220> FEATURE:
<223> OTHER INFORMATION: Synthetic Polynucleotide

<400> SEQUENCE: 862
accgattgtc ggcattttcg gtcataatca ttatgaatct a                 41

<210> SEQ ID NO 863
<211> LENGTH: 41
<212> TYPE: DNA
<213> ORGANISM: Artificial
<220> FEATURE:
<223> OTHER INFORMATION: Synthetic Polynucleotide

<400> SEQUENCE: 863
tttaggacaa atgctttaaa caatcaggtc ttatgaatct a                 41

<210> SEQ ID NO 864
<211> LENGTH: 43
<212> TYPE: DNA
<213> ORGANISM: Artificial
<220> FEATURE:
<223> OTHER INFORMATION: Synthetic Polynucleotide

```
<400> SEQUENCE: 864
ccaacaggag cgaaccagac cggagccttt acttatgaat cta            43

<210> SEQ ID NO 865
<211> LENGTH: 41
<212> TYPE: DNA
<213> ORGANISM: Artificial
<220> FEATURE:
<223> OTHER INFORMATION: Synthetic Polynucleotide

<400> SEQUENCE: 865
acgctaacac ccacaagaat tgaaatagc ttatgaatct a               41

<210> SEQ ID NO 866
<211> LENGTH: 41
<212> TYPE: DNA
<213> ORGANISM: Artificial
<220> FEATURE:
<223> OTHER INFORMATION: Synthetic Polynucleotide

<400> SEQUENCE: 866
aacagttttg taccaaaaac attttatttc ttatgaatct a              41

<210> SEQ ID NO 867
<211> LENGTH: 43
<212> TYPE: DNA
<213> ORGANISM: Artificial
<220> FEATURE:
<223> OTHER INFORMATION: Synthetic Polynucleotide

<400> SEQUENCE: 867
caaccgtttc aaatcaccat caattcgagc cattatgaat cta            43

<210> SEQ ID NO 868
<211> LENGTH: 41
<212> TYPE: DNA
<213> ORGANISM: Artificial
<220> FEATURE:
<223> OTHER INFORMATION: Synthetic Polynucleotide

<400> SEQUENCE: 868
ttagtatcac aatagataag tccacgagca ttatgaatct a              41

<210> SEQ ID NO 869
<211> LENGTH: 41
<212> TYPE: DNA
<213> ORGANISM: Artificial
<220> FEATURE:
<223> OTHER INFORMATION: Synthetic Polynucleotide

<400> SEQUENCE: 869
taatcagcgg attgaccgta atcgtaaccg ttatgaatct a              41

<210> SEQ ID NO 870
<211> LENGTH: 43
<212> TYPE: DNA
<213> ORGANISM: Artificial
<220> FEATURE:
<223> OTHER INFORMATION: Synthetic Polynucleotide

<400> SEQUENCE: 870
caactgttgc gccattcgcc attcaaacat cattatgaat cta            43

<210> SEQ ID NO 871
```

```
<211> LENGTH: 41
<212> TYPE: DNA
<213> ORGANISM: Artificial
<220> FEATURE:
<223> OTHER INFORMATION: Synthetic Polynucleotide

<400> SEQUENCE: 871
cttttacaaa atcgtcgcta ttagcgatag ttatgaatct a                     41

<210> SEQ ID NO 872
<211> LENGTH: 41
<212> TYPE: DNA
<213> ORGANISM: Artificial
<220> FEATURE:
<223> OTHER INFORMATION: Synthetic Polynucleotide

<400> SEQUENCE: 872
gtcgacttcg gccaacgcgc ggggtttttc ttatgaatct a                     41

<210> SEQ ID NO 873
<211> LENGTH: 43
<212> TYPE: DNA
<213> ORGANISM: Artificial
<220> FEATURE:
<223> OTHER INFORMATION: Synthetic Polynucleotide

<400> SEQUENCE: 873
gcaattcaca tattcctgat tatcaaagtg tattatgaat cta                   43

<210> SEQ ID NO 874
<211> LENGTH: 41
<212> TYPE: DNA
<213> ORGANISM: Artificial
<220> FEATURE:
<223> OTHER INFORMATION: Synthetic Polynucleotide

<400> SEQUENCE: 874
cagaagatta gataatacat ttgtcgacaa ttatgaatct a                     41

<210> SEQ ID NO 875
<211> LENGTH: 42
<212> TYPE: DNA
<213> ORGANISM: Artificial
<220> FEATURE:
<223> OTHER INFORMATION: Synthetic Polynucleotide

<400> SEQUENCE: 875
caaatcaagt tttttggggt cgaaacgtgg attatgaatc ta                    42

<210> SEQ ID NO 876
<211> LENGTH: 41
<212> TYPE: DNA
<213> ORGANISM: Artificial
<220> FEATURE:
<223> OTHER INFORMATION: Synthetic Polynucleotide

<400> SEQUENCE: 876
aaagcactaa atcggaaccc taatccagtt ttatgaatct a                     41

<210> SEQ ID NO 877
<211> LENGTH: 43
<212> TYPE: DNA
<213> ORGANISM: Artificial
<220> FEATURE:
<223> OTHER INFORMATION: Synthetic Polynucleotide

<400> SEQUENCE: 877
```

```
cccgatttag agcttgacgg ggaaaaagaa tattatgaat cta                43
```

<210> SEQ ID NO 878
<211> LENGTH: 42
<212> TYPE: DNA
<213> ORGANISM: Artificial
<220> FEATURE:
<223> OTHER INFORMATION: Synthetic Polynucleotide

<400> SEQUENCE: 878

```
aacgtggcga gaaggaagg gaaaccagta attatgaatc ta                  42
```

<210> SEQ ID NO 879
<211> LENGTH: 41
<212> TYPE: DNA
<213> ORGANISM: Artificial
<220> FEATURE:
<223> OTHER INFORMATION: Synthetic Polynucleotide

<400> SEQUENCE: 879

```
taaaagggac attctggcca acaaagcatc ttatgaatct a                  41
```

<210> SEQ ID NO 880
<211> LENGTH: 43
<212> TYPE: DNA
<213> ORGANISM: Artificial
<220> FEATURE:
<223> OTHER INFORMATION: Synthetic Polynucleotide

<400> SEQUENCE: 880

```
acccttctga cctgaaagcg taagacgctg agttatgaat cta                43
```

<210> SEQ ID NO 881
<211> LENGTH: 42
<212> TYPE: DNA
<213> ORGANISM: Artificial
<220> FEATURE:
<223> OTHER INFORMATION: Synthetic Polynucleotide

<400> SEQUENCE: 881

```
gcacagacaa tatttttgaa tggggtcagt attatgaatc ta                 42
```

<210> SEQ ID NO 882
<211> LENGTH: 8064
<212> TYPE: DNA
<213> ORGANISM: Artificial
<220> FEATURE:
<223> OTHER INFORMATION: p8064 scaffold sequence for microtubule-like
      DNA origami structure

<400> SEQUENCE: 882

```
tgatagacgg ttttcgccc tttgacgttg gagtccacgt tctttaatag tggactcttg   60
ttccaaactg gaacaacact caaccctatc tcgggctatt cttttgattt ataagggatt  120
ttgccgattt cggaaccacc atcaaacagg attttcgcct gctggggcaa accagcgtgg  180
accgcttgct gcaactctct cagggccagg cggtgaaggg caatcagctg ttgcccgtct  240
cactggtgaa aagaaaaacc accctggcgc ccaatacgca aaccgcctct ccccgcgcgt  300
tggccgattc attaatgcag ctggcacgac aggtttcccg actggaaagc gggcagtgag  360
cgcaacgcaa ttaatgtgag ttagctcact cattaggcac cccaggcttt acactttatg  420
cttccggctc gtatgttgtg tggaattgtg agcggataac aatttcacac aggaaacagc  480
tatgaccatg attacgaatt cgagctcggt acccggggat cctcaactgt gaggaggctc  540
```

```
acggacgcga agaacaggca cgcgtgctgg cagaaacccc cggtatgacc gtgaaaacgg      600
cccgccgcat tctggccgca gcaccacaga gtgcacaggc gcgcagtgac actgcgctgg      660
atcgtctgat gcagggggca ccggcaccgc tggctgcagg taacccggca tctgatgccg      720
ttaacgattt gctgaacaca ccagtgtaag ggatgtttat gacgagcaaa gaaacccttta     780 cccattacca gccgcagggc aacagtgacc cggctcatac cgcaaccgcg cccggcggat      840
tgagtgcgaa agcgcctgca atgaccccgc tgatgctgga cacctccagc cgtaagctgg      900
ttgcgtggga tggcaccacc gacggtgctg ccgttggcat tcttgcggtt gctgctgacc      960
agaccagcac cacgctgacg ttctacaagt ccggcacgtt ccgttatgag gatgtgctct     1020
ggccggaggc tgccagcgac gagacgaaaa acggaccgc gtttgccgga acggcaatca      1080
gcatcgttta actttaccct tcatcactaa aggccgcctg tgcggctttt tttacgggat     1140
ttttttatgt cgatgtacac aaccgcccaa ctgctggcgg caaatgagca gaaatttaag     1200
tttgatccgc tgtttctgcg tctcttttc cgtgagagct atcccttcac cacggagaaa      1260
gtctatctct cacaaattcc gggactggta acatggcgc tgtacgtttc gccgattgtt      1320
tccggtgagg ttatccgttc ccgtggcggc tccacctctg aaagcttggc actggccgtc     1380
gttttacaac gtcgtgactg ggaaaaccct ggcgttaccc aacttaatcg ccttgcagca     1440
catccccctt tcgccagctg gcgtaatagc gaagaggccc gcaccgatcg cccttcccaa     1500
cagttgcgca gcctgaatgg cgaatggcgc tttgcctggt tccggcacc agaagcggtg      1560 ccggaaagct ggctggagtg cgatcttcct gaggccgata ctgtcgtcgt cccctcaaac     1620
tggcagatgc acggttacga tgcgcccatc tacaccaacg tgacctatcc cattacggtc     1680
aatccgccgt ttgttcccac ggagaatccg acgggttgtt actcgctcac atttaatgtt     1740
gatgaaagct ggctacagga aggccagacg cgaattattt ttgatggcgt tcctattggt     1800
taaaaaatga gctgatttaa caaaaattta atgcgaattt taacaaaata ttaacgttta     1860
caatttaaat atttgcttat acaatcttcc tgttttttggg gcttttctga ttatcaaccg     1920
gggtacatat gattgacatg ctagttttac gattaccgtt catcgattct cttgtttgct     1980
ccagactctc aggcaatgac ctgatagcct ttgtagatct ctcaaaaata gctaccctct     2040
ccggcattaa tttatcagct agaacggttg aatatcatat tgatggtgat ttgactgtct     2100 ccggccttc tcacccttt gaatctttac ctacacatta ctcaggcatt gcatttaaaa       2160
tatatgaggg ttctaaaaat tttatccttt gcgttgaaat aaaggcttct cccgcaaaag     2220
tattacaggg tcataatgtt tttggtacaa ccgatttagc tttatgctct gaggctttat     2280
tgcttaattt tgctaattct ttgccttgcc tgtatgattt attggatgtt aatgctacta     2340
ctattagtag aattgatgcc accttttcag ctcgcgcccc aaatgaaaat atagctaaac     2400
aggttattga ccatttgcga aatgtatcta atggtcaaac taaatctact cgttcgcaga     2460
attgggaatc aactgttata tggaatgaaa cttccagaca ccgtacttta gttgcatatt     2520
taaaacatgt tgagctacag cattatattc agcaattaag ctctaagcca tccgcaaaaa     2580
tgacctctta tcaaaaggag caattaaagg tactctctaa tcctgacctg ttggagtttg     2640
cttccggtct ggttcgcttt gaagctcgaa ttaaaacgcg atatttgaag tctttcgggc     2700
ttcctcttaa tctttttgat gcaatccgct ttgcttctga ctataatagt cagggtaaag     2760
acctgatttt tgatttatgg tcattctcgt tttctgaact gtttaaagca tttgagggg      2820 attcaatgaa tatttatgac gattccgcag tattggacgc tatccagtct aaacatttta     2880
```

```
ctattacccc ctctggcaaa acttcttttg caaaagcctc tcgctatttt ggttttatc    2940
gtcgtctggt aaacgagggt tatgatagtg ttgctcttac tatgcctcgt aattcctttt    3000
ggcgttatgt atctgcatta gttgaatgtg gtattcctaa atctcaactg atgaatcttt    3060
ctacctgtaa taatgttgtt ccgttagttc gttttattaa cgtagatttt tcttcccaac    3120
gtcctgactg gtataatgag ccagttctta aaatcgcata aggtaattca caatgattaa    3180
agttgaaatt aaaccatctc aagcccaatt tactactcgt tctggtgttt ctcgtcaggg    3240
caagccttat tcactgaatg agcagctttg ttacgttgat ttgggtaatg aatatccggt    3300
tcttgtcaag attactcttg atgaaggtca gccagcctat gcgcctggtc tgtacaccgt    3360
tcatctgtcc tctttcaaag ttggtcagtt cggttccctt atgattgacc gtctgcgcct    3420
cgttccggct aagtaacatg gagcaggtcg cggatttcga cacaatttat caggcgatga    3480
tacaaatctc cgttgtactt tgtttcgcgc ttggtataat cgctgggggt caaagatgag    3540
tgttttagtg tattcttttg cctctttcgt tttaggttgg tgccttcgta gtggcattac    3600
gtatttttacc cgtttaatgg aaacttcctc atgaaaaagt ctttagtcct caaagcctct    3660
gtagccgttg ctaccctcgt tccgatgctg tctttcgctg ctgagggtga cgatcccgca    3720
aaagcggcct ttaactccct gcaagcctca gcgaccgaat atatcggtta tgcgtgggcg    3780
atggttgttg tcattgtcgg cgcaactatc ggtatcaagc tgtttaagaa attcacctcg    3840
aaagcaagct gataaaccga tacaattaaa ggctcctttt ggagcctttt ttttggagat    3900
tttcaacgtg aaaaaattat tattcgcaat cctttagtt gttcctttct attctcactc    3960
cgctgaaact gttgaaagtt gtttagcaaa atcccataca gaaaattcat ttactaacgt    4020
ctggaaagac gacaaaactt tagatcgtta cgctaactat gagggctgtc tgtggaatgc    4080
tacaggcgtt gtagtttgta ctggtgacga aactcagtgt tacggtacat gggttcctat    4140
tgggcttgct atccctgaaa atgagggtgg tggctctgag ggtggcggtt ctgagggtgg    4200
cggttctgag ggtggcggta ctaaacctcc tgagtacggt gatacaccta ttccgggcta    4260
tacttatatc aaccctctcg acggcactta tccgcctggt actgagcaaa accccgctaa    4320
tcctaatcct tctcttgagg agtctcagcc tcttaatact ttcatgtttc agaataatag    4380
gttccgaaat aggcagggggcattaactgt ttatacgggc actgttactc aaggcactga    4440
ccccgttaaa acttattacc agtacactcc tgtatcatca aaagccatgt atgacgctta    4500
ctggaacggt aaattcagag actgcgcttt ccattctggc tttaatgagg atttatttgt    4560
ttgtgaatat caaggccaat cgtctgacct gcctcaacct cctgtcaatg ctggcggcgg    4620
ctctggtggt ggttctggtg gcggctctga gggtggtggc tctgagggtg gcggttctga    4680
gggtggcggc tctgagggag gcggttccgg tggtggctct ggttccgtg attttgatta    4740
tgaaaagatg gcaacgctaa taagggggc tatgaccgaa aatgccgatg aaaacgcgct    4800
acagtctgac gctaaaggca aacttgattc tgtcgctact gattacggtg ctgctatcga    4860
tggtttcatt ggtgacgttt ccggccttgc taatggtaat ggtgctactg gtgattttgc    4920
tggctctaat tcccaaatgg ctcaagtcgg tgacggtgat aattcacctt taatgaataa    4980
tttccgtcaa tatttacctt ccctccctca atcggttgaa tgtcgccctt ttgtctttgg    5040
cgctggtaaa ccatatgaat tttctattga ttgtgacaaa ataaacttat tccgtggtgt    5100
ctttgcgttt cttttatatg ttgccacctt tatgtatgta ttttctacgt ttgctaacat    5160
actgcgtaat aaggagtctt aatcatgcca gttcttttgg gtattccgtt attattgcgt    5220
ttcctcggtt tccttctggt aactttgttc ggctatctgc ttacttttct taaaaagggc    5280
```

```
ttcggtaaga tagctattgc tatttcattg tttcttgctc ttattattgg gcttaactca    5340
attcttgtgg gttatctctc tgatattagc gctcaattac cctctgactt tgttcagggt    5400
gttcagttaa ttctcccgtc taatgcgctt ccctgttttt atgttattct ctctgtaaag    5460
gctgctattt tcattttttga cgttaaacaa aaaatcgttt cttatttgga ttgggataaa    5520
taatatggct gtttattttg taactggcaa attaggctct ggaaagacgc tcgttagcgt    5580
tggtaagatt caggataaaa ttgtagctgg gtgcaaaata gcaactaatc ttgatttaag    5640
gcttcaaaac ctcccgcaag tcgggaggtt cgctaaaacg cctcgcgttc ttagaatacc    5700
ggataagcct tctatatctg atttgcttgc tattgggcgc ggtaatgatt cctacgatga    5760
aaataaaaac ggcttgcttg ttctcgatga gtgcggtact tggtttaata cccgttcttg    5820
gaatgataag gaaagacagc cgattattga ttggtttcta catgctcgta aattaggatg    5880
ggatattatt tttcttgttc aggacttatc tattgttgat aaacaggcgc gttctgcatt    5940
agctgaacat gttgtttatt gtcgtcgtct ggacagaatt actttacctt ttgtcggtac    6000
tttatattct cttattactg gctcgaaaat gcctctgcct aaattacatg ttggcgttgt    6060
taaatatggc gattctcaat taagccctac tgttgagcgt tggctttata ctggtaagaa    6120
tttgtataac gcatatgata ctaaacaggc tttttctagt aattatgatt ccggtgttta    6180 ttcttatttta acgccttatt tatcacacgg tcggtatttc aaaccattaa atttaggtca    6240
gaagatgaaa ttaactaaaa tatatttgaa aaagttttct cgcgttcttt gtcttgcgat    6300
tggatttgca tcagcattta catatagtta tataacccaa cctaagccgg aggttaaaaa    6360
ggtagtctct cagacctatg attttgataa attcactatt gactcttctc agcgtcttaa    6420
tctaagctat cgctatgttt tcaaggattc taagggaaaa ttaattaata gcgacgattt    6480
acagaagcaa ggttattcac tcacatatat tgatttatgt actgtttcca ttaaaaaagg    6540
taattcaaat gaaattgtta aatgtaatta attttgtttt cttgatgttt gtttcatcat    6600
cttcttttgc tcaggtaatt gaaatgaata attcgcctct gcgcgatttt gtaacttggt    6660
attcaaagca atcaggcgaa tccgttattg tttctcccga tgtaaaaggt actgttactg    6720
tatattcatc tgacgttaaa cctgaaaatc tacgcaattt cttatttct gttttacgtg    6780 caaataattt tgatatggta ggttctaacc cttccattat tcagaagtat aatccaaaca    6840
atcaggatta tattgatgaa ttgccatcat ctgataatca ggaatatgat gataattccg    6900
ctccttctgg tggtttcttt gttccgcaaa atgataatgt tactcaaact tttaaaatta    6960
ataacgttcg ggcaaaggat ttaatacgag ttgtcgaatt gtttgtaaag tctaatactt    7020
ctaaatcctc aaatgtatta tctattgacg gctctaatct attagttgtt agtgctccta    7080
aagatatttt agataacctt cctcaattcc tttcaactgt tgatttgcca actgaccaga    7140
tattgattga gggtttgata tttgaggttc agcaaggtga tgctttagat ttttcatttg    7200
ctgctggctc tcagcgtggc actgttgcag gcggtgttaa tactgaccgc ctcacctctg    7260
ttttatcttc tgctggtggt tcgttcggta ttttaatgg cgatgtttta gggctatcag    7320
ttcgcgcatt aaagactaat agccattcaa aaatattgtc tgtgccacgt attcttacgc    7380
tttcaggtca gaagggttct atctctgttg gccagaatgt cccttttatt actggtcgtg    7440
tgactggtga atctgccaat gtaaataatc catttcagac gattgagcgt caaaatgtag    7500
gtatttccat gagcgttttt cctgttgcaa tggctggcgg taatattgtt ctggatatta    7560
ccagcaaggc cgatagtttg agttcttcta ctcaggcaag tgatgttatt actaatcaaa    7620
```

```
gaagtattgc tacaacggtt aatttgcgtg atggacagac tcttttactc ggtggcctca    7680
ctgattataa aaacacttct caggattctg gcgtaccgtt cctgtctaaa atccctttaa    7740
tcggcctcct gtttagctcc cgctctgatt ctaacgagga agcacgtta tacgtgctcg     7800 tcaaagcaac catagtacgc gccctgtagc ggcgcattaa gcgcggcggg tgtggtggtt    7860
acgcgcagcg tgaccgctac acttgccagc gccctagcgc ccgctccttt cgctttcttc    7920
ccttcctttc tcgccacgtt cgccggcttt ccccgtcaag ctctaaatcg ggggctccct    7980
ttagggttcc gatttagtgc tttacggcac ctcgacccca aaaaacttga tttgggtgat    8040
ggttcacgta gtgggccatc gccc                                          8064
```

<210> SEQ ID NO 883
<211> LENGTH: 6912
<212> TYPE: DNA
<213> ORGANISM: Artificial
<220> FEATURE:
<223> OTHER INFORMATION: M13mp18 scaffold sequence for drift markers and Exchange-PAINT DNAorigami structures

<400> SEQUENCE: 883

```
ttcccttcct ttctcgccac gttcgccggc tttccccgtc aagctctaaa tcggggctc      60 cctttagggt tccgatttag tgctttacgg cacctcgacc ccaaaaaact tgatttgggt    120
gatggttcac gtagtgggcc atcgccctga tagacggttt ttcgcccttt gacgttggag    180
tccacgttct ttaatagtgg actcttgttc caaactggaa caacactcaa ccctatctcg    240
ggctattctt ttgatttata agggattttg ccgatttcgg aaccaccatc aaacaggatt    300
ttcgcctgct ggggcaaacc agcgtggacc gcttgctgca actctctcag gccaggcgg     360 tgaagggcaa tcagctgttg cccgtctcac tggtgaaaag aaaaaccacc ctggcgccca    420
atacgcaaac cgcctctccc cgcgcgttgg ccgattcatt aatgcagctg gcacgacagg    480
tttcccgact ggaaagcggg cagtgagcgc aacgcaatta atgtgagtta gctcactcat    540
taggcacccc aggctttaca ctttatgctt ccggctcgta tgttgtgtgg aattgtgagc    600
ggataacaat ttcacacagg aaacagctat gaccatgatt acgaattcga gctcggtacc    660
cggggatcct ctagagtcga cctgcaggca tgcaagcttg gcactggccg tcgttttaca    720
acgtcgtgac tgggaaaacc ctggcgttac ccaacttaat cgccttgcag cacatccccc    780
tttcgccagc tggcgtaata gcgaagaggc ccgcaccgat cgcccttccc aacagttgcg    840
cagcctgaat ggcgaatggc gctttgcctg gtttccggca ccagaagcgg tgccggaaag    900
ctggctggag tgcgatcttc ctgaggccga tactgtcgtc gtcccctcaa actggcagat    960
gcacggttac gatgcgccca tctacaccaa cgtgacctat cccattacgg tcaatccgcc   1020
gtttgttccc acgagaatc cgacgggttg ttactcgctc acatttaatg ttgatgaaag    1080
ctggctacag gaaggccaga cgcgaattat ttttgatggc gttcctattg gttaaaaaat   1140
gagctgattt aacaaaaatt taatgcgaat tttaacaaaa tattaacgtt tacaatttaa   1200
atatttgctt atacaatctt cctgttttg ggcttttct gattatcaac cggggtacat     1260
atgattgaca tgctagtttt acgattaccg ttcatcgatt ctcttgtttg ctccagactc    1320
tcaggcaatg acctgatagc ctttgtagat ctctcaaaaa tagctaccct ctccggcatt    1380
aatttatcag ctagaacggt tgaatatcat attgatggtg atttgactgt ctccggcctt    1440
tctcaccctt ttgaatcttt acctacacat tactcaggca ttgcatttaa atatatgag     1500 ggttctaaaa atttttatcc ttgcgttgaa ataaaggctt ctcccgcaaa agtattacag    1560
```

```
ggtcataatg ttttggtac aaccgattta gctttatgct ctgaggcttt attgcttaat    1620
tttgctaatt ctttgccttg cctgtatgat ttattggatg ttaatgctac tactattagt    1680
agaattgatg ccaccttttc agctcgcgcc ccaaatgaaa atatagctaa acaggttatt    1740
gaccatttgc gaaatgtatc taatggtcaa actaaatcta ctcgttcgca gaattgggaa    1800
tcaactgtta tatggaatga aacttccaga caccgtactt tagttgcata tttaaaacat    1860
gttgagctac agcattatat tcagcaatta agctctaagc catccgcaaa aatgacctct    1920
tatcaaaagg agcaattaaa ggtactctct aatcctgacc tgttggagtt tgcttccggt    1980
ctggttcgct ttgaagctcg aattaaaacg cgatatttga agtctttcgg gcttcctctt    2040 aatcttttg atgcaatccg ctttgcttct gactataata gtcagggtaa agacctgatt    2100
tttgatttat ggtcattctc gttttctgaa ctgtttaaag catttgaggg ggattcaatg    2160
aatatttatg acgattccgc agtattggac gctatccagt ctaaacatttt tactattacc    2220 ccctctggca aaacttcttt tgcaaaagcc tctcgctatt ttggttttta tcgtcgtctg    2280
gtaaacgagg gttatgatag tgttgctctt actatgcctc gtaattcctt ttggcgttat    2340
gtatctgcat tagttgaatg tggtattcct aaatctcaac tgatgaatct ttctacctgt    2400
aataatgttg ttccgttagt tcgttttatt aacgtagatt tttcttccca acgtcctgac    2460
tggtataatg agccagttct taaaatcgca taggtaatt cacaatgatt aaagttgaaa    2520
ttaaaccatc tcaagcccaa tttactactc gttctggtgt ttctcgtcag gcaagccttt    2580
attcactgaa tgagcagctt tgttacgttg atttgggtaa tgaatatccg gttcttgtca    2640
agattactct tgatgaaggt cagccagcct atgcgcctgg tctgtacacc gttcatctgt    2700
cctctttcaa agttggtcag ttcggttccc ttatgattga ccgtctgcgc ctcgttccgg    2760
ctaagtaaca tggagcaggt cgcggatttc gacacaattt atcaggcgat gatacaaatc    2820
tccgttgtac tttgtttcgc gcttggtata atcgctgggg gtcaaagatg agtgttttag    2880
tgtattcttt tgcctctttc gttttaggtt ggtgccttcg tagtggcatt acgtatttta    2940
cccgtttaat ggaaacttcc tcatgaaaaa gtctttagtc ctcaaagcct ctgtagccgt    3000 tgctacccte gttccgatgc tgtctttcgc tgctgagggt gacgatcccg caaaagcggc    3060
ctttaactcc ctgcaagcct cagcgaccga atatatcggt tatgcgtggg cgatggttgt    3120
tgtcattgtc ggcgcaacta tcggtatcaa gctgtttaag aaattcacct cgaaagcaag    3180
ctgataaacc gatacaatta aaggctcctt ttggagcctt ttttttggag attttcaacg    3240
tgaaaaaatt attattcgca attcctttag ttgttccttt ctattctcac tccgctgaaa    3300
ctgttgaaag ttgtttagca aaatcccata cagaaaattc atttactaac gtctggaaag    3360
acgacaaaac tttagatcgt tacgctaact atgagggctg tctgtggaat gctacaggcg    3420
ttgtagtttg tactggtgac gaaactcagt gttacggtac atgggttcct attgggcttg    3480
ctatccctga aaatgagggt ggtggctctg agggtggcgg ttctgagggt ggcggttctg    3540
agggtggcgg tactaaacct cctgagtacg gtgatacacc tattccgggc tatacttata    3600
tcaaccctct cgacggcact tatccgcctg gtactgagca aaaccccgct aatcctaatc    3660
cttctcttga ggagtctcag cctcttaata ctttcatgtt tcagaataat aggttccgaa    3720
ataggcaggg ggcattaact gtttatacgg gcactgttac tcaaggcact gaccccgtta    3780
aaacttatta ccagtacact cctgtatcat caaaagccat gtatgacgct tactggaacg    3840
gtaaattcag agactgcgct ttccattctg gctttaatga ggatttattt gtttgtgaat    3900
atcaaggcca atcgtctgac ctgcctcaac ctcctgtcaa tgctggcggc ggctctggtg    3960
```

```
gtggttctgg tggcggctct gagggtggtg gctctgaggg tggcggttct gagggtggcg    4020
gctctgaggg aggcggttcc ggtggtggct ctggttccgg tgattttgat tatgaaaaga    4080
tggcaaacgc taataagggg gctatgaccg aaaatgccga tgaaaacgcg ctacagtctg    4140
acgctaaagg caaacttgat tctgtcgcta ctgattacgg tgctgctatc gatggtttca    4200
ttggtgacgt ttccggcctt gctaatggta atggtgctac tggtgatttt gctggctcta    4260
attcccaaat ggctcaagtc ggtgacggtg ataattcacc tttaatgaat aatttccgtc    4320
aatatttacc ttccctccct caatcggttg aatgtcgccc ttttgtcttt ggcgctggta    4380
aaccatatga attttctatt gattgtgaca aaataaactt attccgtggt gtctttgcgt    4440
ttcttttata tgttgccacc tttatgtatg tattttctac gtttgctaac atactgcgta    4500
ataaggagtc ttaatcatgc cagttctttt gggtattccg ttattattgc gtttcctcgg    4560
tttccttctg gtaactttgt tcggctatct gcttactttt cttaaaaagg gcttcggtaa    4620
gatagctatt gctatttcat tgtttcttgc tcttattatt gggcttaact caattcttgt    4680
gggttatctc tctgatatta gcgctcaatt accctctgac tttgttcagg gtgttcagtt    4740
aattctcccg tctaatgcgc ttccctgttt ttatgttatt ctctctgtaa aggctgctat    4800
tttcattttt gacgttaaac aaaaaatcgt ttcttatttg gattgggata aataatatgg    4860
ctgtttattt tgtaactggc aaattaggct ctggaaagac gctcgttagc gttggtaaga    4920
ttcaggataa aattgtagct gggtgcaaaa tagcaactaa tcttgattta aggcttcaaa    4980
acctcccgca agtcgggagg ttcgctaaaa cgcctcgcgt tcttagaata ccggataagc    5040
cttctatatc tgatttgctt gctattgggc gcggtaatga ttcctacgat gaaaataaaa    5100
acggcttgct tgttctcgat gagtgcggta cttggtttaa tacccgttct tggaatgata    5160
aggaaagaca gccgattatt gattggtttc tacatgctcg taaattagga tgggatatta    5220
tttttcttgt tcaggactta tctattgttg ataaacaggc gcgttctgca ttagctgaac    5280
atgttgttta ttgtcgtcgt ctggacagaa ttactttacc ttttgtcggt actttatatt    5340
ctcttattac tggctcgaaa atgcctctgc ctaaattaca tgttggcgtt gttaaatatg    5400
gcgattctca attaagccct actgttgagc gttggcttta tactggtaag aatttgtata    5460
acgcatatga tactaaacag gcttttttct agtaattatga ttccggtgtt tattcttatt    5520
taacgcctta tttatcacac ggtcggtatt tcaaaccatt aaatttaggt cagaagatga    5580
aattaactaa aatatatttg aaaaagtttt ctcgcgttct ttgtcttgcg attggatttg    5640
catcagcatt tacatatagt tatataaccc aacctaagcc ggaggttaaa aaggtagtct    5700
ctcagaccta tgattttgat aaattcacta ttgactcttc tcagcgtctt aatctaagct    5760
atcgctatgt tttcaaggat tctaagggaa aattaattaa tagcgacgat ttacagaagc    5820
aaggttattc actcacatat attgatttat gtactgtttc cattaaaaaa ggtaattcaa    5880
atgaaattgt taaatgtaat taattttgtt ttcttgatgt ttgtttcatc atcttctttt    5940
gctcaggtaa ttgaaatgaa taattcgcct ctgcgcgatt ttgtaacttg gtattcaaag    6000
caatcaggcg aatccgttat tgtttctccc gatgtaaaag gtactgttac tgtatattca    6060
tctgacgtta aacctgaaaa tctacgcaat ttctttattt ctgttttacg tgcaaataat    6120
tttgatatgg taggttctaa cccttccatt attcagaagt ataatccaaa caatcaggat    6180
tatattgatg aattgccatc atctgataat caggaatatg atgataattc cgctccttct    6240
ggtggtttct ttgttccgca aaatgataat gttactcaaa cttttaaaat taataacgtt    6300
```

-continued

```
cgggcaaagg atttaatacg agttgtcgaa ttgtttgtaa agtctaatac ttctaaatcc     6360
tcaaatgtat tatctattga cggctctaat ctattagttg ttagtgctcc taaagatatt     6420
ttagataacc ttcctcaatt cctttcaact gttgatttgc caactgacca gatattgatt     6480
gagggtttga tatttgaggt tcagcaaggt gatgctttag attttcatt tgctgctggc      6540 tctcagcgtg gcactgttgc aggcggtgtt aatactgacc gcctcacctc tgttttatct     6600
tctgctggtg gttcgttcgg tattttaat ggcgatgttt tagggctatc agttcgcgca      6660
ttaaagacta atagccattc aaaaatattg tctgtgccac gtattcttac gctttcaggt     6720
cagaagggtt ctatctctgt tggccagaat gtccctttta ttactggtcg tgtgactggt     6780
gaatctgcca atgtaaataa tccatttcag acgattgagc gtcaaaatgt aggtatttcc     6840
atgagcgttt ttcctgttgc aatggctggc ggtaatattg ttctggatat taccagcaag     6900
gccgatagtt tg                                                         6912
```

<210> SEQ ID NO 884
<211> LENGTH: 10
<212> TYPE: DNA
<213> ORGANISM: Artificial
<220> FEATURE:
<223> OTHER INFORMATION: Synthetic Polynucleotide

<400> SEQUENCE: 884
ctagatgtat          10

<210> SEQ ID NO 885
<211> LENGTH: 10
<212> TYPE: DNA
<213> ORGANISM: Artificial
<220> FEATURE:
<223> OTHER INFORMATION: Synthetic Polynucleotide

<400> SEQUENCE: 885
tatgtagatc          10

<210> SEQ ID NO 886
<211> LENGTH: 10
<212> TYPE: DNA
<213> ORGANISM: Artificial
<220> FEATURE:
<223> OTHER INFORMATION: Synthetic Polynucleotide

<400> SEQUENCE: 886
gtaatgaaga          10

<210> SEQ ID NO 887
<211> LENGTH: 10
<212> TYPE: DNA
<213> ORGANISM: Artificial
<220> FEATURE:
<223> OTHER INFORMATION: Synthetic Polynucleotide

<400> SEQUENCE: 887
gtagattcat          10

<210> SEQ ID NO 888
<211> LENGTH: 10
<212> TYPE: DNA
<213> ORGANISM: Artificial
<220> FEATURE:
<223> OTHER INFORMATION: Synthetic Polynucleotide

<400> SEQUENCE: 888
ctttacctaa                                                            10

<210> SEQ ID NO 889
<211> LENGTH: 10
<212> TYPE: DNA
<213> ORGANISM: Artificial
<220> FEATURE:
<223> OTHER INFORMATION: Synthetic Polynucleotide

<400> SEQUENCE: 889
gtactcaatt                                                            10

<210> SEQ ID NO 890
<211> LENGTH: 10
<212> TYPE: DNA
<213> ORGANISM: Artificial
<220> FEATURE:
<223> OTHER INFORMATION: Synthetic Polynucleotide

<400> SEQUENCE: 890
catcctaatt                                                            10

<210> SEQ ID NO 891
<211> LENGTH: 10
<212> TYPE: DNA
<213> ORGANISM: Artificial
<220> FEATURE:
<223> OTHER INFORMATION: Synthetic Polynucleotide

<400> SEQUENCE: 891
gatccattat                                                            10

<210> SEQ ID NO 892
<211> LENGTH: 10
<212> TYPE: DNA
<213> ORGANISM: Artificial
<220> FEATURE:
<223> OTHER INFORMATION: Synthetic Polynucleotide

<400> SEQUENCE: 892
caccttatta                                                            10

<210> SEQ ID NO 893
<211> LENGTH: 10
<212> TYPE: DNA
<213> ORGANISM: Artificial
<220> FEATURE:
<223> OTHER INFORMATION: Synthetic Polynucleotide

<400> SEQUENCE: 893
ccttctctat                                                            10

<210> SEQ ID NO 894
<211> LENGTH: 10
<212> TYPE: DNA
<213> ORGANISM: Artificial
<220> FEATURE:
<223> OTHER INFORMATION: Synthetic Polynucleotide

<400> SEQUENCE: 894
gtatcatcaa                                                            10

<210> SEQ ID NO 895
<211> LENGTH: 10
<212> TYPE: DNA

```
<213> ORGANISM: Artificial
<220> FEATURE:
<223> OTHER INFORMATION: Synthetic Polynucleotide

<400> SEQUENCE: 895
gaatcactat                                                          10

<210> SEQ ID NO 896
<211> LENGTH: 11
<212> TYPE: DNA
<213> ORGANISM: Artificial
<220> FEATURE:
<223> OTHER INFORMATION: Synthetic Polynucleotide

<400> SEQUENCE: 896
ttatacatct a                                                        11

<210> SEQ ID NO 897
<211> LENGTH: 11
<212> TYPE: DNA
<213> ORGANISM: Artificial
<220> FEATURE:
<223> OTHER INFORMATION: Synthetic Polynucleotide

<400> SEQUENCE: 897
ttatctacat a                                                        11

<210> SEQ ID NO 898
<211> LENGTH: 12
<212> TYPE: DNA
<213> ORGANISM: Artificial
<220> FEATURE:
<223> OTHER INFORMATION: Synthetic Polynucleotide

<400> SEQUENCE: 898
ttgatctaca ta                                                       12

<210> SEQ ID NO 899
<211> LENGTH: 11
<212> TYPE: DNA
<213> ORGANISM: Artificial
<220> FEATURE:
<223> OTHER INFORMATION: Synthetic Polynucleotide

<400> SEQUENCE: 899
tttcttcatt a                                                        11

<210> SEQ ID NO 900
<211> LENGTH: 11
<212> TYPE: DNA
<213> ORGANISM: Artificial
<220> FEATURE:
<223> OTHER INFORMATION: Synthetic Polynucleotide

<400> SEQUENCE: 900
ttatgaatct a                                                        11

<210> SEQ ID NO 901
<211> LENGTH: 11
<212> TYPE: DNA
<213> ORGANISM: Artificial
<220> FEATURE:
<223> OTHER INFORMATION: Synthetic Polynucleotide

<400> SEQUENCE: 901
ttttaggtaa a                                                        11
```

```
<210> SEQ ID NO 902
<211> LENGTH: 11
<212> TYPE: DNA
<213> ORGANISM: Artificial
<220> FEATURE:
<223> OTHER INFORMATION: Synthetic Polynucleotide

<400> SEQUENCE: 902
ttaattgagt a                                                          11

<210> SEQ ID NO 903
<211> LENGTH: 11
<212> TYPE: DNA
<213> ORGANISM: Artificial
<220> FEATURE:
<223> OTHER INFORMATION: Synthetic Polynucleotide

<400> SEQUENCE: 903
ttaattagga t                                                          11

<210> SEQ ID NO 904
<211> LENGTH: 11
<212> TYPE: DNA
<213> ORGANISM: Artificial
<220> FEATURE:
<223> OTHER INFORMATION: Synthetic Polynucleotide

<400> SEQUENCE: 904
ttataatgga t                                                          11

<210> SEQ ID NO 905
<211> LENGTH: 11
<212> TYPE: DNA
<213> ORGANISM: Artificial
<220> FEATURE:
<223> OTHER INFORMATION: Synthetic Polynucleotide

<400> SEQUENCE: 905
tttaataagg t                                                          11

<210> SEQ ID NO 906
<211> LENGTH: 11
<212> TYPE: DNA
<213> ORGANISM: Artificial
<220> FEATURE:
<223> OTHER INFORMATION: Synthetic Polynucleotide

<400> SEQUENCE: 906
ttatagagaa g                                                          11

<210> SEQ ID NO 907
<211> LENGTH: 11
<212> TYPE: DNA
<213> ORGANISM: Artificial
<220> FEATURE:
<223> OTHER INFORMATION: Synthetic Polynucleotide

<400> SEQUENCE: 907
ttttgatgat a                                                          11

<210> SEQ ID NO 908
<211> LENGTH: 11
<212> TYPE: DNA
<213> ORGANISM: Artificial
<220> FEATURE:
```

<223> OTHER INFORMATION: Synthetic Polynucleotide

<400> SEQUENCE: 908
ttatagtgat t                                                        11

<210> SEQ ID NO 909
<211> LENGTH: 11
<212> TYPE: DNA
<213> ORGANISM: Artificial
<220> FEATURE:
<223> OTHER INFORMATION: Synthetic Polynucleotide

<400> SEQUENCE: 909
ttatacatct a                                                        11

<210> SEQ ID NO 910
<211> LENGTH: 11
<212> TYPE: DNA
<213> ORGANISM: Artificial
<220> FEATURE:
<223> OTHER INFORMATION: Synthetic Polynucleotide

<400> SEQUENCE: 910
ttatctacat a                                                        11

<210> SEQ ID NO 911
<211> LENGTH: 11
<212> TYPE: DNA
<213> ORGANISM: Artificial
<220> FEATURE:
<223> OTHER INFORMATION: Synthetic Polynucleotide

<400> SEQUENCE: 911
tttcttcatt a                                                        11

<210> SEQ ID NO 912
<211> LENGTH: 11
<212> TYPE: DNA
<213> ORGANISM: Artificial
<220> FEATURE:
<223> OTHER INFORMATION: Synthetic Polynucleotide

<400> SEQUENCE: 912
ttatgaatct a                                                        11

<210> SEQ ID NO 913
<211> LENGTH: 21
<212> TYPE: DNA
<213> ORGANISM: Artificial
<220> FEATURE:
<223> OTHER INFORMATION: Synthetic Polynucleotide

<400> SEQUENCE: 913
gaatcggtca cagtacaacc g                                             21